United States Patent
Tresch et al.

(10) Patent No.: US 10,294,488 B2
(45) Date of Patent: May 21, 2019

(54) HERBICIDE-METABOLIZING CYTOCHROME P450 MONOOXYGENASES

(71) Applicant: BASF SE, Ludwigshafen (DE)

(72) Inventors: Stefan Tresch, Kirchheim (DE); Doreen Schachtschabel, Mannheim (DE); Maciej Pasternak, Ludwigshafen (DE); Liliana Parra Rapado, Offenburg (DE); Jens Lerchl, Golm (DE); Thomas Mietzner, Annweiler (DE); Martin Laforest, St.-Jean-sur-Richelieu (CA)

(73) Assignee: BASF SE, Ludwigshafen (DE)

( * ) Notice: Subject to any disclaimer, the term of this patent is extended or adjusted under 35 U.S.C. 154(b) by 545 days.

(21) Appl. No.: 14/653,090

(22) PCT Filed: Dec. 13, 2013

(86) PCT No.: PCT/IB2013/060902
§ 371 (c)(1),
(2) Date: Jun. 17, 2015

(87) PCT Pub. No.: WO2014/097085
PCT Pub. Date: Jun. 26, 2014

(65) Prior Publication Data
US 2015/0322453 A1 Nov. 12, 2015

Related U.S. Application Data

(60) Provisional application No. 61/738,437, filed on Dec. 18, 2012.

(30) Foreign Application Priority Data

Dec. 18, 2012 (EP) .................... 12197818

(51) Int. Cl.
C12N 9/02 (2006.01)
C12N 15/82 (2006.01)
A01N 57/16 (2006.01)

(52) U.S. Cl.
CPC ......... C12N 15/8274 (2013.01); A01N 57/16 (2013.01); C12N 9/0071 (2013.01); C12N 9/0079 (2013.01); C12Y 114/00 (2013.01)

(58) Field of Classification Search
CPC ............ C12N 15/8274; C12N 15/8275; C12N 15/8278; C12N 15/8277; A01H 5/10; A01H 5/12; A01H 5/00
See application file for complete search history.

(56) References Cited

U.S. PATENT DOCUMENTS

| 5,169,770 A | 12/1992 | Chee et al. |
| 5,322,783 A | 6/1994 | Tomes et al. |
| 5,376,543 A | 12/1994 | Chee et al. |
| 5,455,818 A | 10/1995 | Ohashi |
| 5,633,435 A * | 5/1997 | Barry .................. C12N 9/1092 435/320.1 |
| 5,693,507 A | 12/1997 | Daniell et al. |
| 5,932,479 A | 8/1999 | Daniell et al. |
| 5,990,387 A | 11/1999 | Tomes et al. |
| 6,444,879 B1 * | 9/2002 | Sernyk ..................... A01H 5/10 435/430 |
| 6,653,529 B2 | 11/2003 | Peng et al. |
| 6,781,033 B2 | 8/2004 | Staub et al. |
| 8,338,337 B2 | 12/2012 | Song et al. |
| 8,841,298 B2 | 9/2014 | Song et al. |
| 2008/0148432 A1 | 6/2008 | Abad |
| 2009/0011936 A1 * | 1/2009 | Hawkes ............... C12N 9/0077 504/136 |
| 2009/0049567 A1 | 2/2009 | Olhoft et al. |
| 2009/0217415 A1 * | 8/2009 | Dam .................. C12N 15/8274 800/278 |
| 2010/0319082 A1 * | 12/2010 | Moreno-Sevilla ....... A01H 5/10 800/263 |
| 2011/0201501 A1 | 8/2011 | Song et al. |

(Continued)

FOREIGN PATENT DOCUMENTS

| EP | 0397687 A1 | 11/1990 |
| EP | 0424047 A1 | 4/1991 |

(Continued)

OTHER PUBLICATIONS

Bernasconi, Paul, et al. "A naturally occurring point mutation confers broad range tolerance to herbicides that target acetolactate synthase." Journal of Biological Chemistry 270.29 (1995): 17381-17385 (Year: 1995).*

Van Lohuizen, Maarten, et al. "Sequence similarity between the mammalian bmi-1 proto-oncogene and the *Drosophila* regulatory genes Psc and Su (z) 2." Nature 353.6342 (1991): 353. (Year: 1991).*

Bernhardt, Rita, and Vlada B. Urlacher. "Cytochromes P450 as promising catalysts for biotechnological application: chances and limitations." Applied microbiology and biotechnology 98.14 (2014): 6185-6203. (Year: 2014).*

(Continued)

Primary Examiner — Weihua Fan
(74) Attorney, Agent, or Firm — Marshall, Gerstein & Borun LLP

(57) ABSTRACT

The present invention refers to method for producing a transgenic plant with increased herbicide tolerance or resistance as compared to a corresponding non-transformed wild type plant, comprising transforming a plant cell or a plant cell nucleus or a plant tissue with a nucleic acid molecule encoding an *Alopecurus* cytochrome P450 monooxygenase, as well as to the nucleic acid, and plants with increased herbicide tolerance or resistance comprising the nucleic acid of the invention. Furthermore, the present invention refers to methods of controlling weeds at a locus which contains a plant with increased herbicide tolerance or resistance comprising the nucleic acid of the invention.

Figure 1:
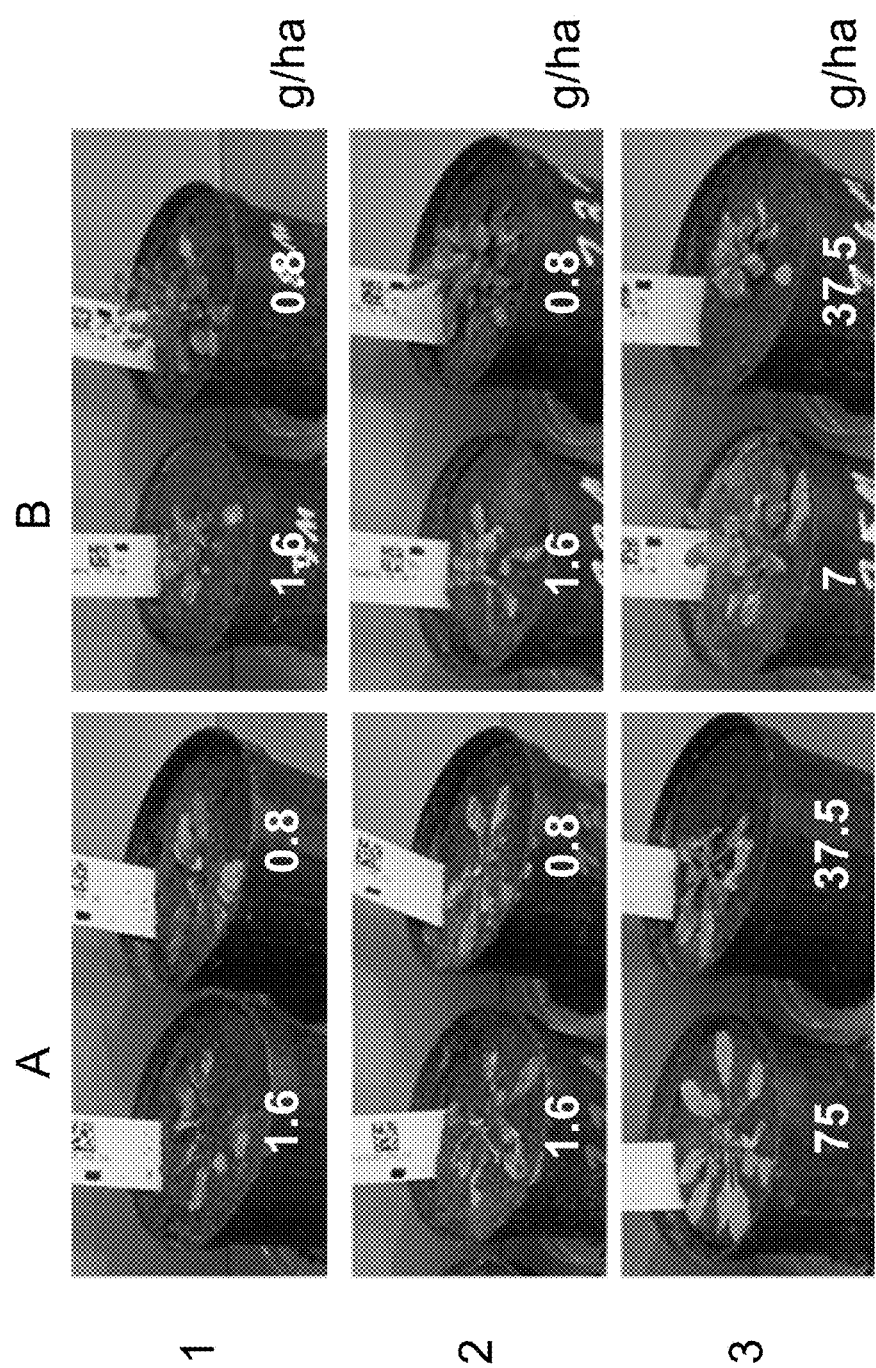

13 Claims, 2 Drawing Sheets
Specification includes a Sequence Listing.

(56) References Cited

U.S. PATENT DOCUMENTS

| | | |
|---|---|---|
| 2012/0071322 A1 | 3/2012 | Song et al. |
| 2012/0149576 A1 | 6/2012 | Saijo et al. |

FOREIGN PATENT DOCUMENTS

| | | |
|---|---|---|
| EP | 2325170 A1 | 5/2011 |
| WO | WO-93/07256 A1 | 4/1993 |
| WO | WO-2004/040973 A2 | 5/2004 |
| WO | WO-2007/103567 A2 | 9/2007 |
| WO | WO-2008/009908 A1 | 1/2008 |
| WO | WO-2008/071918 A1 | 6/2008 |
| WO | WO-2008/124495 A2 | 10/2008 |
| WO | WO-2008/150473 A2 | 12/2008 |
| WO | WO-2009/090401 A2 | 7/2009 |
| WO | WO-2009/090402 A2 | 7/2009 |
| WO | WO-2010/029311 A2 | 3/2010 |
| WO | WO-2010/049269 A1 | 5/2010 |
| WO | WO-2010/049270 A1 | 5/2010 |
| WO | WO-2010/130970 A1 | 11/2010 |
| WO | WO-2010/139657 A1 | 12/2010 |
| WO | WO-2010/139658 A1 | 12/2010 |
| WO | WO-2010/143743 A1 | 12/2010 |
| WO | WO-2010/145992 A1 | 12/2010 |
| WO | WO-2011/057989 A1 | 5/2011 |
| WO | WO-2011/058036 A1 | 5/2011 |
| WO | WO-2011/085211 A1 | 7/2011 |
| WO | WO-2011/117151 A1 | 9/2011 |
| WO | WO-2011/117152 A1 | 9/2011 |
| WO | WO-2011/117195 A1 | 9/2011 |
| WO | WO-2011/117210 A1 | 9/2011 |
| WO | WO-2011/117211 A1 | 9/2011 |
| WO | WO-2011/117273 A1 | 9/2011 |
| WO | WO-2012/084755 A1 | 6/2012 |
| WO | WO-2012/085265 A1 | 6/2012 |
| WO | WO-2012/168241 A1 | 12/2012 |
| WO | WO-2012/168397 A1 | 12/2012 |
| WO | WO-2014/097085 A1 | 6/2014 |
| WO | WO-2015/022639 A2 | 2/2015 |

OTHER PUBLICATIONS

Li, Qinfan, et al. "Mechanism of the plant cytochrome P450 for herbicide resistance: a modelling study." Journal of enzyme inhibition and medicinal chemistry 28.6 (2013): 1182-1191 (Year: 2013).*

Siminszky, Balazs. "Plant cytochrome P450-mediated herbicide metabolism." Phytochemistry Reviews 5.2-3 (2006): 445-458. (Year : 2006).*

De Block, Marc, Dirk De Brouwer, and Paul Tenning. "Transformation of *Brassica napus* and *Brassica oleracea* using Agrobacterium tumefaciens and the expression of the bar and neo genes in the transgenic plants." Plant Physiology91.2 (1989): 694-701. (Year: 1989).*

Letouzé, Anne, and Jacques Gasquez. "Enhanced activity of several herbicide-degrading enzymes: a suggested mechanism responsible for multiple resistance in blackgrass (*Alopecurus myosuroides* Huds.)." Agronomie 23.7 (2003): 601-608 (Year: 2003).*

Bevan et al., "Binary *Agrobacterium* vectors for plant transformation", *Nucleic Acids Research*, 12(22):8711-8721 (1984).

De Block et al., "Transformation of *Brassica napus* and *Bassica oleracea* using *Agrobacterium tumetaciens* and the expression of the bar and neo genes in the transgenic plants", *Plant Physiol*, 91:694-701 (1989).

De Castro Silca Filho et al., "Mitochondrial and chloroplast targeting sequences in tandem modify protein import specificty in plant organelles", *Plant Mol. Biol.*, 30:769-780 (1996).

Della-Cioppa et al., "Protein trafficking in plant cells", *Plant Physiol.*, 84:965-968 (1987).

Fischer et al., "A general cloning strategy for divergent plant cytochrome P450 genes and its application in *Lolium rigidum* and *Ocimum basilicum*", *Theor. Appl. Genet.*, 103:1014-1021 (2001).

Geneseq Accession No. CAW56825.1, "Process for the production of a fine chemical" dated Mar. 27, 2009.

Hajukiewicz et al., "The small, versatile pPZP family of *Agrobacterium* binary vectors for plant transformation", *Plant Mol. Biol.*, 25:989-994 (1994).

Hall et al., "Mechanism of resistance to chlorotoluron in two biotypes of the grass weed *Alopecurus myosuroides*", Pesticide Biochemistry and Physiology, 53:180-192(1995).

Heijne et al., "CHLPEP—a database of chloroplast transit peptides", *Plant Molecular Biology Reporter*, 9(2):104-126 (1991).

Hellens et al., "A guide to *Agrobacterium* binary Ti vectors", *Trends in Plant Science*, 5(10):446-451 (2000).

Hoefgen et al., "Biochemical and genetic analysis of different patatin isoforms expressed in various organs of potato (*Solanum tuberosum*)", *Plant Science*, 66:221-230 (1990).

Hoefgen et al., "Storage of competent cells for *Agrobacterium* transformation", *Nucl. Acids Res.*, 16(20):9877 (1988).

Keegstra et al,. "Chloroplastic precursors and their transport across the envelope membranes", *Annu. Rev. Plant Physiol. Plant Mol. Biol.*, 40:471-501 (1989).

Kemp et al., "Herbicide resistance in *Alopecurus myosuroides*", Managing resistance to agrochemicals ACS Symposium Series, 421:376-393 (1990).

Kermode, "Mechanisms of intracellular protein transport and targeting in plant cells", *Critical Reviews in Plant Science*, 15(4):285-423 (1996).

Lamb et al., "Cytochrome P450 complement (CYPome) of the avermectin-producer *Streptomyces avermitilis* and comparison to that of *Streptomyces coelicolor* A3(2)", *Biochemical and Biophysical Research Communications*, 307:610-619(2003).

Lamb et al., "Ferredoxins form two sulonylurea herbicide monooxygenase systems in *Streptomyces griseolus*", *Biochemistry*, 30(2): 447-455 (1991).

Lawrence et al., "Alterations in the *Chlamydomonas* plastocyanin transit peptide have distinct effects on in vitro import and in vivo protein accumulation", *Journal of Biological Chemistry*, 272(33):20357-20363(1997).

Letouzé et al., "Enhanced activity of several herbicide-degrading enzymes: a suggested mechanism responsible for multiple resistance in blackgrass (*Alopecurus myosuroides* Huds.)", *Agronomie*, 23:601-608 (2003).

Lubben et al., "Transport of proteins into chloroplasts", *Photosynthesis Research*, 17:173-194 (1988).

Maliga P., "Plastid transformation in higher plants", *Annu. Rev. Plant Biol.*, 55:289-313 (2004).

Moloney et al., "High efficiency transformation of *Brassica napus* using *Agrobacterium* vectors", *Plant Cell Reports*, 8:238-242 (1989).

Nelson, "Progress in tracing the evolutionary paths of cytochrome P450", *Biochimica et Biophysica Acta*, 1814:14-18 (2011).

Pan et al., "Map-based cloning of a novel rice cytochrome P450 gene CYP81A6 that confers resistance to two different classes of herbicides", *Plant Mol Biol*, 61:933-943(2006).

Roemer et al., "Expression of the genes encoding the early carotenoid biosynthetic enzymes in *capsicum annuum*", *Biophysical and Biochemical Research Communications*, 196(3):1414-1421(1993).

Schmidt et al., "A novel operon organization involving the genes for chorismate synthase (aromatic biosynthese pathway) and ribosomal GTPase center proteins (L11, L1, L10, L12: rplKAJL) in *Cyanobacterium synechocystis* PCC 6803", *Journal of Biological Chemistry*, 268(36):27447-27457(1993).

Schmidt et al., "High efficiency *Agrobacterium tumefaciens*-mediated transformation of *Arabidopsis thaliana* leaf and cotyledon explants", *Plant Cell Reports*, 7:583-586 (1988).

Thies et al., "Xenobiotic Biotransformation in Unicellular Green Algae", *Plant Physiol*, 122:361-370 (1996).

Werck-Reichhart et al., "Cytochromes P450 for engineering herbicide tolerance", *Trends in Plant Science*, 5(3):116-123 (2005).

Yuan et al., "Non-target-site herbicide resistance: a family business", *Trends in Plant Science*, 12(1):6-13 (2006).

Zhao et al., "Immunological characterization and chloroplast localization of the tryptophan biosynthetic enzymes of the flowering

(56) References Cited

OTHER PUBLICATIONS plant *Arabidopsis thaliana*", *Journal of Biological Chemistry*, 270(11):6081-6087 (1996).

* cited by examiner

HERBICIDE-METABOLIZING CYTOCHROME P450 MONOOXYGENASES

This application is a National Stage application of International Application No. PCT/IB2013/060902, filed Dec. 13, 2013, which claims the benefit of U.S. Provisional Application No. 61/738,437, filed 18 Dec. 2012, and which claims priority to European Patent Application No. 12197818.3, filed 18 Dec. 2012, both of which are hereby incorporated herein by reference in their entirety.

REFERENCE TO SEQUENCE LISTING SUBMITTED VIA EFS-WEB

This application was filed electronically via EFS-Web and includes an electronically submitted sequence in .txt format. The .txt file contains a sequence listing entitled "74210-371_Seqlisting.txt" created on Jun. 9, 2015, and is 303,381 bytes in size. The sequence listing contained in this .txt file is part of the specification and is hereby incorporated by reference herein in its entirety.

FIELD OF THE INVENTION

The present invention relates to *Alopecurus* cytochrome P450 monooxygenases which are able to metabolize herbicides, as well as polynucleotides encoding this enzyme. The invention also relates to transgenic plants producing these enzymes which are resistant and/or tolerant to herbicide activity, when treated therewith.

BACKGROUND OF THE INVENTION

Cytochrome P450 monooxygenases (hereinafter "CYP450s") form a large diverse gene family with about 246 isoforms in *Arabidopsis* and 372 identified in rice. CYP450s are hemoproteins that convert a broad range of substrates to more or less bioactive products. The reaction cycle catalyzed by CYP450s requires the sequential input of two reducing equivalents (i.e., two electrons and two protons). The reducing equivalents for the CYP450-catalyzed reaction are supplied by either NADPH or NADH, depending on the type of redox system concerned, and electron transfer is mediated by two co-factors, one of which is FAD; the other being either FMN or an iron-sulfur $FeS_2$ redoxin (ferredoxin) or, in the microsomal system, cytochrome b5. In particular, the majority of plant CYP450s utilize an electron transport chain which consists of an FAD-containing NADPH-dependent oxidoreductase (Werck-Reichhart, Trends in plant science 5 (2000) 116-123). The mitochondrial system in mammalia bears many similarities with the plant P450 electron transport chain and both systems are generally referred to as Class I (see Lewis and Hlavica, Biochimica et Biophysica Acta 1460 (2000) 353-374, as well as references contained therein). CYP450s are critical in numerous plant metabolic pathways, including biosynthesis of hormones, secondary metabolites and lipids, particularly lignin and pigment biosynthesis, detoxification of harmful compounds, and are considered important in the evolution of land plants. Inhibitors of CYP450 activity include 1-aminobenzo-triazole, tetcyclacis, piperonyl butoxide, cinnamonic acid, and tridiphane.

Several approaches can lead to herbicide tolerant plants: a) modification of the target molecule of the herbicide, b) metabolic approach, i.e. making the compound non-hazardous. For the metabolic solution, one or more enzymes are needed, that catalyze the conversion of the herbicide to a non toxic compound. One source of such enzymes can be microorganisms isolated from nature. Bacteria, especially those of the order Actinomycetales, are known for their potential to detoxify soil by metabolizing xenobiotics, including herbicides (Cork et al, 1991; Schrijver et al., 1999; Caracciolo et al., 2010). These detoxifying reactions can be catalyzed by O-demethylases from *Pseudomonas maltophilia* DI-6, like it was shown for the herbicide Dicamba (Chakraborty et al., 2005; Wang et al., 1997).

In many other cases those reactions are catalyzed by CYP450's. Those can be plant derived (Pan et al., 2006), from algal (Thies et al., 1996) or microbial origin (O'Keefe et al., 1991). Among bacteria, especially actinomycetes offer a broad spectrum of CYP450's. The genome analysis of *Streptomyes coelicolor* revealed 18 CYP450's (Lamb et al., 2002), the *Streptomyes avermitilis* genome revealed 33 (Lamb et al., 2003). According to Nelson (2011), actinobacteria hold the largest number of CYP450's per genome.

Current enzymes available for metabolizing herbicides, such as, for example, saflufenacil, e.g. those described in WO2010/143743 particularly when expressed in plants, do not have particularly high activity. Thus, there is the need for the identification of further enzymes which can be used to metabolize herbicides.

The present inventors have characterized an *Alopecurus* species utilizing a mechanism of metabolizing herbicides. Furthermore, the inventors have isolated and characterized the novel herbicidemetabolizing CYP450 monooxygenases from this grass species.

KEY TO SEQUENCE LISTING

TABLE 1

| Name | Genus | SEQ ID NO | type | SEQ ID NO | type |
|---|---|---|---|---|---|
| Am_CYP01 | Alopecurus myosurcides | 1 | nucleic acid | 2 | amino acid |
| Am_CYP03 | Alopecurus myosurcides | 3 | nucleic acid | 4 | amino acid |
| Am_CYP03b | Alopecurus myosurcides | 5 | nucleic acid | 6 | amino acid |
| Am_CYP15 | Alopecurus myosurcides | 7 | nucleic acid | 8 | amino acid |
| Q9ATV4 | Lolium rigidum | | | 9 | amino acid |
| B9F5T6 | Oryza sativa | | | 10 | amino acid |
| Q94HA6 | Oryza sativa | | | 11 | amino acid |
| Q9ATV6 | Lolium rigidum | | | 12 | amino acid |
| B9F5T8 | Oryza sativa | | | 13 | amino acid |
| C0KHM1 | Poa annus | | | 14 | amino acid |
| Q94HA5 | Oryza sativa | | | 15 | amino acid |
| F2EH65 | Hordeum vulgare | | | 16 | amino acid |
| Q2LA61 | Oryza sativa | | | 17 | amino acid |
| F2DYW1 | Hordeum vulgare | | | 18 | amino acid |
| Q6F4F4 | Lolium rigidum | | | 19 | amino acid |

TABLE 1-continued

| Name | Genus | SEQ ID NO | type | SEQ ID NO | type |
|---|---|---|---|---|---|
| Q6F4F3 | Lolium rigidum | | | 20 | amino acid |
| Q6F4F2 | Lolium rigidum | | | 21 | amino acid |
| F2DH14 | Hordeum vulgare | | | 22 | amino acid |
| Q9ATV5 | Lolium rigidum | | | 23 | amino acid |
| Q0DND2 | Oryza sativa | | | 24 | amino acid |
| B6SSF2 | Zea mays | | | 25 | amino acid |
| Am_CYP04 | Alopecurus myosurcides | 26 | nucleic acid | 27 | amino acid |
| Q9ATU5 | Lolium rigidum | | | 28 | amino acid |
| Q8LL74 | Zea mays | | | 29 | amino acid |
| Q9FDZ1 | Oryza sativa | | | 30 | amino acid |
| Q9AX23 | Oryza sativa | | | 31 | amino acid |
| Q615Q4 | Oryza sativa | | | 32 | amino acid |
| A2WUP8 | Oryza sativa | | | 33 | amino acid |
| Q9ATU3 | Lolium rigidum | | | 34 | amino acid |
| B9FP88 | Oryza sativa | | | 35 | amino acid |
| Q9ATU2 | Lolium rigidum | | | 36 | amino acid |
| C5XEE4 | Sorghum bicolor | | | 37 | amino acid |
| C5XEE3 | Sorghum bicolor | | | 38 | amino acid |
| Q9ATU4 | Lolium rigidum | | | 39 | amino acid |
| Q8LGM8 | Zea mays | | | 40 | amino acid |
| C4J0D4 | Zea mays | | | 41 | amino acid |
| Q9ATU1 | Lolium rigidum | | | 42 | amino acid |
| B8AC00 | Oryza sativa | | | 43 | amino acid |
| Am_CYP12 | Alopecurus myosurcides | 44 | nucleic acid | 45 | amino acid |
| B8B662 | Oryza sativa | | | 46 | amino acid |
| B6SSZ4 | Zea mays | | | 47 | amino acid |
| B4FMT5 | Zea mays | | | 48 | amino acid |
| C5X3A1 | Sorghum bicolor | | | 49 | amino acid |
| B9FWV1 | Oryza sativa | | | 50 | amino acid |
| Q6T485 | Triticum aestivum | | | 51 | amino acid |
| A3BMK1 | Oryza sativa | | | 52 | amino acid |
| B8A062 | Zea mays | | | 53 | amino acid |
| C5X3A3 | Sorghum bicolor | | | 54 | amino acid |
| Q8L4Q4 | Oryza sativa | | | 55 | amino acid |
| B8B554 | Oryza sativa | | | 56 | amino acid |
| Q8LIR5 | Oryza sativa | | | 57 | amino acid |
| B9FUF2 | Oryza sativa | | | 58 | amino acid |
| B8B553 | Oryza sativa | | | 59 | amino acid |
| Q8LHV0 | Oryza sativa | | | 60 | amino acid |
| F2DQ95 | Hordeum vulgare | | | 61 | amino acid |
| C4JB42 | Zea mays | | | 62 | amino acid |
| Q0D4C4 | Oryza sativa | | | 63 | amino acid |
| B8ARP1 | Oryza sativa | | | 64 | amino acid |
| F2DL54 | Hordeum vulgare | | | 65 | amino acid |
| Q6DV71 | Triticum aestivum | | | 66 | amino acid |
| Q0D4C5 | Oryza sativa | | | 67 | amino acid |
| A2YP19 | Oryza sativa | | | 68 | amino acid |
| C5X3A2 | Sorghum bicolor | | | 69 | amino acid |
| Am_CYP01 | Alopecurus myosurcides | 70 | Nucleic acid | | |
| Am_CYP03 | Alopecurus myosurcides | 71 | Nucleic acid | | |
| Am_CYP03b | Alopecurus myosurcides | 72 | Nucleic acid | | |
| Am_CYP04 | Alopecurus myosurcides | 73 | Nucleic acid | | |
| Am_CYP12 | Alopecurus myosurcides | 74 | Nucleic acid | | |

LEGEND TO THE DRAWING

FIG. 1:

Phenotype of wildtype plants (A) and transgenic plants expressing Am_CYP03 (B) treated with specified herbicides at different application rates (g/ha). Transgenic plants, expressing a protein with SEQ ID 4 were much less injured compared to non-trangenic plants. 1=saflufenacil, 2=1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 3=Chlorotoluron

FIG. 2:

Phenotype of wildtype plants (A) and transgenic plants expressing Am_CYP04 (B) treated with specified herbicides at different application rates (g/ha). Transgenic plants, expressing a protein with SEQ ID 27 were much less injured compared to non-trangenic plants. 1=saflufenacil, 2=1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 3=Chlorotoluron

SUMMARY OF THE INVENTION

Accordingly, in one embodiment, the present invention provides a method for producing a plant having an increased herbicide tolerance or resistance as compared to a corresponding wild type plant whereby the method comprises at least the following step: increasing or generating in a plant the activity of an *Alopecurus* CYP450, or a homolog thereof.

Accordingly, the invention provides a transgenic plant that over-expresses a recombinant *Alopecurus* CYP450 polynucleotide, or a homolog thereof, in the sub-cellular compartment and tissue as indicated herein. The transgenic plant of the invention demonstrates an improved or increased herbicide tolerance or resistance as compared to a wild type variety of the plant.

Accordingly, the invention provides a method for producing a plant with increased herbicide tolerance or resistance as compared to a corresponding wild type plant comprising at least one of the steps selected from the group consisting of: (i) increasing or generating the activity of a polypeptide comprising at least one polypeptide motif or consensus sequence comprising the sequence of SEQ ID NO: 2, 4, 6, 8, 27, or 45, or a homolog thereof; or (ii) increasing or generating the activity of an expression product of one or more isolated and/or recombinant polynucleotide(s) comprising one or more polynucleotide(s) comprising the sequence of SEQ ID NO: 1, 3, 5, 7, 26, or 44, or a homolog thereof.

The invention further provides a method for increasing herbicide tolerance or resistance of a crop plant, the method comprising the following steps: (i) increasing or generating of the expression of at least one polynucleotide; and/or (ii) increasing or generating the expression of an expression product encoded by at least one polynucleotide; and/or (iii) increasing or generating one or more activities of an expression product encoded by at least one polynucleotide, wherein the polynucleotide is selected from the group consisting of:

(a) an isolated and/or a recombinant polynucleotide encoding the polypeptide comprising the sequence of SEQ ID NO: 2, 4, 6, 8, 27, or 45, or a homolog thereof;
(b) an isolated and/or a recombinant polynucleotide comprising the sequence of SEQ ID NO: 1, 3, 5, 7, 26, or 44, or a homolog thereof;
(c) an isolated and/or a recombinant polynucleotide, which, as a result of the degeneracy of the genetic code, can be derived from a polypeptide comprising the sequence of SEQ ID NO: 2, 4, 6, 8, 27, or 45, or a homolog thereof and confers an increased herbicide tolerance or resistance as compared to a corresponding, e.g. non-transformed, wild type plant cell, a transgenic plant or a part thereof;
(d) an isolated and/or a recombinant polynucleotide having 30 or more, for example 50%, 60%, 70%, 80%, 85%, 90%, 95%, 97%, 98%, or 99% (percent) or more identity with the sequence of a polynucleotide comprising the sequence of SEQ ID NO: 1, 3, 5, 7, 26, or 44, or a homolog thereof and conferring an increased herbicide tolerance or resistance as compared to a corresponding, e.g. non-transformed, wild type plant cell, a transgenic plant or a part thereof;
(e) an isolated and/or a recombinant polynucleotide encoding a polypeptide having 30 or more, for example 50%, 60%, 70%, 80%, 85%, 90%, 95%, 97%, 98%, or 99% or more identity with the amino acid sequence of the polypeptide encoded by the polynucleotide of (a) to (c) and conferring an increased herbicide tolerance or resistance as compared to a corresponding, e.g. non-transformed, wild type plant cell, a transgenic plant or a part thereof;
(f) an isolated and/or a recombinant polynucleotide which hybridizes with an isolated and/or a recombinant polynucleotide of (a) to (c) under stringent hybridization conditions and confers an increased herbicide tolerance or resistance as compared to a corresponding, e.g. non-transformed, wild type plant cell, a transgenic plant or a part thereof;
(g) an isolated and/or a recombinant polynucleotide encoding a polypeptide which can be isolated with the aid of monoclonal or polyclonal antibodies made against a polypeptide encoded by one of the polynucleotides of (a) to (e) and which has the activity represented by the polynucleotide comprising the sequence of SEQ ID NO: 1, 3, 5, 7, 26, or 44, or a homolog thereof;

Furthermore, the invention relates to a method for producing a transgenic plant with increased herbicide tolerance or resistance as compared to a corresponding, e.g. non-transformed, wild type plant, comprising transforming a plant cell or a plant cell nucleus or a plant tissue to produce such a plant, with an isolated and/or a recombinant polynucleotide selected from the group consisting of:

(a) an isolated and/or a recombinant polynucleotide encoding the polypeptide comprising the sequence of SEQ ID NO: 2, 4, 6, 8, 27, or 45, or a homolog thereof;
(b) an isolated and/or a recombinant polynucleotide comprising the sequence of SEQ ID NO: 1, 3, 5, 7, 26, or 44, or a homolog thereof;
(c) an isolated and/or a recombinant polynucleotide, which, as a result of the degeneracy of the genetic code, can be derived from a polypeptide comprising the sequence of SEQ ID NO: 2, 4, 6, 8, 27, or 45, or a homolog thereof and confers an increased herbicide tolerance or resistance as compared to a corresponding, e.g. non-transformed, wild type plant cell, a transgenic plant or a part thereof;
(d) an isolated and/or a recombinant polynucleotide having 30 or more, for example 50%, 60%, 70%, 80%, 85%, 90%, 95%, 97%, 98%, or 99% (percent) or more identity with the sequence of a polynucleotide comprising the sequence of SEQ ID NO: 1, 3, 5, 7, 26, or 44, or a homolog thereof and conferring an increased herbicide tolerance or resistance as compared to a corresponding, e.g. non-transformed, wild type plant cell, a transgenic plant or a part thereof;
(e) an isolated and/or a recombinant polynucleotide encoding a polypeptide having 30 or more, for example 50%, 60%, 70%, 80%, 85%, 90%, 95%, 97%, 98%, or 99% or more identity with the amino acid sequence of the polypeptide encoded by the polynucleotide of (a) to (c) and conferring an increased herbicide tolerance or resistance as compared to a corresponding, e.g. non-transformed, wild type plant cell, a transgenic plant or a part thereof;
(f) an isolated and/or a recombinant polynucleotide which hybridizes with an isolated and/or a recombinant polynucleotide of (a) to (c) under stringent hybridization conditions and confers an increased herbicide tolerance or resistance as compared to a corresponding, e.g. non-transformed, wild type plant cell, a transgenic plant or a part thereof;
(g) an isolated and/or a recombinant polynucleotide encoding a polypeptide which can be isolated with the aid of monoclonal or polyclonal antibodies made against a polypeptide encoded by one of the polynucleotides of (a) to (e) and which has the activity represented by the polynucleotide comprising the sequence of SEQ ID NO: 1, 3, 5, 7, 26, or 44, or a homolog thereof.

The invention further provides a method for controlling weeds at a locus for growth of a plant, the method comprising: (a) applying a herbicide composition to the locus; and (b) planting a seed at the locus, wherein the seed is capable of producing a plant that comprises a recombinant polynucleotide operably linked to a promoter operable in plant cells, the promoter capable of expressing a *Alopecurus* CYP450 polypeptide encoded by the polynucleotide and comprising the sequence of SEQ ID NO: 2, 4, 6, 8, 27, or 45, or a homolog thereof, the expression of the *Alopecurus* CYP450 polypeptide conferring to the plant tolerance to herbicides.

In some aspects, the present invention provides a method for controlling weeds at a locus for growth of a plant, the method comprising: applying an herbicidal composition to the locus; wherein said locus is: (a) a locus that contains: a plant or a seed capable of producing said plant; or (b) a locus that is to be after said applying is made to contain the plant or the seed; wherein the plant or the seed comprises in at least some of its cells a recombinant polynucleotide operably linked to a promoter operable in plant cells, the promoter capable of expressing a *Alopecurus* CYP450 polypeptide encoded by the polynucleotide and comprising the sequence of SEQ ID NO: 2, 4, 6, 8, 27, or 45, or a homolog thereof, the expression of the *Alopecurus* CYP450 polypeptide conferring to the plant tolerance to herbicides.

DETAILED DESCRIPTION OF THE PREFERRED EMBODIMENTS

Definition Collection

An "herbicide tolerance or resistance-increasing activity" according to the invention refers to an activity of a CYP450 from *Alopecurus* comprising the sequence of SEQ ID NO: 2, 4, 6, 8, 27, or 45, or a homolog thereof. A polypeptide conferring a herbicide tolerance or resistance-increasing activity can be encoded by a nucleic acid sequence comprising the sequence of SEQ ID NO: 1, 3, 5, 7, 26, or 44, or a homolog thereof, and/or comprises or consists of a polypeptide comprising the sequence of SEQ ID NO: 2, 4, 6, 8, 27, or 45, or a homolog thereof.

A "transgenic plant", as used herein, refers to a plant which contains a foreign nucleotide sequence inserted into either its nuclear genome or organelle genome. It encompasses further the offspring generations i.e. the T1-, T2- and consecutively generations or BC1-, BC2- and consecutively generation as well as crossbreeds thereof with non-transgenic or other transgenic plants.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into a organism, transient or stable. Furthermore such an increase can be reached by the introduction of the inventive nucleic acid sequence or the encoded protein in the correct cell compartment for example into the nucleus or cytoplasmic respectively or into plastids either by transformation and/or targeting.

For the purposes of the description of the present invention, the terms "cytoplasmic" and "non-targeted" shall indicate, that the nucleic acid of the invention is expressed without the addition of a non-natural transit peptide encoding sequence. A non-natural transit peptide encoding sequence is a sequence which is not a natural part of a nucleic acid of the invention, e.g. of the nucleic acids depicted in SEQ ID NO: 1, 3, 5, 7, 26, or 44, or a homolog thereof, but is rather added by molecular manipulation steps which are well known to the person skilled in the art or as for example described hereinafter. Therefore the terms "cytoplasmic" and "non-targeted" shall not exclude a targeted localization to any cell compartment for the products of the inventive nucleic acid sequences by their naturally occurring sequence properties within the background of the transgenic organism. The sub-cellular location of the mature polypeptide derived from the enclosed sequences can be predicted by a skilled person for the organism (plant) by using software tools like TargetP (Emanuelsson et al., (2000), Predicting sub-cellular localization of proteins based on their N-terminal amino acid sequence. J. Mol. Biol. 300, 1005-1016), ChloroP (Emanuelsson et al. (1999), ChloroP, a neural network-based method for predicting chloroplast transit peptides and their cleavage sites. Protein Science, 8: 978-984) or other predictive software tools (Emanuelsson et al. (2007), locating proteins in the cell using TargetP, SignalP, and related tools (Nature Protocols 2, 953-971).

The term "organelle" according to the invention shall mean for example "mitochondria", "plastid" or endoplasmic reticulum (ER). The term "plastid" according to the invention is intended to include various forms of plastids including proplastids, chloroplasts, chromoplasts, gerontoplasts, leucoplasts, amyloplasts, elaioplasts and etioplasts, preferably chloroplasts. They all have as a common ancestor the aforementioned proplasts.

The term "introduced" in the context of this specification shall mean the insertion of a nucleic acid sequence into the organism by means of a "transfection", "transduction" or preferably by "transformation".

A plastid, such as a chloroplast, has been "transformed" by an exogenous (preferably foreign) nucleic acid sequence if nucleic acid sequence has been introduced into the plastid that means that this sequence has crossed the membrane or the membranes of the plastid. The foreign DNA may be integrated (covalently linked) into plastid DNA making up the genome of the plastid, or it may remain not integrated (e.g., by including a chloroplast origin of replication). "Stably" integrated DNA sequences are those, which are inherited through plastid replication, thereby transferring new plastids, with the features of the integrated DNA sequence to the progeny.

As used herein, "plant" is meant to include not only a whole plant but also a part thereof i.e., one or more cells, and tissues, including for example, leaves, stems, shoots, roots, flowers, fruits and seeds.

The term "herbicide tolerance or resistance" as used herein it is intended that a plant that is tolerant or resistant to at least one herbicide at a level that would normally kill, or inhibit the growth of, a normal or wild-type plant.

Any increase in herbicide tolerance or resistance is an improved herbicide tolerance or resistance in accordance with the invention. For example, the improvement in herbicide tolerance or resistance can comprise a 1.5×, 2×, 2.5×, 3×, 5×, 10×, 20×, 30×, 40×, 50×, 75×, 100×, 150×, 200× or greater increase in any measurable parameter.

Generally, the term "herbicide" is used herein to mean an active ingredient that kills, controls or otherwise adversely modifies the growth of plants. More specifically, the term "herbicide" is meant to include any molecule that, when exogenously applied to a plant, has a deleterious effect on said plant. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by the herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicideresistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

Examples of herbicides that are particularly useful for the present invention include saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4; herein also referred to as benzoxazinone-derivatives as described in WO2010/145992), benzobicyclon, chlorotoluron, pendimethalin, mesotrione, sulcotrione, tefuryltrione, tembotrione, 4-hydroxy-3-[[2-(2-methoxyethoxy)methyl]-6-(trifluoromethyl)-3-pyridinyl]carbonyl]-bicyclo[3.2.1]-oct-3-en-2-one (bicyclopyrone), ketospiradox or the free acid thereof, benzofenap, pyrasulfotole, pyrazolynate, pyrazoxyfen, topramezone, [2-chloro-3-(2-methoxyethoxy)-4-(methylsulfonyl) phenyl](l-ethyl-5-hydroxy-1H-pyrazol-4-yl)-methanone, (2,3-dihydro-3,3,4-trimethyl-1,1-dioxidobenzo[b]thien-5-yl)(5-hydroxy-1-methyl-1H-pyrazol-4-yl)-methanone, isoxachlortole, isoxaflutole, α-(cyclopropylcarbonyl)-2-(methylsulfonyl)-β-oxo-4-chloro-benzenepropanenitrile, and α-(cyclopropylcarbonyl)-2-(methylsulfonyl)-β-oxo-4-(trifluoromethyl)-benzenepropanenitrile.

Other herbicidal compounds useful for the present invention may further include herbicides to which the crop plant is naturally tolerant, or to which it is resistant via expression of one or more additional transgenes.

Unless already included in the section above, the herbicides that can be in applied in conjunction with the herbicide-resistant plant according to the present invention further include compounds:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuronmethyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone; among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquatdimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyrethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napropanilide and napropamide, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8

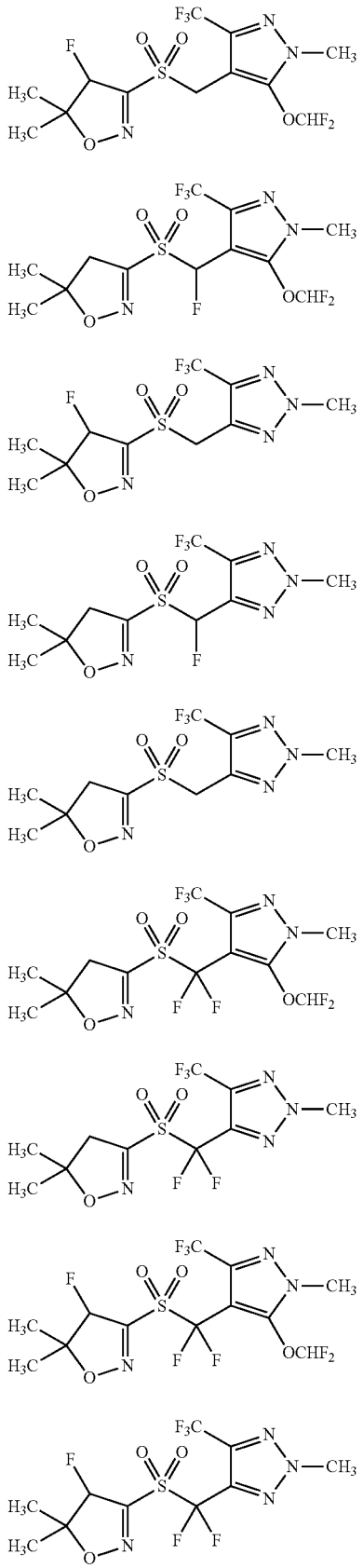

the isoxazoline compounds of the formula (I) I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, triaziflam, isoxaben and 1-Cyclohexyl-5-pentafluorphenyloxy-1⁴-[1,2,4,6]thiatriazin-3-ylamine;

b12) from the group of the decoupler herbicides: dinoseb, dinoterb and DNOC and its salts;

b13) from the group of the auxinic herbicides: 2,4-D and its salts and esters such as clacyfos, 2,4-DB and its salts and esters, aminocyclopyrachlor and its salts and esters, aminopyralid and its salts such as aminopyralid-tris (2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, MCPP and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Moreover, it may be useful to apply herbicides listed SUPRA in combination with safeners. Safeners are chemical compounds which prevent or reduce damage on useful plants without having a major impact on the herbicidal action of herbicides towards unwanted plants. They can be applied either before sowings (e.g. on seed treatments, shoots or seedlings) or in the pre-emergence application or post-emergence application of the useful plant.

Furthermore, the safeners and the herbicides can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

The compounds of groups b1) to b15) and the Safeners are known Herbicides and Safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

Preferred examples of herbicides include, but are not limited to, saflufenacil, 1,5-dimethyl-6-thioxo-3-(2,2,7-trifluoro-3-oxo-4-(prop-2-ynyl)-3,4-dihydro-2H-benzo[b][1,4] oxazin-6-yl)-1,3,5-triazinane-2,4-dione (CAS 1258836-72-4) herbicide (as disclosed in WO2010/145992, and herein also referred as benzoxazinone-derivative), chlorotoluron, pendimethalin, flumioxazin, butafenacil, acifluorfen, lactofen, bifenox, diuron, sulfentrazone.

Other preferred examples of herbicides include anellated heterocyclic compounds, herein also referred to as coumarone-derivative herbicides, such as those disclosed in WO2010/049270, WO2010/049269, WO2010/139657, WO2010/139658, EP2325170, WO2011/057989, WO2011/058036, WO2011/117195, WO2011/117211, WO2011/117210, WO2011/117273, WO2011/117151, WO2011/117152, WO2010/029311, WO2009/090401, WO2009/090402, WO2008/071918, WO2008/009908, WO 2012/084755, WO 2012/085265, PCT/EP2012/060846, PCT/EP2012/060600, WO2010130970.

In one embodiment of the present invention, the herbicide, preferably the anellated heterocycle, useful for the present invention refers to a substituted pyridine compound of formula I:

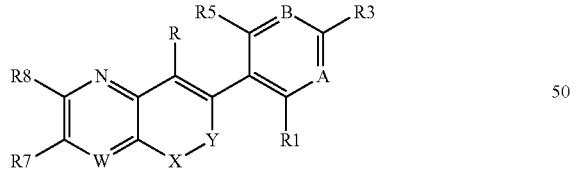

wherein
R is hydroxy or O—$R^A$, where $R^A$ is $C_1$-$C_8$-alkyl, $C_2$-$C_8$-alkenyl, $C_2$-$C_8$-alkynyl, aryl-$C_1$-$C_4$-alkyl, $C_1$-$C_8$-alkylcarbonyl, $C_1$-$C_8$-alkoxycarbonyl, $C_1$-$C_8$-alkylthiocarbonyl or $C_1$-$C_8$-alkylsulfonyl, where the aryl moiety is unsubstituted or substituted by one to five R and each $R^a$ is independently halogen, cyano, nitro, G-$C_8$-alkyl, $C_1$-$C_8$-haloalkyl, $C_1$-$C_8$-alkoxy or $C_1$-$C_8$-haloalkoxy;
$R^1$ is cyano, halogen, nitro, $C_1$-$C_6$-alkyl, $C_2$-$C_6$-alkenyl, $C_2$-$C_6$-alkynyl, $C_1$-$C_6$-alkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, S(O)$_n$$R^b$, Z-phenoxy or Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^c$;
Z is independently a covalent bond or G-$C_4$-alkylene;
n is independently 0, 1 or 2;
$R^b$ is independently $C_1$-$C_8$-alkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-haloalkyl;
$R^c$ is independently Z—CN, Z—OH, Z—$NO_2$, Z-halogen, oxo (=O), =N—$R^d$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-haloalkoxy, Z—$C_3$-$C_{10}$-cycloalkyl, O—Z—$C_3$-$C_{10}$-cycloalkyl, Z—C(=O)—$R^d$, $NR^iR^{ii}$, Z-(tri-$C_1$-$C_4$-alkyl)silyl, Z-phenyl or S(O)$_n$$R^b$; or two groups $R^c$ may together form a ring which has 3 to 6 ring members and, in addition to carbon atoms, may contain heteroatoms selected from the group consisting of O, N and S and may be unsubstituted or substituted by further groups $R^c$;
$R^d$ is independently hydrogen, OH, $C_1$-$C_8$-alkyl, $C_1$-$C_4$-haloalkyl, Z—$C_3$-$C_6$-cycloalkyl, $C_2$-$C_8$-alkenyl, Z—$C_5$-$C_6$-cycloalkenyl, $C_2$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy, $NR^iR^{ii}$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups R;
$R^i$, $R^{ii}$ independently of one another are hydrogen, $C_1$-$C_8$-alkyl, $C_1$-$C_4$-haloalkyl, $C_3$-$C_8$-alkenyl, $C_3$-$C_8$-alkynyl, Z—$C_3$-$C_6$-cycloalkyl, Z—$C_1$-$C_8$-alkoxy, Z—$C_1$-$C_8$-haloalkoxy, Z—C(=O)—$R^d$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z;
$R^i$ and $R^{ii}$ together with the nitrogen atom to which they are attached may also form a 5- or 6-membered monocyclic or 9- or 10-membered bicyclic heterocycle which contains 1, 2, 3 or 4 heteroatoms selected from the group consisting of O, N and S;
A is N or C—$R^2$;
B is N or C—$R^4$;
$R^2$, $R^3$ independently of one another are hydrogen, Z-halogen, Z—CN, Z—OH, Z—NQ, $C_1$-$C_8$-alkyl, $C_1$-$C_4$-haloalkyl, $C_2$-$C_8$-alkenyl, $C_2$-$C_8$-alkynyl, $C_2$-$C_8$-haloalkenyl, $C_2$-$C_8$-haloalkynyl, Z—$C_1$-$C_8$-alkoxy, Z—$C_1$-$C_8$-haloalkoxy, Z—$C_1$-$C_4$-alkoxy-$C_1$-$C_4$-alkoxy, Z—$C_1$-$C_4$-alkythio, Z—$C_1$-$C_4$-alkylthio-$C_1$-$C_4$-alkylthio, Z—$C_1$-$C_6$-haloalkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, Z—$C_3$-$C_{10}$-cycloalkyl, O—Z—$C_3$-$C_{10}$-cycloalkyl, Z—C(=O)—$R^d$, $NR^iR^{ii}$, Z-(tri-$C_1$-$C_4$-alkyl)silyl, S(O)$_n$$R^b$, Z-phenyl, $Z^1$-phenyl, Z-heterocyclyl or $Z^1$-heterocyclyl, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^c$;

$R^2$ together with the group attached to the adjacent carbon atom may also form a 5- to 10-membered saturated or partially or fully unsaturated mono- or bicyclic ring which, in addition to carbon atoms, may contain 1, 2 or 3 heteroatoms selected from the group consisting of O, N and S and may be substituted by further groups $R^c$;

$Z^1$ is independently a covalent bond, $C_1$-$C_4$-alkyleneoxy, $C_1$-$C_4$-oxyalkylene or $C_1$-$C_4$-alkyleneoxy-$C_1$-$C_4$-alkylene;

$R^4$, $R^5$ independently of one another are hydrogen, halogen or $Q$-$C_4$-alkyl;

W is N or C—$R^6$;

$R^6$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy or $C_1$-$C_4$-haloalkylthio;

$R^7$, $R^8$ independently of one another are hydrogen, halogen or $C_1$-$C_4$-alkyl;

X is O, $NR^z$ or $CR^xR^y$;

$R^x$, $R^y$ independently of one another are hydrogen, $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl or halogen; or $R^x$ and $R^y$ are together a $C_2$-$C_5$-alkylene or $C_2$-$C_5$-alkenylene chain and form a 3-, 4-, 5- or 6-membered saturated, partially unsaturated or fully unsaturated monocyclic ring together with the carbon atom they are bonded to, wherein 1 or 2 of any of the $CH_2$ or CH groups in the $C_2$-$C_5$-alkylene or $C_2$-$C_5$-alkenylene chain may be replaced by 1 or 2 heteroatoms independently selected from O or S;

$R^z$ is $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl Y is CO or $SO_2$.

where in the groups $R^1$, $R^2$ and $R^3$ and their subsubstituents, the carbon chains and/or the cyclic groups may be partially or fully substituted by groups $R^c$, or an agriculturally suitable salt or N-oxide thereof.

According to a preferred embodiment of the invention preference is also given to those compounds of formula I, wherein the variables, either independently of one another or in combination with one another, have the following meanings:

Preferably, R is hydroxy or O—$R^A$, where $R^A$ is $C_1$-$C_8$-alkyl, $C_2$-$C_8$-alkenyl, $C_2$-$C_8$-alkynyl, aryl-$C_1$-$C_4$-alkyl, $C_1$-$C_8$-alkylcarbonyl, $C_1$-$C_8$-alkoxycarbonyl, $C_1$-$C_8$-alkylthiocarbonyl or $C_1$-$C_8$-alkylsulfonyl, where the aryl moiety is unsubstituted.

More preferably, R is hydroxy or O—$R^A$, where $R^A$ is $C_1$-$C_8$-alkylcarbonyl.

In one embodiment, R is hydroxy.

In one embodiment, R is O—$R^A$, where $R^A$ is $C_1$-$C_8$-alkylcarbonyl.

In another embodiment, R is selected from the group consisting of hydroxy, methoxy, allyloxy, propargyloxy, cyclopropylcarbonyloxy, benzyloxy, prop-2-ylcarbonyloxy, 2-methyl-prop-2-ylcarbonyloxy, methoxycarbonyloxy, ethoxycarbonyloxy, methylthiocarbonyloxy, ethylthiocarbonyloxy, ethylthiocarbonyloxy and methylsulfonyloxy.

Preferably, R is selected from the group consisting of hydroxy, cyclopropylcarbonyloxy, and 2-methyl-prop-2-ylcarbonyloxy, In particular, R is hydroxy or 2-methyl-prop-2-ylcarbonyloxy In one embodiment, R is hydroxy.

In one embodiment, R is 2-methyl-prop-2-ylcarbonyloxy $R^i$ and $R^{ii}$ are preferably $C_1$-$C_8$-alkyl, $C_1$-$C_4$-haloalkyl, Z—$C_3$-$C_6$-cycloalkyl, Z—$C_1$-$C_8$-alkoxy, Z—$C_1$-$C_8$-haloalkoxy, Z-phenyl, Z—C(=O)—$R^d$ or Z-hetaryl. Preference is given here to $CH_3$, $C_2H_5$, n-propyl, $CH(CH_3)_2$, butyl, 2-choroethyl, cyclopentyl, cyclohexyl, 2-ethoxymethyl, 2-chloroethoxy, phenyl, pyrimidines or triazines, which rings are unsubstituted or substituted. Preferred substituents are $C_1$-$C_4$-alkylcarbonyl or $C_1$-$C_4$-haloalkylcarbonyl, in particular C(=O)—$CH_3$, C(=O)—$C_2H_5$, C(=O)—$C_3H_7$, C(=O)—$CH(CH_3)_2$, butylcarbonyl and C(=O)—$CH_2Cl$. Particularly preferred aspects of group $NRR^{ii}$ are N(di-$C_1$-$C_4$-alkyl), in particular $N(CH_3)$—$C_1$-$C_4$-alkyl, such as $N(CH_3)_2$, $N(CH_3)CH_2CH_3$, $N(CH_3)C_3H_7$ and $N(CH_3)CH(CH_3)_2$.

Further particularly preferred aspects of $NRR^{ii}$ are NH-aryl, where aryl is preferably phenyl which is substituted—in particular in the 2- and 6-position—by one to three identical or different groups selected from the group consisting of halogen, $CH_3$, halo-$C_1$-$C_2$-alkyl, halo-$C_1$-$C_2$-alkoxy and carboxyl, such as 2-Cl,6-COOH—$C_6H_3$, 2,6-$Cl_2$-$C_6H_3$, 2,6-$F_2$—$C_6H_3$, 2,6-$Cl_2$ 3-$C_6H_2$, 2-$CF_3$,6-$CH_2CHF_2$—$C_6H_3$, 2-$CF_3$,6-$OCF_3$—$C_6H_3$ and 2-$CF_3$, 6-$CH_2CHF_2$—$C_6H_3$.

For the compounds of the formula I, the groups R are preferably selected from the group consisting of halogen, oxo (=O), =N—$R^d$, $C_1$-$C_4$-alkyl, $C_1$-$C_4$-haloalkyl, $C_2$-$C_6$-alkenyl, $C_2$-$C_6$-alkynyl, Z—$C_1$-$C_4$-haloalkoxy, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkylthio-$C_1$-$C_4$-alkyl, Z—C(=O)—$R^d$ and $S(O)_n R^b$, where $R^b$ is preferably $C_1$-$C_4$-alkyl or $C_1$-$C_4$-haloalkyl and n is 0, 1 or 2.

Particularly preferably, $R^c$ is a group selected from the group consisting of halogen, $C_1$-$C_4$-alkyl, $C_3$-$C_6$-acycloalkyl, $C_1$-$C_4$-haloalkyl, $C_1$-$C_4$-alkoxy, $C_1$-$C_4$-alkylthio, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-haloalkoxy, $C_1$-$C_4$-haloalkylthio, $C_3$-$C_4$-alkenyl, $C_3$-$C_4$-alkynyl and =N—$C_1$-$C_4$-alkoxy.

Two groups $R^c$ together may form a ring which preferably has three to seven ring members and, in addition to carbon atoms, may also contain heteroatoms from the group consisting of O, N and S and which may be unsubstituted or substituted by further groups R. These substituents $R^c$ are preferably selected from the group consisting of halogen, $C_1$-$C_4$-alkyl, $C_1$-$C_4$-alkoxy and $C_1$-$C_4$-haloalkyl.

Groups $R^d$ preferred for the compounds of the formula I are selected from the group consisting of OH, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy and $NR^iR^{ii}$.

Groups $R^c$ and $R^d$ are selected independently of one another if a plurality of such groups is present.

In a preferred embodiment of the compounds of the formula I, R is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkythio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, $S(O)_n R^b$.

In a particularly preferred embodiment of the compounds of the formula I, R is halogen, CN, $NO_2$, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$-alkoxy, $S(O)_n$—$C_1$-$C_4$-alkyl and $S(O)_n$—$C_1$-$C_4$-haloalkyl. Particularly preferably, $R^1$ is selected from the group consisting of F, Cl, Br, $NO_2$, $CH_3$, $CHF_2$, $CF_3$, $OCH_3$, $OCF_3$, $SCF_3$, $SO_2CH_3$, $SO_2$ $CH_2CH_3$, $OCH_2CH_2OCH_3$, $CH_2OCH_2CH_2OCH_3$ and $CH_2OCH_2CF_3$. Particularly preferably, R is selected from the group consisting of F, Cl, Br, $NO_2$, $CH_3$, $CF_3$, $OCH_3$, $OCF_3$, $SCF_3$, $SO_2CH_3$, $SO_2$ $CH_2CH_3$, $OCH_2CH_2OCH_3$, $CH_2OCH_2CH_2OCH_3$ and $CH_2OCH_2CF_3$.

In a further preferred embodiment of the HPPD-inhibiting herbicides of the formula I, A is C—$R^2$, B is CR4, X is CRxRy, Y is SO2 and W is CR6. These compounds correspond to the formula I.1 where the variables have the meanings defined at the outset and preferably the meanings mentioned as preferred.

More preferably, in the compounds of the formula I.1, the group $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, I, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or $R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio, or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.

R4 is H
R5 is H or halogen
R6 is H
R7 is H
R8 is H
Rx, Ry is H or CH3
B is N or CH Particularly preferably, in the compounds of the formula I.1, the group $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or $R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.

In a preferred embodiment of the compounds of the formula I.1, $R^2$ is $Z^1$-heterocyclyl where heterocyclyl is a 5- or 6-membered monocyclic or 9- or 10-membered bicyclic, saturated, partially unsaturated or aromatic heterocycle which contains 1, 2, 3 or 4 heteroatoms selected from the group consisting of O, N and S, cyclic groups being unsubstituted or partially or fully substituted by $R^b$.

$R^2$ is in this case preferably a 3- to 7-membered monocyclic or 9- or 10-membered bicyclic saturated, partially unsaturated or aromatic heterocycle which is attached via Z and contains 1, 2, 3 or 4 heteroatoms selected from the group consisting of O, N and S, where the cyclic groups are unsubstituted or partially or fully substituted by groups R.

In a further preferred aspect of the compounds of the formula I.1, $R^2$ is a 3- to 7-membered monocyclic or 9- or 10-membered bicyclic saturated, partially unsaturated or aromatic heterocycle which is attached directly or via $C_1$-$C_4$-alkyleneoxy, $C_1$-$C_4$-oxyalkylene or $C_1$-$C_4$-alkyleneoxy-$C_1$-$C_4$-alkylene, which contains 1, 2, 3 or 4 heteroatoms selected from the group consisting of O, N and S and which may be substituted as defined at the outset.

A preferred aspect of group $R^2$ relates to five- or six-membered saturated or partially unsaturated heterocycles, such as, for example, isoxazoline, tetrazolone, 1,2-dihydrotetrazolone, 1,4-dihydrotetrazolone, tetrahydrofuran, dioxolane, piperidine, morpholine and piperazine. Particular preference is given to 3-isoxazoline, 5-isoxazoline, 1-tetrazolone, 2-tetrazolone, [1,3]dioxolane-2 and N-morpholine. Especially preferred are: 4,5-dihydroisoxazole-3, unsubstituted or substituted by 5-$CH_3$, 5-$CH_2F$ or 5-$CHF_2$; 4,5-dihydroisoxazole-5, unsubstituted or substituted by 3-$CH_3$, 3-$OCH_3$, 3—$CH_2OCH_3$, 3-$CH_2SCH_3$; 1-methyl-5-oxo-1,5-dihydrotetrazole-2; 4-methyl-5-oxo-4,5-dihydrotetrazole-1 and N-morpholine.

A further preferred aspect of group R relates to five- or six-membered aromatic heterocycles, such as, for example, isoxazole, pyrazole, thiazole, furyl, pyridine, pyrimidine and pyrazine. Particular preference is given to 3-isoxazole, 5-isoxazole, 3-pyrazole, 5-pyrazole, 2-thiazole, 2-oxazole, 2-furyl. Especially preferred are: 3-isoxazole, 5-methyl-3-isoxazole, 5-isoxazole, 3-methyl-5-isoxazole, 1-methyl-1H-pyrazole-3,2-methyl-2H-pyrazole-3 and thiazole-2.

In a preferred aspect of the compounds of the formula I, the groups R independently of one another are Z—CN, Z—OH, Z—$NO_2$, Z-halogen, oxo (=O), =N—$R^d$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-haloalkoxy, Z—$C_3$-$C_{10}$-cycloalkyl, O—Z—$C_3$-$C_{10}$-cycloalkyl, Z—C(=O)—$R^d$, $NR^iR^{ii}$, Z-(tri-$C_1$-$C_4$-alkyl)silyl, Z-phenyl or $S(O)_n R^b$.

In a preferred aspect of heterocyclic groups $R^2$, the groups $R^c$ independently of one another are preferably $C_1$-$C_4$-alkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-alkylthio or $C_1$-$C_4$-alkylsulfonyl. Especially preferred are $CH_3$, $C_2H_5$, $CH_2F$, $CF_2H$, $CF_3$, $OCH_3$, $CH_2OCH_3$, $CH_2SCH_3$, $SCH_3$ and $SO_2CH_3$.

The group $R^b$ is preferably $C_1$-$C_8$-alkyl.

In a preferred aspect, the group $Z^1$ is a covalent bond.

In a further preferred aspect, the group $Z^1$ is $C_1$-$C_4$-alkyleneoxy, in particular $OCH_2$ or $OCH_2CH_2$.

In a further preferred aspect, the group $Z^1$ is $C_1$-$C_4$-oxyalkylene, in particular $CH_2O$ or $CH_2CH_2O$.

In a further preferred aspect, the group $Z^1$ is $C_1$-$C_4$-alkyleneoxy-$C_1$-$C_4$-alkylene, in particular $OCH_2OCH_2$ or $OCH_2CH_2OCH_2$.

Particularly preferred aspects of heterocycles attached via $Z^1$ include tetrahydrofuran-2-ylmethoxymethyl and [1,3]dioxolan-2-ylmethoxy.

In another preferred embodiment of the compounds of the formula I.1, $R^2$ is a group selected from the group consisting of halogen, $C_1$-$C_8$-alkyl, $C_2$-$C_6$-haloalkyl, $C_1$-$C_4$-alkoxy-$C_1$-$C_4$-alkyl, $C_2$-$C_8$-alkenyl, $C_2$-$C_8$-alkynyl, $C_2$-$C_8$-haloalkenyl, $C_2$-$C_8$-haloalkynyl, $C_1$-$C_6$-alkoxy, Z—$C_1$-$C_4$-alkoxy-$C_1$-$C_4$-alkoxy, Z—$C_1$-$C_4$-haloalkoxy-$C_1$-$C_4$-alkoxy, Z—$C_1$-$C_6$-haloalkoxy, $C_2$-$C_8$-alkenyloxy, $C_2$-$C_8$-alkynyloxy, Z—$C_1$-$C_4$-alkythio, Z—$C_1$-$C_6$-haloalkylthio, Z—C(=O)—$R^d$ or $S(O)_n R^d$, $C_1$-$C_4$-cycloalkyl-$C_1$-$C_4$-alkoxy-$C_1$-$C_4$-alkyl, $C_1$-$C_4$-cycloalkyl-$C_1$-$C_4$-alkoxy.

In yet another preferred embodiment of the compounds of the formula I.1, $R^2$ is a group selected from the group consisting of halogen, $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_8$-alkyl, $S(O)_2$—$C_1$-$C_8$-haloalkyl and N—($C_1$-$C_4$-alkyl) amino-N-sulfonyl-$C_1$-$C_4$-alkyl.

In a particularly preferred aspect of these compounds of the formula I.1, R is a group selected from the group consisting of $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_1$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_4$-alkyl and $S(O)_2$—$C_1$-$C_6$-haloalkyl.

Particularly preferred groups $R^2$ include $C_2$-$C_4$-alkenyl, $C_2$-$C_4$-alkynyl, $C_1$-$C_2$-haloalkoxy-$C_1$-$C_2$-alkyl, $C_3$-$C_4$-alkenyloxy, $C_3$-$C_4$-alkynyloxy, $C_1$-$C_4$-alkylsulfonyl, $C_1$-$C_4$-alkoxy, $C_1$-$C_4$-alkoxycarbonyl and $S(O)_2$—$C_1$-$C_4$-alkyl, chlorine, bromine. Special preference is given to CH=$CH_2$, CH=CHCH$_3$, $CH_2OCH_2CF_3$, $OC_2H_5$, $OCH_2CH$=$CH_2$, $OCH_2C$≡CH, $OCH_2CH_2OCH_3$, $COOCH_3$, $COOC_2H_5$ and $SO_2CH_3$, $SO_2C_2H_5$ and $SO_2CH(CH_3)_2$, cyclopropyl-methoxy-methyl (cyPr—$CH_2$—O—$CH_2$—), difluoromethoxy ($CHF_2$—O—); and 1,1,1-triflouroethoxy ($CF_3CH_2$—O—).

In a further preferred aspect, $R^2$ together with the group attached to the adjacent carbon atom forms a five- to ten-membered saturated, partially unsaturated or fully unsaturated mono- or bicyclic ring which, in addition to carbon atoms, may contain 1, 2 or 3 heteroatoms selected from the group consisting of O, N and S and which may be substituted by further groups $R^3$.

In a particularly preferred aspect, $R^2$ together with $R^1$ or $R^3$ forms a five- to ten-membered mono- or bicyclic, saturated, partially unsaturated or fully unsaturated ring which contains 1, 2, 3 or 4 heteroatoms selected from the group consisting of O, N and S and which may be partially or fully substituted by groups $R^c$. Suitable are, for example, the following: 4-dihydro-2H-thiopyrano[2,3-b]pyridine 1,1-dioxide, 3,4-dihydro-2H-thiopyrano[3,2-b]pyridine 1,1-dioxide, 2,3-dihydro-[1,4]dithiino[2,3-b]pyridine 1,1,4,4-tetraoxide, 1H-thiazolo[5,4-b]pyridin-2-one, 2,3-dihydrothieno[2,3-b]pyridine 1,1-dioxide, 1,8-naphthyridine, 1,5-naphthyridine, 1,7-naphthyridine and isothiazolo[5,4-b]pyridine Preferably, $R^2$ together with $R^1$ or $R^3$ forms a five- or six-membered monocyclic, saturated or partially unsaturated ring.

In a further preferred embodiment of the compounds of the formula I (in particular of the formula I.1), $R^3$ is hydrogen, cyano, halogen, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy or $S(O)_n R^b$.

In a particularly preferred embodiment of the compounds of the formula I (in particular of the formula I.1), $R^3$ is hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_n$—$C_1$-$C_4$-alkyl and $S(O)_n$—$C_1$-$C_4$-haloalkyl, where n is preferably 0 or 2. Particularly preferably, R is selected from the group consisting of H, F, Cl, Br, CN, $NO_2$, $CH_3$, $CF_3$, $CHF_2$, $OCH_3$, $OCF_3$, $OCHF_2$, $SCH_3$, $SCF_3$, $SCHF_2$, $SO_2CH_3$ and $SO_2CH_2CH_3$.

In further preferred aspects of the formula I.1, the groups R, $R^2$ and $R^3$ together form a substitution pattern selected from the group consisting of:
$R^1$=Cl, $R^2$=H, $R^3$=Cl;
$R^1$=Cl, $R^2$=H, $R^3$=$CF_3$;
$R^1$=Cl, $R^2$=H, $R^3$=$SO_2CH_3$;
$R^1$=Cl, $R^2$=H, $R^3$=$OCH_3$;
$R^1$=Cl, $R^2$=H, $R^3$=$CH_3$;
$R^1$=$CH_3$, $R^2$=H, $R^3$=Cl;
$R^1$=$CH_3$, $R^2$=H, $R^3$=$CF_3$;
$R^1$=$CH_3$, $R^2$=H, $R^3$=$SO_2CH_3$;
$R^1$=$CH_3$, $R^2$=H, $R^3$=$OCH_3$;
$R^1$=$CF_3$, $R^2$=H, $R^3$=$CH_3$;
$R^1$=$CF_3$, $R^2$=H, $R^3$=Cl;
$R^1$=$CF_3$, $R^2$=H, $R^3$=$CF_3$;
$R^1$=$CF_3$, $R^2$=H, $R^3$=$SO_2CH_3$;
$R^1$=$CF_3$, $R^2$=H, $R^3$=$OCH_3$;
$R^1$=$SO_2CH_3$, $R^2$=H, $R^3$=$CH_3$,
$R^1$=$SO_2CH_3$, $R^2$=H, $R^3$=Cl;
$R^1$=$SO_2CH_3$, $R^2$=H, $R^3$=$CF_3$;
$R^1$=$SO_2CH_3$, $R^2$=H, $R^3$=$SO_2CH_3$;
$R^1$=$SO_2CH_3$, $R^2$=H, $R^3$=$OCH_3$; and $R^1$=$SO_2CH_3$, $R^2$=H, $R^3$=$CH_3$.

In a further preferred embodiment of the HPPD-inhibiting herbicides of the formula I, A is N, B is CR4, X is CRxRy, Y is SO2 and W is CR6. These compounds correspond to the formula I.2

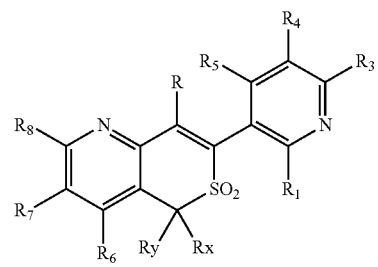

where the variables have the meanings defined at the outset and preferably the meanings mentioned as preferred.

More preferably, in the compounds of the formula I.2, the group
$R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, I, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or
$R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio, or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.
R4 is H
R5 is H or halogen
R6 is H
R7 is H
R8 is H
Rx, Ry is H or CH3

Particularly preferably, in the compounds of the formula I.1, the group

R$^1$ is halogen, C$_1$-C$_4$-alkyl, C$_1$-C$_4$-haloalkyl, C$_1$-C$_4$-alkoxy-C$_1$-C$_4$-alkyl, C$_1$-C$_4$-alkoxy-C$_1$-C$_4$-alkoxy-C$_1$-C$_4$-alkyl, C$_1$-C$_4$-alkoxy, C$_1$-C$_4$-haloalkoxy, C$_1$-C$_4$-alkylthio, C$_1$-C$_4$-haloalkylthio or C$_1$-C$_4$-alkylsulfonyl, in particular F, Cl, Br, NO$_2$, CH$_3$, CF$_3$, OCH$_3$, OCF$_3$, OCHF$_2$, SCF$_3$, SCHF$_2$, SO$_2$CH$_3$, or CH$_2$OCH$_2$CH$_2$OCH$_3$; and/or R$^3$ is H, halogen, CN, NO$_2$, C$_1$-C$_4$-alkyl, C$_1$-C$_4$-haloalkyl, C$_1$-C$_4$-alkoxy, C$_1$-C$_4$-alkylthio or C$_1$-C$_4$-alkylsulfonyl, in particular H, F, Cl, Br, CN, NO$_2$, CH$_3$, CH$_2$CH$_3$, CF$_3$, CHF$_2$, OCH$_3$, OCF$_3$, OCHF$_2$, SCH$_3$, SO$_2$CH$_3$ or SO$_2$CH$_2$CH$_3$.

In a further preferred embodiment of the compounds of the formula I (in particular of the formula I.2), R$^3$ is hydrogen, cyano, halogen, nitro, C$_1$-C$_4$-alkyl, C$_1$-C$_4$-haloalkyl, C$_1$-C$_4$-alkoxy, C$_1$-C$_4$-haloalkoxy, C$_2$-C$_4$-alkenyl, C$_2$-C$_4$-alkynyl, C$_2$-C$_4$-alkenyloxy, C$_2$-C$_4$-alkynyloxy or S(O)$_n$R$^b$.

In a particularly preferred embodiment of the compounds of the formula I (in particular of the formula I.2), R$^3$ is hydrogen, halogen, CN, NO$_2$, C$_1$-C$_4$-alkyl, C$_1$-C$_4$-haloalkyl, C$_1$-C$_4$-alkoxy, C$_1$-C$_4$-haloalkoxy, S(O)$_n$—C$_1$-C$_4$-alkyl and S(O)$_n$—C$_1$-C$_4$-haloalkyl, where n is preferably 0 or 2. Particularly preferably, R$^3$ is selected from the group consisting of H, F, Cl, Br, CN, NO, CH$_3$, CF$_3$, CHF$_2$, OCH$_3$, OCF$_3$, OCHF$_2$, SCH$_3$, SCF$_3$, SCHF$_2$, SO$_2$CH$_3$ and SO$_2$CH$_2$CH$_3$.

In further preferred aspects of the formula I.1, the groups R, R$^2$ and R$^3$ together form a substitution pattern selected from the group consisting of:
R$^1$=Cl, R$^3$=Cl;
R$^1$=Cl, R$^3$=CF$_3$;
R$^1$=Cl, R$^3$=SO$_2$CH$_3$;
R$^1$=Cl, R$^3$=OCH$_3$;
R$^1$=Cl, R$^3$=CH$_3$;
R$^1$=CH$_3$, R$^3$=Cl;
R$^1$=CH$_3$, R$^3$=CF$_3$;
R$^1$=CH$_3$, R$^3$=SO$_2$CH$_3$;
R$^1$=CH$_3$, R$^3$=OCH$_3$;
R$^1$=CF$_3$, R$^3$=CH$_3$;
R$^1$=CF$_3$, R$^3$=Cl;
R$^1$=CF$_3$, R$^3$=CF$_3$;
R$^1$=CF$_3$, R$^3$=SO$_2$CH$_3$;
R$^1$=CF$_3$, R$^3$=OCH$_3$;
R$^1$=SO$_2$CH$_3$, R$^3$=CH$_3$,
R$^1$=SO$_2$CH$_3$, R$^3$=Cl;
R$^1$=SO$_2$CH$_3$, R$^3$=CF$_3$;
R$^1$=SO$_2$CH$_3$, R$^3$=SO$_2$CH$_3$;
R$^1$=SO$_2$CH$_3$, R$^3$=OCH$_3$; and
R$^1$=SO$_2$CH$_3$, R$^3$=CH$_3$.

Further particularly preferred herbicides useful for the present invention, comprise azines of formula (I)

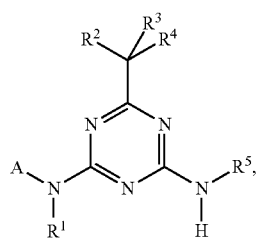

I wherein

A is phenyl, which is substituted by two to five substituents selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;

R$^1$ H, CN, C$_1$-C$_6$-alkyl, C$_1$-C$_6$-alkoxy-C$_1$-C$_6$-alkyl, C$_1$-C$_6$-alkoxy, (C$_1$-C$_6$-alkyl)carbonyl, (C$_1$-C$_6$-alkoxy)carbonyl, (C$_1$-C$_6$-alkyl)sulfonyl or phenylsulfonyl,
wherein the phenyl is unsubstituted or substituted by one to five substituents selected from the group consisting of halogen, CN, NO$_2$, C$_1$-C$_6$-alkyl, C$_1$-C$_6$-haloalkyl and C$_1$-C$_6$-alkoxy;

R$^2$ H, halogen, CN, C$_1$-C$_6$-alkyl, C$_1$-C$_6$-haloalkyl, C$_2$-C$_6$-alkenyl, C$_3$-C$_6$-alkynyl, C$_3$-C$_6$-cycloalkyl, C$_3$-C$_6$-cycloalkenyl, OH, C$_1$-C$_6$-alkoxy or C$_1$-C$_6$-alkoxy-C$_1$-C$_6$-alkyl;

R$^3$ H, halogen, CN, C$_1$-C$_6$-alkyl, C$_1$-C$_6$-haloalkyl or C$_1$-C$_6$-alkoxy;

R$^4$ H, halogen, CN, C$_1$-C$_6$-alkyl or C$_1$-C$_6$-haloalkyl; or

R$^3$ and R$^4$ together with the carbon atom to which they are attached form a moiety selected from the group consisting of carbonyl, C$_2$-C$_6$-alkenyl, C$_3$-C$_6$-cycloalkyl, C$_3$-C$_6$-cycloalkenyl and three- to six-membered heterocyclyl,
wherein the C$_3$-C$_6$-cycloalkyl, C$_3$-C$_6$-cycloalkenyl, or three- to six-membered heterocyclyl is unsubstituted or substituted by one to three substituents selected from halogen, CN, C$_1$-C$_6$-alkyl and C$_1$-C$_6$-alkoxy; and R$^5$ H, CN, C$_1$-C$_6$-alkyl, C$_1$-C$_6$-alkoxy-C$_1$-C$_6$-alkyl, C$_1$-C$_6$-alkoxy, (C$_1$-C$_6$-alkyl)carbonyl, (C$_1$-C$_6$-alkoxy)carbonyl, (C$_1$-C$_6$-alkyl)sulfonyl or phenylsulfonyl,
wherein the phenyl is unsubstituted or substituted by one to five substituents selected from the group consisting of halogen, CN, NO$_2$, C$_1$-C$_6$-alkyl, C$_1$-C$_6$-haloalkyl and C$_1$-C$_6$-alkoxy;

including their agriculturally acceptable salts or N-oxides.

Further particularly preferred herbicides useful for the present invention, comprise triazines of formula (I)

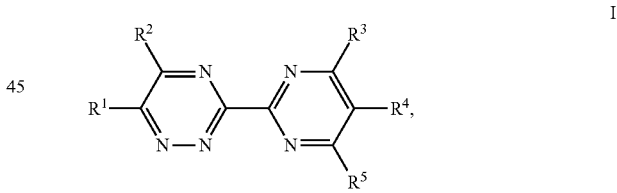

I wherein

R$^1$ is hydrogen, C$_1$-C$_{10}$-alkyl, C$_2$-C$_{10}$-alkenyl, C$_2$-C$_{10}$-alkynyl, C$_1$-C$_8$-haloalkyl, C$_2$-C$_8$-haloalkenyl, C$_2$-C$_8$-haloalkynyl, C$_1$-C$_8$-alkoxy, C$_1$-C$_8$-alkoxy-C$_1$-C$_8$-alkyl, C$_1$-C$_8$-alkylthio, C$_1$-C$_8$-alkylthio-C$_1$-C$_8$-alkyl, hydroxy-C$_1$-C$_{10}$-alkyl, aminocarbonyl, (C$_1$-C$_6$-alkyl)aminocarbonyl, di(C$_1$-C$_6$-alkyl)aminocarbonyl, C$_3$-C$_6$-cycloalkyl, C$_3$-C$_6$-cycloalkyl-C$_1$-C$_8$-alkyl, C$_3$-C$_6$-cycloalkyl-C$_1$-C$_8$-haloalkyl, C$_3$-C$_6$-cycloalkyl-C$_2$-C$_8$-alkenyl or C$_3$-C$_6$-cycloalkyl-C$_2$-C$_8$-haloalkenyl,
which cycloalkyls are unsubstituted or substituted by one to five substituents selected from the group consisting of halogen, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl and C$_2$-C$_6$-haloalkynyl;

R$^2$ is halogen, CN, OH, SH, C$_1$-C$_6$-alkoxy, C$_1$-C$_6$-alkylthio, C$_1$-C$_6$-alkoxy-C$_1$-C$_4$-alkoxy, C$_1$-C$_6$-alkoxy-C$_1$-

$C_4$-alkylthio, $C_1$-$C_6$-alkylthio-$C_1$-$C_4$-alkoxy, $C_1$-$C_6$-alkyltio-$C_1$-$C_4$-alkylthio, $C_1$-$C_6$-alkoxycarbonyl-$C_1$-$C_6$-alkoxy, $C_1$-$C_6$-alkoxycarbonyloxy, $C_1$-$C_6$-alkylthiocarbonyl-oxy, aminocarbonyloxy, ($C_1$-$C_6$-alkyl)aminocarbonyloxy, di($C_1$-$C_6$-alkyl) aminocarbonyloxy, a 5-membered heteroaryl having 1 to 4 nitrogen atoms, which heteroaryl is attached to the triazine ring via a nitrogen atom, and which heteroaryl is unsubstituted or substituted by 1 to 4 substituents selected from the group consisting of halogen, CN, $NO_2$, OH, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-haloalkyl, $C_2$-$C_6$-haloalkenyl, $C_2$-$C_6$-haloalkynyl, $C_1$-$C_6$-alkoxy, $C_1$-$C_6$-alkylthio, $C_1$-$C_6$-alkoxycarbonyl, $C_1$-$C_6$-alkylthiocarbonyl, $C_1$-$C_6$-alkoxy-$C_1$-$C_4$-alkyl, $C_1$-$C_6$-alkylthio-$C_1$-$C_4$-alkyl, hydroxy-carbonyl, thiocarboxy, $C_1$-$C_6$-alkoxycarbonyl-$C_1$-$C_4$-alkyl, $C_1$-$C_6$-alkylthiocarbonyl-$C_1$-$C_4$-alkyl, $NH_2$, ($C_1$-$C_6$-alkyl)amino and di($C_1$-$C_6$-alkyl)amino, phenoxy or phenyl-$C_1$-$C_4$-alkoxy, which phenyls are unsubstituted or substituted by one to five substituents selected from the group consisting of halogen, CN, $NO_2$, $C_1$-$C_4$-alkyl, $C_1$-$C_4$-alkoxy, $C_1$-$C_4$-haloalkyl and $C_1$-$C_4$-haloalkoxy;

$R^3$, $R^4$ and $R^5$ independently of one another are hydrogen, halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylsulfonyl, ($C_1$-$C_6$-alkyl)amino or di($C_1$-$C_6$-alkyl)amino;

including their agriculturally acceptable salts or, provided that the triazines of formula I have a carboxyl group, their agriculturally acceptable derivatives.

Preferred are the triazines of the formula (I), wherein $R^1$ is hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-alkoxy, $C_1$-$C_6$-alkoxy-$C_1$-$C_4$-alkyl, $C_1$-$C_6$-alkylthio, $C_1$-$C_6$-alkylthio-$C_1$-$C_4$-alkyl, aminocarbonyl, ($C_1$-$C_6$-alkyl)aminocarbonyl, di($C_1$-$C_6$-alkyl)aminocarbonyl, $C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_2$-$C_6$-alkenyl or $C_3$-$C_6$-cycloalkyl-$C_2$-$C_6$-haloalkenyl, which cycloalkyls are unsubstituted or substituted by one to five substituents selected from the group consisting of halogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl and $C_2$-$C_6$-haloalkynyl;

$R^2$ is halogen, CN, OH, SH, $C_1$-$C_6$-alkoxy, $C_1$-$C_6$-alkylthio, $C_1$-$C_6$-alkoxy-$C_1$-$C_4$-alkoxy, $C_1$-$C_6$-alkoxy-$C_1$-$C_4$-alkylthio, $C_1$-$C_6$-alkylthio-$C_1$-$C_4$-alkoxy, $C_1$-$C_6$-alkyltio-$C_1$-$C_4$-alkylthio, $C_1$-$C_6$-alkoxycarbonyl-$C_1$-$C_6$-alkoxy, $C_1$-$C_6$-alkoxycarbonyloxy, $C_1$-$C_6$-alkylthiocarbonyl-oxy, aminocarbonyloxy, ($C_1$-$C_6$-alkyl)aminocarbonyloxy, di($C_1$-$C_6$-alkyl) aminocarbonyloxy or a 5-membered heteroaryl having 1 to 4 nitrogen atoms, which heteroaryl is attached to the triazine ring via a nitrogen atom, and which heteroaryl is unsubstituted or substituted by 1 to 4 substituents selected from the group consisting of halogen, CN, $NO_2$, OH, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-haloalkyl, $C_2$-$C_6$-haloalkenyl, $C_2$-$C_6$-haloalkynyl, $C_1$-$C_6$-alkoxy, $C_1$-$C_6$-alkylthio, $C_1$-$C_6$-alkoxycarbonyl, $C_1$-$C_6$-alkylthiocarbonyl, $C_1$-$C_6$-alkoxy-$C_1$-$C_4$-alkyl, $C_1$-$C_6$-alkylthio-$C_1$-$C_4$-alkyl, hydroxy-carbonyl, thiocarboxy, $C_1$-$C_6$-alkoxycarbonyl-$C_1$-$C_4$-alkyl, $C_1$-$C_6$-alkylthiocarbonyl-$C_1$-$C_4$-alkyl, $NH_2$, ($C_1$-$C_6$-alkyl)amino and di($C_1$-$C_6$-alkyl)amino;

$R^3$, $R^4$ and $R^5$ independently of one another are hydrogen, halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylsulfonyl, ($C_1$-$C_6$-alkyl)amino or di($C_1$-$C_6$-alkyl)amino;

including their agriculturally acceptable salts or, provided that the triazines of formula I have a carboxyl group, their agriculturally acceptable derivatives.

Further particularly preferred herbicides useful for the present invention, comprise pyrazol amide compounds of formula (I)

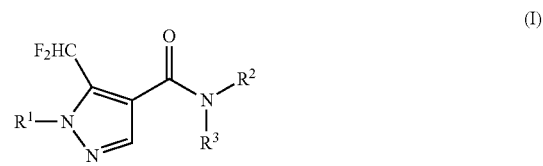

(I)

wherein $R^1$ is H, $C_1$-$C_{10}$-alkyl, $C_1$-$C_{10}$-haloalkyl, $C_2$-$C_{10}$-hydroxyalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl, $C_1$-$C_6$-alkylsulfinyl-$C_1$-$C_6$-alkyl, $C_1$-$C_6$-haloalkylsulfinyl-$C_1$-$C_6$-alkyl, $C_1$-$C_6$-alkylsulfonyl-$C_1$-$C_6$-alkyl, $C_1$-$C_6$-haloalkylsulfonyl-$C_1$-$C_6$-alkyl, $C_3$-$C_6$-cycloalkyl, 1-methylcycloprop-1-yl, 2-methylcycloprop-1-yl, 2,2-dimethylcycloprop-1-yl, 2,2,3,3-tetramethylcycloprop-1-yl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, $C_2$-$C_{10}$-alkenyl, $C_2$-$C_{10}$-haloalkenyl, $C_2$-$C_{10}$-hydroxyalkenyl, $C_3$-$C_{10}$-alkadienyl, $C_3$-$C_6$-alkynyl, $C_3$-$C_6$-haloalkynyl, $CH_2CN$, $CH(CN)_2$, N,N-di-($C_1$-$C_6$)-alkylamino-$C_1$-$C_6$-alkyl, $C_1$-$C_6$-dialkoxy-$C_1$-$C_6$-alkyl, $C_1$-$C_6$-dialkylthio-$C_1$-$C_6$-alkyl, $C_1$-$C_3$-alkoxy-$C_1$-$C_3$-alkylthio-$C_1$-$C_6$-alkyl, or a heterocyclic group selected from the formulae H1, H2 or H3

(H1)

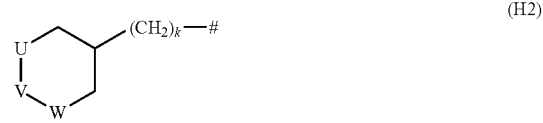

(H2)

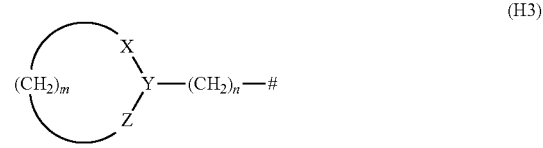

(H3)

wherein each of Q and R in the formula H1 is O or S;

U-V-W in the formula H2 is selected from the group consisting of $CH_2$—$CH_2$—O, $CH_2$—$CH_2$—NH, $CH_2$—$CH_2$—N($CH_3$), $CH_2$—O—$CH_2$, $CH_2$—NH—$CH_2$, $CH_2$—N($CH_3$)—$CH_2$, O—$CH_2$—O, O—$CH_2$—S, and S—$CH_2$—S;

k in the formula H2 is 0 or 1;

X—Y—Z in the formula H3 is selected from the group consisting of CH$_2$—N—CH$_2$, O—CH—CH$_2$, O—CH—O, S—CH—CH$_2$, S—CH—S, and O—CH—S;

m in the formula H3 is 1, 2 or 3;

n in the formula H3 is 0, 1 or 2, with the proviso that, when n is 0, X—Y—Z is not CH$_2$—N—CH$_2$;

in each of the formulae H1, H2 or H3 denotes the bonding site to the remainder of the formula I;

$R^2$ is hydrogen, $C_1$-$C_4$-alkyl, $C_3$-$C_6$-cycloalkyl or $C_1$-$C_4$-alkoxy; and $R^3$ is hydrogen, $C_1$-$C_4$-alkyl, $C_3$-$C_6$-cycloalkyl or $C_1$-$C_4$-alkoxy;

or an agriculturally acceptable salt thereof.

Further particularly preferred herbicides useful for the present invention, comprise pyrazol amide compounds of formula (II):

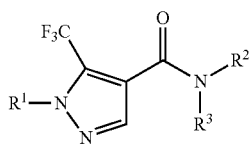

(II)

wherein $R^1$ is $C_5$-$C_{10}$-alkyl, $C_1$-$C_{10}$-haloalkyl, $C_2$-$C_{10}$-hydroxyalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio-$C_1$-$C_6$-alkyl, $C_1$-$C_6$-haloalkylthio-$C_1$-$C_6$-alkyl, $C_1$-$C_6$-alkylsulfinyl-$C_1$-$C_6$-alkyl, $C_1$-$C_6$-haloalkylsulfinyl-$C_1$-$C_6$-alkyl, $C_1$-$C_6$-alkylsulfonyl-$C_1$-$C_6$-alkyl, $C_1$-$C_6$-haloalkylsulfonyl-$C_1$-$C_6$-alkyl, $C_3$-$C_4$-cycloalkyl, 1-methylcycloprop-1-yl, 2-methylcycloprop-1-yl, 2,2-dimethylcycloprop-1-yl, 2,2,3,3-tetramethylcycloprop-1-yl, $C_3$-$C_6$-halocycloalkyl, $C_3$-$C_6$-cycloalkyl-$C_1$-$C_6$-alkyl, $C_2$-$C_{10}$-alkenyl, $C_2$-$C_{10}$-hydroxyalkenyl, $C_3$-$C_{10}$-alkadienyl, $C_2$-$C_6$-haloalkenyl, $C_3$-$C_6$-alkynyl, $C_3$-$C_6$-haloalkynyl, CH$_2$CN, CH(CN)$_2$, N,N-di-($C_1$-$C_6$)-alkylamino-$C_1$-$C_6$-alkyl, $C_1$-$C_6$-dialkoxy-$C_1$-$C_6$ alkyl, $C_1$-$C_6$-dialkylthio-$C_1$-$C_6$ alkyl, $C_1$-$C_3$-alkoxy-$C_1$-$C_3$-alkylthio-$C_1$-$C_6$ alkyl, or a heterocyclic group selected from the formulae H1, H2 or H3

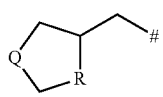

(H1)

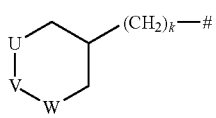

(H2)

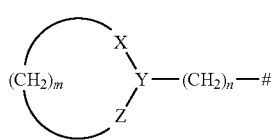

(H3)

wherein each of Q and R in the formula H1 is O or S;

U—V—W in the formula H2 is selected from the group consisting of CH$_2$—CH$_2$—O, CH$_2$—CH$_2$—NH, CH$_2$—CH$_2$—N(CH$_3$), CH$_2$—O—CH$_2$, CH$_2$—NH—CH$_2$, CH$_2$—N(CH$_3$)—CH$_2$, O—CH$_2$—O, O—CH$_2$—S, and S—CH$_2$—S;

k in the formula H2 is 0 or 1;

X—Y—Z in the formula H3 is selected from the group consisting of CH$_2$—N—CH$_2$, O—CH—CH$_2$, O—CH—O, S—CH—CH$_2$, S—CH—S, and O—CH—S;

m in the formula H3 is 1, 2 or 3;

n in the formula H$_3$ is 0, 1 or 2, with the proviso that, when n is 0, X—Y—Z is not CH$_2$—N—CH$_2$;

in each of the formulae H1, H2 or H3 denotes the bonding site to the remainder of the formula I;

$R^2$ is hydrogen, $C_1$-$C_4$-alkyl, $C_3$-$C_6$-cycloalkyl or $C_1$-$C_4$-alkoxy; and $R^3$ is hydrogen, $C_1$-$C_4$-alkyl, $C_3$-$C_6$-cycloalkyl or $C_1$-$C_4$-alkoxy;

or an agriculturally acceptable salt thereof.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms "gene(s)", "polynucleotide", "nucleic acid sequence", "nucleotide sequence", or "nucleic acid molecule(s)" as used herein include known types of modifications, for example, methylation, "caps", substitutions of one or more of the naturally occurring nucleotides with an analogue. Preferably, the DNA or RNA sequence comprises a coding sequence encoding the herein defined polypeptide. As also used herein, the terms "nucleic acid" and "nucleic acid molecule" are intended to include DNA molecules (e.g. cDNA or genomic DNA) and RNA molecules (e.g. mRNA) and analogs of the DNA or RNA generated using nucleotide analogs. The nucleic acid molecule can be single-stranded or double-stranded.

An "isolated" nucleic acid molecule is one that is substantially separated from other nucleic acid molecules, which are present in the natural source of the nucleic acid. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated herbicide resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A "coding sequence" is a nucleotide sequence, which is transcribed into an RNA, e.g. a regulatory RNA, such as a miRNA, a ta-siRNA, co-suppression molecule, an RNAi, a ribozyme, etc. or into a mRNA which is translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

As used in the present context a nucleic acid molecule may also encompass the untranslated sequence located at the 3' and at the 5' end of the coding gene region, for example 2000, preferably less, e.g. 500, preferably 200, especially preferable 100, nucleotides of the sequence upstream of the 5' end of the coding region and for example 300, preferably less, e.g. 100, preferably 50, especially preferable 20, nucleotides of the sequence downstream of the 3' end of the coding gene region.

"Polypeptide" refers to a polymer of amino acid (amino acid sequence) and does not refer to a specific length of the molecule. Thus, peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. An "isolated" polynucleotide or nucleic acid molecule is separated from other polynucleotides or nucleic acid molecules, which are present in the natural source of the nucleic acid molecule. An isolated and/or a recombinant nucleic acid molecule may be a chromosomal fragment of several kb, or preferably, a molecule only comprising the coding region of the gene. Accordingly, an isolated and/or a recombinant nucleic acid molecule of the invention may comprise chromosomal regions, which are adjacent 5' and 3' or further adjacent chromosomal regions, but preferably comprises no such sequences which naturally flank the nucleic acid molecule sequence in the genomic or chromosomal context in the organism from which the nucleic acid molecule originates (for example sequences which are adjacent to the regions encoding the 5'- and 3'-UTRs of the nucleic acid molecule). An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of a protein in which the polypeptide is separated from some of the cellular components of the cells in which it is naturally or recombinantly produced.

The terms "comprise" or "comprising" and grammatical variations thereof when used in this specification are to be taken to specify the presence of stated features, integers, steps or components or groups thereof, but not to preclude the presence or addition of one or more other features, integers, steps, components or groups thereof.

In accordance with the invention, a protein or polypeptide has the "activity of a CYP450 protein if its de novo activity, or its increased expression directly or indirectly leads to and confers increased herbicide tolerance or resistance, as compared to a corresponding, e.g. non-transformed, wild type plant and the protein has the above mentioned activity of a CYP450.

Throughout the specification the activity or preferably the biological activity of such a protein or polypeptide or an nucleic acid molecule or sequence encoding such protein or polypeptide is identical or similar if it still has the biological or enzymatic activity of a protein comprising the sequence of SEQ ID NO: 2, 4, 6, 8, 27, or 45, or a homolog thereof, or which has 10% or more of the original enzymatic activity, preferably 20%, 30%, 40%, 50%, particularly preferably 60%, 70%, 80% most particularly preferably 90%, 95%, 98%, 99% or more in comparison to a protein comprising the sequence of SEQ ID NO: 2, 4, 6, 8, 27, or 45, or a homolog thereof.

In another embodiment the biological or enzymatic activity of a protein comprising the sequence of SEQ ID NO: 2, 4, 6, 8, 27, or 45, or a homolog thereof, has 100% or more of the original enzymatic activity, preferably 110%, 120%, 130%, 150%, particularly preferably 150%, 200%, 300% or more in comparison to a protein comprising the sequence of SEQ ID NO: 2, 4, 6, 8, 27, or 45, or a homolog thereof.

The terms "increased", "raised", "extended", "enhanced", "improved" or "amplified" relate to a corresponding change of a property in a plant, an organism, a part of an organism such as a tissue, seed, root, leave, flower etc. or in a cell and are interchangeable. Preferably, the overall activity in the volume is increased or enhanced in cases if the increase or enhancement is related to the increase or enhancement of an activity of a gene product, independent whether the amount of gene product or the specific activity of the gene product or both is increased or enhanced or whether the amount, stability or translation efficacy of the nucleic acid sequence or gene encoding for the gene product is increased or enhanced.

The terms "increase" include the change of said property in only parts of the subject of the present invention, for example, the modification can be found in compartment of a cell, like a organelle, or in a part of a plant, like tissue, seed, root, leave, flower etc. but is not detectable if the overall subject, i.e. complete cell or plant, is tested. Accordingly, the term "increase" means that the specific activity of an enzyme as well as the amount of a compound or metabolite, e.g. of a polypeptide, a nucleic acid molecule of the invention or an encoding mRNA or DNA, can be increased in a volume. The term "increase" includes, that a compound or an activity, especially an activity, is introduced into a cell, the cytoplasm or a sub-cellular compartment or organellede novo or that the compound or the activity, especially an activity, has not been detected before, in other words it is "generated". Accordingly, in the following, the term "increasing" also comprises the term "generating" or "stimulating". The increased activity manifests itself in increased herbicide tolerance or resistance, as compared to a corresponding, e.g. non-transformed, wild type plant cell, plant or part thereof.

Under "change of a property" it is understood that the activity, expression level or amount of a gene product or the metabolite content is changed in a specific volume relative to a corresponding volume of a control, reference or wild type, including the de novo creation of the activity or expression.

"Amount of protein or mRNA" is understood as meaning the molecule number of polypeptides or mRNA molecules in an organism, especially a plant, a tissue, a cell or a cell compartment. "Increase" in the amount of a protein means the quantitative increase of the molecule number of said protein in an organism, especially a plant, a tissue, a cell or a cell compartment such as an organelle like a plastid or mitochondria or part thereof—for example by one of the methods described herein below—in comparison to a wild type, control or reference.

The increase in molecule number amounts preferably to 1% or more, preferably to 10% or more, more preferably to 30% or more, especially preferably to 50%, 70% or more, very especially preferably to 100%, most preferably to 500% or more. However, ade novo expression is also regarded as subject of the present invention.

The terms "wild type", "control" or "reference" are exchangeable and can be a cell or a part of organisms such as an organelle like a chloroplast or a tissue, or an organism, in particular a plant, which was not modified or treated according to the herein described process according to the invention. Accordingly, the cell or a part of organisms such as an organelle like a chloroplast or a tissue, or an organism, in particular a plant used as wild type, control or reference corresponds to the cell, organism, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property.

Preferably, any comparison is carried out under analogous conditions. The term "analogous conditions" means that all conditions such as, for example, culture or growing conditions, soil, nutrient, water content of the soil, temperature, humidity or surrounding air or soil, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-" -organelle, -cell, -tissue or -organism, in particular plant, relates to an organelle, cell, tissue or organism, in particular plant, which is nearly genetically identical to the organelle, cell, tissue or organism, in particular plant, of the present invention or a part thereof preferably 90% or more, e.g. 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a subject, e.g. an organelle, a cell, a tissue, an organism, in particular a plant, which is genetically identical to the organism, in particular plant, cell, a tissue or organelle used according to the process of the invention except that the responsible or activity conferring nucleic acid molecules or the gene product encoded by them are amended, manipulated, exchanged or introduced according to the inventive process. In case, a control, reference or wild type differing from the subject of the present invention only by not being subject of the process of the invention can not be provided, a control, reference or wild type can be an organism in which the cause for the modulation of an activity conferring the enhanced tolerance or resistance to herbicides as compared to a corresponding, e.g. non-transformed, wild type plant cell, plant or part thereof or expression of the nucleic acid molecule of the invention as described herein has been switched back or off, e.g. by knocking out the expression of responsible gene product, e.g. by antisense or RNAi or miRNA inhibition, by inactivation of an activator or agonist, by activation of an inhibitor or antagonist, by inhibition through adding inhibitory antibodies, by adding active compounds as e.g. hormones, by introducing negative dominant mutants, etc. A gene production can for example be knocked out by introducing inactivating point mutations, which lead to an enzymatic activity inhibition or a destabilization or an inhibition of the ability to bind to cofactors etc. Accordingly, preferred reference subject is the starting subject of the present process of the invention. Preferably, the reference and the subject matter of the invention are compared after standardization and normalization, e.g. to the amount of total RNA, DNA, or protein or activity or expression of reference genes, like housekeeping genes, such as ubiquitin, actin or ribosomal proteins.

The term "expression" refers to the transcription and/or translation of a codogenic gene segment or gene. As a rule, the resulting product is an mRNA or a protein.

The increase or modulation according to this invention can be constitutive, e.g. due to a stable permanent transgenic expression or to a stable mutation in the corresponding endogenous gene encoding the nucleic acid molecule of the invention or to a modulation of the expression or of the behavior of a gene conferring the expression of the polypeptide of the invention, or transient, e.g. due to an transient transformation or temporary addition of a modulator such as a agonist or antagonist or inducible, e.g. after transformation with a inducible construct carrying the nucleic acid molecule of the invention under control of a inducible promoter and adding the inducer, e.g. tetracycline or as described herein below.

Less influence on the regulation of a gene or its gene product is understood as meaning a reduced regulation of the enzymatic activity leading to an increased specific or cellular activity of the gene or its product. An increase of the enzymatic activity is understood as meaning an enzymatic activity, which is increased by 10% or more, advantageously 20%, 30% or 40% or more, especially advantageously by 50%, 60% or 70% or more in comparison with the starting organism. This leads to increased herbicide tolerance or resistance, as compared to a corresponding, e.g. non-transformed, wild type plant or part thereof.

The increase in activity of the polypeptide amounts in a cell, a tissue, an organelle, an organ or an organism, preferably a plant, or a part thereof preferably to 5% or more, preferably to 20% or to 50%, especially preferably to 70%, 80%, 90% or more, very especially preferably are to 100%, 150% or 200%, most preferably are to 250% or more in comparison to the control, reference or wild type. In one embodiment the term increase means the increase in amount in relation to the weight of the organism or part thereof (w/w).

By "vectors" is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) are integrated into the genome of a host cell or a organelle upon introduction into the host cell, and thereby are replicated along with the host or organelle genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

As used herein, "operatively linked" is intended to mean that the nucleotide sequence of interest is linked to the regulatory sequence(s) in a manner which allows for expression of the nucleotide sequence (e.g. in an in vitro transcription/translation system or in a host cell when the vector is introduced into the host cell). The term "regulatory sequence" is intended to include promoters, enhancers, and other expression control elements (e.g. polyadenylation signals). Such regulatory sequences are described, for example, in Goeddel, Gene Expression Technology: Methods in Enzymology 185, Academic Press, San Diego, Calif. (1990), and Gruber and Crosby, in: Methods in Plant Molecular Biology and Biotechnology, eds. Glick and Thompson, Chapter 7, 89-108, CRC Press; Boca Raton, Fla., including the references therein. Regulatory sequences include those that direct constitutive expression of a nucleotide sequence in many types of host cells and those that direct expression of the nucleotide sequence only in certain host cells or under certain conditions.

"Transformation" is defined herein as a process for introducing heterologous DNA into a plant cell, plant tissue, or plant. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time. Transformed plant cells, plant tissue, or plants are understood to encompass not only the end product of a transformation process, but also transgenic progeny thereof.

The terms "transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extra-chromosomal molecule. Such an extra-chromosomal molecule can be auto-replicating. Transformed cells, tissues, or plants are understood to encompass not only the end product of a transformation process, but also transgenic progeny thereof. A "non-transformed", "non-transgenic" or "non-recombinant" host refers to a wild-type organism, e.g. a bacterium or plant, which does not contain the heterologous nucleic acid molecule.

The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

As used herein, "recombinant," when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if that nucleotide sequence has been removed from it natural text and cloned into any type of artificial nucleic acid vector. The term recombinant also can refer to an organism having a recombinant material, e.g., a plant that comprises a recombinant nucleic acid can be considered a recombinant plant.

For the purposes of the invention "transgenic" or "recombinant" means with regard for example to a nucleic acid sequence, an expression cassette (=gene construct, nucleic acid construct) or a vector containing the nucleic acid sequence according to the invention or an organism transformed by said nucleic acid sequences, expression cassette or vector according to the invention all those constructions produced by genetic engineering methods in which either
(a) the nucleic acid sequence comprising the sequence of SEQ ID NO: 1, 3, 5, 7, 26, or 44, or a homolog thereof, or its derivatives or parts thereof; or
(b) a genetic control sequence functionally linked to the nucleic acid sequence described under (a), for example a 3'- and/or 5'-genetic control sequence such as a promoter or terminator, or
(c) (a) and (b);
are not found in their natural, genetic environment or have been modified by genetic engineering methods, wherein the modification may by way of example be a substitution, addition, deletion, inversion or insertion of one or more nucleotide residues.

"Natural genetic environment" means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette— for example the naturally occurring combination of the natural promoter of the nucleic acid sequence according to the invention with the corresponding gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815.

The term "transgenic plants" used in accordance with the invention also refers to the progeny of a transgenic plant, for example the $T_1$, $T_2$, $T_3$ and subsequent plant generations or the $BC_1$, $BC_2$, $BC_3$ and subsequent plant generations. Thus, the transgenic plants according to the invention can be raised and selfed or crossed with other individuals in order to obtain further transgenic plants according to the invention. Transgenic plants may also be obtained by propagating transgenic plant cells vegetatively. The present invention also relates to transgenic plant material, which can be derived from a transgenic plant population according to the invention. Such material includes plant cells and certain tissues, organs and parts of plants in all their manifestations, such as seeds, leaves, anthers, fibers, tubers, roots, root hairs, stems, embryo, calli, cotelydons, petioles, harvested material, plant tissue, reproductive tissue and cell cultures, which are derived from the actual transgenic plant and/or can be used for bringing about the transgenic plant. Any transformed plant obtained according to the invention can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention. As mentioned before, the present invention is in principle applicable to any plant and crop that can be transformed with any of the transformation method known to those skilled in the art.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structurally equivalents can, for example, be identified by testing the binding of said polypeptide to antibodies or computer based predictions. Structurally equivalent have the similar immunological characteristic, e.g. comprise similar epitopes.

As used herein, the terms "gene" and "recombinant gene" refer to nucleic acid molecules comprising an open reading frame encoding the polypeptide of the invention or comprising the nucleic acid molecule of the invention or encoding the polypeptide used in the process of the present invention, preferably from a crop plant or from a microorgansim useful for the method of the invention. Such natural variations can typically result in 1 to 5% variance in the nucleotide sequence of the gene. Any and all such nucleotide variations and resulting amino acid polymorphisms in genes encoding a polypeptide of the invention or comprising the nucleic acid molecule of the invention that are the result of natural variation and that do not alter the functional activity as described are intended to be within the scope of the invention.

SPECIFIC EMBODIMENTS

Accordingly, this invention provides measures and methods to produce plants with increased herbicide tolerance or resistance.

Accordingly, the present invention provides transgenic plants showing increased tolerance or resistance to one or more herbicides as compared to the corresponding origin or the wild type plant and methods for producing such transgenic plants with increased herbicide tolerance or resistance.

One or more enhanced herbicide tolerance-related phenotypes are increased in accordance with the invention by increasing or generating the activity of an *Alopecurus* CYP450 enzyme.

The nucleic acid molecule of the present invention or used in accordance with the present invention, encodes a protein conferring an activity of an *Alopecurus* CYP450 enzyme.

Accordingly, in one embodiment, the present invention relates to a nucleic acid molecule that encodes a polypeptide with an herbicide tolerance or resistance-increasing activity which is encoded by a nucleic acid sequence comprising the sequence of SEQ ID NO: 1, 3, 5, 7, 26, or 44, or a homolog thereof, and/or which is a protein comprising or consisting of a polypeptide comprising the sequence of SEQ ID NO: 2, 4, 6, 8, 27, or 45, or a homolog thereof.

The increase or generation of said "activity" is for example conferred by the increase of activity or of amount in a cell or a part thereof of one or more expression products of said nucleic acid molecule, e.g. proteins, or by de novo expression, i.e. by the generation of said "activity" in the plant.

In one embodiment, said herbicide tolerance or resistance-increasing activity is increased by increasing the amount and/or the specific activity of a CYP450 protein comprising the sequence of SEQ ID NO: 2, 4, 6, 8, 27, or 45, or a homolog thereof.

Accordingly, in one embodiment, an increased herbicide tolerance or resistance as compared to a correspondingly non-modified, e.g. a non-transformed, wild type plant is conferred according to method of the invention, by increasing or generating the activity of a polypeptide comprising the sequence of SEQ ID NO: 2, 4, 6, 8, 27, or 45, or a homolog thereof, or encoded by the nucleic acid molecule (or gene) the sequence of SEQ ID NO: 1, 3, 5, 7, 26, or 44, or a homolog of said nucleic acid molecule or polypeptide.

Thus, in one embodiment, the present invention provides a method for producing a plant showing increased or improved herbicide resistance or tolerance as compared to the corresponding origin or wild type plant, by increasing or generating the activity of an *Alopecurus* CYP450 enzyme, e.g. which is conferred by one or more polynucleotide(s) comprising the sequence of SEQ ID NO: 1, 3, 5, 7, 26, or 44, or a homolog thereof, or by one or more protein(s), each comprising a polypeptide encoded by one or more nucleic acid sequence(s) comprising the sequence of SEQ ID NO: 1, 3, 5, 7, 26, or 44, or a homolog thereof, or by one or more protein(s) each comprising a polypeptide comprising the sequence of SEQ ID NO: 2, 4, 6, 8, 27, or 45, or a homolog thereof, and (b) optionally, growing the plant cell, plant or part thereof under conditions which permit the development of the plant cell, the plant or the part thereof, and (c) regenerating a plant with increased herbicide tolerance or resistance, as compared to a corresponding, e.g. non-transformed, wild type plant or a part thereof.

Accordingly, in one further embodiment, the said method for producing a plant or a part thereof for the regeneration of said plant, the plant showing an increased herbicide tolerance or resistance, said method comprises (i) growing the plant or part thereof together with a, e.g. non-transformed, wild type plant under conditions of herbicide treatment; and (ii) selecting a plant with increased herbicide tolerance or resistance as compared to a corresponding, e.g.

non-transformed, wild type plant, for example after the, e.g. non-transformed, wild type plant shows visual symptoms of deficiency and/or death.

Further, the present invention relates to a method for producing a plant with increased herbicide tolerance or resistance as compared to a corresponding origin or wild type plant, e.g. a transgenic plant, which comprises: (a) increasing or generating, in a plant cell nucleus, a plant cell, a plant or a part thereof, the activity of an *Alopecurus* CYP450 polypeptide of the present invention, e.g. by the methods mentioned herein; and (b) cultivating or growing the plant cell, the plant or the part thereof under conditions which permit the development of the plant cell, the plant or the part thereof; and (c) recovering a plant from said plant cell nucleus, said plant cell, or said plant part, which shows increased herbicide tolerance or resistance as compared to a corresponding, e.g. non-transformed, origin or wild type plant; and (d) optionally, selecting the plant or a part thereof, showing increased herbicide tolerance or resistance, as compared to a corresponding, e.g. non-transformed, wild type plant cell, e.g. which shows visual symptoms of deficiency and/or death.

Furthermore, the present invention also relates to a method for the identification of a plant with an increased herbicide tolerance or resistance comprising screening a population of one or more plant cell nuclei, plant cells, plant tissues or plants or parts thereof for said "activity", comparing the level of activity with the activity level in a reference; identifying one or more plant cell nuclei, plant cells, plant tissues or plants or parts thereof with the activity increased compared to the reference, optionally producing a plant from the identified plant cell nuclei, cell or tissue.

In one further embodiment, the present invention also relates to a method for the identification of a plant with an increased herbicide tolerance or resistance comprising screening a population of one or more plant cell nuclei, plant cells, plant tissues or plants or parts thereof for the expression level of an nucleic acid coding for an polypeptide conferring said activity, comparing the level of expression with a reference; identifying one or more plant cell nuclei, plant cells, plant tissues or plants or parts thereof with the expression level increased compared to the reference, optionally producing a plant from the identified plant cell nuclei, cell or tissue.

Accordingly, in a preferred embodiment, the present invention provides a method for producing a transgenic cell for the regeneration or production of a plant with increased herbicide tolerance or resistance, as compared to a corresponding, e.g. non-transformed, wild type cell by increasing or generating the activity of an *Alopecurus* CYP450 polypeptide of the present invention. The cell can be for example a host cell, e.g. a transgenic host cell. A host cell can be for example a microorganism, e.g. derived from fungi or bacteria, or a plant cell particular useful for transformation.

Thus, the present invention fulfills the need to identify new, unique genes capable of conferring increased herbicide tolerance or resistance to plants, upon expression or overexpression of exogenous genes. Accordingly, the present invention provides novel CYP450 enzymes comprising the sequence of SEQ ID NO: 2, 4, 6, 8, 27, or 45, or a homolog thereof.

In one embodiment the increase in activity of the polypeptide amounts in an organelle such as a plastid. In another embodiment the increase in activity of the polypeptide amounts in the cytoplasm.

The specific activity of a polypeptide encoded by a nucleic acid molecule of the present invention or of the polypeptide of the present invention can be tested as described in the examples. In particular, the expression of a protein in question in a cell, e.g. a plant cell in comparison to a control is an easy test and can be performed as described in the state of the art.

Accordingly, in one embodiment, the process of the present invention for producing a plant with increased herbicide tolerance or resistance comprises increasing or generating the activity of a gene product conferring the activity of a CYP450 enzyme from *Alopecurus* or its functional equivalent or its homolog, e.g. the increase of (a) a gene product of a gene comprising the nucleic acid molecule comprising the sequence of SEQ ID NO: 1, 3, 5, 7, 26, or 44, or a functional equivalent or a homologue thereof; or (b) a polypeptide comprising a polypeptide, a consensus sequence or a polypeptide motif comprising the sequence of SEQ ID NO: 2, 4, 6, 8, 27, or 45 or a functional equivalent or a homologue thereof, preferably a homologue or functional equivalent comprising the sequence of SEQ ID NO: 9, 10, 11, 12, 13, 14, 15, 16, 17, 18, 19, 20, 21, 22, 23, 24, 25, 28, 29, 30, 31, 32, 33, 34, 35, 36, 37, 38, 39, 40, 41, 42, 43, 46, 47, 48, 49, 50, 51, 52, 53, 54, 55, 56, 57, 58, 59, 60, 61, 62, 63, 64, 65, 66, 67, 68, or 69.

Accordingly, an activity of a CYP450 polypeptide from *Alopecurus* is increased in one or more specific compartment(s) or organelle(s) of a cell or plant and confers said increased herbicide tolerance or resistance. For example, said activity can be increased in plastids or mitochondria of a plant cell, thus conferring increase of herbicide tolerance or resistance in a corresponding plant.

In one embodiment, an activity conferred by an expression of a gene described herein or its expression product; i.e. by a CYP450 polypeptide of the present invention is increased or generated in the plastid.

In one embodiment, an activity conferred by the expression of a gene described herein or its expression product; i.e. by a CYP450 polypeptide of the present invention is increased or generated in the mitochondria.

In one embodiment, an activity conferred by the expression of a gene described herein or its expression product; i.e. by a CYP450 polypeptide of the present invention is increased or generated in the cytoplasm.

In one embodiment, an activity conferred by the expression of a gene described herein or its expression product; i.e. by a CYP450 polypeptide of the present invention is increased or generated in the endoplasmic reticulum.

As the terms "cytoplasmic" and "non-targeted" shall not exclude a targeted localisation to any cell compartment for the products of the inventive nucleic acid sequences by their naturally occurring sequence properties within the background of the transgenic organism, in one embodiment, an activity as disclosed herein as being conferred by a polypeptide shown in SEQ ID NO: 2, 4, 6, 8, 27, or 45, or a homolog thereof is increase or generated non-targeted. For the purposes of the description of the present invention, the term "cytoplasmic" shall indicate, that the nucleic acid of the invention is expressed without the addition of a non-natural transit peptide encoding sequence. A non-natural transient peptide encoding sequence is a sequence which is not a natural part of a nucleic acid of the invention but is rather added by molecular manipulation steps which are well-known to the person skilled in the art. Therefore the term "cytoplasmic" shall not exclude a targeted localisation to any cell compartment for the products of the inventive nucleic acid sequences by their naturally occurring sequence properties.

In another embodiment the present invention is related to a method for producing a, e.g. transgenic, plant with increased herbicide tolerance or resistance, or a part thereof, as compared to a corresponding, e.g. non-transformed, wild type plant, which comprises (a1) increasing or generating the activity of an *Alopecurus* CYP450 polypeptide, e.g. the activity of said gene or the gene product gene, in an organelle of a plant cell, or (a2) increasing or generating the activity of a protein comprising the sequence of SEQ ID NO: 2, 4, 6, 8, 27, or 45, or a homolog thereof or as encoded by the nucleic acid sequences comprising the sequence of SEQ ID NO: 1, 3, 5, 7, 26, or 44, or a homolog thereof, and which is joined to a nucleic acid sequence encoding a transit peptide in the plant cell; or (a3) increasing or generating the activity of a protein comprising the sequence of SEQ ID NO: 2, 4, 6, 8, 27, or 45, or a homolog thereof or as encoded by the nucleic acid sequences comprising the sequence of SEQ ID NO: 1, 3, 5, 7, 26, or 44, or a homolog thereof, and which is joined to a nucleic acid sequence encoding an organelle localization sequence, especially a chloroplast localization sequence, in a plant cell, (a4) increasing or generating the activity of a protein comprising the sequence of SEQ ID NO: 2, 4, 6, 8, 27, or 45, or a homolog thereof or as encoded by the nucleic acid sequences comprising the sequence of SEQ ID NO: 1, 3, 5, 7, 26, or 44, or a homolog thereof, and which is joined to a nucleic acid sequence encoding an mitochondrion localization sequence in a plant cell, and (b) regenerating a plant from said plant cell;

(c) growing the plant under conditions which permit the development of a plant with increased herbicide tolerance or resistance as compared to a corresponding, e.g. non-transformed, wild type plant.

The skilled worker is able to link transit peptide nucleic acid sequences to the nucleic acid sequences comprising the sequence of SEQ ID NO: 1, 3, 5, 7, 26, or 44, or a homolog thereof.

Any transit peptide may be used in accordance with the various embodiments of the present invention. For example, specificucleic acid sequences are encoding transit peptides are disclosed by von Heijne et al. (Plant Molecular Biology Reporter, 9 (2), 104, (1991)) or other transit peptides are disclosed by Schmidt et al. (J. Biol. Chem. 268 (36), 27447 (1993)), Della-Cioppa et al. (Plant. Physiol. 84, 965 (1987)), de Castro Silva Filho et al. (Plant Mol. Biol. 30, 769 (1996)), Zhao et al. (J. Biol. Chem. 270 (11), 6081(1995)), Römer et al. (Biochem. Biophys. Res. Commun. 196 (3), 1414 (1993)), Keegstra et al. (Annu. Rev. Plant Physiol. Plant Mol. Biol. 40, 471(1989)), Lubben et al. (Photosynthesis Res. 17, 173 (1988)) and Lawrence et al. (J. Biol. Chem. 272 (33), 20357 (1997)), which are hereby incorporated by reference. A general review about targeting is disclosed by Kermode Allison R. in Critical Reviews in Plant Science 15 (4), 285 (1996) under the title "Mechanisms of Intracellular Protein Transport and Targeting in Plant Cells".

Additional nucleic acid sequences encoding a transit peptide can be isolated from any organism such as microorganisms such as algae or plants containing plastids, preferably containing chloroplasts. A "transit peptide" is an amino acid sequence, whose encoding nucleic acid sequence is translated together with the corresponding structural gene. That means the transit peptide is an integral part of the translated protein and forms an amino terminal extension of the protein. Both are translated as so called "pre-protein". In general the transit peptide is cleaved off from the pre-protein during or just after import of the protein into the correct cell organelle such as a plastid to yield the mature protein. The transit peptide ensures correct localization of the mature protein by facilitating the transport of proteins through intracellular membranes.

For example, such transit peptides, which are beneficially used in the inventive process, are derived from the nucleic acid sequence encoding a protein selected from the group consisting of ribulose bisphosphate carboxylase/oxygenase, 5-enolpyruvyl-shikimate-3-phosphate synthase, acetolactate synthase, chloroplast ribosomal protein CS17, Cs protein, ferredoxin, plastocyanin, ribulose bisphosphate carboxylase activase, tryptophan synthase, acyl carrier protein, plastid chaperonin-60, cytochrome $c_{552}$, 22-kDA heat shock protein, 33-kDa Oxygen-evolving enhancer protein 1, ATP synthase γ subunit, ATP synthase δ subunit, chlorophyll-a/b-binding proteinII-1, Oxygen-evolving enhancer protein 2, Oxygen-evolving enhancer protein 3, photosystem I: P21, photosystem I: P28, photosystem I: P30, photosystem I: P35, photosystem I: P37, glycerol-3-phosphate acyltransferases, chlorophyll a/b binding protein, CAB2 protein, hydroxymethyl-bilane synthase, pyruvate-orthophosphate dikinase, CAB3 protein, plastid ferritin, ferritin, early light-inducible protein, glutamate-1-semialdehyde aminotransferase, protochlorophyllide reductase, starch-granule-bound amylase synthase, light-harvesting chlorophyll a/b-binding protein of photosystem II, major pollen allergen Lol p 5a, plastid CIpB ATP-dependent protease, superoxide dismutase, ferredoxin NADP oxidoreductase, 28-kDa ribonucleoprotein, 31-kDa ribonucleoprotein, 33-kDa ribonucleoprotein, acetolactate synthase, ATP synthase $CF_0$ subunit 1, ATP synthase $CF_0$ subunit 2, ATP synthase $CF_0$ subunit 3, ATP synthase $CF_0$ subunit 4, cytochrome f, ADP-glucose pyrophosphorylase, glutamine synthase, glutamine synthase 2, carbonic anhydrase, GapA protein, heat-shock-protein hsp21, phosphate translocator, plastid CIpA ATP-dependent protease, plastid ribosomal protein CL24, plastid ribosomal protein CL9, plastid ribosomal protein PsCL18, plastid ribosomal protein PsCL25, DAHP synthase, starch phosphorylase, root acyl carrier protein II, betaine-aldehyde dehydrogenase, GapB protein, glutamine synthetase 2, phosphoribulokinase, nitrite reductase, ribosomal protein L12, ribosomal protein L13, ribosomal protein L21, ribosomal protein L35, ribosomal protein L40, triose phosphate-3-phosphoglyerate-phosphate translocator, ferredoxin-dependent glutamate synthase, glyceraldehyde-3-phosphate dehydrogenase, NADP-dependent malic enzyme and NADP-malate dehydrogenase, chloroplast 30S ribosomal protein PSrp-1, and the like.

In a particularly preferred embodiment, the nucleic acid sequences of the present invention are linked to a nucleic acid encoding a so-called "signal sequence peptide". For the purposes of the present invention, "signal sequence peptide" refers to amino acid sequences of about 15 to about 50 amino acids in length which are known in the art to be generally located at the amino terminus of proteins and which are capable of targeting said proteins to the endoplasmic reticulum. The core of the signal peptide contains a long stretch of hydrophobic amino acids that has a tendency to form a single alpha-helix. In addition, many signal peptides begin with a short positively charged stretch of amino acids, which may help to enforce proper topology of the polypeptide during translocation by what is known as the positive-inside rule. At the end of the signal peptide there is typically a stretch of amino acids that is recognized and cleaved by signal peptidase. However this cleavage site is absent from transmembrane-domains that serve as signal peptides, which are sometimes referred to as signal anchor sequences. Signal peptidase may cleave during, or after completion of, translocation to generate a free signal peptide and a mature protein. The free signal peptides are then digested by specific proteases. Those skilled in the art would readily appreciate that many signal sequence peptides are known (van Heijne, G., J. Mol. Biol. 184: 99-105 (1985)) and that these peptide sequences or analogues thereof can be easily substituted as long as they fulfill the requirements for a signal peptide as described above.

The skilled worker will recognize that various other nucleic acid sequences encoding transit or signal sequence peptides can easily isolated from plastid-localized, mitochondria-localized or endoplasmic reticulum-localized proteins, which are expressed from nuclear genes as precursors and are then targeted to plastids, mitochondria or endoplasmic reticulum. Nucleic acid sequences encoding a transit or signal sequence peptide can be isolated from organelle-targeted proteins from any organism. Preferably, the transit or signal sequence peptide is isolated from an organism selected from the group consisting of the genera *Acetabularia, Arabidopsis, Brassica, Capsicum, Chlamydomonas, Cururbita, Dunaliella, Euglena, Flaveria, Glycine, Helianthus, Hordeum, Lemna, Lolium, Lycopersion, Malus, Medicago, Mesembryanthemum, Nicotiana, Oenotherea, Oryza, Petunia, Phaseolus, Physcomitrella, Pinus, Pisum, Raphanus, Silene, Sinapis, Solanum, Spinacea, Stevia, Synechococcus, Triticum* and *Zea*. More preferably, the nucleic acid sequence encoding the transit or signal sequence peptide is isolated from an organism selected from the group consisting of the species *Acetabularia mediterranea, Arabidopsis thaliana, Brassica campestris, Brassica napus, Capsicum annuum, Chlamydomonas reinhardtii, Cururbita moschata, Dunaliella salina, Dunaliella tertiolecta, Euglena gracilis, Flaveria trinervia, Glycine max, Helianthus annuus, Hordeum vulgare, Lemna gibba, Lolium perenne, Lycopersion esculentum, Malus domestica, Medicago falcata, Medicago sativa, Mesembryanthemum crystallinum, Nicotiana plumbaginifolia, Nicotiana sylvestris, Nicotiana tabacum, Oenotherea hookeri, Oryza sativa, Petunia hybrida, Phaseolus vulgaris, Physcomitrella patens, Pinus tunbergii, Pisum sativum, Raphanus sativus, Silene pratensis, Sinapis alba, Solanum tuberosum, Spinacea oleracea, Stevia rebaudiana, Synechococcus, Synechocystis, Triticum aestivum* and *Zea mays*. Alternatively, nucleic acid sequences coding for transit or signal sequence peptides may be chemically synthesized either in part or wholly according to structure of transit peptide sequences disclosed in the prior art.

Such transit or signal sequence peptides encoding sequences can be used for the construction of other expression constructs. The transit or signal sequence peptides advantageously used in the inventive process and which are part of the inventive nucleic acid sequences and proteins are typically 20 to 120 amino acids, preferably 25 to 110, 30 to 100 or 35 to 90 amino acids, more preferably 40 to 85 amino acids and most preferably 45 to 80 amino acids as for transit peptides, or about 15 to about 50 amino acids as for signal sequence peptides in length and functions post-translational to direct the protein to the plastid, preferably to the chloroplast, the mitochondrion or endoplasmic reticulum. The nucleic acid sequences encoding such transit or signal sequence peptides are localized upstream of nucleic acid sequence encoding the mature protein. For the correct molecular joining of the transit or signal sequence peptide encoding nucleic acid and the nucleic acid encoding the protein to be targeted it is sometimes necessary to introduce additional base pairs at the joining position, which forms restriction enzyme recognition sequences useful for the molecular joining of the different nucleic acid molecules. This procedure might lead to very few additional amino acids at the N-terminal of the mature imported protein, which usually and preferably do not interfere with the protein function. In any case, the additional base pairs at the joining position which forms restriction enzyme recognition sequences have to be chosen with care, in order to avoid the formation of stop codons or codons which encode amino acids with a strong influence on protein folding, like e.g. proline. It is preferred that such additional codons encode small structural flexible amino acids such as glycine or alanine.

As mentioned above the nucleic acid sequence coding for a protein comprising the sequence of SEQ ID NO: 2, 4, 6, 8, 27, or 45, or a homolog thereof, can be joined to a nucleic acid sequence encoding a transit or a signal sequence peptide. The nucleic acid sequence of the gene to be expressed and the nucleic acid sequence encoding the transit or signal sequence peptide are operably linked. Therefore the transit or signal sequence peptide is fused in frame to the nucleic acid sequence coding for a protein comprising the sequence of SEQ ID NO: 2, 4, 6, 8, 27, or 45, or a homolog thereof.

The proteins translated from said inventive nucleic acid sequences are a kind of fusion proteins that means the nucleic acid sequences encoding the transit or signal sequence peptide, are joint to a gene, e.g. the nucleic acid sequences comprising the sequence of SEQ ID NO: 1, 3, 5, 7, 26, or 44, or a homolog thereof. The person skilled in the art is able to join said sequences in a functional manner. Advantageously the transit or signal sequence peptide part is cleaved off from the protein part during the transport preferably into the endoplasmic reticulum or plastids. The skilled worker knows that other short sequences are also useful in the expression of the CYP450 genes of the present invention. Furthermore the skilled worker is aware of the fact that there is not a need for such short sequences in the expression of the genes.

Alternatively to the targeting of the gene, e.g. proteins having the sequences comprising the sequence of SEQ ID NO: 2, 4, 6, 8, 27, or 45, or a homolog thereof, the nucleic acids of the invention can directly be introduced into the plastidic genome.

By transforming the plastids the intraspecies specific transgene flow is blocked, because a lot of species such as corn, cotton and rice have a strict maternal inheritance of plastids. By placing the gene e.g. the genes comprising the sequence of SEQ ID NO: 1, 3, 5, 7, 26, or 44, or a homolog thereof, or active fragments thereof in the plastids of plants, these genes will not be present in the pollen of said plants.

In another embodiment of the invention the gene, e.g. the nucleic acid molecules comprising the sequence of SEQ ID NO: 1, 3, 5, 7, 26, or 44, or a homolog thereof, used in the inventive process are transformed into mitochondria, which are metabolic active.

For a good expression in the plastids the gene, e.g. the nucleic acid sequences comprising the sequence of SEQ ID NO: 1, 3, 5, 7, 26, or 44, or a homolog thereof, are introduced into an expression cassette using a preferably a promoter and terminator, which are active in plastids, preferably a chloroplast promoter. Examples of such promoters include the psbA promoter from the gene from spinach or pea, the rbcL promoter, and the atpB promoter from corn.

In one embodiment, the process of the present invention comprises one or more of the following steps:

(a) stabilizing a protein conferring the increased expression of a protein encoded by the nucleic acid molecule of the invention or of the polypeptide of the invention having the herein-mentioned activity of an *Alopecurus* CYP450 and conferring increased herbicide tolerance or resistance, as compared to a corresponding, e.g. non-transformed, wild type plant cell, plant or part thereof;

(b) stabilizing an mRNA conferring the increased expression of a polynucleotide encoding a polypeptide as mentioned in (a);

(c) increasing the specific activity of a protein conferring the increased expression of a polypeptide as mentioned in (a);

(d) generating or increasing the expression of an endogenous or artificial transcription factor mediating the expression of a protein conferring the increased expression of a polypeptide as mentioned in (a);

(e) stimulating activity of a protein conferring the increased expression of a polypeptide as mentioned in (a), by adding one or more exogenous inducing factors to the organism or parts thereof;

(f) expressing a transgenic gene encoding a protein conferring the increased expression of a polypeptide as mentioned in (a); and/or (g) increasing the copy number of a gene conferring the increased expression of a nucleic acid molecule encoding a polypeptide as mentioned in (a);

(h) increasing the expression of the endogenous gene encoding a polypeptide as mentioned in (a) by adding positive expression or removing negative expression elements, e.g. homologous recombination can be used to either introduce positive regulatory elements like for plants the 35S enhancer into the promoter or to remove repressor elements form regulatory regions. Further gene conversion methods can be used to disrupt repressor elements or to enhance to activity of positive elements-positive elements can be randomly introduced in plants by T-DNA or transposon mutagenesis and lines can be identified in which the positive elements have been integrated near to a gene of the invention, the expression of which is thereby enhanced; and/or (i) modulating growth conditions of the plant in such a manner, that the expression or activity of the gene encoding a polypeptide as mentioned in (a), or the protein itself is enhanced;

(j) selecting of organisms with especially high activity of a polypeptide as mentioned in (a) from natural or from mutagenized resources and breeding them into the target organisms, e.g. the elite crops.

Preferably, said mRNA is encoded by the nucleic acid molecule of the present invention and/or the protein conferring the increased expression of a protein encoded by the nucleic acid molecule of the present invention alone or linked to a transit nucleic acid sequence or transit peptide encoding nucleic acid sequence or the polypeptide having the herein mentioned activity, e.g. conferring with increased herbicide tolerance or resistance, as compared to a corresponding, e.g. non-transformed, wild type plant cell, plant or part thereof after increasing the expression or activity of the encoded polypeptide or having the activity of a polypeptide having an activity as the protein comprising the sequence of SEQ ID NO: 2, 4, 6, 8, 27, or 45, or a homolog thereof In general, the amount of mRNA or polypeptide in a cell or a compartment of an organism correlates with the amount of encoded protein and thus with the overall activity of the encoded protein in said volume. Said correlation is not always linear, the activity in the volume is dependent on the stability of the molecules or the presence of activating or inhibiting co-factors. The activity of the above-mentioned proteins and/or polypeptides encoded by the nucleic acid molecule of the present invention can be increased in various ways. For example, the activity in an organism or in a part thereof, like a cell, is increased via increasing the gene product number, e.g. by increasing the expression rate, like introducing a stronger promoter, or by increasing the stability of the mRNA expressed, thus increasing the translation rate, and/or increasing the stability of the gene product, thus reducing the proteins decayed. Further, the activity or turnover of enzymes can be influenced in such a way that a reduction or increase of the reaction rate or a modification (reduction or increase) of the affinity to the substrate results, is reached. A mutation in the catalytic centre of an polypeptide of the invention, e.g. as enzyme, can modulate the turn over rate of the enzyme, e.g. a knock out of an essential amino acid can lead to a reduced or completely knock out activity of the enzyme, or the deletion or mutation of regulator binding sites can reduce a negative regulation like a feedback inhibition (or a substrate inhibition, if the substrate level is also increased). The specific activity of an enzyme of the present invention can be increased such that the turn over rate is increased or the binding of a co-factor is improved. Improving the stability of the encoding mRNA or the protein can also increase the activity of a gene product. The stimulation of the activity is also under the scope of the term "increased activity".

Moreover, the regulation of the abovementioned nucleic acid sequences may be modified so that gene expression is increased. This can be achieved advantageously by means of heterologous regulatory sequences or by modifying, for example mutating, the natural regulatory sequences which are present. The advantageous methods may also be combined with each other.

In general, an activity of a gene product in an organism or part thereof, in particular in a plant cell or organelle of a plant cell, a plant, or a plant tissue or a part thereof or in a microorganism can be increased by increasing the amount of the specific encoding mRNA or the corresponding protein in said organism or part thereof.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into a organism, transient or stable. Furthermore such an increase can be reached by the introduction of the inventive nucleic acid sequence or the encoded protein in the correct cell compartment for example into the nucleus or cytoplasm respectively or into plastids either by transformation and/or targeting.

In one further embodiment of the process according to the invention, organisms are used in which one of the abovementioned genes, or one of the abovementioned nucleic acids, is mutated in a way that the activity of the encoded gene products is less influenced by cellular factors, or not at all, in comparison with the not mutated proteins. For example, well known regulation mechanisms of enzyme activity are substrate inhibition or feed back regulation mechanisms. Ways and techniques for the introduction of substitution, deletions and additions of one or more bases, nucleotides or amino acids of a corresponding sequence are described herein below in the corresponding paragraphs and the references listed there, e.g. in Sambrook et al., Molecular Cloning, Cold Spring Harbour, N.Y., 1989. The person skilled in the art will be able to identify regulation domains and binding sites of regulators by comparing the sequence of the nucleic acid molecule of the present invention or the expression product thereof with the state of the art by computer software means which comprise algorithms for the identifying of binding sites and regulation domains or by introducing into a nucleic acid molecule or in a protein systematically mutations and assaying for those mutations which will lead to an increased specific activity or an increased activity per volume, in particular per cell.

It can therefore be advantageous to express in an organism a nucleic acid molecule of the invention or a polypeptide of the invention derived from a evolutionary distantly related organism, as e.g. using a prokaryotic gene in a eukaryotic host, as in these cases the regulation mechanism of the host cell may not weaken the activity (cellular or specific) of the gene or its expression product.

The mutation is introduced in such a way that increased herbicide tolerance or resistance, is not adversely affected.

The invention is not limited to specific nucleic acids, specific polypeptides, specific cell types, specific host cells, specific conditions or specific methods etc. as such, but may vary and numerous modifications and variations therein will be apparent to those skilled in the art. It is also to be understood that the terminology used herein is for the purpose of describing specific embodiments only and is not intended to be limiting.

Further, "proteins are generally composed of one or more functional regions, commonly termed domains. Different combinations of domains give rise to the diverse range of proteins found in nature. The identification of domains that occur within proteins can therefore provide insights into their function. Pfam-A entries are high quality, manually curated families. The Pfam database is a large collection of protein families, each represented by multiple sequence alignments and hidden Markov models (HMMs)." (see: The Pfam protein families database: R. D. Finn, et al., Nucleic Acids Research (2010), Database Issue 38:D211-222). The Pfam protein family database is a large collection of more than ten thousand protein families and is available under http://pfam.sanger.ac.uk/. Profile Hidden Markov Models (HMMs) are flexible, probabilistic models that can be used to describe the consensus patterns shared by sets of homologous protein/domain sequences. HMMs in the Pfam database are constructed from an alignment of a representative set of sequences for each protein domain, called a seed alignment.

Accordingly, the present invention relates to a nucleic acid molecule encoding a polypeptide which is 50% or more, preferably 60%, 70%, or 75%, more preferably 80%, 85%, 90%, or 95%, even more preferred 96%, 97%, 98%, 99% or more and most preferred 100% identical to the polypeptide of SEQ ID NO: 2, 4, 6, 8, 27, or 45, and conferring the increase of the herbicide tolerance or resistance of a plant as described herein. The invention also relates to the polypeptide encoded by said polynucleotide.

The present invention also relates to isolated and/or recombinant nucleic acids comprising a nucleic acid molecule selected from the group consisting of:
(a) a nucleic acid molecule encoding the polypeptide comprising the sequence of SEQ ID NO: 2, 4, 6, 8, 27, or 45, or a homolog thereof;
(b) a nucleic acid molecule comprising the sequence of SEQ ID NO: 1, 3, 5, 7, 26, or 44, or a homolog thereof,
(c) a nucleic acid molecule, which, as a result of the degeneracy of the genetic code, can be derived from a polypeptide sequence of SEQ ID NO: 2, 4, 6, 8, 27, or 45, or a homolog thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1, 3, 5, 7, 26, or 44, or a homolog thereof, and confers increased herbicide tolerance or resistance, as compared to a corresponding, e.g. non-transformed, wild type plant cell, a plant or a part thereof;
(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the polypeptide encoded by the nucleic acid molecule of (a), (b), (c) or (d) and having the activity represented by a nucleic acid molecule comprising a polynucleotide of SEQ ID NO: 1, 3, 5, 7, 26, or 44, or a homolog thereof, and confers increased herbicide tolerance or resistance as compared to a corresponding, e.g. non-transformed, wild type plant cell, a plant or a part thereof;
(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;
(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide as depicted in SEQ ID NO: 1, 3, 5, 7, 26, or 44, or a homolog thereof;
(h) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having 15 nt, preferably 20 nt, 30 nt, 50 nt, 100 nt, 200 nt, 500 nt, 750 nt or 1000 nt or more of a nucleic acid molecule complementary to a nucleic acid molecule sequence characterized in (a) to (e) and encoding a polypeptide having the activity represented by a protein comprising a polypeptide as depicted SEQ ID NO: 2, 4, 6, 8, 27, or 45, or a homolog thereof.

In one embodiment, the nucleic acid molecule according to (a), (b), (c), (d), (e), (f), (g), (h), is at least in one or more nucleotides different from the sequence depicted in SEQ ID NO: 1, 3, 5, 7, 26, or 44, and encodes a protein which differs at least in one or more amino acids from the protein sequences depicted in SEQ ID NO: 2, 4, 6, 8, 27, or 45.

In one embodiment the invention relates to homologs of the aforementioned sequences, which can be isolated advantageously from yeast, fungi, viruses, algae, bacteria, such as *Acetobacter* (subgen. *Acetobacter*) *aceti; Acidithiobacillus ferrooxidans; Acinetobacter* sp.; *Actinobacillus* sp; *Aeromonas salmonicida; Agrobacterium tumefaciens; Aquifex aeolicus; Arcanobacterium pyogenes; Aster yellows phytoplasma; Bacillus* sp.; *Bifidobacterium* sp.; *Borrelia burgdorferi; Brevibacterium linens; Brucella melitensis; Buchnera* sp.; *Butyrivibrio fibrisolvens; Campylobacterjejuni; Caulobacter crescentus; Chlamydia* sp.; *Chlamydophila* sp.; *Chlorobium limicola; Citrobacter rodentium; Clostridium* sp.; *Comamonas testosteroni; Corynebacterium* sp.; *Cox-* iella burnetii; Deinococcus radiodurans; Dichelobacter nodosus; Edwardsiella ictaluri; Enterobacter sp.; Erysipelothrix rhusiopathiae; E. coli; Flavobacterium sp.; Francisella tularensis; Frankia sp. Cp11; Fusobacterium nucleatum; Geobacillus stearothermophilus; Gluconobacter oxydans; Haemophilus sp.; Helicobacter pylori; Klebsiella pneumoniae; Lactobacillus sp.; Lactococcus lactis; Listeria sp.; Mannheimia haemolytica; Mesorhizobium loti; Methylophaga thalassica; Microcystis aeruginosa; Microscilla sp. PRE1; Moraxella sp. TA 144; Mycobacterium sp.; Mycoplasma sp.; Neisseria sp.; Nitrosomonas sp.; Nostoc sp. PCC 7120; Novosphingobium aromaticivorans; Oenococcus oeni; Pantoea citrea; Pasteurella multocida; Pediococcus pentosaceus; Phormidium foveolarum; Phytoplasma sp.; Plectonema boryanum; Prevotella ruminicola; Propionibacterium sp.; Proteus vulgaris; Pseudomonas sp.; Ralstonia sp.; Rhizobium sp.; Rhodococcus equi; Rhodothermus marinus; Rickettsia sp.; Riemerella anatipestifer; Ruminococcus flavefaciens; Salmonella sp.; Selenomonas ruminantium; Serratia entomophila; Shigella sp.; Sinorhizobium meliloti; Staphylococcus sp.; Streptococcus sp.; Streptomyces sp.; Synechococcus sp.; Synechocystis sp. PCC 6803; Thermotoga maritima; Treponema sp.; Ureaplasma urealyticum; Vibrio cholerae; Vibrio parahaemolyticus; Xylella fastidiosa; Yersinia sp.; Zymomonas mobilis preferably Salmonella sp. or E. coli or plants, preferably from yeasts such as from the genera Saccharomyces, Pichia, Candida, Hansenula, Torulopsis or Schizosaccharomyces or plants such as A. thaliana, maize, wheat, rye, oat, triticale, rice, barley, soybean, peanut, cotton, borage, sunflower, linseed, primrose, rapeseed, canola and turnip rape, manihot, pepper, sunflower, tagetes, solanaceous plant such as potato, tobacco, eggplant and tomato, Vicia species, pea, alfalfa, bushy plants such as coffee, cacao, tea, Salix species, trees such as oil palm, coconut, perennial grass, such as ryegrass and fescue, and forage crops, such as alfalfa and clover and from spruce, pine or fir for example. More preferably homologs of aforementioned sequences can be isolated from S. cerevisiae, E. coli or Synechocystis sp. or plants, preferably Brassica napus, Glycine max, Zea mays cotton or Oryza sativa. In a particularly preferred embodiment, the homolog refers to a polypeptide comprising the sequence of SEQ ID NO: 9, 10, 11, 12, 13, 14, 15, 16, 17, 18, 19, 20, 21, 22, 23, 24, 25, 28, 29, 30, 31, 32, 33, 34, 35, 36, 37, 38, 39, 40, 41, 42, 43, 46, 47, 48, 49, 50, 51, 52, 53, 54, 55, 56, 57, 58, 59, 60, 61, 62, 63, 64, 65, 66, 67, 68, or 69.

The proteins of the present invention are preferably produced by recombinant DNA techniques. For example, a nucleic acid molecule encoding the protein is cloned into an expression vector, for example in to a binary vector, the expression vector is introduced into a host cell, for example the A. thaliana wild type NASC N906 or any other plant cell as described in the examples see below, and the protein is expressed in said host cell. Examples for binary vectors are pBIN19, pBI101, pBinAR (Höfgen and Willmitzer, Plant Science 66, 221 (1990)), pGPTV, pCAMBIA, pBIB-HYG, pBecks, pGreen or pPZP (Hajukiewicz, P. et al., Plant Mol. Biol. 25, 989 (1994), and Hellens et al, Trends in Plant Science 5, 446 (2000)).

In one embodiment as decribed in more detail SUPRA, the protein of the present invention is preferably targeted to an compartment of the cell, e.g. to the endoplasmic reticulum or in the plastids. Ways of introducing nucleic acids into the endoplasmic reticulum or plastids and producing proteins in this compartment are known to the person skilled in the art have been also described in this application. In one embodiment, the polypeptide of the invention is a protein localized after expression e.g. non-targeted, mitochondrial or plastidic, for example it is fused to a transit or signal sequence peptide as decribed above for plastidic or endoplasmic reticulum localisation. In another embodiment the protein of the present invention is produced without further targeting signal (e.g. as mentioned herein), e.g. in the cytoplasm of the cell. Ways of producing proteins in the cytoplasm are known to the person skilled in the art. Ways of producing proteins without artificial targeting are known to the person skilled in the art.

Advantageously, the nucleic acid sequences according to the invention or the gene construct together with at least one reporter gene are cloned into an expression cassette, which is introduced into the organism via a vector or directly into the genome. This reporter gene should allow easy detection via a growth, fluorescence, chemical, bioluminescence or tolerance assay or via a photometric measurement. Examples of reporter genes which may be mentioned are antibiotic- or herbicide-tolerance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxyglucose-6-phosphate phosphatase gene, the β-glucuronidase gene, β-lactamase gene, the neomycin phosphotransferase gene, the hygromycin phosphotransferase gene, a mutated acetohydroxyacid synthase (AHAS) gene (also known as acetolactate synthase (ALS) gene), a gene for a D-amino acid metabolizing enzyme or the BASTA (=gluphosinate-tolerance) gene. These genes permit easy measurement and quantification of the transcription activity and hence of the expression of the genes. In this way genome positions may be identified which exhibit differing productivity. For expression a person skilled in the art is familiar with different methods to introduce the nucleic acid sequences into different organelles such as the preferred plastids. Such methods are for example disclosed by Maiga P. (Annu. Rev. Plant Biol. 55, 289 (2004)), Evans T. (WO 2004/040973), McBride K. E. et al. (U.S. Pat. No. 5,455,818), Daniell H. et al. (U.S. Pat. No. 5,932,479 and U.S. Pat. No. 5,693,507) and Straub J. M. et al. (U.S. Pat. No. 6,781,033). A preferred method is the transformation of microspore-derived hypocotyl or cotyledonary tissue (which are green and thus contain numerous plastids) leaf tissue and afterwards the regeneration of shoots from said transformed plant material on selective medium. As methods for the transformation bombarding of the plant material or the use of independently replicating shuttle vectors are well known by the skilled worker. But also a PEG-mediated transformation of the plastids or Agrobacterium transformation with binary vectors is possible. Useful markers for the transformation of plastids are positive selection markers for example the chloramphenicol-, streptomycin-, kanamycin-, neomycin-, amikamycin-, spectinomycin-, triazine- and/or lincomycin-tolerance genes. As additional markers named in the literature often as secondary markers, genes coding for the tolerance against herbicides such as phosphinothricin (=glufosinate, BASTA™, Liberty™, encoded by the bar gene), glyphosate (=N(phosphonomethyl)glycine, Roundup™, encoded by the 5-enolpyruvylshikimate-3-phosphate synthase gene=epsps), sulfonylureas (like Staple™, encoded by the acetolactate synthase (ALS) gene), imidazolinones [=IMI, like imazethapyr, imazamox, Clearfield™, encoded by the acetohydroxyacid synthase (AHAS) gene, also known as acetolactate synthase (ALS) gene] or bromoxynil (=Buctril™, encoded by the oxy gene) or genes coding for antibiotics such as hygromycin or G418 are useful for further selection. Such secondary markers are useful in the case when most genome copies are transformed. In addition negative selection markers such as the bacterial cytosine deaminase (encoded by the codA gene) are also useful for the transformation of plastids.

To increase the possibility of identification of transformants it is also desirable to use reporter genes other then the aforementioned tolerance genes or in addition to said genes. Reporter genes are for example β-galactosidase-, β-glucuronidase-(GUS), alkaline phosphatase- and/or green-fluorescent protein-genes (GFP).

In a preferred embodiment a nucleic acid construct, for example an expression cassette, comprises upstream, i.e. at the 5' end of the encoding sequence, a promoter and downstream, i.e. at the 3' end, a polyadenylation signal and optionally other regulatory elements which are operably linked to the intervening encoding sequence with one of the nucleic acids of SEQ ID NO: 1, 3, 5, 7, 26, or 44, or a homolog thereof. By an operable linkage is meant the sequential arrangement of promoter, encoding sequence, terminator and optionally other regulatory elements in such a way that each of the regulatory elements can fulfill its function in the expression of the encoding sequence in due manner. In one embodiment the sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 8693 (1987).

A nucleic acid construct, for example an expression cassette may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a host organism, for example a plant, the expression cassette is advantageously inserted into a vector such as by way of example a plasmid, a phage or other DNA which allows optimal expression of the genes in the host organism. Examples of suitable plasmids are: in *E. coli* pLG338, pACYC184, pBR series such as e.g. pBR322, pUC series such as pUC18 or pUC19, M113mp series, pKC30, pRep4, pHS1, pHS2, pPLc236, pMBL24, pLG200, pUR290, pIN-III113-B1, λgt11 or pBdCl; in *Streptomyces* pIJ101, pIJ364, pIJ702 or pIJ361; in *Bacillus* pUB110, pC194 or pBD214; in *Corynebacterium* pSA77 or pAJ667; in fungi pALS1, pIL2 or pBB116; other advantageous fungal vectors are described by Romanos M. A. et al., Yeast 8, 423 (1992) and by van den Hondel, C.A.M.J.J. et al. [(1991) "Heterologous gene expression in filamentous fungi"] as well as in "More Gene Manipulations" in "Fungi" in Bennet J. W. & Lasure L. L., eds., pp. 396-428, Academic Press, San Diego, and in "Gene transfer systems and vector development for filamentous fungi" [van den Hondel, C.A.M.J.J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2 μM, pAG-1, YEp6, YEp13 or pEMBLYe23. Examples of algal or plant promoters are pLGV23, pGHlac+, pBIN19, pAK2004, pVKH or pDH51 (see Schmidt, R. and Willmitzer, L., Plant Cell Rep. 7, 583 (1988)). The vectors identified above or derivatives of the vectors identified above are a small selection of the possible plasmids. Further plasmids are well known to those skilled in the art and may be found, for example, in "Cloning Vectors" (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press, Ch. 6/7, pp. 71-119). Advantageous vectors are known as shuttle vectors or binary vectors which replicate in *E. coli* and *Agrobacterium*.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

A nucleic acid sequence can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

The invention further provides an isolated recombinant expression vector comprising a nucleic acid encoding a polypeptide comprising the sequence of SEQ ID NO: 2, 4, 6, 8, 27, or 45, or a homolog thereof, wherein expression of the vector in a host cell results in increased herbicide tolerance or resistance, as compared to a wild type variety of the host cell.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein.

The recombinant expression vectors of the invention can be designed for expression of the polypeptide of the invention in plant cells. For example, nucleic acid molecules of the present invention can be expressed in plant cells (see Schmidt R., and Willmitzer L., Plant Cell Rep. 7 (1988); Plant Molecular Biology and Biotechnology, C Press, Boca Raton, Fla., Chapter 6/7, p. 71-119 (1993); White F. F., Jenes B. et al., Techniques for Gene Transfer, in: Transgenic Plants, Vol. 1, Engineering and Utilization, eds. Kung und Wu R., 128-43, Academic Press: 1993; Potrykus, Annu. Rev. Plant Physiol. Plant Molec. Biol. 42, 205 (1991) and references cited therein). Suitable host cells are discussed further in Goeddel, Gene Expression Technology: Methods in Enzymology 185, Academic Press: San Diego, Calif. (1990). By way of example the plant expression cassette can be installed in the pRT transformation vector ((a) Toepfer et al., Methods Enzymol. 217, 66 (1993), (b) Toepfer et al., Nucl. Acids. Res. 15, 5890 (1987)). Alternatively, a recombinant vector (=expression vector) can also be transcribed and translated in vitro, e.g. by using the T7 promoter and the T7 RNA polymerase.

In an further embodiment of the present invention, the nucleic acid molecules of the invention are expressed in plants and plants cells such as unicellular plant cells (e.g. algae) (see Falciatore et al., Marine Biotechnology 1 (3), 239 (1999) and references therein) and plant cells from higher plants (e.g., the spermatophytes, such as crop plants), for example to regenerate plants from the plant cells. A nucleic acid molecule depicted in SEQ ID NO: 1, 3, 5, 7, 26, or 44, or a homolog thereof may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contains the nucleic acid of the invention, followed by breeding of the transformed gametes. Other suitable methods for transforming or transfecting host cells including plant cells can be found in Sambrook et al., supra, and other laboratory manuals such as Methods in Molecular Biology, 1995, Vol. 44, *Agrobacterium* protocols, ed: Gartland and Davey, Humana Press, Totowa, N.J.

In one embodiment of the present invention, transfection of a nucleic acid molecule coding for a polypeptide comprising the sequence of SEQ ID NO: 2, 4, 6, 8, 27, or 45, or a homolog thereof into a plant is achieved by *Agrobacterium* mediated gene transfer. *Agrobacterium* mediated plant transformation can be performed using for example the GV3101 (pMP90) (Koncz and Schell, Mol. Gen. Genet. 204, 383 (1986)) or LBA4404 (Clontech) *Agrobacterium tumefaciens* strain. Transformation can be performed by standard transformation and regeneration techniques (Deblaere et al., Nucl. Acids Res. 13, 4777 (1994), Gelvin, Stanton B. and Schilperoort Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick Bernard R., Thompson John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., Plant Cell Report 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994). Additionally, transformation of soybean can be performed using for example a technique described in European Patent No. 424 047, U.S. Pat. No. 5,322,783, European Patent No. 397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (see, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced nucleic acid molecule coding for a polypeptides depicted in SEQ ID NO: 2, 4, 6, 8, 27, or 45, or homologs thereof, may be maintained in the plant cell stably if it is incorporated into a non-chromosomal autonomous replicon or integrated into the plant chromosomes or organelle genome. Alternatively, the introduced nucleic acid molecule may be present on an extra-chromosomal non-replicating vector and be transiently expressed or transiently active.

In one embodiment, a homologous recombinant microorganism can be created wherein the nucleic acid molecule is integrated into a chromosome, a vector is prepared which contains at least a portion of a nucleic acid molecule coding for a protein depicted in SEQ ID NO: 2, 4, 6, 8, 27, or 45, or a homolog thereof into which a deletion, addition, or substitution has been introduced to thereby alter, e.g., unctionally disrupt, the gene. For example, the gene is a yeast gene, like a gene of *S. cerevisiae*, or of *Synechocystis*, or a bacterial gene, like an *E. coli* gene, but it can be a homolog from a related plant or even from a mammalian or insect source. The vector can be designed such that, upon homologous recombination, the endogenous nucleic acid molecule coding for a protein depicted in SEQ ID NO: 2, 4, 6, 8, 27, or 45, or a homolog thereof is mutated or otherwise altered but still encodes a functional polypeptide (e.g., the upstream regulatory region can be altered to thereby alter the expression of the endogenous nucleic acid molecule). In a preferred embodiment the biological activity of the protein of the invention is increased upon homologous recombination. To create a point mutation via homologous recombination, DNA-RNA hybrids can be used in a technique known as chimeraplasty (Cole-Strauss et al., Nucleic Acids Research 27 (5), 1323 (1999) and Kmiec, Gene Therapy American Scientist. 87 (3), 240 (1999)). Homologous recombination procedures in *Physcomitrella patens* are also well known in the art and are contemplated for use herein.

Whereas in the homologous recombination vector, the altered portion of the nucleic acid molecule coding for a protein depicted in SEQ ID NO: 2, 4, 6, 8, 27, or 45, or a homolog thereof is flanked at its 5' and 3' ends by an additional nucleic acid molecule of the gene to allow for homologous recombination to occur between the exogenous gene carried by the vector and an endogenous gene, in a microorganism or plant. The additional flanking nucleic acid molecule is of sufficient length for successful homologous recombination with the endogenous gene. Typically, several hundreds of base pairs up to kilobases of flanking DNA (both at the 5' and 3' ends) are included in the vector. See, e.g., Thomas K. R., and Capecchi M. R., Cell 51, 503 (1987) for a description of homologous recombination vectors or Strepp et al., PNAS, 95 (8), 4368 (1998) for cDNA based recombination in *Physcomitrella patens*. The vector is introduced into a microorganism or plant cell (e.g. via polyethylene glycol mediated DNA transformation), and cells in which the introduced gene has homologously recombined with the endogenous gene are selected using art-known techniques.

Whether present in an extra-chromosomal non-replicating vector or a vector that is integrated into a chromosome, the nucleic acid molecule coding for amino acid molecules depicted in SEQ ID NO: 2, 4, 6, 8, 27, or 45, or a homolog thereof preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., EMBO J. 3, 835 (1984)) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., Nucl. Acids Research 15, 8693 (1987)). Examples of plant expression vectors include those detailed in: Becker D. et al., Plant Mol. Biol. 20, 1195 (1992); and Bevan M. W., Nucl. Acid. Res. 12, 8711 (1984); and "Vectors for Gene Transfer in Higher Plants" in: Transgenic Plants, Vol. 1, Engineering and Utilization, eds. Kung and Wu R., Academic Press, 1993, S. 15-38.

The host organism (=transgenic organism) advantageously contains at least one copy of the nucleic acid according to the invention and/or of the nucleic acid construct according to the invention.

In principle all plants can be used as host organism. Preferred transgenic plants are, for example, selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants such as plants advantageously selected from the group of the genus peanut, oilseed rape, canola, sunflower, safflower, olive, sesame, hazelnut, almond, avocado, bay, pumpkin/squash, linseed, soya, pistachio, borage, maize, wheat, rye, oats, sorghum and millet, triticale, rice, barley, cassava, potato, sugarbeet, egg plant, alfalfa, and perennial grasses and forage plants, oil palm, vegetables (brassicas, root vegetables, tuber vegetables, pod vegetables, fruiting vegetables, onion vegetables, leafy vegetables and stem vegetables), buckwheat, Jerusalem artichoke, broad bean, vetches, lentil, dwarf bean, lupin, clover and Lucerne for mentioning only some of them.

In one embodiment of the invention transgenic plants are selected from the group comprising cereals, soybean, rapeseed (including oil seed rape, especially canola and winter oil seed rape), cotton, sugarcane, sugar beet and potato, especially corn, soy, rapeseed (including oil seed rape, especially canola and winter oil seed rape), cotton, wheat and rice.

In another embodiment of the invention the transgenic plant is a gymnosperm plant, especially a spruce, pine or fir.

In one embodiment, the host plant is selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants and in particular plants mentioned herein above as host plants such as the families and genera mentioned above for example preferred the species *Anacardium occidentale, Calendula officinalis Carthamus tinctorius, Cichorium intybus, Cynara scolymus, Helianthus annus, Tagetes lucida, Tagetes erecta, Tagetes tenuifolia Daucus carota; Corylus avellana, Corylus colurng Borago officinalis, Brassica napus, Brassica rapa* ssp., *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis Brassica oleracea, Arabidopsis thaliana, Anana comosus, Ananas ananas, Bromelia comosa Carica papaya, Cannabis sative, Ipomoea batatus, Ipomoea pandurata, Convolvulus batatas, Convolvulus tiliaceus, Ipomoea fastigiata, Ipomoea tiliacea, Ipomoea triloba, Convolvulus panduratus, Beta vulgaris, Beta vulgaris* var. *altissima, Beta vulgaris* var. *vulgaris, Beta maritima, Beta vulgaris* var. *perennis, Beta vulgaris* var. *conditiva, Beta vulgaris* var. *esculenta Cucurbita maxima, Cucurbita mixta, Cucurbita pepo, Cucurbita moschatc Olea europaea, Manihot utilissima, Janipha manihot, Jatropha manihot., Manihot aipil, Manihot dulcis, Manihot manihot, Manihot melanobasis, Manihot esculenta Ricinus communis, Pisum sativum, Pisum arvense, Pisum humile Medicago sativa, Medicago falcata, Medicago varia, Glycine max Dolichos soja, Glycine gracilis, Glycine hispida, Phaseolus max, Soja hispida, Soja max, Cocos nucifera, Pelargonium grossularioides, Oleum cocoas Laurus nobilis, Persea americana, Arachis hypogaea Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense, Linum trigynum, Punica granatum, Gossypium hirsutum, Gossypium arboreum, Gossypium barbadense, Gossypium herbaceum, Gossypium thurber Musa nana, Musa acuminata, Musa paradisiaca, Musa* spp., *Elaeis guineensis, Papaver orientale, Papaver rhoeas, Papaver dubium Sesamum indicum, Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata, Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum, Avena sativa, Avena fatua, Avena byzantina, Avena fatua* var. *sativa, Avena hybrida, Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet Panicum militaceum, Zea mays, Triticum aestivum, Triticum durum, Triticum turgidum, Triticum hybernum, Triticum macha, Triticum sativum* or *Triticum vulgare, Cofea* spp., *Coffea arabica, Coffea canephora, Coffea liberica, Capsicum annuum, Capsicum annuum* var. *glabriusculum, Capsicum frutescens, Capsicum annuum, Nicotiana tabacum, Solanum tuberosum Solanum melongena, Lycopersicon esculentum, Lycopersicon*

*lycopersicum., Lycopersicon pyriforme, Solanum integrifolium, Solanum lycopersicum Theobroma cacaoor Camellia sinensis.*

Anacardiaceae such as the genera *Pistacia, Mangifera, Anacardium* e.g. the species *Pistacia vera* [pistachios, Pistazie], *Mangifer indica* [Mango] or *Anacardium occidentale* [Cashew]; Asteraceae such as the genera *Calendula, Carthamus, Centaurea, Cichorium, Cynara, Helianthus, Lactuca, Locusta, Tagetes, Valeriana* e.g. the species *Calendula officinalis* [Marigold], *Carthamus tinctorius* [safflower], *Centaurea cyanus* [cornflower], *Cichorium intybus* [blue daisy], *Cynara scolymus* [Artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta*[lettuce], *Tagetes lucida, Tagetes erecta* or *Tagetes tenuifolia* [Marigold]; Apiaceae such as the genera *Daucus* e.g. the species *Daucus carota* [carrot]; Betulaceae such as the genera *Corylus* e.g. the species *Corylus avellana* or *Corylus colurna* [hazelnut]; Boraginaceae such as the genera *Borago* e.g. the species *Borago officinalis* [borage]; Brassicaceae such as the genera *Brassica, Melanosinapis Sinapis, Arabadopsis* e.g. the species *Brassica napus, Brassica rapa*ssp. [canola, oilseed rape, turnip rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis*[mustard], *Brassica oleracea* [fodder beet] or *Arabidopsis thaliana*; Bromeliaceae such as the genera *Anana, Bromelia* e.g. the species *Anana comosus, Ananas ananas*or *Bromelia comosa* [pineapple]; Caricaceae such as the genera *Carica* e.g. the species *Carica papaya* [papaya]; Cannabaceae such as the genera *Cannabis* e.g. the species *Cannabis sative* [hemp], Convolvulaceae such as the genera *Ipomea, Convolvulus* e.g. the species *Ipomoea batatus, Ipomoea pandurata, Convolvulus batatas, Convolvulus tiliaceus, Ipomoea fastigiata, Ipomoea tiliacea, Ipomoea trilobao*r *Convolvulus panduratus*[sweet potato, Man of the Earth, wild potato], Chenopodiaceae such as the genera *Beta*, i.e. the species *Beta vulgaris, Beta vulgaris* var. *altissime Beta vulgaris* var. *Vulgaris, Beta maritima, Beta vulgaris* var. *perennis, Beta vulgaris* var. *conditiva*or *Beta vulgaris* var. *esculenta*[sugar beet]; Cucurbitaceae such as the genera *Cucubita* e.g. the species *Cucurbita maxima, Cucurbita mixta, Cucurbita pepo*or *Cucurbita moschata* [pumpkin, squash]; Elaeagnaceae such as the genera *Elaeagnus* e.g. the species *Olea europaea* [olive]; Ericaceae such as the genera *Kalmia* e.g. the species *Kalmia latifolia, Kalmia an-gustifolia, Kalmia microphylla, Kalmia polifolia Kalmia occidentalis, Cistus chamaerhodendros* or *Kalmia lucida* [American laurel, broad-leafed laurel, calico bush, spoon wood, sheep laurel, alpine laurel, bog laurel, western bog-laurel, swamp-laurel]; Euphorbiaceae such as the genera *Manihot, Janipha, Jatropha, Ricinus* e.g. the species *Manihot utilissima, Janipha manihot, Jatropha manihot., Manihot aipil, Manihot dulcis, Manihot manihot, Manihot melanobasis, Manihot esculent* [manihot, arrowroot, tapioca, cassava] or *Ricinus communis*[castor bean, Castor Oil Bush, Castor Oil Plant, Palma Christi, Wonder Tree]; Fabaceae such as the genera *Pisum, Albizia, Cathormion Feuillea, Inga, Pithecolobium, Acacia, Mimosa, Medicajo, Glycine, Dolichos, Phaseolus, Soja* e.g. the species *Pisum sativum, Pisum arvense, Pisum humile*[pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feulleea lebbeck, Mimosa lebbeck, Mimosa speciosa*[bastard logwood, silk tree, East Indian Walnut], *Medicago sativa, Medicago falcata, Medicago varia*[alfalfa] *Glycine max Dolichos soja, Glycine gracilis, Glycine hispida, Phaseolus* max, *Soja hispida*or *Soja* max [soybean]; Geraniaceae such as the genera *Pelargonium, Cocos, Oleum* e.g. the species *Cocos nucifera, Pelargonium grossularioides*or *Oleum cocois* [coconut]; Gramineae such as the genera *Saccharum* e.g. the species *Saccharum officinarum*; Juglandaceae such as the genera *Juglans, Wallia* e.g. the species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra*or *Wallia nigra* [walnut, black walnut, common walnut, persian walnut, white walnut, butternut, black walnut]; Lauraceae such as the genera *Persea, Laurus* e.g. the species laurel *Laurus nobilis* [bay, laurel, bay laurel, sweet bay], *Persea americana Persea americana, Persea gratissima*or *Persea persea* [avocado]; Leguminosae such as the genera *Arachis* e.g. the species *Arachis hypogaea* [peanut]; Linaceae such as the genera *Linum, Adenolinum* e.g. the species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [flax, linseed]; Lythrarieae such as the genera *Punica* e.g. the species *Punica granatum* [pomegranate]; Malvaceae such as the genera *Gossypium* e.g. the species *Gossypium hirsutum, Gossypium arboreum, Gossypium barbadense, Gossypium herbaceum*or *Gossypium thurberi* [cotton]; Musaceae such as the genera *Musa* e.g. the species *Musa nana, Musa acuminata, Musa paradisiaca, Musa* spp. [banana]; Onagraceae such as the genera *Camissonia, Oenothera* e.g. the species *Oenothera biennis*or *Camissonia brevipes*[primrose, evening primrose]; Palmae such as the genera *Elacis* e.g. the species *Elaeis guineensis* [oil plam]; Papaveraceae such as the genera *Papaver* e.g. the species *Papaver orientale, Papaver rhoeas, Papaver dubium*[poppy, oriental poppy, corn poppy, field poppy, shirley poppies, field poppy, long-headed poppy, long-pod poppy]; Pedaliaceae such as the genera *Sesamum* e.g. the species *Sesamum indicum* [sesame]; Piperaceae such as the genera *Piper, Artanthe, Peperomia, Steffensia* e.g. the species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [Cayenne pepper, wild pepper]; Poaceae such as the genera *Hordeum, Secale, Avena, Sorghum, Andropogon, Holcus, Panicum, Oryza, Zea, Triticum* e.g. the species *Hordeum vulgare, Hordeum jubatum, Hordeum murinum, Hordeum secalinum, Hordeum distichon Hordeum aegiceras, Hordeum hexastichon., Hordeum hexastichum, Hordeum irregulare, Hordeum sativum, Hordeum secalinum*[barley, pearl barley, foxtail barley, wall barley, meadow barley], *Secale cereale* [rye], *Avena sativa, Avena fatua, Avena byzantina, Avena fatua* var. *sativa, Avena hybrida* [oat], *Sorghum bicolor, Sorghum halepense, Sorghum saccharatum, Sorghum vulgare, Andropogon drummondii, Holcus bicolor, Holcus sorghum, Sorghum aethiopicum, Sorghum arundi-*

*naceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum* [*Sorghum*, millet], *Oryza sativa, Oryza latifolia*[rice], *Zea mays* [corn, maize] *Triticum aestivum, Triticum durum, Triticum turgidum, Triticum hybernum, Triticum macha, Triticum sativumor Triticum vulgare* [wheat, bread wheat, common wheat], Proteaceae such as the genera *Macadamia* e.g. the species *Macadamia intergrifolia* [macadamia]; Rubiaceae such as the genera *Coffea* e.g. the species *Cofea* spp., *Coffea arabica, Coffea canephoraor Coffea liberica* [coffee]; Scrophulariaceae such as the genera *Verbascum* e.g. the species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentumor Verbascum thapsus*[mullein, white moth mullein, nettleleaved mullein, dense-flowered mullein, silver mullein, long-leaved mullein, white mullein, dark mullein, greek mullein, orange mullein, purple mullein, hoary mullein, great mullein]; Solanaceae such as the genera *Capsicum, Nicotiana, Solanum, Lycopersicon* e.g. the species *Capsicum annuum, Capsicum annuum* var. *glabriusculum, Capsicum frutescens*[pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [egg-plant](*Lycopersicon esculentum, Lycopersicon lycopersicum., Lycopersicon pyriforme, Solanum integrifoliumor Solanum lycopersicum* [tomato]; Sterculiaceae such as the genera *Theobroma* e.g. the species *Theobroma cacao* [cacao]; Theaceae such as the genera *Camellia* e.g. the species *Camellia sinensis*) [tea].

The introduction of the nucleic acids according to the invention, the expression cassette or the vector into organisms, plants for example, can in principle be done by all of the methods known to those skilled in the art. The introduction of the nucleic acid sequences gives rise to recombinant or transgenic organisms.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in Jenes B. et al., Techniques for Gene Transfer, in: Transgenic Plants, Vol. 1, Engineering and Utilization, eds. Kung S. D and Wu R., Academic Press (1993) 128-143 and in Potrykus, Annu. Rev. Plant Physiol. Plant Molec. Biol. 42, 205 (1991). The nucleic acids or the construct to be expressed is preferably cloned into a vector which is suitable for transforming *Agrobacterium tumefaciens*, for example pBin19 (Bevan et al., Nucl. Acids Res. 12, 8711 (1984)). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. 16, 9877 (1988) or is known inter alia from White F. F., Vectors for Gene Transfer in Higher Plants; in Transgenic Plants, Vol. 1, Engineering and Utilization, eds. Kung S. D. and Wu R., Academic Press, 1993, pp. 15-38.

Agrobacteria transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassava, arrowroot, *tagetes*, alfalfa, lettuce and the various tree, nut and vine species, in particular oil-containing crop plants such as soybean, peanut, castor oil plant, sunflower, corn, cotton, flax, oilseed rape, coconut, oil palm, safflower (*Carthamus tinctorius*) or cocoa bean, or in particular corn, wheat, soybean, rice, cotton and canola, e.g. by bathing bruised leaves or chopped leaves in an agrobacterial solution and then culturing them in suitable media.

The genetically modified plant cells may be regenerated by all of the methods known to those skilled in the art. Appropriate methods can be found in the publications referred to above by Kung S. D. and Wu R., Potrykus or Höfgen and Willmitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms— or reproductive material derived from such organisms.

In one embodiment of the invention host plants for the nucleic acid, expression cassette or vector according to the invention are selected from the group comprising corn, soy, oil seed rape (including canola and winter oil seed rape), cotton, wheat and rice.

A further embodiment of the invention relates to the use of a nucleic acid construct, e.g. an expression cassette, containing one or more DNA sequences encoding one or more polypeptides shown in SEQ ID NO: 2, 4, 6, 8, 27, or 45, or a homolog thereof or comprising one or more nucleic acid molecules as depicted in SEQ ID NO: 1, 3, 5, 7, 26, or 44, or a homolog thereof or encoding or DNA sequences hybridizing therewith for the transformation of plant cells, tissues or parts of plants.

In doing so, depending on the choice of promoter, the nucleic acid molecules of the present invention can be expressed specifically in the leaves, in the seeds, the nodules, in roots, in the stem or other parts of the plant. Those transgenic plants overproducing sequences, e.g. as depicted in SEQ ID NO: 1, 3, 5, 7, 26, or 44, or a homolog thereof, the reproductive material thereof, together with the plant cells, tissues or parts thereof are a further object of the present invention.

The expression cassette or the nucleic acid sequences or construct according to the invention containing nucleic acid molecules or sequences as depicted in SEQ ID NO: 1, 3, 5, 7, 26, or 44, or a homolog thereof can, moreover, also be employed for the transformation of the organisms identified by way of example above such as bacteria, yeasts, filamentous fungi and plants.

Within the framework of the present invention, increased herbicide tolerance or resistance, relates to, for example, the artificially acquired trait of increased herbicide tolerance or resistance, by comparison with the non-genetically modified initial plants e.g. the trait acquired by genetic modification of the target organism, and due to functional over-expression of one or more polypeptide (sequences) of SEQ ID NO: 2, 4, 6, 8, 27, or 45, or a homolog thereof, e.g. encoded by the corresponding nucleic acid molecules as depicted in SEQ ID NO: 1, 3, 5, 7, 26, or 44, and/or homologs, in the organisms according to the invention, advantageously in the transgenic plant according to the invention or produced according to the method of the invention, at least for the duration of at least one plant generation.

A constitutive expression of the polypeptide sequences of SEQ ID NO: 2, 4, 6, 8, 27, or 45, or a homolog thereof, encoded by the corresponding nucleic acid molecule as depicted in SEQ ID NO: 1, 3, 5, 7, 26, or 44, or a homolog thereof is, moreover, advantageous. On the other hand, however, an inducible expression may also appear desirable. Expression of the polypeptide sequences of the invention can be either direct to the cytoplasm or the organelles, preferably the plastids of the host cells, preferably the plant cells.

The activity of the protein encoded by the sequences of SEQ ID NO: 2, 4, 6, 8, 27, or 45, or a homolog thereof, encoded by the corresponding nucleic acid molecule as depicted in SEQ ID NO: 1, 3, 5, 7, 26, or 44, or a homolog thereof can be determined, for example, in vitro as described in EXAMPLE 2. In addition, a functional expression of the sequences of SEQ ID NO: 2, 4, 6, 8, 27, or 45, or a homolog thereof, encoded by the corresponding nucleic acid molecule as depicted in SEQ ID NO: 1, 3, 5, 7, 26, or 44, and/or homologs modified in nature and level and its effect on herbicide tolerance or resistance, but also on the metabolic pathways performance can be tested on test plants in greenhouse trials (see EXAMPLE 3 and 4).

An additional object of the invention comprises transgenic organisms such as transgenic plants transformed by an expression cassette containing sequences of as depicted in SEQ ID NO: 1, 3, 5, 7, 26, or 44, or a homolog thereof according to the invention or DNA sequences hybridizing therewith, as well as transgenic cells, tissue, parts and reproduction material of such plants. Particular preference is given in this case to transgenic crop plants such as by way of example barley, wheat, rye, oats, corn, soybean, rice, cotton, sugar beet, oilseed rape and canola, sunflower, flax, hemp, thistle, potatoes, tobacco, tomatoes, tapioca, cassava, arrowroot, alfalfa, lettuce and the various tree, nut and vine species.

In one embodiment of the invention transgenic plants transformed by an expression cassette containing or comprising nucleic acid molecules or sequences as depicted in SEQ ID NO: 1, 3, 5, 7, 26, or 44, or a homolog thereof, according to the invention or DNA sequences hybridizing therewith are selected from the group comprising corn, soy, oil seed rape (including canola and winter oil seed rape), cotton, wheat and rice.

For the purposes of the invention plants are mono- and dicotyledonous plants, mosses or algae, especially plants, for example in one embodiment monocotyledonous plants, or for example in another embodiment dicotyledonous plants. A further refinement according to the invention are transgenic plants as described above which contain a nucleic acid sequence or construct according to the invention or a expression cassette according to the invention.

However, transgenic also means that the nucleic acids according to the invention are located at their natural position in the genome of an organism, but that the sequence, e.g. the coding sequence or a regulatory sequence, for example the promoter sequence, has been modified in comparison with the natural sequence. Preferably, transgenic/recombinant is to be understood as meaning the transcription of one or more nucleic acids or molecules of the invention and being shown in SEQ ID NO: 1, 3, 5, 7, 26, or 44, or a homolog thereof, occurs at a non-natural position in the genome. In one embodiment, the expression of the nucleic acids or molecules is homologous. In another embodiment, the expression of the nucleic acids or molecules is heterologous. This expression can be transiently or of a sequence integrated stably into the genome.

Advantageous inducible plant promoters are by way of example the PRP1 promoter (Ward et al., Plant. Mol. Biol. 22361 (1993)), a promoter inducible by benzenesulfonamide (EP 388 186), a promoter inducible by tetracycline (Gatz et al., Plant J. 2, 397 (1992)), a promoter inducible by salicylic acid (WO 95/19443), a promoter inducible by abscisic acid (EP 335 528) and a promoter inducible by ethanol or cyclohexanone (WO 93/21334). Other examples of plant promoters which can advantageously be used are the promoter of cytoplasmic FBPase from potato, the ST-LSI promoter from potato (Stockhaus et al., EMBO J. 8, 2445 (1989)), the promoter of phosphoribosyl pyrophosphate amidotransferase from *Glycine max* (see also gene bank accession number U87999) or a nodienespecific promoter as described in EP 249 676.

Such promoters are known to the person skilled in the art or can be isolated from genes which are induced under the conditions mentioned above. In one embodiment, seed-specific promoters may be used for monocotylodonous or dicotylodonous plants.

In principle all natural promoters with their regulation sequences can be used like those named above for the expression cassette according to the invention and the method according to the invention. Over and above this, synthetic promoters may also advantageously be used. In the preparation of an expression cassette various DNA fragments can be manipulated in order to obtain a nucleotide sequence, which usefully reads in the correct direction and is equipped with a correct reading frame. To connect the DNA fragments (=nucleic acids according to the invention) to one another adaptors or linkers may be attached to the fragments. The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which shown in SEQ ID NO: 1, 3, 5, 7, 26, or 44, or a homolog thereof and a region for transcription termination. Different termination regions can be exchanged for one another in any desired fashion.

A nucleic acid molecule of the present invention, e.g., a nucleic acid molecule encoding a polypeptide which confers increased herbicide tolerance or resistance, in plants, can be isolated using standard molecular biological techniques and the sequence information provided herein. For example, an *A. thaliana* polypeptide encoding cDNA can be isolated from a *A. thaliana* c-DNA library or a *Synechocystis* sp., *Brassica napus, Glycine max, Zea mays* or *Oryza sativa* polpypeptide encoding cDNA can be isolated from a *Synechocystis* sp., *Brassica napus, Glycine max, Zea mays* or *Oryza sativa* c-DNA library respectively using all or portion of one of the sequences shown in SEQ ID NO: 1, 3, 5, 7, 26, or 44, or a homolog thereof. Moreover, a nucleic acid molecule encompassing all or a portion of one of the sequences of SEQ ID NO: 1, 3, 5, 7, 26, or 44, or a homolog thereof can be isolated by the polymerase chain reaction using oligonucleotide primers designed based upon this sequence. For example, mRNA can be isolated from plant cells (e.g., by the guanidiniumthiocyanate extraction procedure of Chirgwin et al., Biochemistry 18, 5294 (1979)) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO: 1, 3, 5, 7, 26, or 44, or a homolog thereof. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, the genes employed in the present invention can be prepared by standard synthetic techniques, e.g., using a commercially available automated DNA synthesizer.

In a embodiment, an isolated and/or a recombinant nucleic acid molecule of the invention comprises one of the nucleotide sequences or molecules as shown in SEQ ID NO: 1, 3, 5, 7, 26, or 44, or a homolog thereof. Moreover, the nucleic acid molecule of the invention can comprise only a portion of the coding region of one of the sequences or molecules of a nucleic acid as shown in SEQ ID NO: 1, 3, 5, 7, 26, or 44, or a homolog thereof, for example, a fragment which can be used as a probe or primer or a fragment encoding a biologically active portion of a polypeptide according to invention.

Portions of proteins encoded by the polypeptide according to the invention or a polypeptide encoding nucleic acid molecules of the invention are preferably biologically active portions described herein. As used herein, the term "biologically active portion of" a polypeptide is intended to include a portion, e.g. a domain/motif, of increased herbicide tolerance or resistance, in a plant. To determine whether a polypeptide according to the invention, or a biologically active portion thereof, results in an increased herbicide tolerance or resistance, an analysis of a plant comprising the polypeptide may be performed. Such analysis methods are well known to those skilled in the art, as detailed in the Examples. More specifically, nucleic acid fragments encoding biologically active portions of a polypeptide can be prepared by isolating a portion of one of the sequences of the nucleic acid molecules listed in SEQ ID NO: 1, 3, 5, 7, 26, or 44, or a homolog thereof expressing the encoded portion of the polypeptide or peptide thereof (e.g., by recombinant expression in vitro) and assessing the activity of the encoded portion.

Biologically active portions of the polypeptide according to the invention are encompassed by the present invention and include peptides comprising amino acid sequences derived from the amino acid sequence of the polypeptide encoding gene, or the amino acid sequence of a protein homologous to the polypeptide according to the invention, which include fewer amino acids than a full length polypeptide according to the invention or the full length protein which is homologous to the polypeptide according to the invention, and exhibits at least some enzymatic or biological activity of the polypeptide according to the invention. Typically, biologically active portions (e.g., peptides which are, for example, 5, 10, 15, 20, 30, 35, 36, 37, 38, 39, 40, 50, 100 or more amino acids in length) comprise a domain or motif with at least one activity of the polypeptide according to the invention. Moreover, other biologically active portions in which other regions of the protein are deleted can be prepared by recombinant techniques and evaluated for one or more of the activities described herein. Preferably, the biologically active portions of the polypeptide according to the invention include one or more selected domains/motifs or portions thereof having biological activity.

The term "biological active portion" or "biological activity" means a polypeptide as depicted in SEQ ID NO: 2, 4, 6, 8, 27, or 45, or a homolog thereof or a portion of said polypeptide which still has at least 10% or 20%, preferably 30%, 40%, 50% or 60%, especially preferably 70%, 75%, 80%, 90% or 95% of the enzymatic or biological activity of the natural or starting enzyme or protein.

In the process according to the invention nucleic acid sequences or molecules can be used, which, if appropriate, contain synthetic, non-natural or modified nucleotide bases, which can be incorporated into DNA or RNA. Said synthetic, non-natural or modified bases can for example increase the stability of the nucleic acid molecule outside or inside a cell. The nucleic acid molecules of the invention can contain the same modifications as aforementioned.

As used in the present context the term "nucleic acid molecule" may also encompass the untranslated sequence or molecule located at the 3' and at the 5' end of the coding gene region, for example at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. It is often advantageous only to choose the coding region for cloning and expression purposes.

Preferably, the nucleic acid molecule used in the process according to the invention or the nucleic acid molecule of the invention is an isolated and/or recombinant nucleic acid molecule. In one embodiment, the nucleic acid molecule of the invention is the nucleic acid molecule used in the process of the invention.

In various embodiments, the isolated and/or recombinant nucleic acid molecule used in the process according to the invention may, for example comprise less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid molecule originates.

The nucleic acid molecules used in the process, for example the polynucleotide of the invention or of a part thereof can be isolated using molecular-biological standard techniques and the sequence information provided herein. Also, for example a homologous sequence or homologous, conserved sequence regions at the DNA or amino acid level can be identified with the aid of comparison algorithms. The former can be used as hybridization probes under standard hybridization techniques (for example those described in Sambrook et al., supra) for isolating further nucleic acid sequences useful in this process.

A nucleic acid molecule encompassing a complete sequence of the nucleic acid molecules used in the process, for example the polynucleotide of the invention, or a part thereof may additionally be isolated by polymerase chain reaction, oligonucleotide primers based on this sequence or on parts thereof being used. For example, a nucleic acid molecule comprising the complete sequence or part thereof can be isolated by polymerase chain reaction using oligonucleotide primers which have been generated on the basis of this very sequence. For example, mRNA can be isolated from cells (for example by means of the guanidinium thiocyanate extraction method of Chirgwin et al., Biochemistry 18, 5294(1979)) and cDNA can be generated by means of reverse transcriptase (for example Moloney, MLV reverse transcriptase, available from Gibco/BRL, Bethesda, Md., or AMV reverse transcriptase, obtainable from Seikagaku America, Inc., St. Petersburg, Fla.).

Synthetic oligonucleotide primers for the amplification by means of polymerase chain reaction can be generated on the basis of a sequence shown herein, using known methods.

Moreover, it is possible to identify a conserved protein by carrying out protein sequence alignments with the polypeptide encoded by the nucleic acid molecules of the present invention, in particular with the sequences encoded by the nucleic acid molecule shown in SEQ ID NO: 1, 3, 5, 7, 26, or 44, or a homolog thereof, from which conserved regions, and in turn, degenerate primers can be derived. Conserved regions are those, which show a very little variation in the amino acid in one particular position of several homologs from different origin. Moreover, it is possible to identify conserved regions from various organisms by carrying out protein sequence alignments with the polypeptide encoded by the nucleic acid of the present invention, in particular with the sequences of the polypeptide molecule shown in SEQ ID NO: 2, 4, 6, 8, 27, or 45, or a homolog thereof, from which conserved regions, and in turn, degenerate primers can be derived.

Conserved domains can be identified from all sequences and are described using a subset of the standard Prosite notation, e.g. the pattern Y-x(21,23)-[FW] means that a conserved tyrosine is separated by minimum 21 and maximum 23 amino acid residues from either a phenylalanine or tryptophane. Patterns can match at least 80% of the investigated proteins. Conserved patterns can be identified with the software tool MEME version 3.5.1 or manually. MEME is described by Timothy L. Bailey and Charles Elkan (Proceedings of the Second International Conference on Intelligent Systems for Molecular Biology, pp. 28-36, AAAI Press, Menlo Park, Calif., 1994). The source code for the stand-alone program is publicly available from the San Diego Supercomputer centre. The Prosite patterns of the conserved domains can be used to search for protein sequences matching this pattern. Various established Bioinformatic centres provide public internet portals for using those patterns in database searches (e.g. PIR (Protein Information Resource, located at Georgetown University Medical Center) or ExPASy (Expert Protein Analysis System)). Alternatively, stand-alone software is available, like the program Fuzzpro, which is part of the EMBOSS software package. For example, the program Fuzzpro not only allows searching for an exact pattern-protein match but also allows setting various ambiguities in the performed search.

Degenerate primers can then be utilized by PCR for the amplification of fragments of novel proteins having above-mentioned activity, e.g. conferring increased herbicide tolerance or resistance, as compared to a corresponding, e.g. non-transformed, wild type plant cell, plant or part thereof after increasing the expression or activity or having the activity of a protein as shown in SEQ ID NO: 2, 4, 6, 8, 27, or 45, or a homolog thereof or further functional homologs of the polypeptide of the invention from other organisms.

These fragments can then be utilized as hybridization probe for isolating the complete gene sequence. As an alternative, the missing 5' and 3' sequences can be isolated by means of RACE-PCR. A nucleic acid molecule according to the invention can be amplified using cDNA or, as an alternative, genomic DNA as template and suitable oligonucleotide primers, following standard PCR amplification techniques. The nucleic acid molecule amplified thus can be cloned into a suitable vector and characterized by means of DNA sequence analysis. Oligonucleotides, which correspond to one of the nucleic acid molecules used in the process can be generated by standard synthesis methods, for example using an automatic DNA synthesizer.

Nucleic acid molecules which are advantageous for the process according to the invention can be isolated based on their homology to the nucleic acid molecules disclosed herein using the sequences or part thereof as or for the generation of a hybridization probe and following standard hybridization techniques under stringent hybridization conditions. In this context, it is possible to use, for example, isolated one or more nucleic acid molecules of at least 15, 20, 25, 30, 35, 40, 50, 60 or more nucleotides, preferably of at least 15, 20 or 25 nucleotides in length which hybridize under stringent conditions with the above-described nucleic acid molecules, in particular with those which encompass a nucleotide sequence of the nucleic acid molecule used in the process of the invention or encoding a protein used in the invention or of the nucleic acid molecule of the invention. Nucleic acid molecules with 30, 50, 100, 250 or more nucleotides may also be used.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)) or in Current Protocols in Molecular Biology, John Wiley & Sons, N. Y. (1989), 6.3.1-6.3.6.

According to the invention, DNA as well as RNA molecules of the nucleic acid of the invention can be used as probes. Further, as template for the identification of functional homologues Northern blot assays as well as Southern blot assays can be performed. The Northern blot assay advantageously provides further information about the expressed gene product: e.g. expression pattern, occurrence of processing steps, like splicing and capping, etc. The Southern blot assay provides additional information about the chromosomal localization and organization of the gene encoding the nucleic acid molecule of the invention.

A preferred, non-limiting example of stringent hybridization conditions are hybridizations in 6× sodium chloride/sodium citrate (=SSC) at approximately 45° C., followed by one or more wash steps in 0.2×SSC, 0.1% SDS at 50 to 65° C., for example at 50° C., 55° C. or 60° C. The skilled worker knows that these hybridization conditions differ as a function of the type of the nucleic acid and, for example when organic solvents are present, with regard to the temperature and concentration of the buffer. The temperature under "standard hybridization conditions" differs for example as a function of the type of the nucleic acid between 42° C. and 58° C., preferably between 45° C. and 50° C. in an aqueous buffer with a concentration of 0.1×, 0.5×, 1×, 2×, 3×, 4× or 5×SSC (pH 7.2). If organic solvent(s) is/are present in the abovementioned buffer, for example 50% formamide, the temperature under standard conditions is approximately 40° C., 42° C. or 45° C. The hybridization conditions for DNA:DNA hybrids are preferably for example 0.1×SSC and 20° C., 25° C., 30° C., 35° C., 40° C. or 45° C., preferably between 30° C. and 45° C. The hybridization conditions for DNA:RNA hybrids are preferably for example 0.1×SSC and 30° C., 35° C., 40° C., 45° C., 50° C. or 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows to determine the hybridization conditions required with the aid of textbooks, for example the ones mentioned above, or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

A further example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Further, the conditions during the wash step can be selected from the range of conditions delimited by low-stringency conditions (approximately 2×SSC at 50° C.) and high-stringency conditions (approximately 0.2×SSC at 50° C., preferably at 65° C.) (20×SSC: 0.3 M sodium citrate, 3 M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Relevant factors like 1) length of treatment, 2) salt conditions, 3) detergent conditions, 4) competitor DNAs, 5) temperature and 6) probe selection can be combined case by case so that not all possibilities can be mentioned herein.

Thus, in a preferred embodiment, Northern blots are prehybridized with Rothi-Hybri-Quick buffer (Roth, Karlsruhe) at 68° C. for 2 h. Hybridization with radioactive labelled probe is done overnight at 68° C. Subsequent washing steps are performed at 68° C. with 1×SSC. For Southern blot assays the membrane is prehybridized with Rothi-Hybri-Quick buffer (Roth, Karlsruhe) at 68° C. for 2 h. The hybridzation with radioactive labelled probe is conducted over night at 68° C. Subsequently the hybridization buffer is discarded and the filter shortly washed using 2×SSC; 0.1% SDS. After discarding the washing buffer new 2×SSC; 0.1% SDS buffer is added and incubated at 68° C. for 15 minutes. This washing step is performed twice followed by an additional washing step using 1×SSC; 0.1% SDS at 68° C. for 10 min.

Some examples of conditions for DNA hybridization (Southern blot assays) and wash step are shown herein below:
(1) Hybridization conditions can be selected, for example, from the following conditions:
    (a) 4×SSC at 65° C.,
    (b) 6×SSC at 45° C.,
    (c) 6×SSC, 100 mg/ml denatured fragmented fish sperm DNA at 68° C.,
    (d) 6×SSC, 0.5% SDS, 100 mg/ml denatured salmon sperm DNA at 68° C.,
    (e) 6×SSC, 0.5% SDS, 100 mg/ml denatured fragmented salmon sperm DNA, 50% formamide at 42° C.,
    (f) 50% formamide, 4×SSC at 42° C.,
    (g) 50% (v/v) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
    (h) 2× or 4×SSC at 50° C. (low-stringency condition), or
    (i) 30 to 40% formamide, 2× or 4×SSC at 42° C. (low-stringencycondition).
(2) Wash steps can be selected, for example, from the following conditions:
    (a) 0.015 M NaCl/0.0015 M sodium citrate/0.1% SDS at 50° C.
    (b) 0.1×SSC at 65° C.
    (c) 0.1×SSC, 0.5% SDS at 68° C.
    (d) 0.1×SSC, 0.5% SDS, 50% formamide at 42° C.
    (e) 0.2×SSC, 0.1% SDS at 42° C.
    (f) 2×SSC at 65° C. (low-stringency condition).

Polypeptides having above-mentioned activity, i.e. conferring increased herbicide tolerance or resistance, as compared to a corresponding, e.g. non-transformed, wild type plant cell, plant or part thereof, derived from other organisms, can be encoded by other DNA sequences which hybridize to the sequences shown in SEQ ID NO: 1, 3, 5, 7, 26, or 44, or a homolog thereof, under relaxed hybridization conditions and which code on expression for peptides conferring the increased herbicide tolerance or resistance, as compared to a corresponding, e.g. non-transformed, wild type plant cell, plant or part thereof.

Further, some applications have to be performed at low stringency hybridization conditions, without any consequences for the specificity of the hybridization. For example, a Southern blot analysis of total DNA could be probed with a nucleic acid molecule of the present invention and washed at low stringency (55° C. in 2×SSPE, 0.1% SDS). The hybridization analysis could reveal a simple pattern of only genes encoding polypeptides of the present invention or used in the process of the invention, e.g. having the hereinmentioned activity of enhancing the increased herbicide tolerance or resistance, as compared to a corresponding, e.g. non-transformed, wild type plant cell, plant or part thereof. A further example of such low-stringent hybridization conditions is 4×SSC at 50° C. or hybridization with 30 to 40% formamide at 42° C. Such molecules comprise those which are fragments, analogues or derivatives of the polypeptide of the invention or used in the process of the invention and differ, for example, by way of amino acid and/or nucleotide deletion(s), insertion(s), substitution (s), addition(s) and/or recombination (s) or any other modification(s) known in the art either alone or in combination from the above-described amino acid sequences or their underlying nucleotide sequence(s). However, it is preferred to use high stringency hybridization conditions.

Hybridization should advantageously be carried out with fragments of at least 5, 10, 15, 20, 25, 30, 35 or 40 bp, advantageously at least 50, 60, 70 or 80 bp, preferably at least 90, 100 or 110 bp. Most preferably are fragments of at least 15, 20, 25 or 30 bp. Preferably are also hybridizations with at least 100 or 200 bp, very especially preferably at least 400 bp in length. In an especially preferred embodiment, the hybridization should be carried out with the entire nucleic acid sequence with conditions described above.

The terms "fragment", "fragment of a sequence" or "part of a sequence" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence or molecule referred to or hybridizing with the nucleic acid molecule of the invention or used in the process of the invention under stringent conditions, while the maximum size is not critical. In some applications, the maximum size usually is not substantially greater than that required to provide the desired activity and/or function (s) of the original sequence.

Typically, the truncated amino acid sequence or molecule will range from about 5 to about 310 amino acids in length. More typically, however, the sequence will be a maximum of about 250 amino acids in length, preferably a maximum of about 200 or 100 amino acids. It is usually desirable to select sequences of at least about 10, 12 or 15 amino acids, up to a maximum of about 20 or 25 amino acids.

The term "epitope" relates to specific immunoreactive sites within an antigen, also known as antigenic determinates. These epitopes can be a linear array of monomers in a polymeric composition such as amino acids in a protein—or consist of or comprise a more complex secondary or tertiary structure. Those of skill will recognize that immunogens (i.e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive.

In one embodiment the present invention relates to a epitope of the polypeptide of the present invention or used in the process of the present invention and confers an increased herbicide tolerance or resistance as compared to a corresponding, e.g. non-transformed, wild type plant cell, plant or part thereof.

The term "one or several amino acids" relates to at least one amino acid but not more than that number of amino acids, which would result in a homology of below 50% identity. Preferably, the identity is more than 70% or 80%, more preferred are 85%, 90%, 91%, 92%, 93%, 94% or 95%, even more preferred are 96%, 97%, 98%, or 99% identity.

Further, the nucleic acid molecule of the invention comprises a nucleic acid molecule, which is a complement of one of the nucleotide sequences of above mentioned nucleic acid molecules or a portion thereof. A nucleic acid molecule or its sequence which is complementary to one of the nucleotide molecules or sequences shown in SEQ ID NO: 1, 3, 5, 7, 26, or 44, or a homolog thereof, is one which is sufficiently complementary to one of the nucleotide molecules or sequences shown in SEQ ID NO: 1, 3, 5, 7, 26, or 44, or a homolog thereof such that it can hybridize to one of the nucleotide sequences shown in SEQ ID NO: 1, 3, 5, 7, 26, or 44, or a homolog thereof, thereby forming a stable duplex. Preferably, the hybridization is performed under stringent hybrization conditions. However, a complement of one of the herein disclosed sequences is preferably a sequence complement thereto according to the base pairing of nucleic acid molecules well known to the skilled person. For example, the bases A and G undergo base pairing with the bases T and U or C, resp. and visa versa. Modifications of the bases can influence the base-pairing partner.

The nucleic acid molecule of the invention comprises a nucleotide sequence which is at least about 30%, 35%, 40% or 45%, preferably at least about 50%, 55%, 60% or 65%, more preferably at least about 70%, 80%, or 90%, and even more preferably at least about 95%, 97%, 98%, 99% or more homologous to a nucleotide sequence shown in SEQ ID NO: 1, 3, 5, 7, 26, or 44, or a homolog thereof, or a portion thereof and preferably has above mentioned activity, in particular having a herbicide tolerance or resistance increasing activity after increasing the activity or an activity of a gene as shown in SEQ ID NO: 1, 3, 5, 7, 26, or 44, or a homolog thereof or of a gene product, by for example expression either in the cytosol or cytoplasm or in an organelle such as a plastid or mitochondria or both, preferably in plastids.

In one embodiment, the nucleic acid molecules comprising the sequence of SEQ ID NO: 1, 3, 5, 7, 26, or 44, or a homolog thereof or gene products encoded by said nucleic acid molecules are expressed in combination with a targeting signal as described herein.

The nucleic acid molecule of the invention comprises a nucleotide sequence or molecule which hybridizes, preferably hybridizes under stringent conditions as defined herein, to one of the nucleotide sequences or molecule shown in SEQ ID NO: 1, 3, 5, 7, 26, or 44, or a homolog thereof, or a portion thereof and encodes a protein having above-mentioned activity, e.g. conferring an increased herbicide tolerance or resistance, as compared to a corresponding, e.g. non-transformed, wild type plant cell, plant or part thereof by for example expression either in the cytosol or in an organelle such as a plastid or mitochondria or both, preferably in plastids, and optionally, having the activity of an *Alopecurus* CYP450 enzyme.

Moreover, the nucleic acid molecule of the invention can comprise only a portion of the coding region of one of the sequences shown in SEQ ID NO: 1, 3, 5, 7, 26, or 44, or a homolog thereof, for example a fragment which can be used as a probe or primer or a fragment encoding a biologically active portion of the polypeptide of the present invention or of a polypeptide used in the process of the present invention, i.e. having above-mentioned activity, e.g. conferring an increased herbicide tolerance or resistance, as compared to a corresponding, e.g. non-transformed, wild type plant cell, plant or part thereof f its activity is increased by for example expression either in the cytosol or in an organelle such as a plastid or mitochondria or both, preferably in plastids. The nucleotide sequences determined from the cloning of the present protein-according-to-the-invention-encoding gene allows for the generation of probes and primers designed for use in identifying and/or cloning its homologues in other cell types and organisms. The probe/primer typically comprises substantially purified oligonucleotide. The oligonucleotide typically comprises a region of nucleotide sequence that hybridizes under stringent conditions to at least about 12, 15 preferably about 20 or 25, more preferably about 40, 50 or 75 consecutive nucleotides of a sense strand of one of the sequences set forth, e.g., in SEQ ID NO: 1, 3, 5, 7, 26, or 44, or a homolog thereof, an anti-sense sequence of one of the sequences, e.g., set forth in SEQ ID NO: 1, 3, 5, 7, 26, or 44, or a homolog thereof, or naturally occurring mutants thereof. Primers based on a nucleotide of invention can be used in PCR reactions to clone homologues of the polypeptide of the invention or of the polypeptide used in the process of the invention, e.g. as the primers described in the examples of the present invention, e.g. as shown in the examples. A PCR with primers based on SEQ ID NO: 1, 3, 5, 7, 26, or 44 will result in a fragment of the gene product as shown SEQ ID NO: 2, 4, 6, 8, 27, or 45, or a homolog thereof.

Primer sets are interchangeable. The person skilled in the art knows to combine said primers to result in the desired product, e.g. in a full length clone or a partial sequence. Probes based on the sequences of the nucleic acid molecule of the invention or used in the process of the present invention can be used to detect transcripts or genomic sequences encoding the same or homologous proteins. The probe can further comprise a label group attached thereto, e.g. the label group can be a radioisotope, a fluorescent compound, an enzyme, or an enzyme co-factor. Such probes can be used as a part of a genomic marker test kit for identifying cells which express an polypeptide of the invention or used in the process of the present invention, such as by measuring a level of an encoding nucleic acid molecule in a sample of cells, e.g., detecting mRNA levels or determining, whether a genomic gene comprising the sequence of the polynucleotide of the invention or used in the processes of the present invention has been mutated or deleted.

The nucleic acid molecule of the invention encodes a polypeptide or portion thereof which includes an amino acid sequence which is sufficiently homologous to the amino acid sequence shown in SEQ ID NO: 2, 4, 6, 8, 27, or 45, or a homolog thereof such that the protein or portion thereof maintains the ability to participate in increasing herbicide tolerance or resistance, as compared to a corresponding, e.g. non-transformed, wild type plant cell, plant or part thereof, in particular increasing the activity as mentioned above or as described in the examples in plants is comprised.

As used herein, the language "sufficiently homologous" refers to proteins or portions thereof which have amino acid sequences which include a minimum number of identical or equivalent amino acid residues (e.g., an amino acid residue which has a similar side chain as an amino acid residue in one of the sequences of the polypeptide of the present invention) to an amino acid sequence shown in SEQ ID NO: 2, 4, 6, 8, 27, or 45, or a homolog thereof such that the protein or portion thereof is able to participate in increasing herbicide tolerance or resistance, as compared to a corresponding, e.g. non-transformed, wild type plant cell, plant or part thereof.

In one embodiment, the nucleic acid molecule of the present invention comprises a nucleic acid that encodes a portion of the protein of the present invention. The protein is at least about 30%, 35%, 40%, 45% or 50%, preferably at least about 55%, 60%, 65% or 70%, and more preferably at least about 75%, 80%, 85%, 90%, 91%, 92%, 93% or 94% and most preferably at least about 95%, 97%, 98%, 99% or more homologous to an entire amino acid sequence SEQ ID NO: 2, 4, 6, 8, 27, or 45, and having above-mentioned activity, e.g. conferring an increased herbicide tolerance or resistance, as compared to a corresponding, e.g. non-transformed, wild type plant cell, plant or part thereof by for example expression either in the cytosol or in an organelle such as a plastid or mitochondria or both, preferably in plastids. In a preferred embodiment, such homologs refer to proteins comprising the sequences of SEQ ID NO: 9, 10, 11, 12, 13, 14, 15, 16, 17, 18, 19, 20, 21, 22, 23, 24, 25, 28, 29, 30, 31, 32, 33, 34, 35, 36, 37, 38, 39, 40, 41, 42, 43, 46, 47, 48, 49, 50, 51, 52, 53, 54, 55, 56, 57, 58, 59, 60, 61, 62, 63, 64, 65, 66, 67, 68, or 69.

Portions of proteins encoded by the nucleic acid molecule of the invention are preferably biologically active, preferably having above-mentioned annotated activity, e.g. conferring an increased herbicide tolerance or resistance, as compared to a corresponding, e.g. non-transformed, wild type plant cell, plant or part thereof after increase of activity.

As mentioned herein, the term "biologically active portion" is intended to include a portion, e.g., a domain/motif, that confers an increased herbicide tolerance or resistance, e.g. an increased herbicide tolerance or resistance-related trait, as compared to a corresponding, e.g. non-transformed, wild type plant cell, plant or part thereof or has an immunological activity such that it is binds to an antibody binding specifically to the polypeptide of the present invention or a polypeptide used in the process of the present invention for increasing herbicide tolerance or resistance, as compared to a corresponding, e.g. non-transformed, wild type plant cell, plant or part thereof.

The invention further relates to nucleic acid molecules that differ from one of the nucleotide sequences shown in SEQ ID NO: 1, 3, 5, 7, 26, or 44, or a homolog thereof (and portions thereof) due to degeneracy of the genetic code and thus encode a polypeptide of the present invention, in particular a polypeptide having above mentioned activity, e.g. as that polypeptides depicted by the sequence shown in SEQ ID NO: 2, 4, 6, 8, 27, or 45, or the functional homologues. Advantageously, the nucleic acid molecule of the invention comprises, or in an other embodiment has, a nucleotide sequence encoding a protein comprising, or in an other embodiment having, an amino acid sequence shown in SEQ ID NO: 2, 4, 6, 8, 27, or 45, or the functional homologues. In a still further embodiment, the nucleic acid molecule of the invention encodes a full length protein which is substantially homologous to an amino acid sequence shown in SEQ ID NO: 2, 4, 6, 8, 27, or 45, or the functional homologues.

In addition, it will be appreciated by those skilled in the art that DNA sequence polymorphisms that lead to changes in the amino acid sequences may exist within a population. Such genetic polymorphism in the gene encoding the polypeptide of the invention or comprising the nucleic acid molecule of the invention may exist among individuals within a population due to natural variation.

Nucleic acid molecules corresponding to natural variants homologues of a nucleic acid molecule of the invention, which can also be a cDNA, can be isolated based on their homology to the nucleic acid molecules disclosed herein using the nucleic acid molecule of the invention, or a portion thereof, as a hybridization probe according to standard hybridization techniques under stringent hybridization conditions.

Accordingly, in another embodiment, a nucleic acid molecule of the invention is at least 15, 20, 25 or 30 nucleotides in length. Preferably, it hybridizes under stringent conditions to a nucleic acid molecule comprising a nucleotide sequence of the nucleic acid molecule of the present invention or used in the process of the present invention, e.g. comprising the sequence shown in SEQ ID NO: 1, 3, 5, 7, 26, or 44, or a homolog thereof. The nucleic acid molecule is preferably at least 20, 30, 50, 100, 250 or more nucleotides in length.

The term "hybridizes under stringent conditions" is defined above. In one embodiment, the term "hybridizes under stringent conditions" is intended to describe conditions for hybridization and washing under which nucleotide sequences at least 30%, 40%, 50% or 65% identical to each other typically remain hybridized to each other. Preferably, the conditions are such that sequences at least about 70%, more preferably at least about 75% or 80%, and even more preferably at least about 85%, 90% or 95% or more identical to each other typically remain hybridized to each other.

Preferably, nucleic acid molecule of the invention that hybridizes under stringent conditions to a sequence shown in SEQ ID NO: 1, 3, 5, 7, 26, or 44, or a homolog thereof corresponds to a naturally-occurring nucleic acid molecule of the invention. As used herein, a "naturally-occurring" nucleic acid molecule refers to an RNA or DNA molecule having a nucleotide sequence that occurs in nature (e.g., encodes a natural protein). Preferably, the nucleic acid molecule encodes a natural protein having above-mentioned activity, e.g. conferring increasing herbicide tolerance or resistance, after increasing the expression or activity thereof or the activity of a protein of the invention or used in the process of the invention by for example expression the nucleic acid sequence of the gene product in the cytosol and/or in an organelle such as a plastid or mitochondria, preferably in plastids.

In addition to naturally-occurring variants of the sequences of the polypeptide or nucleic acid molecule of the invention as well as of the polypeptide or nucleic acid molecule used in the process of the invention that may exist in the population, the skilled artisan will further appreciate that changes can be introduced by mutation into a nucleotide sequence of the nucleic acid molecule encoding the polypeptide of the invention or used in the process of the present invention, thereby leading to changes in the amino acid sequence of the encoded said polypeptide, without altering the functional ability of the polypeptide, preferably not decreasing said activity.

For example, nucleotide substitutions leading to amino acid substitutions at "non-essential" amino acid residues can be made in a sequence of the nucleic acid molecule of the invention or used in the process of the invention, e.g. shown in SEQ ID NO: 1, 3, 5, 7, 26, or 44, or a homolog thereof.

A "non-essential" amino acid residue is a residue that can be altered from the wild-type sequence of one without altering the activity of said polypeptide, whereas an "essential" amino acid residue is required for an activity as mentioned above, e.g. leading to increasing herbicide tolerance or resistance, as compared to a corresponding, e.g. non-transformed, wild type plant cell, plant or part thereof in an organism after an increase of activity of the polypeptide. Other amino acid residues, however, (e.g., those that are not conserved or only semi-conserved in the domain having said activity) may not be essential for activity and thus are likely to be amenable to alteration without altering said activity.

Further, a person skilled in the art knows that the codon usage between organisms can differ. Therefore, he may adapt the codon usage in the nucleic acid molecule of the present invention to the usage of the organism or the cell compartment for example of the plastid or mitochondria in which the polynucleotide or polypeptide is expressed. In a particular preferred embodiment, codon-adapted nucleic acid molecules of the present invention comprise the sequence of SEQ ID NO: 70, 71, 72, 73, or 74, which represent codon-adapted nucleic acid molecules corresponding to SEQ ID NO: 1, 3, 5, 24, or 42, respectively.

Accordingly, the invention relates to nucleic acid molecules encoding a polypeptide having above-mentioned activity, in an organism or parts thereof by for example expression either in the cytosol or in an organelle such as a plastid or mitochondria or both, preferably in plastids that contain changes in amino acid residues that are not essential for said activity. Such polypeptides differ in amino acid sequence from a sequence contained in the sequences shown in SEQ ID NO: 2, 4, 6, 8, 27, or 45, or a homolog thereof yet retain said activity described herein. The nucleic acid molecule can comprise a nucleotide sequence encoding a polypeptide, wherein the polypeptide comprises an amino acid sequence at least about 50% identical to an amino acid sequence shown SEQ ID NO: 2, 4, 6, 8, 27, or 45, or a homolog thereof and is capable of participation in increasing herbicide tolerance or resistance, as compared to a corresponding, e.g. non-transformed, wild type plant cell, plant or part thereof after increasing its activity, e.g. its expression by for example expression either in the cytosol or in an organelle such as a plastid or mitochondria or both, preferably in plastids. Preferably, the protein encoded by the nucleic acid molecule is at least about 60% identical to the sequence shown in SEQ ID NO: 2, 4, 6, 8, 27, or 45, or a homolog thereof, more preferably at least about 70% identical to one of the sequences shown in SEQ ID NO: 2, 4, 6, 8, 27, or 45, or a homolog thereof, even more preferably at least about 80%, 90%, 95% homologous to the sequence shown in SEQ ID NO: 2, 4, 6, 8, 27, or 45, or a homolog thereof, and most preferably at least about 96%, 97%, 98%, or 99% identical to the sequence shown in SEQ ID NO: 2, 4, 6, 8, 27, or 45, or a homolog thereof.

To determine the percentage homology (=identity, herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions×100). The terms "homology" and "identity" are thus to be considered as synonyms.

For the determination of the percentage homology (=identity) of two or more amino acids or of two or more nucleotide sequences several computer software programs have been developed. The homology of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of homologies of different sequences is the standard blast program, which is included in the Biomax pedant software (Biomax, Munich, Federal Republic of Germany). This leads unfortunately sometimes to suboptimal results since blast does not always include complete sequences of the subject and the querry. Nevertheless as this program is very efficient it can be used for the comparison of a huge number of sequences. The following settings are typically used for such a comparisons of sequences: —p Program Name [String]; —d Database [String]; default=nr; —i Query File [File In]; default=stdin; —e Expectation value (E) [Real]; default=10.0; —m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; —o BLAST report Output File [File Out] Optional; default=stdout; —F Filter query sequence (DUST with blastn, SEG with others) [String]; default=T; —G Cost to open a gap (zero invokes default behavior) [Integer]; default=0; —E Cost to extend a gap (zero invokes default behavior) [Integer]; default=0; —X X dropoff value for gapped alignment (in bits) (zero invokes default behavior); blastn 30, megablast 20, tblastx 0, all others 15 [Integer];

default=0; —I Show GI's in deflines [T/F]; default=F; —q Penalty for a nucleotide mismatch (blastn only) [Integer]; default=-3; —r Reward for a nucleotide match (blastn only) [Integer]; default=1; —v Number of database sequences to show one-line descriptions for (V) [Integer]; default=500; —b Number of database sequence to show alignments for (B) [Integer]; default=250; —f Threshold for extending hits, default if zero; blastp 11, blastn 0, blastx 12, tblastn 13; tblastx 13, megablast 0 [Integer]; default=0; —g Perform gapped alignment (not available with tblastx) [T/F]; default=T; —Q Query Genetic code to use [Integer]; default=1; —D DB Genetic code (for tblast[nx] only) [Integer]; default=1; —a Number of processors to use [Integer]; default=1; —O SeqAlign file [File Out] Optional; —J Believe the query defline [T/F]; default=F; —M Matrix [String]; default=BLOSUM62; —W Word size, default if zero (blastn 11, megablast 28, all others 3) [Integer]; default=0; —z Effective length of the database (use zero for the real size) [Real]; default=0; —K Number of best hits from a region to keep (off by default, if used a value of 100 is recommended) [Integer]; default=0; —P 0 for multiple hit, 1 for single hit [Integer]; default=0; —Y Effective length of the search space (use zero for the real size) [Real]; default=0; —S Query strands to search against database (for blast[nx], and tblastx); 3 is both, 1 is top, 2 is bottom [Integer]; default=3; —T Produce HTML output [T/F]; default=F; —l Restrict search of database to list of GI's [String] Optional; —U Use lower case filtering of FASTA sequence [T/F] Optional; default=F; —y X dropoff value for ungapped extensions in bits (0.0 invokes default behavior); blastn 20, megablast 10, all others 7 [Real]; default=0.0; —Z X dropoff value for final gapped alignment in bits (0.0 invokes default behavior); blastn/megablast 50, tblastx 0, all others 25 [Integer]; default=0; —R PSI-TBLASTN checkpoint file [File In] Optional; —n MegaBlast search [T/F]; default=F; —L Location on query sequence [String] Optional; —A Multiple Hits window size, default if zero (blastn/megablast 0, all others 40 [Integer]; default=0; —w Frame shift penalty (OOF algorithm for blastx) [Integer]; default=0; —t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously, the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence homology are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which has 80% homology with sequence SEQ ID NO: 1 at the nucleic acid level is understood as meaning a sequence which, upon comparison with the sequence SEQ ID NO: 1 by the above program "Needle" with the above parameter set, has a 80% homology.

Homology between two polypeptides is understood as meaning the identity of the amino acid sequence over in each case the entire sequence length which is calculated by comparison with the aid of the above program "Needle" using Matrix: EBLOSUM62, Gap_penalty: 8.0, Extend_penalty: 2.0.

For example a sequence which has a 80% homology with sequence SEQ ID NO: 2 at the protein level is understood as meaning a sequence which, upon comparison with the sequence SEQ ID NO: 2 by the above program "Needle" with the above parameter set, has a 80% homology.

Functional equivalents derived from the nucleic acid sequence as shown in SEQ ID NO: 1, 3, 5, 7, 26, or 44, or a homolog thereof according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 2, 4, 6, 8, 27, or 45, or a homolog thereof according to the invention and encode polypeptides having essentially the same properties as the polypeptide as shown in SEQ ID NO: 2, 4, 6, 8, 27, or 45, or a homolog thereof.

Functional equivalents derived from one of the polypeptides as shown in SEQ ID NO: 2, 4, 6, 8, 27, or 45, or a homolog thereof according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 2, 4, 6, 8, 27, or 45, or a homolog thereof according to the invention and having essentially the same properties as the polypeptide as shown in SEQ ID NO: 2, 4, 6, 8, 27, or 45, or a homolog thereof.

"Essentially the same properties" of a functional equivalent is above all understood as meaning that the functional equivalent has above mentioned activity, by for example expression either in the cytosol or in an organelle such as a plastid or mitochondria or both, preferably in plastids while increasing the amount of protein, activity or function of said functional equivalent in an organism, e.g. a microorgansim, a plant or plant tissue or animal tissue, plant or animal cells or a part of the same.

A nucleic acid molecule encoding an homologous to a protein sequence of SEQ ID NO: 2, 4, 6, 8, 27, or 45, or a homolog thereof can be created by introducing one or more nucleotide substitutions, additions or deletions into a nucleotide sequence of the nucleic acid molecule of the present invention, in particular of SEQ ID NO: 1, 3, 5, 7, 26, or 44, or a homolog thereof such that one or more amino acid substitutions, additions or deletions are introduced into the encoded protein. Mutations can be introduced into the encoding sequences of SEQ ID NO: 1, 3, 5, 7, 26, or 44, or a homolog thereof by standard techniques, such as site-directed mutagenesis and PCR-mediated mutagenesis.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophane), beta-branched side chains (e.g., threonine, valine, isoleucine) and aromatic side chains (e.g., tyrosine, phenylalanine, tryptophane, histidine).

Thus, a predicted nonessential amino acid residue in a polypeptide of the invention or a polypeptide used in the process of the invention is preferably replaced with another amino acid residue from the same family. Alternatively, in another embodiment, mutations can be introduced randomly along all or part of a coding sequence of a nucleic acid molecule of the invention or used in the process of the invention, such as by saturation mutagenesis, and the resultant mutants can be screened for activity described herein to identify mutants that retain or even have increased above mentioned activity, e.g. conferring increased herbicide tolerance or resistance, as compared to a corresponding, e.g. non-transformed, wild type plant cell, plant or part thereof.

Following mutagenesis of one of the sequences as shown herein, the encoded protein can be expressed recombinantly and the activity of the protein can be determined using, for example, assays described herein.

The highest homology of the nucleic acid molecule used in the process according to the invention was found for the following database entries by Gap search.

Homologues of the nucleic acid sequences used, with the sequence shown in SEQ ID NO: 1, 3, 5, 7, 26, or 44, or a homolog thereof, comprise also allelic variants with at least approximately 30%, 35%, 40% or 45% homology, by preference at least approximately 50%, 60% or 70%, more preferably at least approximately 90%, 91%, 92%, 93%, 94% or 95% and even more preferably at least approximately 96%, 97%, 98%, 99% or more homology with one of the nucleotide sequences shown or the abovementioned derived nucleic acid sequences or their homologues, derivatives or analogues or parts of these. Allelic variants encompass in particular functional variants which can be obtained by deletion, insertion or substitution of nucleotides from the sequences shown, preferably from SEQ ID NO: 1, 3, 5, 7, 26, or 44, or a homolog thereof, or from the derived nucleic acid sequences, the intention being, however, that the enzyme activity or the biological activity of the resulting proteins synthesized is advantageously retained or increased.

In one embodiment of the present invention, the nucleic acid molecule of the invention or used in the process of the invention comprises the sequences shown in any of the SEQ ID NO: 1, 3, 5, 7, 26, or 44, or a homolog thereof. It is preferred that the nucleic acid molecule comprises as little as possible other nucleotides not shown in any one of SEQ ID NO: 1, 3, 5, 7, 26, or 44, or a homolog thereof. In one embodiment, the nucleic acid molecule comprises less than 500, 400, 300, 200, 100, 90, 80, 70, 60, 50 or 40 further nucleotides. In a further embodiment, the nucleic acid molecule comprises less than 30, 20 or 10 further nucleotides. In one embodiment, the nucleic acid molecule use in the process of the invention is identical to the sequences shown in SEQ ID NO: 1, 3, 5, 7, 26, or 44, or a homolog thereof.

Also preferred is that the nucleic acid molecule used in the process of the invention encodes a polypeptide comprising the sequence shown in SEQ ID NO: 2, 4, 6, 8, 27, or 45, or a homolog thereof. In one embodiment, the nucleic acid molecule encodes less than 150, 130, 100, 80, 60, 50, 40 or 30 further amino acids. In a further embodiment, the encoded polypeptide comprises less than 20, 15, 10, 9, 8, 7, 6 or 5 further amino acids. In one embodiment used in the inventive process, the encoded polypeptide is identical to the sequences shown in SEQ ID NO: 2, 4, 6, 8, 27, or 45, or a homolog thereof.

In one embodiment, the nucleic acid molecule of the invention or used in the process encodes a polypeptide comprising the sequence shown in SEQ ID NO: 2, 4, 6, 8, 27, or 45, or a homolog thereof comprises less than 100 further nucleotides. In a further embodiment, said nucleic acid molecule comprises less than 30 further nucleotides. In one embodiment, the nucleic acid molecule used in the process is identical to a coding sequence of the sequences shown in SEQ ID NO: 1, 3, 5, 7, 26, or 44, or a homolog thereof.

Polypeptides (=proteins), which still have the essential biological or enzymatic activity of the polypeptide of the present invention conferring increased herbicide tolerance or resistance, as compared to a corresponding, e.g. non-transformed, wild type plant cell, plant or part thereof i.e. whose activity is essentially not reduced, are polypeptides with at least 10% or 20%, by preference 30% or 40%, especially preferably 50% or 60%, very especially preferably 80% or 90 or more of the wild type biological activity or enzyme activity, advantageously, the activity is essentially not reduced in comparison with the activity of a polypeptide shown in SEQ ID NO: 2, 4, 6, 8, 27, or 45, or a homolog thereof expressed under identical conditions.

Homologues of SEQ ID NO: 1, 3, 5, 7, 26, or 44, or of the derived sequences of SEQ ID NO: 2, 4, 6, 8, 27, or 45, or a homolog thereof also mean truncated sequences, cDNA, single-stranded DNA or RNA of the coding and noncoding DNA sequence. Homologues of said sequences are also understood as meaning derivatives, which comprise noncoding regions such as, for example, UTRs, terminators, enhancers or promoter variants. The promoters upstream of the nucleotide sequences stated can be modified by one or more nucleotide substitution(s), insertion(s) and/or deletion(s) without, however, interfering with the functionality or activity either of the promoters, the open reading frame (=ORF) or with the 3'-regulatory region such as terminators or other 3'-regulatory regions, which are far away from the ORF. It is furthermore possible that the activity of the promoters is increased by modification of their sequence, or that they are replaced completely by more active promoters, even promoters from heterologous organisms. Appropriate promoters are known to the person skilled in the art and are mentioned herein below.

In addition to the nucleic acid molecules encoding the polypeptide according to the invention described above, another aspect of the invention pertains to negative regulators of the activity of a nucleic acid molecule comprising the sequence of SEQ ID NO: 1, 3, 5, 7, 26, or 44, or a homolog thereof. Antisense polynucleotides thereto are thought to inhibit the downregulating activity of those negative regulators by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a negative regulator of the activity of a nucleic acid molecules encoding a polypeptide having at least 80% sequence identity with the polypeptide selected from the group according to SEQ ID NO: 2, 4, 6, 8, 27, or 45, or a homolog thereof.

The antisense nucleic acid can be complementary to an entire negative regulator strand, or to only a portion thereof. In an embodiment, the antisense nucleic acid molecule is antisense to a "noncoding region" of the coding strand of a nucleotide sequence encoding the polypeptide according to the invention. The term "noncoding region" refers to 5' and 3' sequences that flank the coding region that are not translated into amino acids (i.e., also referred to as 5' and 3' untranslated regions). The antisense nucleic acid molecule can be complementary to only a portion of the noncoding region of a mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. Typically, the antisense molecules of the present invention comprise an RNA having 60-100% sequence identity with at least 14 consecutive nucleotides of a noncoding region of one of the nucleic acid of SEQ ID NO: 1, 3, 5, 7, 26, or 44, or a homolog thereof. Preferably, the sequence identity will be at least 70%, more preferably at least 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)-uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl)-uracil, acp3 and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual b-units, the strands run parallel to each other (Gaultier et al., Nucleic Acids. Res. 15, 6625 (1987)). The antisense nucleic acid molecule can also comprise a 2'-o-methylribonucleotide (Inoue et al., Nucleic Acids Res. 15, 6131 (1987)) or a chimeric RNA-DNA analogue (Inoue et al., FEBS Lett. 215, 327 (1987)).

The antisense nucleic acid molecules of the invention are typically administered to a cell or generated in situ such that they hybridize with or bind to cellular mRNA and/or genomic DNA. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of the polypeptide according to the invention polypeptide. By "ribozyme" is meant a catalytic RNA-based enzyme with ribonuclease activity which is capable of cleaving a single-stranded nucleic acid, such as an mRNA, to which it has a complementary region. Ribozymes (e.g., hammerhead ribozymes described in Haselhoff and Gerlach, Nature 334, 585 (1988)) can be used to catalytically cleave the mRNA transcripts to thereby inhibit translation of the mRNA. A ribozyme having specificity for the polypeptide according to the invention-encoding nucleic acid can be designed based upon the nucleotide sequence of the polypeptide according to the invention cDNA, as disclosed herein or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in the polypeptide according to the invention-encoding mRNA. See, e.g. U.S. Pat. Nos. 4,987,071 and 5,116,742 to Cech et al. alternatively, the mRNA can be used to select a catalytic RNA having a specific ribonuclease activity from a pool of RNA molecules. See, e.g. Bartel D., and Szostak J. W., Science 261, 1411 (1993). In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, e.g. U.S. Pat. Nos. 6,025,167, 5,773,260 and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide according to SEQ ID NO: 2, 4, 6, 8, 27, or 45, or a homolog thereof or a polypeptide having at least 70% sequence identity with a polypeptide according to SEQ ID NO: 2, 4, 6, 8, 27, or 45, or a homolog thereof. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides or ribonucleotide analogs, such as 2'-O-methyl ribosyl residues, or combinations thereof. See, e.g. U.S. Pat. Nos. 4,130,641 and 4,024,222. A dsRNA polyriboinosinic acid: polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g. U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., Science 238, 645 (1987), and Cooney et al., Science 241, 456 (1988)) and co-suppression (Napoli et al., The Plant Cell 2,279, 1990,) are known in the art. Partial and full-length cDNAs have been used for the c-osuppression of endogenous plant genes. See, e.g. U.S. Pat. Nos. 4,801,340, 5,034,323, 5,231,020, and 5,283,184; Van der Kroll et al., The Plant Cell 2, 291, (1990); Smith et al., Mol. Gen. Genetics 224, 477 (1990), and Napoli et al., The Plant Cell 2, 279 (1990).

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of one of the nucleic acids as depicted in SEQ ID NO: 1, 3, 5, 7, 26, or 44, or a homolog thereof. The regions of identity can comprise introns and and/or exons and untranslated regions. The introduced sense polynucleotide may be present in the plant cell transiently, or may be stably integrated into a plant chromosome or extra-chromosomal replicon.

Further, embodiment of the invention is an expression vector comprising a nucleic acid molecule comprising a nucleic acid molecule selected from the group consisting of:

(a) a nucleic acid molecule encoding the polypeptide comprising the sequence of SEQ ID NO: 2, 4, 6, 8, 27, or 45, or a homolog thereof;

(b) a nucleic acid molecule comprising the sequence of SEQ ID NO: 1, 3, 5, 7, 26, or 44, or a homolog thereof, (c) a nucleic acid molecule, which, as a result of the degeneracy of the genetic code, can be derived from a polypeptide sequence of SEQ ID NO: 2, 4, 6, 8, 27, or 45, or a homolog thereof, and confers increased herbicide tolerance or resistance, as compared to a corresponding, e.g. non-transformed, wild type plant cell, a plant or a part thereof;

(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1, 3, 5, 7, 26, or 44, or a homolog thereof, and confers increased herbicide tolerance or resistance, as compared to a corresponding, e.g. non-transformed, wild type plant cell, a plant or a part thereof;

(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the polypeptide encoded by the nucleic acid molecule of (a), (b), (c) or (d) and having the activity represented by a nucleic acid molecule comprising a polynucleotide of SEQ ID NO: 1, 3, 5, 7, 26, or 44, or a homolog thereof, and confers increased herbicide tolerance or resistance as compared to a corresponding, e.g. non-transformed, wild type plant cell, a plant or a part thereof;

(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;

(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide as depicted in SEQ ID NO: 1, 3, 5, 7, 26, or 44, or a homolog thereof;

(h) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having 15 nt, preferably 20 nt, 30 nt, 50 nt, 100 nt, 200 nt, 500 nt, 750 nt or 1000 nt or more of a nucleic acid molecule complementary to a nucleic acid molecule sequence characterized in (a) to (e) and encoding a polypeptide having the activity represented by a protein comprising a polypeptide as depicted SEQ ID NO: 2, 4, 6, 8, 27, or 45, or a homolog thereof.

The invention further provides an isolated recombinant expression vector comprising the nucleic acid molecule of the invention, wherein expression of the vector or nucleic acid molecule, respectively in a host cell results in an increased herbicide tolerance or resistance, as compared to the corresponding, e.g. non-transformed, wild type of the host cell.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* T-DNA such as the gene 3 known as octopine synthase of the Ti-plasmid pTiACH5 (Gielen et al., EMBO J. 3, 835 1(984)) or functional equivalents thereof but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., Nucl. Acids Research 15, 8693 (1987)).

Plant gene expression has to be operably linked to an appropriate promoter conferring gene expression in a timely, cell or tissue specific manner. Preferred are promoters driving constitutive expression (Benfey et al., EMBO J. 8, 2195 (1989)) like those derived from plant viruses like the 35 S CaMV (Franck et al., Cell 21, 285 (1980)), the 19S CaMV (see also U.S. Pat. No. 5,352,605 and PCT Application No. WO 84/02913) or plant promoters like those from Rubisco small subunit described in U.S. Pat. No. 4,962,028. Other promoters, e.g. super-promoter (Ni et al., Plant Journal 7, 661 (1995)), Ubiquitin promoter (Callis et al., J. Biol. Chem., 265, 12486 (1990); U.S. Pat. No. 5,510,474; U.S. Pat. No. 6,020,190; Kawalleck et al., Plant. Molecular Biology, 21, 673 (1993)) or 34S promoter (GenBank Accession numbers M59930 and X16673) were similar useful for the present invention and are known to a person skilled in the art. Developmental stage-preferred promoters are preferentially expressed at certain stages of development. Tissue and organ preferred promoters include those that are preferentially expressed in certain tissues or organs, such as leaves, roots, seeds, or xylem.

Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., BiEssays 10, 108 (1989). Examples of seed preferred promoters include, but are not limited to, cellulose synthase (celA), Cim1, gamma-zein, globulin-1, maize 19 kD zein (cZ19B1), and the like.

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086, 169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional advantageous regulatory sequences are, for example, included in the plant promoters such as CaMV/35S (Franck et al., Cell 21 285 (1980)), PRP1 (Ward et al., Plant. Mol. Biol. 22, 361 (1993)), SSU, OCS, lib4, usp, STLS1, B33, LEB4, nos, ubiquitin, napin or phaseolin promoter. Also advantageous in this connection are inducible promoters such as the promoters described in EP 388 186 (benzyl sulfonamide inducible), Gatz et al., Plant J. 2, 397 (1992) (tetracyclin inducible), EP-A-0 335 528 (abscisic acid inducible) or WO 93/21334 (ethanol or cyclohexenol inducible). Additional useful plant promoters are the cytoplasmic FBPase promoter or ST-LSI promoter of potato (Stockhaus et al., EMBO J. 8, 2445 (1989)), the phosphorybosyl phyrophoshate amido transferase promoter of *Glycine max* (gene bank accession No. U87999) or the node-specific promoter described in EP-A-0 249 676. Additional particularly advantageous promoters are seed specific promoters which can be used for monocotyledones or dicotyledones and are described in U.S. Pat. No. 5,608,152 (napin promoter from rapeseed), WO 98/45461 (phaseolin promoter from *Arabidopsis*), U.S. Pat. No. 5,504,200 (phaseolin promoter from *Phaseolus vulgaris*), WO 91/13980 (Bce4 promoter from *Brassica*) and Baeumlein et al., Plant J., 2 (2), 233 (1992) (LEB4 promoter from leguminosa). Said promoters are useful in dicotyledones. The following promoters are useful for example in monocotyledones Ipt-2- or Ipt-1-promoter from barley (WO 95/15389 and WO 95/23230) or hordein promoter from barley. Other useful promoters are described in WO 99/16890. It is possible in principle to use all natural promoters with their regulatory sequences like those mentioned above for the novel process. It is also possible and advantageous in addition to use synthetic promoters.

The gene construct may also comprise further genes which are to be inserted into the organisms and which are for example involved in herbicide tolerance or resistance increase. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of same promoter as the sequences of the nucleic acid of SEQ ID NO: 1, 3, 5, 7, 26, or 44, or their homologs.

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or over-expressed only after induction, or that it is immediately expressed and/or over-expressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

Other preferred sequences for use in plant gene expression cassettes are targeting-sequences necessary to direct the gene product in its appropriate cell compartment (for review see Kermode, Crit. Rev. Plant Sci. 15 (4), 285 (1996) and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, Annu. Rev. Plant Physiol. Plant Mol. Biol. 48, 89 (1997)). Chemically inducible promoters are especially suitable if gene expression is wanted to occur in a time specific manner.

Table 2 lists several examples of promoters that may be used to regulate transcription of the nucleic acid coding sequences of the present invention.

TABLE 2

Examples of tissue-specific and inducible promoters in plants

| Expression | Reference |
|---|---|
| Cor78 - Cold, drought, salt, ABA, wounding-inducible | Ishitani, et al., Plant Cell 9, 1935 (1997) Yamaguchi-Shinozaki and Shinozaki, Plant Cell 6, 251 (1994) |
| Rci2A - Cold, dehydration-inducible | Capel et al., Plant Physiol 115, 569 (1997) |
| Rd22 - Drought, salt | Yamaguchi-Shinozaki and Shinozaki, Mol. Gen. Genet. 238, 17 (1993) |
| Cor15A - Cold, dehydration, ABA | Baker et al., Plant Mol. Biol. 24, 701 (1994) |
| GH3 - Auxin inducible | Liu et al., Plant Cell 6, 645 (1994) |
| ARSK1 - Root, salt inducible | Hwang and Goodman, Plant J. 8, 37 (1995; |
| PtxA - Root, salt inducible | GenBank accession X67427 |
| SbHRGP3 - Root specific | Ahn et al., Plant Cell 8, 1477 (1998). |
| KST1 - Guard cell specific | Plesch et al., Plant Journal. 28(4), 455-(2001) |
| KAT1 - Guard cell specific | Plesch et al., Gene 249, 83 (2000) Nakamura et al., Plant Physiol. 109, 371 (1995) |
| salicylic acid inducible | PCT Application No. WO 95/19443 |
| tetracycline inducible | Gatz et al., Plant J. 2, 397 (1992) |
| Ethanol inducible | PCT Application No. WO 93/21334 |
| Pathogen inducible PRP1 | Ward et al., Plant. Mol. Biol. 22, 361-(1993) |
| Heat inducible hsp80 | U.S. Pat. No. 5,187,267 |
| Cold inducible alpha-amylase | PCT Application No. WO 96/12814 |
| Wound-inducible pinII | European Patent No. 375 091 |
| RD29A - salt-inducible | Yamaguchi-Shinozalei et al. Mol. Gen. Genet. 236, 331 (1993) |
| Plastid-specific viral RNA-polymerase | PCT Application No. WO 95/16783, PCT Application WO 97/06250 |

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, Cell 43, 729 (1985)).

In one embodiment, the language "substantially free of cellular material" includes preparations of a protein having less than about 30% (by dry weight) of contaminating material (also referred to herein as a "contaminating polypeptide"), more preferably less than about 20% of contaminating material, still more preferably less than about 10% of contaminating material, and most preferably less than about 5% contaminating material.

The nucleic acid molecules, polypeptides, polypeptide homologs, fusion polypeptides, primers, vectors, and host cells described herein can be used in one or more of the following methods: identification of S. cerevisiae, E. coli or Brassica napus, Glycine max, Zea mays or Oryza sativa and related organisms; mapping of genomes of organisms related to S. cerevisiae, E. coli; identification and localization of S. cerevisiae, E. coli or Brassica napus, Glycine max, Zea mays or Oryza sativa sequences of interest; evolutionary studies; determination of polypeptide regions required for function; modulation of a polypeptide activity; modulation of the metabolism of one or more cell functions; modulation of the transmembrane transport of one or more compounds; modulation of herbicide tolerance or resistance, and modulation of expression of polypeptide nucleic acids.

The nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

There are a number of mechanisms by which the alteration of the polypeptide of the invention may directly affect herbicide tolerance or resistance.

The effect of the genetic modification in plants regarding herbicide tolerance or resistance can be assessed by treating the modified plant with respective herbicides as, e.g., described in EXAMPLE 4, and then analyzing the growth characteristics and/or metabolism of the plant in comparison to non-modified plants. Such analysis techniques are well known to one skilled in the art, and include evaluation of the plant phenotype, dry weight, fresh weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, Vol. 17; Rehm et al., 1993 Biotechnology, Vol. 3, Chapter III: Product recovery and purification, page 469-714, VCH: Weinheim; Belter P. A. et al., 1988, Bioseparations: downstream processing for biotechnology, John Wiley and Sons; Kennedy J. F., and Cabral J.

M. S., 1992, Recovery processes for biological materials, John Wiley and Sons; Shaeiwitz J. A. and Henry J. D., 1988, Biochemical separations, in Ul-mann's Encyclopedia of Industrial Chemistry, Vol. B3, Chapter 11, page 1-27, VCH: Weinheim; and Dechow F. J., 1989, Separation and purification techniques in biotechnology, Noyes Publications).

For example, plant expression vectors comprising the nucleic acids disclosed herein, or fragments thereof, can be constructed and transformed into an appropriate plant cell such as rape, maize, cotton, rice, wheat, sugar cane, sugar beet, soy bean, *Arabidopsis thaliana*, potato, *Medicago truncatula*, etc., using standard protocols. The resulting transgenic cells and/or plants derived therefrom can then be assayed for generation or alteration of their herbicide tolerance or resistance.

The present invention also provides antibodies that specifically bind to the polypeptide according to the invention, or a portion thereof, as encoded by a nucleic acid described herein. Antibodies can be made by many well-known methods (see, e.g. Harlow and Lane, "Antibodies; A Laboratory Manual", Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., Bio/Technology 10, 163 (1992); Bebbington et al., Bio/Technology 10, 169 (1992).

Gene expression in plants is regulated by the interaction of protein transcription factors with specific nucleotide sequences within the regulatory region of a gene. One example of transcription factors are polypeptides that contain zinc finger (ZF) motifs. Each ZF module is approximately 30 amino acids long folded around a zinc ion. The DNA recognition domain of a ZF protein is a α-helical structure that inserts into the major grove of the DNA double helix. The module contains three amino acids that bind to the DNA with each amino acid contacting a single base pair in the target DNA sequence. ZF motifs are arranged in a modular repeating fashion to form a set of fingers that recognize a contiguous DNA sequence. For example, a three-fingered ZF motif will recognize 9 bp of DNA. Hundreds of proteins have been shown to contain ZF motifs with between 2 and 37 ZF modules in each protein (Isalan M. et al., Biochemistry 37 (35), 12026 (1998); Moore M. et al., Proc. Natl. Acad. Sci. USA 98 (4), 1432 (2001) and Moore M. et al., Proc. Natl. Acad. Sci. USA 98 (4), 1437 (2001); US patents U.S. Pat. No. 6,007,988 and U.S. Pat. No. 6,013,453).

The regulatory region of a plant gene contains many short DNA sequences (cis-acting elements) that serve as recognition domains for transcription factors, including ZF proteins. Similar recognition domains in different genes allow the coordinate expression of several genes encoding enzymes in a metabolic pathway by common transcription factors. Variation in the recognition domains among members of a gene family facilitates differences in gene expression within the same gene family, for example, among tissues and stages of development and in response to environmental conditions.

Typical ZF proteins contain not only a DNA recognition domain but also a functional domain that enables the ZF protein to activate or repress transcription of a specific gene. Experimentally, an activation domain has been used to activate transcription of the target gene (U.S. Pat. No. 5,789,538 and patent application WO 95/19431), but it is also possible to link a transcription repressor domain to the ZF and thereby inhibit transcription (patent applications WO 00/47754 and WO 01/002019). It has been reported that an enzymatic function such as nucleic acid cleavage can be linked to the ZF (patent application WO 00/20622).

The invention provides a method that allows one skilled in the art to isolate the regulatory region of one or more polypeptide according to the invention-encoding genes from the genome of a plant cell and to design zinc finger transcription factors linked to a functional domain that will interact with the regulatory region of the gene. The interaction of the zinc finger protein with the plant gene can be designed in such a manner as to alter expression of the gene and preferably thereby to confer increasing herbicide tolerance or resistance.

In particular, the invention provides a method of producing a transgenic plant with a coding nucleic acid, wherein expression of the nucleic acid(s) in the plant results in in increasing herbicide tolerance or resistance, as compared to a wild type plant comprising: (a) transforming a plant cell with an expression vector comprising a encoding nucleic acid, and (b) generating from the plant cell a transgenic plant with enhanced increased herbicide tolerance or resistance as compared to a wild type plant. For such plant transformation, binary vectors such as pBinAR can be used (Höfgen and Willmitzer, Plant Science 66, 221 (1990)). Moreover suitable binary vectors are for example pBIN19, pBI101, pGPTV or pPZP (Hajukiewicz P. et al., Plant Mol. Biol., 25, 989 (1994)).

Alternate methods of transfection include the direct transfer of DNA into developing flowers via electroporation or *Agrobacterium* mediated gene transfer. *Agrobacterium* mediated plant transformation can be performed using for example the GV3101 (pMP90) (Koncz and Schell, Mol. Gen. Genet. 204, 383 (1986)) or LBA4404 (Ooms et al., Plasmid, 7, 15 (1982); Hoekema et al., Nature, 303, 179 (1983)) *Agrobacterium tumefaciens* strain. Transformation can be performed by standard transformation and regeneration techniques (Deblaere et al., Nucl. Acids. Res. 13, 4777 (1994); Gelvin and Schilperoort, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick B. R. and Thompson J. E., Methods in Plant Molecular Biology and Biotechnology, Boca Raton: CRC Press, 1993.-360 S., ISBN 0-8493-5164-2). For example, rapeseed can be transformed via cotyledon or hypocotyl transformation (Moloney et al., Plant Cell Reports 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994)). Additionally, transformation of soybean can be performed using for example a technique described in European Patent No. 424 047, U.S. Pat. No. 5,322,783, European Patent No. 397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique (see, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

As described above, the present invention teaches compositions and methods for increasing the herbicide tolerance of a crop plant or seed as compared to a wild-type variety of the plant or seed. In a preferred embodiment, the herbicide tolerance of a crop plant or seed is increased such that the plant or seed can withstand a herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Post-emergent weed control methods useful in various embodiments hereof utilize about >0.3× application rates of herbicides; in some embodiments, this can be about, for example, >0.3×, >0.4×, >0.5×, >0.6×, >0.7×, >0.8×, >0.9×, or >1× of herbicides. In one embodiment, herbicide-tolerant plants of the present invention have tolerance to a post-emergant application of a herbicide at an amount of about 25 to about 200 g ai/ha. In some embodiments, wherein the herbicide-tolerant plant is a dicot (e.g., soy, cotton), the post-emergant application of the herbicides is at an amount of about 50 g ai/ha. In another embodiment, wherein the herbicide-tolerant plant is a monocot (e.g., maize, rice, sorghum), the post-emergant application of the herbicides is at an amount of about 200 g ai/ha. In other embodiments, wherein the herbicides-tolerant plant is a Brassica (e.g., canola), the post-emergant application of the herbicides is at an amount of about 25 g ai/ha. In post-emergent weed control methods hereof, in some embodiments, the method can utilize herbicides application rates at about 7 to 10 days post-emergent. In another embodiment, the application rate can exceed Ix herbicides; in some embodiments, the rate can be up to 4× herbicides, though more typically it will be about 2.5× or less, or about 2× or less, or about 1× or less.

Furthermore, the present invention provides methods that involve the use of at least one herbicide, optionally in combination with one or more other herbicidal compounds, and, optionally, a safener, as described in detail supra.

In these methods, the herbicide can be applied by any method known in the art including, but not limited to, seed treatment, soil treatment, and foliar treatment. Prior to application, the herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to herbicide, a wide variety of formulations can be employed for protecting plants from weeds, so as to enhance plant growth and reduce competition for nutrients. A herbicide can be used by itself for pre-emergence, post-emergence, pre-planting, and at-planting control of weeds in areas surrounding the crop plants described herein, or a herbicide formulation can be used that contains other additives. The herbicide can also be used as a seed treatment. Additives found in a herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates, and liquid concentrates. The herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

Herbicide-tolerant plants of the invention can be used in conjunction with an herbicide to which they are tolerant. Herbicides can be applied to the plants of the invention using any techniques known to those skilled in the art. Herbicides can be applied at any point in the plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergent application of herbicides. In one embodiment, the post-emergent application of the herbicides is about 7 to 10 days following planting of safener-treated seeds. In some embodiments, the safener is cloquintocet, dichlormid, fluxofenim, or combinations thereof.

Methods of Controlling Weeds or Undesired Vegetation

In other aspects, the present invention provides a method for controlling weeds at a locus for growth of a plant or plant part thereof, the method comprising: applying a composition comprising a herbicides to the locus.

In some aspects, the present invention provides a method for controlling weeds at a locus for growth of a plant, the method comprising: applying an herbicide composition to the locus; wherein said locus is: (a) a locus that contains: a plant or a seed capable of producing said plant; or (b) a locus that is to be after said applying is made to contain the plant or the seed; wherein the plant or the seed comprises in at least some of its cells a recombinant polynucleotide operably linked to a promoter operable in plant cells, the promoter capable of expressing a Alopecurus CYP450 polypeptide encoded by the polynucleotide and comprising the sequence of SEQ ID NO: 2, 4, 6, 8, 27, or 45, or a homolog thereof, the expression of said Alopecurus CYP450 polypeptide conferring to the plant tolerance to herbicides.

The present invention further provides a method for controlling weeds at a locus for growth of a plant, the method comprising: applying an herbicidal composition to the locus; wherein said locus is: (a) a locus that contains: a plant or a seed capable of producing said plant; or (b) a locus that is to be after said applying is made to contain the plant or the seed; wherein the plant or the seed comprises in at least some of its cells a recombinant polynucleotide operably linked to a promoter operable in plant cells, the promoter capable of expressing a Alopecurus CYP450 polypeptide encoded by the polynucleotide and comprising the sequence of SEQ ID NO: 2, 4, 6, 8, 27, or 45, or a homolog thereof, the expression of the Alopecurus CYP450 polypeptide conferring to the plant tolerance to herbicides Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides can be used to control the growth of weeds that may be found growing in the vicinity of the herbicide-tolerant plants invention. In embodiments of this type, an herbicide can be applied to a plot in which herbicide-tolerant plants of the invention are growing in vicinity to weeds. An herbicide to which the herbicide-tolerant plant of the invention is tolerant can then be applied to the plot at a concentration sufficient to kill or inhibit the growth of the weed. Concentrations of herbicide sufficient to kill or inhibit the growth of weeds are known in the art and are disclosed above.

In other embodiments, the present invention provides a method for controlling weeds in the vicinity of a herbicides-tolerant plant of the invention. The method comprises applying an effective amount of a herbicides to the weeds and to the auxinic herbicide-tolerant plant, wherein the plant has increased tolerance to auxinic herbicide when compared to a wild-type plant. In some embodiments, the herbicides-tolerant plants of the invention are preferably crop plants, including, but not limited to, sunflower, alfalfa, *Brassica* sp., soybean, cotton, safflower, peanut, tobacco, tomato, potato, wheat, rice, maize, *sorghum*, barley, rye, millet, and *sorghum*.

In other aspects, herbicide(s) can also be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed Treatment formulations may additionally comprise binders and optionally colorants.

Binders can be added to improve the adhesion of the active materials on the seeds after treatment. In one embodiments, suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers. Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The term seed treatment comprises all suitable seed treatment techniques known in the art, such as seed dressing, seed coating, seed dusting, seed soaking, and seed pelleting. In one embodiment, the present invention provides a method of treating soil by the application, in particular into the seed drill: either of a granular formulation containing the herbicides as a composition/formulation (e.g., a granular formulation), with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising one herbicide and, optionally, at least one other herbicide such as, e.g., an AHAS-inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In some embodiments, the seed treatment application with herbicides or with a formulation comprising the herbicides is carried out by spraying or dusting the seeds before sowing of the plants and before emergence of the plants.

In other embodiments, in the treatment of seeds, the corresponding formulations are applied by treating the seeds with an effective amount of herbicides or a formulation comprising the herbicides.

In other aspects, the present invention provides a method for combating undesired vegetation or controlling weeds comprising contacting the seeds of the herbicides-tolerant plants of the present invention before sowing and/or after pregermination with herbicides. The method can further comprise sowing the seeds, for example, in soil in a field or in a potting medium in greenhouse. The method finds particular use in combating undesired vegetation or controlling weeds in the immediate vicinity of the seed. The control of undesired vegetation is understood as the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepiclium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solarium, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In other embodiments, in the treatment of seeds, the corresponding formulations are applied by treating the seeds with an effective amount of herbicides or a formulation comprising the herbicides.

In still further aspects, treatment of loci, plants, plant parts, or seeds of the present invention comprises application of an agronomically acceptable composition that does not contain an A.I. In one embodiment, the treatment comprises application of an agronomically acceptable composition that does not contain a herbicides A.I. In some embodiments, the treatment comprises application of an agronomically acceptable composition that does not contain a herbicides A.I., wherein the composition comprises one or more of agronomically-acceptable carriers, diluents, excipients, plant growth regulators, and the like. In other embodiments, the treatment comprises application of an agronomically acceptable composition that does not contain a herbicides A.I., wherein the composition comprises an adjuvant. In one embodiment, the adjuvant is a surfactant, a spreader, a sticker, a penetrant, a drift-control agent, a crop oil, an emulsifier, a compatibility agent, or combinations thereof.

In one embodiment, the present invention relates to a method for the identification of a gene product conferring in increasing herbicide tolerance or resistance, as compared to a corresponding, e.g. non-transformed, wild type cell in a cell of an organism for example plant, comprising the following steps:
(a) contacting, e.g. hybridizing, some or all nucleic acid molecules of a sample, e.g. cells, tissues, plants or microorganisms or a nucleic acid library, which can contain a candidate gene encoding a gene product conferring increased herbicide tolerance or resistance with a nucleic acid molecule as shown in SEQ ID NO: 1, 3, 5, 7, 26, or 44, or a functional homologue thereof;
(b) identifying the nucleic acid molecules, which hybridize under relaxed stringent conditions with said nucleic acid molecule, in particular to the nucleic acid molecule sequence shown in SEQ ID NO: 1, 3, 5, 7, 26, or 44, or a homolog thereof, and, optionally, isolating the full length cDNA clone or complete genomic clone;
(c) identifying the candidate nucleic acid molecules or a fragment thereof in host cells, preferably in a plant cell;
(d) increasing the expressing of the identified nucleic acid molecules in the host cells for which increased herbicide tolerance or resistance are desired;
(e) assaying the level of increased herbicide tolerance or resistance of the host cells; and
(f) identifying the nucleic acid molecule and its gene product which confers increased herbicide tolerance or resistance, in the host cell compared to the wild type.

Relaxed hybridization conditions are: After standard hybridization procedures washing steps can be performed at low to medium stringency conditions usually with washing conditions of 40°-55° C. and salt conditions between 2×SSC and 0.2×SSC with 0.1% SDS in comparison to stringent washing conditions as e.g. 60° to 68° C. with 0.1% SDS. Further examples can be found in the references listed above for the stringend hybridization conditions. Usually washing steps are repeated with increasing stringency and length until a useful signal to noise ratio is detected and depend on many factors as the target, e.g. its purity, GC-content, size etc, the probe, e.g. its length, is it a RNA or a DNA probe, salt conditions, washing or hybridization temperature, washing or hybridization time etc.

In another embodiment, the present invention relates to a method for the identification of a gene product the expression of which confers increased herbicide tolerance or resistance, in a cell, comprising the following steps:
(a) identifying a nucleic acid molecule in an organism, which is at least 20%, preferably 25%, more preferably 30%, even more preferred are 35%. 40% or 50%, even more preferred are 60%, 70% or 80%, most preferred are 90% or 95% or more homolog to the nucleic acid molecule as shown in SEQ ID NO: 2, 4, 6, 8, 27, or 45, or a homolog thereofor being encoded by a nucleic acid molecule comprising a polynucleotide as shown in SEQ ID NO: 1, 3, 5, 7, 26, or 44, or a homologue thereof as described herein, for example via homology search in a data bank;
(b) enhancing the expression of the identified nucleic acid molecules in the host cells;
(c) assaying the level of enhancement of in increasing herbicide tolerance or resistance, in the host cells; and
(d) identifying the host cell, in which the enhanced expression confers in increasing herbicide tolerance or resistance, in the host cell compared to a wild type.

Further, the nucleic acid molecule disclosed herein, in particular the nucleic acid molecule shown in SEQ ID NO: 1, 3, 5, 7, 26, or 44, may be sufficiently homologous to the sequences of related species such that these nucleic acid molecules may serve as markers for the construction of a genomic map in related organism or for association mapping. Furthermore natural variation in the genomic regions corresponding to nucleic acids disclosed herein, in particular the nucleic acid molecule shown in SEQ ID NO: 1, 3, 5, 7, 26, or 44, or homologous thereof may lead to variation in the activity of the proteins disclosed herein, in particular the proteins comprising polypeptides as shown in SEQ ID NO: 2, 4, 6, 8, 27, or 45, and their homolgous and in consequence in a natural variation of an increased herbicide tolerance or resistance.

In consequence natural variation eventually also exists in form of more active allelic variants leading already to a relative increase in herbicide tolerance or resistance. Different variants of the nucleic acids molecule disclosed herein, in particular the nucleic acid comprising the nucleic acid molecule as shown SEQ ID NO: 1, 3, 5, 7, 26, or 44, or a homolog thereof, which corresponds to different levels of increased herbicide tolerance or resistance can be identified and used for marker assisted breeding for an increased herbicide tolerance or resistance, Accordingly, the present invention relates to a method for breeding plants with an increased herbicide tolerance or resistance, comprising
(a) selecting a first plant variety with an increased herbicide tolerance or resistance, based on increased expression of a nucleic acid of the invention as disclosed herein, in particular of a nucleic acid molecule comprising a nucleic acid molecule as shown in SEQ ID NO: 1, 3, 5, 7, 26, or 44, or a homolog thereof, or a polypeptide comprising a polypeptide as shown in SEQ ID NO: 2, 4, 6, 8, 27, or 45, or a homolog thereof, or a homologue thereof as described herein;
(b) associating the level of increased herbicide tolerance or resistance with the expression level or the genomic structure of a gene encoding said polypeptide or said nucleic acid molecule;
(c) crossing the first plant variety with a second plant variety, which significantly differs in its level of increased herbicide tolerance or resistance; and
(d) identifying, which of the offspring varieties has got increased levels of herbicide tolerance or resistance, In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a herbicidal composition to the descendent plant.

In another embodiment, the invention refers to harvestable parts of the transgenic plant according to the present invention. Preferably, the harvestable parts comprise the CYP450 nucleic acid or CYP450 protein of the present invention. The harvestable parts may be seeds, roots, leaves and/or flowers comprising the CYP450 nucleic acid or CYP450 protein or parts thereof. Preferred parts of soy plants are soy beans comprising the CYP450 nucleic acid or CYP450 protein of the present invention.

In another embodiment, the invention refers to products derived from a transgenic plant according to the present invention, parts thereof or harvestable parts thereof. A preferred plant product is fodder, seed meal, oil, or seed-treatment-coated seeds. Preferably, the meal and/or oil comprises the CYP450 nucleic acids or CYP450 proteins according to the present invention.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

In another embodiment, the present invention relates to a kit comprising the nucleic acid molecule, the vector, the host cell, the polypeptide, or the antisense, RNAi, snRNA, dsRNA, siRNA, miRNA, ta-siRNA, cosuppression molecule, or ribozyme molecule, or the viral nucleic acid molecule, the antibody, plant cell, the plant or plant tissue, the harvestable part, the propagation material and/or the compound and/or agonist identified according to the method of the invention.

The compounds of the kit of the present invention may be packaged in containers such as vials, optionally with/in buffers and/or solution. If appropriate, one or more of said components might be packaged in one and the same container. Additionally or alternatively, one or more of said components might be adsorbed to a solid support as, e.g. a nitrocellulose filter, a glas plate, a chip, or a nylon membrane or to the well of a micro titerplate. The kit can be used for any of the herein described methods and embodiments, e.g. for the production of the host cells, transgenic plants, pharmaceutical compositions, detection of homologous sequences, identification of antagonists or agonists, as food or feed or as a supplement thereof or as supplement for the treating of plants, etc. Further, the kit can comprise instructions for the use of the kit for any of said embodiments. In one embodiment said kit comprises further a nucleic acid molecule encoding one or more of the aforementioned protein, and/or an antibody, a vector, a host cell, an antisense nucleic acid, a plant cell or plant tissue or a plant. In another embodiment said kit comprises PCR primers to detect and discriminate the nucleic acid molecule to be reduced in the process of the invention, e.g. of the nucleic acid molecule of the invention.

In a further embodiment, the present invention relates to a method for the production of an agricultural composition providing the nucleic acid molecule for the use according to the process of the invention, the nucleic acid molecule of the invention, the vector of the invention, the antisense, RNAi, snRNA, dsRNA, siRNA, miRNA, ta-siRNA, cosuppression molecule, ribozyme, or antibody of the invention, the viral nucleic acid molecule of the invention, or the polypeptide of the invention or comprising the steps of the method according to the invention for the identification of said compound or agonist; and formulating the nucleic acid molecule, the vector or the polypeptide of the invention or the agonist, or compound identified according to the methods or processes of the present invention or with use of the subject matters of the present invention in a form applicable as plant agricultural composition.

In another embodiment, the present invention relates to a method for the production of the plant culture composition comprising the steps of the method of the present invention; and formulating the compound identified in a form acceptable as agricultural composition.

Under "acceptable as agricultural composition" is understood, that such a composition is in agreement with the laws regulating the content of fungicides, plant nutrients, herbicides, etc. Preferably such a composition is without any harm for the protected plants and the animals (humans included) fed therewith. Said polypeptide or nucleic acid molecule or the genomic structure of the genes encoding said polypeptide or nucleic acid molecule of the invention.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes and variations may be made therein without departing from the scope of the invention. The invention is further illustrated by the following examples, which are not to be construed in any way as limiting. On the contrary, it is to be clearly understood that various other embodiments, modifications and equivalents thereof, which, after reading the description herein, may suggest themselves to those skilled in the art without departing from the spirit of the present invention and/or the scope of the claims.

In one embodiment, the increased herbicide tolerance or resistance results in an increase of the production of a specific ingredient including, without limitation, an enhanced and/or improved sugar content or sugar composition, an enhanced or improved starch content and/or starch composition, an enhanced and/or improved oil content and/or oil composition (such as enhanced seed oil content), an enhanced or improved protein content and/or protein composition (such as enhanced seed protein content), an enhanced and/or improved vitamin content and/or vitamin composition, or the like.

EXAMPLES

Example 1: Identification of Genes Encoding Enzymes with Activity Towards Compound Metabolism Isolation of RNA and cDNA Synthesis Leaf tissue of *Alopecurus myosuroides* was harvested, frozen and grounded in liquid nitrogen and total RNA was extracted using an Ambion RNAqueous-Midi kit (AM1911, Ambion) with the Plant RNA Isolation Aid (AM9690, Ambion) as per manufacturer's recommendation. The last elution was done with 10 ul of elution solution. To validate the quality of the extracted RNA 1 uL of the final product was run on a Bioanalyzer 2100 using the RNA 6000 Nano kit with the Plant RNA Nano method. The final solution, containing purified RNA, was stored at −80° C. until library preparation. RNA sequencing libraries were produced using Illumina TruSeq RNA Sample preparation kits V2 (RS-122-2001) from Illumina according to the instructions of the manufacturer. Briefly, 1 μg of total RNA was first purified twice on a poly-dT column. During the second elution step, RNA was fragmented and primed for cDNA synthesis. The material was reverse transcribed, RNA was removed and the second strand was produced. After rendering the ends of the fragment blunt, 3' ends were adenylated and Illumina sequencing-specific bar-coded adaptors were ligated at both ends of the fragments. The DNA fragments bearing adaptors at both ends were enriched by 15 cycle PCR amplification. Libraries are pooled prior to sequencing.

Sequencing

The pooled libraries were first put on a flowcell using a TruSeq PE Cluster kit V3 (PE-401-3001) on the cBot and clusters are amplified on the device. Afterwards, the flowcell is transferred onto the Illumina Hiseq machine and the material on the flowcell is then sequenced using Illumina TruSeq SBS Kit V3 (FC-401-3001) as per manufacturer's recommendation.

EST Assembly and Calculation of Expression Level

The quality of the data produced by the Illumina Hiseq sequencer was evaluated using FASTQC (http://www.bioinformatics.babraham.ac.uk/projects/fastqc/). These sequences were further analyzed to remove any Illumina adaptor sequences and trimmed to remove sequences or parts of sequences not meeting a minimal quality threshold of 15 using CutAdapt (http://code.google.com/p/cutadapt/). Sequence reads were assembled using CLC bio algorithm (version 4.01). Short read alignments were performed using the software Tophat (http://tophat.cbcb.umd.edu/) and expression values were calculated and compared using Cufflinks (http://cufflinks.cbcb.umd.edu/).

Example 2. Detection of Herbicide Degradation by Biochemical Assay

Yeast Expression System:

The cDNA of CYP450 monooxygenase genes were synthesized with an optimized codon usage for yeast, cloned via uniqueBamHI-SalI restriction sites in the low copy pESC-ura expression vector (Agilent Technologies). Constructs were transformed into *S. cerevisiae* wild type strain BJ5459 (MATa ura3-5 trp lys2-801 leu2Δ1 his3Δ200 pep4Δ::HIS3 prb1Δ1.6R can1 GAL cir$^+$; ATCC 208284) using a Yeast Maker Transformation System from Clontech and verified by colony PCR. Positive clones were selected on minimal synthetic-defined media (SD) supplemented with appropriate dropout solution. The strain had no obvious phenotypes. Cells were induced in SG-Ura medium (same composition as SD but with galactose instead of glucose) for 24 h (Pompon et al., Methods in Enzymology 272:51-64 (1996); Urban et al., Eur. J. Biochem. 222:853-850 (1994)). Optimal heterologous protein expression was assayed using Western Blot analysis.

Analysis of Xenobiotic Metabolism:

96 deep well growth plates (STARLAB GmbH) charged with 700 μL SDA medium are inoculated with the respective yeast strains from cryostock and incubated at 30° C., 400 rpm. After 48 h, an aliquot is transferred into a new plate with fresh SDA medium 400 rpm. After 4 h the cultures are spun down, the supernatant discarded and the pellets resuspended in 700 μL pre-warmed SGA media to induce protein expression at 30° C. and 400 rpm. After an incubation time of 24 h, 7 μL herbicide solution (500 μM DMSO stock solution) or solvent control is added to the yeast culture incubated for additional 24 h. The herbicide conversion is stopped by adding 700 μL acetonitrile followed by ultrasonification. The homogenate is prepared for UPLC-MS/MS analysis. The degradation rate was calculated by the determination of the recovery of the herbicide in reference to the control.

The Results are Shown in the Following Table 3:

TABLE 3

Degradation rate of listed herbicidal compounds within 24 h in transgenic yeast cells expressing cytochrome P450 gene of interest

| Name | Seq ID | | | | |
|---|---|---|---|---|---|
| | 4 AmCYP03_1 | 6 AmCYP03b | 27 AmCYP04 | 45 AmCYP12_1 | 2 AmCYP01 |
| 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione | 23 | 21 | 24 | 20 | 17 |

TABLE 3-continued

Degradation rate of listed herbicidal compounds within 24 h in transgenic yeast cells expressing cytochrome P450 gene of interest

| Name | Seq ID 4 AmCYP03_1 | 6 AmCYP03b | 27 AmCYP04 | 45 AmCYP12_1 | 2 AmCYP01 |
|---|---|---|---|---|---|
| Coumarone-derivative 1 | 25 | 18 | 31 | 10 | 0 |
| Chlorotoluron | 32 | 29 | 26 | 22 | 18 |
| pendimethalin | 24 | 24 | 25 | 16 | 13 |
| saflufenacil | 10 | 9 | 18 | 20 | 20 |
| Coumarone-derivative 2 | 16 | 7 | 0 | 24 | 0 |
| Coumarone-derivative 3 | 0 | 0 | 9 | 27 | 0 |
| Coumarone-derivative 4 | 4 | 7 | 12 | 4 | 0 |
| Coumarone-derivative 5 | 2 | 17 | 22 | 15 | 14 |
| Coumarone-derivative 6 | 2 | 0 | 0 | 4 | 1 |
| Coumarone-derivative 7 | 14 | 6 | 7 | 5 | 0 |
| Coumarone-derivative 8 | 10 | 0 | 0 | 3 | 0 |
| Coumarone-derivative 9 | 12 | 5 | 18 | 0 | 0 |
| Coumarone-derivative 10 | 15 | 9 | 19 | 0 | 0 |
| Coumarone-derivative 11 | 0 | 18 | 0 | 0 | 0 |

Legend to Coumarone-Derivatives 1-11 of Table 3 (IUPAC Nomenclature)

1. 1-(2,2-difluoroethyl)-2,2-dioxo-3-(2,4,6-trichloro-3-pyridyl)pyrido[3,2-c]thiazin-4-ol
2. 4-[1-(2,2-difluoroethyl)-4-hydroxy-2,2-dioxo-pyrido[3,2-c]thiazin-3-yl]-3-(trifluoromethyl)benzonitrile
3. 6,6-dioxo-7-[2-(trifluoromethyl)phenyl]-5H-thiopyrano[4,3-b]pyridin-8-ol
4. 3-[2-chloro-6-(trifluoromethyl)phenyl]-2,2-dioxo-oxathiino[5,6-b]pyridin-4-ol
5. 7-(2,6-dichloro-3-pyridyl)-5,5-dimethyl-6,6-dioxo-thiopyrano[4,3-b]pyridin-8-ol
6. 7-[2,4-dichloro-3-(3-methyl-4,5-dihydroisoxazol-5-yl)phenyl]-5,5-dimethyl-6,6-dioxo-thiopyrano[4,3-b]pyridin-8-ol
7. 7-[2,4-dichloro-3-(2-methoxyethoxymethyl)phenyl]-5,5-dimethyl-6,6-dioxo-thiopyrano[4,3-b]pyridin-8-ol
8. 7-[6-methoxy-2-(trifluoromethyl)-3-pyridyl]-5,5-dimethyl-6,6-dioxo-thiopyrano[4,3-b]pyridin-8-ol
9. 1-(2,2-difluoroethyl)-2,2-dioxo-3-(2,4,6-trichloro-3-pyridyl)pyrido[3,2-c]thiazin-4-ol
10. N-[2,6-dichloro-3-(8-hydroxy-5,5-dimethyl-6,6-dioxo-thiopyrano[4,3-b]pyridin-7-yl)phenyl]-N-methyl-methanesulfonamide
11. 7-(3,6-dichloro-2-methyl-phenyl)-5,5-dimethyl-6,6-dioxo-thiopyrano[4,3-b]pyridin-8-ol Example 3. Engineering Herbicide Tolerant Plants Having Additional Cytochrome P450 Genes Herbicide tolerant soybean (*Glycine max*) or corn (*Zea mays*) plants are generated as described by Olhoft et al. (US patent 2009/0049567). For transformation of soybean or *Arabidopsis thaliana*, CYP450 monooxygenase genes of the present invention are cloned with standard cloning techniques as described in Sambrook et al. (Molecular cloning (2001) Cold Spring Harbor Laboratory Press) in a binary vector containing resistance marker gene cassette (AHAS) and CYP450 monooxygenase sequence (marked as GOI) in between ubiquitin promoter (PcUbi) and nopaline synthase terminator (NOS) sequence. For corn transformation, CYP450 monooxygenase sequences are cloned with standard cloning techniques as described in Sambrook et al. (Molecular cloning (2001) Cold Spring Harbor Laboratory Press) in a binary vector containing resistance marker gene cassette (AHAS) and CYP450 monooxygenase sequence (marked as GOI) in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with Agrobacteria, the explants are transferred to shoot introduction media without selection for one week. The explants were subsequently transferred to a shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing CYP450 monooxygenase sequences are introduced into maize immature embryos via *Agrobacterium*-mediated transformation.

Transformed cells were selected in selection media supplemented with 0.5-1.5 μM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse Arabidopsis thaliana are transformed with CYP450 monooxygenase sequences by floral dip method as described by McElver and Singh (WO 2008/124495). Transgenic Arabidopsis plants were subjected to TaqMan analysis for analysis of the number of integration loci. Transformation of Oryza sativa (rice) are done by protoplast transformation as described by Peng et al. (U.S. Pat. No. 6,653,529)

Example 4: Demonstration of Herbicide Tolerance

T0 or T1 transgenic plant of soybean, corn, and rice containing CYP450 monooxygenase sequences are tested for improved tolerance to herbicides in greenhouse studies and mini-plot studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), flumioxazin, butafenacil, acifluorfen, lactofen, bifenox, diuron, sulfentrazone, tepraloxydim, coumarone-derivative herbicides, azine-derivative herbicides.

For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly and grown in the same containers, or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Figure 2:
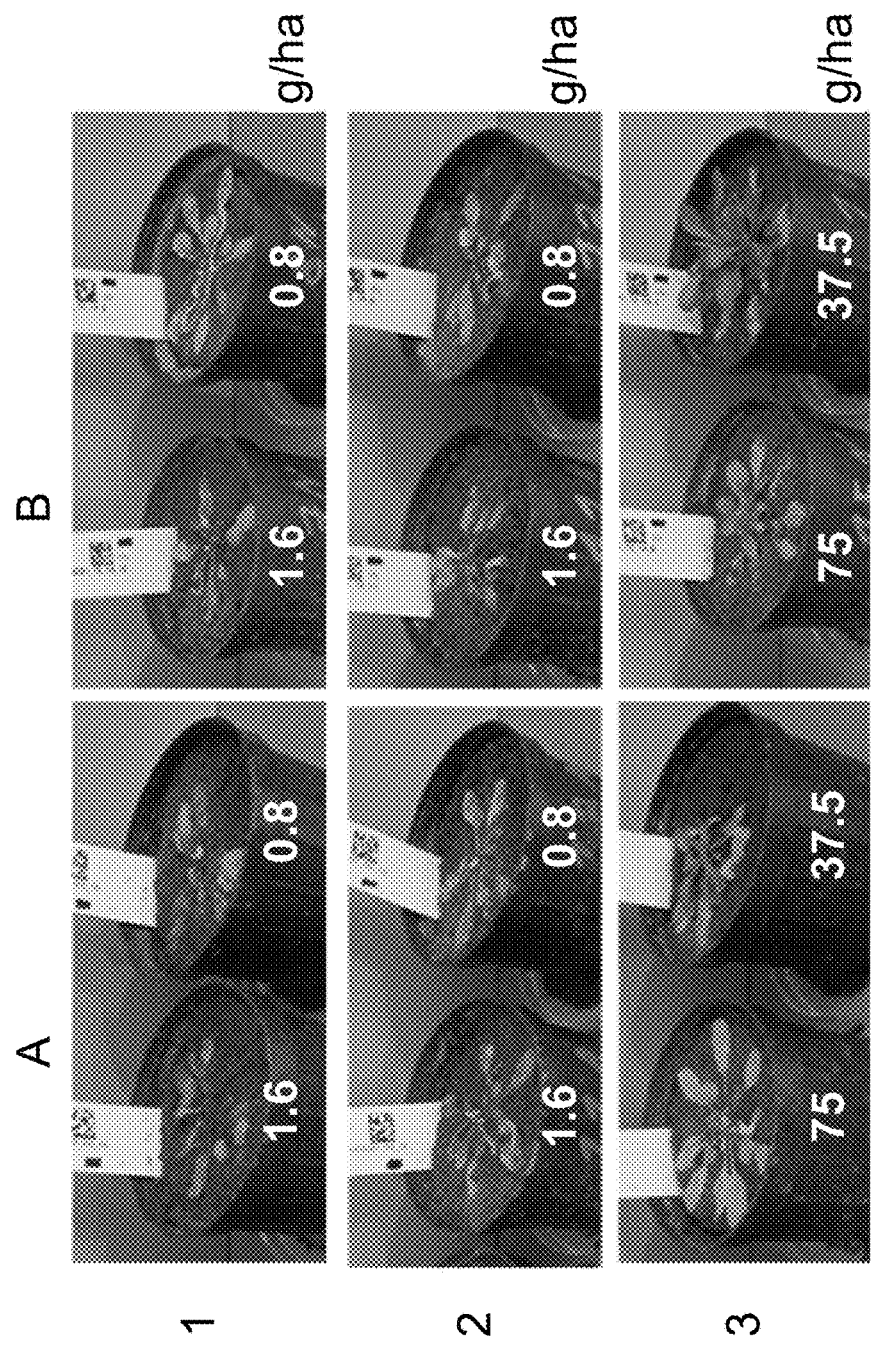

Transgenic Arabidopsis thaliana plants were assayed for improved tolerance to saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), chlorotoluron, pendimethalin, flumioxazin, butafenacil, acifluorfen, lactofen, bifenox, diuron, sulfentrazon, tepraloxydim, coumarone-derivative herbicides, azine-derivative herbicides in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia Plantarum 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*$m^2$*$s^{-1}$ with 14:10 h light: dark photoperiod. Growth inhibition is evaluated seven to ten days after seeding in comparison to wild type plants. Additionally, transgenic T1 Arabidopsis plants were tested for improved tolerance to herbicides in greenhouse studies with the following herbicides: saflufenacil, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), chlorotoluron, pendimethalin, flumioxazin, butafenacil, acifluorfen, lactofen, bifenox, diuron, sulfentrazone, tepraloxydim, coumarone-derivative herbicides, azine-derivative herbicides. The results are shown in FIGS. 1 and 2.

Example 5: Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368,800) as directed by the manufacturer. Isolated DNA was PCR amplified using the appropriate forward and reverse primer. PCR amplification was performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C.

PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

The invention claimed is:

1. A method for producing a transgenic plant with increased herbicide tolerance or resistance as compared to a corresponding non-transformed wild type plant, comprising transforming a plant cell or a plant cell nucleus or a plant tissue with a nucleic acid molecule comprising a recombinant polynucleotide encoding a polypeptide having 90% or more identity with the amino acid sequence of SEQ ID NO: 4; and regenerating a transgenic plant from that transformed plant cell nucleus, plant cell or plant tissue with increased herbicide tolerance or resistance, wherein expression of the recombinant polynucleotide confers an increased herbicide tolerance or resistance thereto as compared to a corresponding non-transformed, wild type plant.

2. A recombinant nucleic acid construct comprising
a nucleic acid molecule encoding a polypeptide having 90% or more identity with the amino acid sequence of SEQ ID NO: 4, and
a heterologous regulatory element operably linked thereto;
wherein the recombinant nucleic acid construct confers increased herbicide tolerance or resistance to a plant cell, plant or part thereof transformed therewith as compared to a corresponding non-transformed, wild type plant cell, plant or part thereof.

3. A vector comprising the nucleic acid construct of claim 2.

4. A plant, a plant cell, or a plant part comprising the nucleic acid construct of claim 2 and having increased herbicide tolerance or resistance as compared to a corresponding non-transformed, wild type plant, wild type plant cell, or wild type plant part.

5. The plant, plant cell, or plant part of claim 4, wherein the plant, plant cell, or plant part is derived from a monocotyledonous plant.

6. The plant, plant cell, or plant part of claim 4, wherein the plant, plant cell, or plant part is derived from a dicotyledonous plant.

7. The plant, plant cell, or plant part of claim 4, wherein the corresponding plant is selected from the group consisting of, wheat, rye, oat, triticale, rice, barley, soybean, peanut, cotton, oil seed rape, canola, winter oil seed rape, *manihot*, pepper, sunflower, sugar cane, sugar beet, flax, borage, safflower, linseed, primrose, rapeseed, turnip rape, *tagetes*, potato, tobacco, eggplant, tomato, *Vicia* species, pea, alfalfa, coffee, cacao, tea, *Salix* species, oil palm, coconut, perennial grass, forage crops and *Arabidopsis thaliana*.

8. The plant, plant cell, or plant part of claim 4, wherein the corresponding plant is selected from the group consisting of corn, soy, oil seed rape, canola, winter oil seed rape, cotton, wheat and rice.

9. A transgenic plant comprising one or more plant cell nuclei, plant cells, progeny, seed or pollen comprising the nucleic acid construct of claim 2.

10. A transgenic plant, transgenic plant cell nucleus, transgenic plant cell, or transgenic plant part comprising a transgene comprising the recombinant nucleic acid construct of claim 2, wherein said transgenic plant, transgenic plant cell nucleus, transgenic plant cell, or transgenic plant part is genetically homozygous for the transgene, and wherein the transgene confers increased herbicide tolerance or resistance thereto as compared to a corresponding non-transformed wild type plant, wild type plant cell nucleus, wild type plant cell, or wild type plant part.

11. A composition comprising the nucleic acid construct of claim 2 and an agriculturally acceptable carrier.

12. A method for controlling weeds at a locus for growth of a plant, the method comprising: (a) applying a herbicide composition to the locus; and (b) planting a seed at the locus, wherein the seed is capable of producing a plant that comprises the recombinant nucleic acid construct of claim 2, wherein expression thereof confers to the plant tolerance to the herbicide.

13. A method for controlling weeds at a locus for growth of a plant, the method comprising: applying an herbicidal composition to the locus; wherein said locus is: (a) a locus that contains: a plant or a seed capable of producing said plant; or (b) a locus that is to be after said applying is made to contain the plant or the seed; wherein the plant or the seed comprises in at least some of its cells the recombinant nucleic acid construct of claim 2, wherein expression thereof confers to the plant tolerance to the herbicide.

* * * * *

UNITED STATES PATENT AND TRADEMARK OFFICE
CERTIFICATE OF CORRECTION

PATENT NO. : 10,294,488 B2
APPLICATION NO. : 14/653090
DATED : May 21, 2019
INVENTOR(S) : Stefan Tresch et al.

It is certified that error appears in the above-identified patent and that said Letters Patent is hereby corrected as shown below:

In the Claims

At Column 287, Line 41, "of," should be -- of maize, --.

Signed and Sealed this
Twenty-third Day of April, 2024

*Katherine Kelly Vidal*

Katherine Kelly Vidal
*Director of the United States Patent and Trademark Office*

SEQUENCE LISTING

<160> NUMBER OF SEQ ID NOS: 74

<210> SEQ ID NO 1
<211> LENGTH: 1848
<212> TYPE: DNA

<213> ORGANISM: Alopecurus

<400> SEQUENCE: 1

| | | | | | |
|---|---|---|---|---|---|
| caacgcagac | aacaggggga | cacgacatcg | ccacaactat | gatgatggat | aaggcctaca | 60 |
| ttgccatctt | cttcttcttc | actttcgtct | tcctgctccg | ccaaattcta | cgaggaaaga | 120 |
| cgagcaatgg | cgacaacaac | agggcgtgc | agctaccgcc | gagccctcca | gctatcccgt | 180 |
| tcctcggcca | cctccacctc | gtggcaaaaa | agccgttaca | cgccacgctg | cgcggcctcg | 240 |
| ccgaccacta | cgggccgatc | ttctcgctgc | gcctaggcgc | gcgtaacgcc | gtggtggtgt | 300 |
| cctccgcggc | gtgcgccacg | gagtgcttca | cggagcacga | cgtgatattc | gccaaccggc | 360 |
| cccagttccc | ctcgcagcag | ctcgtctcct | tcggcggcac | ctcgctcatc | ttctccagct | 420 |
| acggcccgcg | ctggcgcacc | ctccgccgcg | tcgccgccgt | gcagctgctc | tccccgcacc | 480 |
| gcgtcgcctg | catgtcaggg | gttatcgcgt | ccgagatccg | cgcaatgacg | cgccggctct | 540 |
| gccgcgcggc | cgccgcaggc | gcccgggtcc | atctgaagcg | gaggctgttc | gagctctccc | 600 |
| tcagcgtgct | catggagacc | atcgccaaca | ccaagggaac | ccggccggtg | gcggacgccg | 660 |
| acacggacat | gtccatggag | gcccaggagt | tcaagaaggt | gatggacgag | atcatcccgt | 720 |
| acatcggctc | cgcaaacatg | tgggacttcc | tgccggtgat | gcgatggttc | gacgtgttcg | 780 |
| gcgtcaggaa | caaaatcctg | gccgtggtga | gcaggaggga | cgcgttcctg | cggcggctca | 840 |
| tcgacgccga | gcgccagagg | ctggaagacg | gcggcggcca | aggtgacaag | aaaagcatga | 900 |
| tcgccgtgct | gctcaccttg | cagaaaacag | agccagaggt | gtacactgat | actatgatca | 960 |
| cgtctctctg | tgcgaattta | tttggagctg | gaactgagac | cacgtcaacc | atgacagaat | 1020 |
| gggcaatgtc | gctcttgctg | aaccacccag | cagtgatcaa | gaaggcccaa | gctgagatcg | 1080 |
| acgcgtccgt | cggaaactcc | cgtctggttg | ctgctgacga | cgtgccccgc | ctcgcctacc | 1140 |
| tccaatgcat | tatcagtgag | acgctccgac | tgtgcccacc | ggcgccattg | ctactggcgc | 1200 |
| acgagtcctc | cgctgactgc | aaggtcgag | gatacaacgt | gccaagagat | actatgctta | 1260 |
| ttgtaagcgc | atatgccata | catagggatc | cggcaacttg | ggaggatccg | acagtgttcc | 1320 |
| gacccgaaag | gtttgaggac | ggcaagggcg | acgagatgtt | ggtgataccg | tttgggatgg | 1380 |
| ggcggcgggg | gtgccccggg | gagacgctcg | cacggcagat | ggttgggatg | gttcttggga | 1440 |
| caatgttgca | gtgcttcgat | tgggaacggg | tggacagcgt | cgaggtggac | atgacggaag | 1500 |
| ggggagggt | caccatgccc | aaggccgtac | ctttggaggc | tatgtgtagc | ccgcgtgcat | 1560 |
| ctatgtgtaa | agtccttgag | aagctctgag | caccgggctt | attagtatgt | acactagact | 1620 |
| gatagcgtgc | ttcgccgcac | cgtacgtggt | tatttggtgt | gttcacgcgt | tgtatgtgtc | 1680 |
| gttgtttttc | aaataatttg | atgtattggc | aactgtctta | cccggaggtg | ctatcatgca | 1740 |
| tagggctttg | aaagacgtgt | aattcgggtg | attctgcttt | tgttattacg | attcggttga | 1800 |
| attgtttatg | ctgaacagga | tggtcaagat | cggaagagca | cacgtctg | | 1848 |

<210> SEQ ID NO 2
<211> LENGTH: 516
<212> TYPE: PRT
<213> ORGANISM: Alopecurus

<400> SEQUENCE: 2

Met Met Met Asp Lys Ala Tyr Ile Ala Ile Phe Phe Phe Thr Phe
1               5                   10                  15

Val Phe Leu Leu Arg Gln Ile Leu Arg Gly Lys Thr Ser Asn Gly Asp
            20                  25                  30

```
Asn Asn Arg Gly Val Gln Leu Pro Pro Ser Pro Ala Ile Pro Phe
         35                  40                  45

Leu Gly His Leu His Leu Val Ala Lys Lys Pro Leu His Ala Thr Leu
     50                  55                  60

Arg Gly Leu Ala Asp His Tyr Gly Pro Ile Phe Ser Leu Arg Leu Gly
 65              70                  75                      80

Ala Arg Asn Ala Val Val Ser Ser Ala Cys Ala Thr Glu Cys
                 85                  90              95

Phe Thr Glu His Asp Val Ile Phe Ala Asn Arg Pro Gln Phe Pro Ser
             100                 105             110

Gln Gln Leu Val Ser Phe Gly Gly Thr Ser Leu Ile Phe Ser Ser Tyr
         115                 120                 125

Gly Pro Arg Trp Arg Thr Leu Arg Arg Val Ala Ala Val Gln Leu Leu
         130                 135                 140

Ser Pro His Arg Val Ala Cys Met Ser Gly Val Ile Ala Ser Glu Ile
145              150                 155                     160

Arg Ala Met Thr Arg Arg Leu Cys Arg Ala Ala Ala Gly Ala Arg
                 165                 170                 175

Val His Leu Lys Arg Arg Leu Phe Glu Leu Ser Leu Ser Val Leu Met
         180                 185                 190

Glu Thr Ile Ala Asn Thr Lys Gly Thr Arg Pro Val Ala Asp Ala Asp
         195                 200                 205

Thr Asp Met Ser Met Glu Ala Gln Glu Phe Lys Lys Val Met Asp Glu
         210                 215                 220

Ile Ile Pro Tyr Ile Gly Ser Ala Asn Met Trp Asp Phe Leu Pro Val
225              230                 235                     240

Met Arg Trp Phe Asp Val Phe Gly Val Arg Asn Lys Ile Leu Ala Val
                 245                 250                 255

Val Ser Arg Arg Asp Ala Phe Leu Arg Arg Leu Ile Asp Ala Glu Arg
         260                 265                 270

Gln Arg Leu Glu Asp Gly Gly Gln Gly Asp Lys Lys Ser Met Ile
         275                 280                 285

Ala Val Leu Leu Thr Leu Gln Lys Thr Glu Pro Glu Val Tyr Thr Asp
         290                 295                 300

Thr Met Ile Thr Ser Leu Cys Ala Asn Leu Phe Gly Ala Gly Thr Glu
305              310                 315                     320

Thr Thr Ser Thr Met Thr Glu Trp Ala Met Ser Leu Leu Asn His
                 325                 330                 335

Pro Ala Val Ile Lys Lys Ala Gln Ala Glu Ile Asp Ala Ser Val Gly
             340                 345                 350

Asn Ser Arg Leu Val Ala Ala Asp Asp Val Pro Arg Leu Ala Tyr Leu
         355                 360                 365

Gln Cys Ile Ile Ser Glu Thr Leu Arg Leu Cys Pro Pro Ala Pro Leu
         370                 375                 380

Leu Leu Ala His Glu Ser Ser Ala Asp Cys Lys Val Gly Gly Tyr Asn
385              390                 395                     400

Val Pro Arg Asp Thr Met Leu Ile Val Ser Ala Tyr Ala Ile His Arg
                 405                 410                 415

Asp Pro Ala Thr Trp Glu Asp Pro Thr Val Phe Arg Pro Glu Arg Phe
             420                 425                 430

Glu Asp Gly Lys Gly Asp Glu Met Leu Val Ile Pro Phe Gly Met Gly
             435                 440                 445
```

```
Arg Arg Gly Cys Pro Gly Glu Thr Leu Ala Arg Gln Met Val Gly Met
    450                 455                 460
Val Leu Gly Thr Met Leu Gln Cys Phe Asp Trp Glu Arg Val Asp Ser
465                 470                 475                 480
Val Glu Val Asp Met Thr Glu Gly Gly Val Thr Met Pro Lys Ala
                485                 490                 495
Val Pro Leu Glu Ala Met Cys Ser Pro Arg Ala Ser Met Cys Lys Val
            500                 505                 510
Leu Glu Lys Leu
        515

<210> SEQ ID NO 3
<211> LENGTH: 1641
<212> TYPE: DNA
<213> ORGANISM: Alopecurus

<400> SEQUENCE: 3
cacgcttccc caaataattg agacgatacg aaatagtacc atggataagg cggcctacat      60
tgccgtcttc tgcttcactt tcctcttcct gctccaccgc atcctacgag gcagcaagag    120
caatggcggc aacagcagca agggcgtgca gctgccgccg agcccccggg ccatcccgtt    180
cctcggccac ctccatctcg tggcggagaa gccgttgcac gccacgctgc cgcgcctcgc    240
cgatcgctat gggccggtct ctcgctgcg cctcggcgcg cgcaacgccc tggtggtgtc    300
cacggcggcc ggcgccaggg agtgcttcac ggagcacgac gtgaccttcg ccaaccggcc    360
ccagttcccc tcgcagctgc tcgtctcctt cggcggcaca tcgctcatcc actccaacta    420
cggcccgcgc tggcgcatcc tccgccgcgt cgccgccgtg cagctgctct ccacgcaccg    480
cgtcgcctgc atgtcggggg tcatcgcggc tgagatccgc gcaatgacgc gccggctctg    540
ccgcgcggcc gccgcaggcg cccgggtcca tctgaagcgg aggctgttcg agctctccct    600
cagcgtgctc atggagacca tcgccaacac caagggaacc cggccggtgg cggacgccga    660
cacggacatg tccatggagg cccaggagtt caagaaggtg atggacgaga tcatcccgta    720
catcggctcc gcaaacatgt gggacttcct gccggtgatg cgatggttcg acgtgttcgg    780
cgtcaggaac aaaatcctgg ccgtggtgag caggagggac gcgttcctgc ggcggctcat    840
cgacgccgag cgccagaggc tggaagacgg cggcggccaa ggtgacaaga aaagcatgat    900
cgccgtgctg ctcaccttgc agaaaacaga gccagaggtg tacactgata ctatgatcac    960
gtctctctgt gcgaatttat ttggagctgg aactgagacc acgtcaacca tgacagaatg   1020
ggcaatgtcg ctcttgctga accacccagc ggtgatcaag aaggcccaag ctgagatcga   1080
cgcgtccgtt ggaaactccc gcctggttgc tgctgacgac gtgccccgcc tcgcctacct   1140
ccaatgcatt atcagtgaga cgctccgatt gtgcccaccg cgccattgc tactggcaca   1200
cgagtcctcc gctgactgca aggtcggagg atacaacgtg ccaagagaca cgatgcttat   1260
tgtaagcgca tatgccatac atagggatcc ggcaacttgg gaggatccga cagtgttccg   1320
acctgaaaga tttgaggacg gcaagggcga cgggatgttg gtgataccgt ttgggatggg   1380
gcggcggggg tgccccgggg agacgctcgc acggcagatg gttgggatgg ttcttgggac   1440
aatgttgcag tgcttcgatt gggaacgggt ggacggcgtc gaggtggaca tgacggaagg   1500
gggagggggtc accatgccca aggccgtacc tttggaggct atgtgtagcc cgcgtgcatc   1560
tatgtgtaaa gtccttgaga agctctgagc accgggctta ttagtatgta cactagactg   1620
atagcgtgct tcgccgcacc g                                              1641
```

<210> SEQ ID NO 4
<211> LENGTH: 515
<212> TYPE: PRT
<213> ORGANISM: Alopecurus

<400> SEQUENCE: 4

```
Met Asp Lys Ala Ala Tyr Ile Ala Val Phe Cys Phe Thr Phe Leu Phe
1               5                   10                  15

Leu Leu His Arg Ile Leu Arg Gly Ser Lys Ser Asn Gly Gly Asn Ser
            20                  25                  30

Ser Lys Gly Val Gln Leu Pro Pro Ser Pro Pro Ala Ile Pro Phe Leu
        35                  40                  45

Gly His Leu His Leu Val Ala Glu Lys Pro Leu His Ala Thr Leu Arg
    50                  55                  60

Arg Leu Ala Asp Arg Tyr Gly Pro Val Phe Ser Leu Arg Leu Gly Ala
65                  70                  75                  80

Arg Asn Ala Leu Val Val Ser Thr Ala Ala Gly Ala Arg Glu Cys Phe
                85                  90                  95

Thr Glu His Asp Val Thr Phe Ala Asn Arg Pro Gln Phe Pro Ser Gln
            100                 105                 110

Leu Leu Val Ser Phe Gly Gly Thr Ser Leu Ile His Ser Asn Tyr Gly
        115                 120                 125

Pro Arg Trp Arg Ile Leu Arg Arg Val Ala Ala Val Gln Leu Leu Ser
    130                 135                 140

Thr His Arg Val Ala Cys Met Ser Gly Val Ile Ala Ala Glu Ile Arg
145                 150                 155                 160

Ala Met Thr Arg Arg Leu Cys Arg Ala Ala Ala Gly Ala Arg Val
                165                 170                 175

His Leu Lys Arg Arg Leu Phe Glu Leu Ser Leu Ser Val Leu Met Glu
            180                 185                 190

Thr Ile Ala Asn Thr Lys Gly Thr Arg Pro Val Ala Asp Ala Asp Thr
        195                 200                 205

Asp Met Ser Met Glu Ala Gln Glu Phe Lys Lys Val Met Asp Glu Ile
    210                 215                 220

Ile Pro Tyr Ile Gly Ser Ala Asn Met Trp Asp Phe Leu Pro Val Met
225                 230                 235                 240

Arg Trp Phe Asp Val Phe Gly Val Arg Asn Lys Ile Leu Ala Val Val
                245                 250                 255

Ser Arg Arg Asp Ala Phe Leu Arg Arg Leu Ile Asp Ala Glu Arg Gln
            260                 265                 270

Arg Leu Glu Asp Gly Gly Gly Gln Gly Asp Lys Lys Ser Met Ile Ala
        275                 280                 285

Val Leu Leu Thr Leu Gln Lys Thr Glu Pro Glu Val Tyr Thr Asp Thr
    290                 295                 300

Met Ile Thr Ser Leu Cys Ala Asn Leu Phe Gly Ala Gly Thr Glu Thr
305                 310                 315                 320

Thr Ser Thr Met Thr Glu Trp Ala Met Ser Leu Leu Leu Asn His Pro
                325                 330                 335

Ala Val Ile Lys Lys Ala Gln Ala Glu Ile Asp Ala Ser Val Gly Asn
            340                 345                 350

Ser Arg Leu Val Ala Ala Asp Val Pro Arg Leu Ala Tyr Leu Gln
        355                 360                 365

Cys Ile Ile Ser Glu Thr Leu Arg Leu Cys Pro Pro Ala Pro Leu Leu
    370                 375                 380
```

Leu Ala His Glu Ser Ser Ala Asp Cys Lys Val Gly Gly Tyr Asn Val
385                 390                 395                 400

Pro Arg Asp Thr Met Leu Ile Val Ser Ala Tyr Ala Ile His Arg Asp
            405                 410                 415

Pro Ala Thr Trp Glu Asp Pro Thr Val Phe Arg Pro Gly Arg Phe Glu
        420                 425                 430

Asp Gly Lys Gly Asp Gly Met Leu Val Ile Pro Phe Gly Met Gly Arg
            435                 440                 445

Arg Gly Cys Pro Gly Glu Thr Leu Ala Arg Gln Met Val Gly Met Val
        450                 455                 460

Leu Gly Thr Met Leu Gln Cys Phe Asp Trp Glu Arg Val Asp Gly Val
465                 470                 475                 480

Glu Val Asp Met Thr Glu Gly Gly Val Thr Met Pro Lys Ala Val
                485                 490                 495

Pro Leu Glu Ala Met Cys Ser Pro Arg Ala Ser Met Cys Lys Val Leu
            500                 505                 510

Glu Lys Leu
        515

<210> SEQ ID NO 5
<211> LENGTH: 1693
<212> TYPE: DNA
<213> ORGANISM: Alopecurus

<400> SEQUENCE: 5
gggggcacac aacacagctc acgcttcccc aaataattga gacgatacga aatagtacca    60
tggataaggc ggcctacatt gccgtcttct gcttcacttt cctcttcctg ctccaccgca   120
tcctacgagg cagcaagagc aatggcggca acagcagcaa gggcgtgcag ctgccgccga   180
gccccccggc catcccgttc ctcggccacc tccatctcgt ggcggagaag ccgttgcacg   240
ccacgctgcg ccgcctcgcc gatcgctatg gccggtctt ctcgctccgc ctcggcgcgc   300
gcaacgccct ggtggtgtcc acggcggccg cgccaggga gtgcttcacg gagcacgacg   360
tgaccttcgc caaccggccc cagttcccct cgcagctgct cgtctccttc ggcggcacat   420
cgctcatcca ctccaactac ggcccgcgct ggcgcaccct ccgccgcgtc gccgccgtgc   480
agctgctctc cacgcaccgc gtcgcctgca tgtcgggggt catcgcgtcc gagatccgcg   540
caatgacgcg ccggctctgc cgcgcggccg ccgcaggcgc ccgggttcat ctgaagcgga   600
ggctgttcga gctctcctc agcgtgctca tggagaccat cgcgaatacc aaggggaccc   660
ggccggtggc ggacgccgac acggacatgt ccttggaggc acaggagttc aagaaggtga   720
tggacgagat catcccgtat atcggcgcgg caaacatgtg ggacttcctg ccggtgatgc   780
gttggttcga cgtgttcggc gtcaggaaca aaatcctggc cgcggtgagc aggagggacg   840
cgttcctgag gcggctcatc gacgctgagc gccagaggct ggaccacggc ggcggccaag   900
gtgacaagaa aagcatgatc gccgtgctgc tcaccttgca gaaaacagag ccagaggtgt   960
acactgatac tatgatcact gctctgtgtg cgaatttatt tgcagctgga acagagacca  1020
cgtcaaccat gacagaatgg gcgatgacac tcttactgaa tcacccagcg gtgatcaaga  1080
aggcccaagc tgagatcgat gggtctgtcg gaaactcccg cttggtcgct gccgacgacc  1140
tgccccgtct cgcctaccte caatgcatta tcagtgaggc gctccgactg tatccaccgg  1200
cgccactgct acttccgcac gagtcctccg ccgactgcaa ggtcggagga tataatgtgc  1260
caagagacac gatgcttatc gtgagtgcat acgccataca tagagatcca gcaatttggg  1320

```
gggatccgac agtgttccga cctgaaaggt ttgaggacgg caagggcgag gggttgttgg    1380
tgataccgtt tgggatggga cggcggggt gccccgggga cgctcgca cgccagatgg      1440 ttgggatggt tcttgggaca atgttgcagt gcttcgattg ggaacgggag acggcatgg     1500 aggtggacat gactgagggg agagggatca ccatggccaa ggccgtgcct ttggaggcta    1560
tgtgtagccc acgtgcaact atgtgtaatt ttcttgagaa gctctgatgg ttgaattttt    1620
tgtatgaaaa ggtccagcag tctattaata atcatcaacg gtggtaaaat tattttaaa    1680 ggtaatacaa att                                                      1693
```

<210> SEQ ID NO 6
<211> LENGTH: 515
<212> TYPE: PRT
<213> ORGANISM: Alopecurus

<400> SEQUENCE: 6

```
Met Asp Lys Ala Ala Tyr Ile Ala Val Phe Cys Phe Thr Phe Leu Phe
1               5                   10                  15

Leu Leu His Arg Ile Leu Arg Gly Ser Lys Ser Asn Gly Gly Asn Ser
            20                  25                  30

Ser Lys Gly Val Gln Leu Pro Pro Ser Pro Ala Ile Pro Phe Leu
        35                  40                  45

Gly His Leu His Leu Val Ala Glu Lys Pro Leu His Ala Thr Leu Arg
    50                  55                  60

Arg Leu Ala Asp Arg Tyr Gly Pro Val Phe Ser Leu Arg Leu Gly Ala
65                  70                  75                  80

Arg Asn Ala Leu Val Val Ser Thr Ala Ala Gly Ala Arg Glu Cys Phe
                85                  90                  95

Thr Glu His Asp Val Thr Phe Ala Asn Arg Pro Gln Phe Pro Ser Gln
            100                 105                 110

Leu Leu Val Ser Phe Gly Gly Thr Ser Leu Ile His Ser Asn Tyr Gly
        115                 120                 125

Pro Arg Trp Arg Thr Leu Arg Arg Val Ala Ala Val Gln Leu Leu Ser
    130                 135                 140

Thr His Arg Val Ala Cys Met Ser Gly Val Ile Ala Ser Glu Ile Arg
145                 150                 155                 160

Ala Met Thr Arg Arg Leu Cys Arg Ala Ala Ala Gly Ala Arg Val
                165                 170                 175

His Leu Lys Arg Arg Leu Phe Glu Leu Ser Leu Ser Val Leu Met Glu
            180                 185                 190

Thr Ile Ala Asn Thr Lys Gly Thr Arg Pro Val Ala Asp Ala Asp Thr
        195                 200                 205

Asp Met Ser Leu Glu Ala Gln Glu Phe Lys Lys Val Met Asp Glu Ile
    210                 215                 220

Ile Pro Tyr Ile Gly Ala Ala Asn Met Trp Asp Phe Leu Pro Val Met
225                 230                 235                 240

Arg Trp Phe Asp Val Phe Gly Val Arg Asn Lys Ile Leu Ala Ala Val
                245                 250                 255

Ser Arg Arg Asp Ala Phe Leu Arg Leu Ile Asp Ala Glu Arg Gln
            260                 265                 270

Arg Leu Asp His Gly Gly Gly Gln Gly Asp Lys Lys Ser Met Ile Ala
        275                 280                 285

Val Leu Leu Thr Leu Gln Lys Thr Glu Pro Glu Val Tyr Thr Asp Thr
    290                 295                 300
```

```
Met Ile Thr Ala Leu Cys Ala Asn Leu Phe Ala Ala Gly Thr Glu Thr
305                 310                 315                 320

Thr Ser Thr Met Thr Glu Trp Ala Met Thr Leu Leu Leu Asn His Pro
            325                 330                 335

Ala Val Ile Lys Lys Ala Gln Ala Glu Ile Asp Gly Ser Val Gly Asn
        340                 345                 350

Ser Arg Leu Val Ala Ala Asp Asp Leu Pro Arg Leu Ala Tyr Leu Gln
    355                 360                 365

Cys Ile Ile Ser Glu Ala Leu Arg Leu Tyr Pro Pro Ala Pro Leu Leu
370                 375                 380

Leu Pro His Glu Ser Ser Ala Asp Cys Lys Val Gly Gly Tyr Asn Val
385                 390                 395                 400

Pro Arg Asp Thr Met Leu Ile Val Ser Ala Tyr Ala Ile His Arg Asp
            405                 410                 415

Pro Ala Ile Trp Gly Asp Pro Thr Val Phe Arg Pro Glu Arg Phe Glu
        420                 425                 430

Asp Gly Lys Gly Glu Gly Leu Leu Val Ile Pro Phe Gly Met Gly Arg
    435                 440                 445

Arg Gly Cys Pro Gly Glu Thr Leu Ala Arg Gln Met Val Gly Met Val
450                 455                 460

Leu Gly Thr Met Leu Gln Cys Phe Asp Trp Glu Arg Glu Asp Gly Met
465                 470                 475                 480

Glu Val Asp Met Thr Glu Gly Arg Gly Ile Thr Met Ala Lys Ala Val
            485                 490                 495

Pro Leu Glu Ala Met Cys Ser Pro Arg Ala Thr Met Cys Asn Phe Leu
        500                 505                 510

Glu Lys Leu
        515

<210> SEQ ID NO 7
<211> LENGTH: 1668
<212> TYPE: DNA
<213> ORGANISM: Alopecurus

<400> SEQUENCE: 7
ctcaaggtga aagaagaaga ctgatcactt ccctagctag ctcgatcgcc acggttaacc    60
atggataagc catacatcgc cgtcctctcc ttcgcccttc tgttcctgct ccactacgtt   120
gtcggcaagg tcagcaatgg caggcgcggc acgaagggcg ccgtgcagct gccgccgagc   180
cctcgtgcct tcccgttcct cggccaccte tacgtcctag agaagccctt ccacgcatcg   240
ctgtgccgcg tcgccgcgcg cctcggcccg gtcttctccc tgcgcctcgg ctcccgccgc   300
gccgtggtgg tgtgctcgtc cgaggccgcc agggagtgct tcacggagca cgacgtgacc   360
ttcgccgacc ggcccaggtt cccttcccag ctgctcgtct ccttcaacgg cgccgcgctc   420
gccacgtcca gctacggccc gcactggcgc aacctccgcc gcgtcgccgc cgtgcagctg   480
ctctccgcgc accgcgtcgc ctgcatgtcc ggcgtcatcg ccgccgagat ccgcgccatg   540
gtgcgccggc tctgccacac agccgcggcg actcccggcg gcgccccgcg ggtccagctg   600
aagcggaggc tcttcgagct ctccctcagc gtgctcatgg agaccatcgc gcagaccaag   660
gggacccgtt ccgaggccga cgccgacacg gacatgtctg tggaggcgca ggagttcaag   720
aacgtgacgg acaagctcac cccgcacctc ggcacggcaa acaagtggga ctacctgccg   780
gtgttgcggt ggttcgacgt gttcggcgtc aggaacaaga tcctggccgc ggtgggctcg   840
```

```
agggacgcgt tcctgcggcg actggtcgac gccgaacgcc gaaggctggc cgacggcggc    900
agcgatggcg acaagaagag tatgatcgct gtgctgctca cgctgcagaa gacggaaccg    960
gagttctaca ccgataccat gatctcggct ctctgtgcga acttgtttgg cgctggaacg   1020
gagaccacat caaccacgac ggagtgggcg atgtcgctgc tgctgaacca cccggcggcg   1080
ctgaagaagg cccaggcaga gatcgacgtg tccgtgggta catcgcgcct ggtgtccgcc   1140
gacgacgtgc cccgcctcgc ctacctgcag tgcatcgtca gcgagacgct ccgcctctac   1200
ccggcggcgc cgctgctgct gccgcaccag tcctccgcgg actgcaaggt cggcggctac   1260
aacgtgccga gcggcacgat gctgatcgtg aacgcgtacg ccatccacag ggacccggcg   1320
gcgtgggacc gcccgctgga gttcaggccg gagaggttcg aggccgggaa ggccgacggg   1380
ctgttcatga taccgttcgg gatggggcgg cggaggtgcc ccggggagac gctagcgctg   1440
cggacgatcg gcatggtcct cgcaacgctg gtgcagtgct cgactggga acgggtggac   1500
ggcgcagagg tggacatgac ggagggcgga gggctcacca tccccaaggc cgtgccgttg   1560
gaggccgtgt gcaggccgcg cgcagtcatg cacgacgtgc ttcagagcct ctgacgagct   1620
tccgtcttgc agttgtttgt gttcgattgg tcatagcatc gtgtgcgg              1668

<210> SEQ ID NO 8
<211> LENGTH: 517
<212> TYPE: PRT
<213> ORGANISM: Alopecurus

<400> SEQUENCE: 8

Met Asp Lys Pro Tyr Ile Ala Val Leu Ser Phe Ala Leu Leu Phe Leu
1               5                   10                  15

Leu His Tyr Val Val Gly Lys Val Ser Asn Gly Arg Arg Gly Thr Lys
            20                  25                  30

Gly Ala Val Gln Leu Pro Pro Ser Pro Arg Ala Phe Pro Phe Leu Gly
        35                  40                  45

His Leu Tyr Val Leu Glu Lys Pro Phe His Ala Ser Leu Cys Arg Val
    50                  55                  60

Ala Ala Arg Leu Gly Pro Val Phe Ser Leu Arg Leu Gly Ser Arg Arg
65                  70                  75                  80

Ala Val Val Cys Ser Ser Glu Ala Ala Arg Glu Cys Phe Thr Glu
                85                  90                  95

His Asp Val Thr Phe Ala Asp Arg Pro Arg Phe Pro Ser Gln Leu Leu
                100                 105                 110

Val Ser Phe Asn Gly Ala Ala Leu Ala Thr Ser Ser Tyr Gly Pro His
            115                 120                 125

Trp Arg Asn Leu Arg Arg Val Ala Ala Val Gln Leu Leu Ser Ala His
        130                 135                 140

Arg Val Ala Cys Met Ser Gly Val Ile Ala Ala Glu Ile Arg Ala Met
145                 150                 155                 160

Val Arg Arg Leu Cys His Thr Ala Ala Thr Pro Gly Gly Ala Pro
                165                 170                 175

Arg Val Gln Leu Lys Arg Arg Leu Phe Glu Leu Ser Leu Ser Val Leu
            180                 185                 190

Met Glu Thr Ile Ala Gln Thr Lys Gly Thr Arg Ser Glu Ala Asp Ala
        195                 200                 205

Asp Thr Asp Met Ser Val Glu Ala Gln Glu Phe Lys Asn Val Thr Asp
    210                 215                 220

Lys Leu Thr Pro His Leu Gly Thr Ala Asn Lys Trp Asp Tyr Leu Pro
```

```
                225                 230                 235                 240

Val Leu Arg Trp Phe Asp Val Phe Gly Val Arg Asn Lys Ile Leu Ala
                        245                 250                 255

Ala Val Gly Ser Arg Asp Ala Phe Leu Arg Arg Leu Val Asp Ala Glu
                        260                 265                 270

Arg Arg Arg Leu Ala Asp Gly Ser Asp Gly Asp Lys Lys Ser Met
                        275                 280                 285

Ile Ala Val Leu Leu Thr Leu Gln Lys Thr Glu Pro Glu Phe Tyr Thr
                        290                 295                 300

Asp Thr Met Ile Ser Ala Leu Cys Ala Asn Leu Phe Gly Ala Gly Thr
        305                 310                 315                 320

Glu Thr Thr Ser Thr Thr Thr Glu Trp Ala Met Ser Leu Leu Leu Asn
                        325                 330                 335

His Pro Ala Ala Leu Lys Lys Ala Gln Ala Glu Ile Asp Val Ser Val
                        340                 345                 350

Gly Thr Ser Arg Leu Val Ser Ala Asp Asp Val Pro Arg Leu Ala Tyr
                        355                 360                 365

Leu Gln Cys Ile Val Ser Glu Thr Leu Arg Leu Tyr Pro Ala Ala Pro
                        370                 375                 380

Leu Leu Leu Pro His Gln Ser Ser Ala Asp Cys Lys Val Gly Gly Tyr
        385                 390                 395                 400

Asn Val Pro Ser Gly Thr Met Leu Ile Val Asn Ala Tyr Ala Ile His
                        405                 410                 415

Arg Asp Pro Ala Ala Trp Asp Arg Pro Leu Glu Phe Arg Pro Glu Arg
                        420                 425                 430

Phe Glu Ala Gly Lys Ala Asp Gly Leu Phe Met Ile Pro Phe Gly Met
                        435                 440                 445

Gly Arg Arg Arg Cys Pro Gly Glu Thr Leu Ala Leu Arg Thr Ile Gly
                        450                 455                 460

Met Val Leu Ala Thr Leu Val Gln Cys Phe Asp Trp Glu Arg Val Asp
        465                 470                 475                 480

Gly Ala Glu Val Asp Met Thr Glu Gly Gly Gly Leu Thr Ile Pro Lys
                        485                 490                 495

Ala Val Pro Leu Glu Ala Val Cys Arg Pro Arg Ala Val Met His Asp
                        500                 505                 510

Val Leu Gln Ser Leu
                        515

<210> SEQ ID NO 9
<211> LENGTH: 517
<212> TYPE: PRT
<213> ORGANISM: Lolium rigidum

<400> SEQUENCE: 9

Met Asp Lys Ala Tyr Ile Ala Ile Leu Ser Cys Ala Phe Leu Phe Leu
1               5                   10                  15

Val His Tyr Val Leu Gly Lys Val Ser Asp Gly Arg Gly Lys Lys
                20                  25                  30

Gly Ala Val Gln Leu Pro Pro Ser Pro Ala Val Pro Phe Leu Gly
            35                  40                  45

His Leu His Leu Val Asp Lys Pro Ile His Ala Thr Met Cys Arg Leu
            50                  55                  60

Ala Ala Arg Leu Gly Pro Val Phe Ser Leu Arg Leu Gly Ser Arg Arg
65                  70                  75                  80
```

```
Ala Val Val Val Ser Ser Glu Cys Ala Arg Glu Cys Phe Thr Glu
             85              90              95

His Asp Val Thr Phe Ala Asn Arg Pro Lys Phe Pro Ser Gln Leu Leu
            100             105             110

Val Ser Phe Asn Gly Thr Ala Leu Val Thr Ser Ser Tyr Gly Pro His
        115             120             125

Trp Arg Asn Leu Arg Arg Val Ala Thr Val Gln Leu Leu Ser Ala His
        130             135             140

Arg Val Ala Cys Met Ser Gly Val Ile Ala Glu Val Arg Ala Met
145             150             155             160

Ala Arg Arg Leu Phe His Ala Ala Glu Ala Ser Pro Asp Gly Ala Ala
                165             170             175

Arg Val Gln Leu Lys Arg Leu Phe Glu Leu Ser Leu Ser Val Leu
            180             185             190

Met Glu Thr Ile Ala Gln Thr Lys Ala Thr Arg Ser Glu Ala Asp Ala
            195             200             205

Asp Thr Asp Met Ser Val Glu Ala Gln Glu Phe Lys Glu Val Val Asp
    210             215             220

Lys Leu Ile Pro His Leu Gly Ala Ala Asn Met Trp Asp Tyr Leu Pro
225             230             235             240

Val Met Arg Trp Phe Asp Val Phe Gly Val Arg Asn Lys Ile Leu His
                245             250             255

Ala Val Ser Arg Arg Asp Ala Phe Leu Arg Arg Leu Ile Asp Ala Glu
                260             265             270

Arg Arg Arg Leu Ala Asp Gly Gly Ser Asp Gly Asp Lys Lys Ser Met
    275             280             285

Ile Ala Val Leu Leu Thr Leu Gln Lys Thr Glu Pro Lys Val Tyr Thr
    290             295             300

Asp Thr Met Ile Thr Ala Leu Cys Ala Asn Leu Phe Gly Ala Gly Thr
305             310             315             320

Glu Thr Thr Ser Thr Thr Thr Glu Trp Ala Met Ser Leu Leu Leu Asn
            325             330             335

His Pro Ala Ala Leu Lys Lys Ala Gln Ala Glu Ile Asp Ala Ser Val
            340             345             350

Gly Thr Ser Arg Leu Val Ser Val Asp Asp Val Pro Ser Leu Ala Tyr
        355             360             365

Leu Gln Cys Ile Val Asn Glu Thr Leu Arg Leu Tyr Pro Ala Ala Pro
    370             375             380

Leu Leu Leu Pro His Glu Ser Ser Ala Asp Cys Lys Val Gly Gly Tyr
385             390             395             400

Asn Val Pro Ala Asp Thr Met Leu Ile Val Asn Ala Tyr Ala Ile His
            405             410             415

Arg Asp Pro Ala Ala Trp Glu His Pro Leu Val Phe Arg Pro Glu Arg
            420             425             430

Phe Glu Asp Gly Lys Ala Glu Gly Leu Phe Met Ile Pro Phe Gly Met
            435             440             445

Gly Arg Arg Arg Cys Pro Gly Glu Thr Leu Ala Leu Arg Thr Ile Gly
    450             455             460

Met Val Leu Ala Thr Leu Val Gln Cys Phe Asp Trp Glu Pro Val Asp
465             470             475             480

Gly Val Asn Val Asp Met Thr Glu Gly Gly Phe Thr Ile Pro Lys
            485             490             495

Ala Val Pro Leu Glu Ala Val Cys Arg Pro Arg Ala Val Met Arg Asp
```

```
                    500                 505                 510

Val Leu Gln Ser Ile
            515

<210> SEQ ID NO 10
<211> LENGTH: 520
<212> TYPE: PRT
<213> ORGANISM: Oryza sativa

<400> SEQUENCE: 10

Met Lys Tyr Ser Thr Ser Val Thr Met Asp Lys Ala Tyr Ile Ala Val
1               5                   10                  15

Phe Ser Ile Val Ile Leu Phe Leu Leu Val Asp Tyr Leu Arg Arg Leu
            20                  25                  30

Arg Gly Gly Gly Thr Ser Asn Gly Lys Asn Lys Gly Met Arg Leu Pro
        35                  40                  45

Pro Gly Leu Pro Ala Val Pro Ile Ile Gly His Leu His Leu Val Lys
    50                  55                  60

Lys Pro Met His Ala Thr Leu Ser Arg Leu Ala Ala Arg His Gly Pro
65                  70                  75                  80

Val Phe Ser Leu Arg Leu Gly Ser Arg Arg Ala Val Val Val Ser Ser
                85                  90                  95

Pro Gly Cys Ala Arg Glu Cys Phe Thr Glu His Asp Val Ala Phe Ala
            100                 105                 110

Asn Arg Pro Arg Phe Glu Ser Gln Leu Leu Met Ser Phe Asp Gly Thr
        115                 120                 125

Ala Leu Ala Met Ala Ser Tyr Gly Pro His Trp Arg Asn Leu Arg Arg
    130                 135                 140

Val Ala Ala Val Gln Leu Leu Ser Ala Arg Arg Val Gly Leu Met Ser
145                 150                 155                 160

Gly Leu Ile Ala Gly Glu Val Arg Ala Met Val Arg Ser Leu Cys Arg
                165                 170                 175

Arg Pro Ala Ala Ala Pro Val Gln Leu Lys Arg Arg Leu Phe Glu
            180                 185                 190

Leu Ser Leu Ser Val Leu Met Glu Thr Ile Ala Gln Ser Lys Ala Thr
        195                 200                 205

Arg Pro Glu Thr Thr Asp Thr Asp Thr Asp Met Ser Met Glu Ala Gln
    210                 215                 220

Glu Tyr Lys Gln Val Val Glu Glu Ile Leu Glu Arg Ile Gly Thr Gly
225                 230                 235                 240

Asn Leu Cys Asp Tyr Leu Pro Ala Leu Arg Trp Phe Asp Val Phe Gly
                245                 250                 255

Val Arg Asn Arg Ile Leu Ala Ala Val Ser Arg Arg Asp Ala Phe Leu
            260                 265                 270

Arg Arg Leu Ile Tyr Ala Ala Arg Trp Arg Met Asp Asp Gly Glu Lys
        275                 280                 285

Lys Ser Met Ile Ala Val Leu Leu Thr Leu Gln Lys Thr Gln Pro Glu
    290                 295                 300

Val Tyr Thr Asp Asn Met Ile Thr Ala Leu Cys Ser Asn Leu Leu Gly
305                 310                 315                 320

Ala Gly Thr Glu Thr Thr Ser Thr Thr Ile Glu Trp Ala Met Ser Leu
                325                 330                 335

Leu Leu Asn His Pro Glu Thr Leu Lys Lys Ala Gln Ala Glu Ile Asp
            340                 345                 350
```

Ala Ser Val Gly Asn Ser Arg Leu Ile Thr Ala Asp Asp Val Pro Arg
            355                 360                 365

Ile Thr Tyr Leu Gln Cys Ile Val Arg Glu Thr Leu Arg Leu Tyr Pro
        370                 375                 380

Ala Ala Pro Met Leu Ile Pro His Glu Ser Ser Ala Asp Cys Glu Val
385                 390                 395                 400

Gly Gly Tyr Ser Val Pro Arg Gly Thr Met Leu Leu Val Asn Ala Tyr
                405                 410                 415

Ala Ile His Arg Asp Pro Ala Ala Trp Glu Pro Glu Arg Phe Val
            420                 425                 430

Pro Glu Arg Phe Glu Gly Gly Gly Cys Asp Gly Asn Leu Ser Met Pro
        435                 440                 445

Phe Gly Met Gly Arg Arg Cys Pro Gly Glu Thr Leu Ala Leu His
    450                 455                 460

Thr Val Gly Leu Val Leu Gly Thr Leu Ile Gln Cys Phe Asp Trp Glu
465                 470                 475                 480

Arg Val Asp Gly Val Glu Val Asp Met Ala Gly Gly Gly Leu Thr
                485                 490                 495

Met Pro Lys Val Val Pro Leu Glu Ala Val Cys Arg Pro Arg Asp Ala
        500                 505                 510

Met Gly Gly Val Leu Arg Glu Leu
        515                 520

<210> SEQ ID NO 11
<211> LENGTH: 512
<212> TYPE: PRT
<213> ORGANISM: Oryza sativa

<400> SEQUENCE: 11

Met Asp Lys Ala Tyr Ile Ala Val Phe Ser Ile Val Ile Leu Phe Leu
1               5                   10                  15

Leu Val Asp Tyr Leu Arg Arg Leu Arg Gly Gly Gly Thr Ser Asn Gly
            20                  25                  30

Lys Asn Lys Gly Met Arg Leu Pro Pro Gly Leu Pro Ala Val Pro Ile
        35                  40                  45

Ile Gly His Leu His Leu Val Lys Lys Pro Met His Ala Thr Leu Ser
    50                  55                  60

Arg Leu Ala Ala Arg His Gly Pro Val Phe Ser Leu Arg Leu Gly Ser
65                  70                  75                  80

Arg Arg Ala Val Val Val Ser Ser Pro Gly Cys Ala Arg Glu Cys Phe
                85                  90                  95

Thr Glu His Asp Val Ala Phe Ala Asn Arg Pro Arg Phe Glu Ser Gln
            100                 105                 110

Leu Leu Met Ser Phe Asp Gly Thr Ala Leu Ala Met Ala Ser Tyr Gly
        115                 120                 125

Pro His Trp Arg Asn Leu Arg Arg Val Ala Ala Val Gln Leu Leu Ser
    130                 135                 140

Ala Arg Arg Val Gly Leu Met Ser Gly Leu Ile Ala Gly Glu Val Arg
145                 150                 155                 160

Ala Met Val Arg Ser Leu Cys Arg Arg Pro Ala Ala Ala Pro Val
                165                 170                 175

Gln Leu Lys Arg Arg Leu Phe Glu Leu Ser Leu Ser Val Leu Met Glu
            180                 185                 190

Thr Ile Ala Gln Ser Lys Ala Thr Arg Pro Glu Thr Thr Asp Thr Asp
        195                 200                 205

-continued

```
Thr Asp Met Ser Met Glu Ala Gln Glu Tyr Lys Gln Val Val Glu Glu
    210                 215                 220

Ile Leu Glu Arg Ile Gly Thr Gly Asn Leu Cys Asp Tyr Leu Pro Ala
225                 230                 235                 240

Leu Arg Trp Phe Asp Val Phe Gly Val Arg Asn Arg Ile Leu Ala Ala
                245                 250                 255

Val Ser Arg Arg Asp Ala Phe Leu Arg Arg Leu Ile Tyr Ala Ala Arg
                260                 265                 270

Trp Arg Met Asp Asp Gly Glu Lys Lys Ser Met Ile Ala Val Leu Leu
            275                 280                 285

Thr Leu Gln Lys Thr Gln Pro Glu Val Tyr Thr Asp Asn Met Ile Thr
    290                 295                 300

Ala Leu Cys Ser Asn Leu Leu Gly Ala Gly Thr Glu Thr Thr Ser Thr
305                 310                 315                 320

Thr Ile Glu Trp Ala Met Ser Leu Leu Leu Asn His Pro Glu Thr Leu
                325                 330                 335

Lys Lys Ala Gln Ala Glu Ile Asp Ala Ser Val Gly Asn Ser Arg Leu
                340                 345                 350

Ile Thr Ala Asp Asp Val Pro Arg Ile Thr Tyr Leu Gln Cys Ile Val
            355                 360                 365

Arg Glu Thr Leu Arg Leu Tyr Pro Ala Ala Pro Met Leu Ile Pro His
    370                 375                 380

Glu Ser Ser Ala Asp Cys Glu Val Gly Gly Tyr Ser Val Pro Arg Gly
385                 390                 395                 400

Thr Met Leu Leu Val Asn Ala Tyr Ala Ile His Arg Asp Pro Ala Ala
                405                 410                 415

Trp Glu Glu Pro Glu Arg Phe Val Pro Glu Arg Phe Glu Gly Gly Gly
                420                 425                 430

Cys Asp Gly Asn Leu Ser Met Pro Phe Gly Met Gly Arg Arg Arg Cys
            435                 440                 445

Pro Gly Glu Thr Leu Ala Leu His Thr Val Gly Leu Val Leu Gly Thr
    450                 455                 460

Leu Ile Gln Cys Phe Asp Trp Glu Arg Val Asp Gly Val Glu Val Asp
465                 470                 475                 480

Met Ala Glu Gly Gly Gly Leu Thr Met Pro Lys Val Val Pro Leu Glu
                485                 490                 495

Ala Val Cys Arg Pro Arg Asp Ala Met Gly Gly Val Leu Arg Glu Leu
            500                 505                 510
```

<210> SEQ ID NO 12
<211> LENGTH: 517
<212> TYPE: PRT
<213> ORGANISM: Lolium rigidum

<400> SEQUENCE: 12

```
Met Asp Lys Ala Tyr Ile Ala Ile Leu Ser Ser Ala Phe Leu Phe Leu
1               5                   10                  15

Val His Tyr Val Leu Gly Lys Val Ser Asp Gly Arg Arg Gly Lys Lys
                20                  25                  30

Gly Ala Val Gln Leu Pro Pro Ser Pro Pro Ala Val Pro Phe Leu Gly
            35                  40                  45

His Leu His Leu Val Glu Lys Pro Ile His Ala Thr Met Cys Arg Leu
    50                  55                  60

Ala Ala Arg Leu Gly Pro Val Phe Ser Leu Arg Leu Gly Ser Arg Arg
```

```
                65                  70                  75                  80
Ala Val Val Ser Ser Ser Glu Cys Ala Arg Glu Cys Phe Thr Glu
                    85                  90                  95

His Asp Val Thr Phe Ala Asn Arg Pro Lys Phe Pro Ser Gln Leu Leu
                    100                 105                 110

Val Ser Phe Asn Gly Thr Ala Leu Val Thr Ser Ser Tyr Gly Pro His
                115                 120                 125

Trp Arg Asn Leu Arg Arg Val Ala Thr Val Gln Leu Leu Ser Ala His
            130                 135                 140

Arg Val Thr Cys Met Ser Gly Val Ile Ala Ala Glu Val Arg Ala Met
145                 150                 155                 160

Ala Arg Arg Leu Phe His Ala Ala Glu Ala Ser Pro Asp Gly Ala Ala
                165                 170                 175

Arg Val Gln Leu Lys Arg Leu Phe Glu Leu Ser Leu Ser Val Leu
                180                 185                 190

Met Glu Thr Ile Ala Gln Thr Lys Ala Thr Arg Ser Glu Ala Asp Ala
            195                 200                 205

Asp Thr Asp Met Ser Leu Glu Ala Gln Glu Phe Lys Glu Val Val Asp
210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Ser Lys Ile Leu His
                245                 250                 255

Ala Val Ser Arg Arg Asp Ala Phe Leu Arg Arg Leu Ile Asn Ala Glu
                260                 265                 270

Arg Arg Arg Leu Ala Asp Gly Gly Ser Asp Gly Asp Lys Lys Ser Met
            275                 280                 285

Ile Ala Val Leu Leu Thr Leu Gln Lys Thr Glu Pro Lys Val Tyr Thr
            290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Pro Ala Ala Leu Lys Lys Ala Gln Ala Glu Ile Asp Ala Ser Val
                340                 345                 350

Gly Thr Ser Arg Leu Val Ser Val Asp Asp Val Pro Ser Leu Ala Tyr
            355                 360                 365

Leu Gln Cys Ile Val Ser Glu Thr Leu Arg Leu Tyr Pro Ala Ala Pro
        370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu Asp Pro Leu Glu Phe Lys Pro Glu Arg
                420                 425                 430

Phe Glu Asp Gly Lys Ala Glu Gly Leu Phe Met Ile Pro Phe Gly Met
            435                 440                 445

Gly Arg Arg Arg Cys Pro Gly Glu Thr Leu Ala Leu Arg Thr Ile Gly
            450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Gly Phe Thr Ile Pro Lys
                485                 490                 495
```

```
Ala Val Pro Leu Glu Ala Val Cys Arg Pro Arg Val Val Met Arg Asp
            500                 505                 510

Val Leu Gln Asn Leu
        515

<210> SEQ ID NO 13
<211> LENGTH: 306
<212> TYPE: PRT
<213> ORGANISM: Oryza sativa

<400> SEQUENCE: 13

Met Ser Leu Glu Ala Gln Glu Phe Lys Gln Val Val Asp Glu Ile Ile
1               5                   10                  15

Pro His Ile Gly Ala Ala Asn Leu Trp Asp Tyr Leu Pro Ala Leu Arg
                20                  25                  30

Trp Phe Asp Val Phe Gly Val Arg Lys Ile Leu Ala Ala Val Ser
            35                  40                  45

Arg Arg Asp Ala Phe Leu Arg Arg Leu Ile Asp Ala Glu Arg Arg
        50                  55                  60

Leu Asp Asp Gly Asp Glu Gly Lys Lys Ser Met Ile Ala Val Leu
65                  70                  75                  80

Leu Thr Leu Gln Lys Thr Glu Pro Glu Val Tyr Thr Asp Asn Met Ile
                85                  90                  95

Thr Ala Leu Thr Ala Asn Leu Phe Ala Gly Thr Glu Thr Thr Ser
                100                 105                 110

Thr Thr Ser Glu Trp Ala Met Ser Leu Leu Asn His Pro Asp Thr
            115                 120                 125

Leu Lys Lys Ala Gln Ala Glu Ile Asp Ala Ser Val Gly Asn Ser Arg
130                 135                 140

Leu Ile Thr Ala Asp Asp Val Thr Arg Leu Gly Tyr Leu Gln Cys Ile
145                 150                 155                 160

Val Arg Glu Thr Leu Arg Leu Tyr Pro Ala Ala Pro Met Leu Leu Pro
                165                 170                 175

His Glu Ser Ser Ala Asp Cys Lys Val Gly Gly Tyr Asn Ile Pro Arg
                180                 185                 190

Gly Ser Met Leu Leu Ile Asn Ala Tyr Ala Ile His Arg Asp Pro Ala
            195                 200                 205

Val Trp Glu Glu Pro Glu Lys Phe Met Pro Glu Arg Phe Glu Asp Gly
        210                 215                 220

Gly Cys Asp Gly Asn Leu Leu Met Pro Phe Gly Met Gly Arg Arg Arg
225                 230                 235                 240

Cys Pro Gly Glu Thr Leu Ala Leu Arg Thr Val Gly Leu Val Leu Gly
                245                 250                 255

Thr Leu Ile Gln Cys Phe Asp Trp Glu Arg Val Asp Gly Val Glu Val
                260                 265                 270

Asp Met Thr Glu Gly Gly Leu Thr Ile Pro Lys Val Val Pro Leu
        275                 280                 285

Glu Ala Met Cys Arg Pro Arg Asp Ala Met Gly Gly Val Leu Arg Glu
    290                 295                 300

Leu Val
305

<210> SEQ ID NO 14
<211> LENGTH: 516
<212> TYPE: PRT
```

<213> ORGANISM: Poa annua

<400> SEQUENCE: 14

Met Asp Lys Thr Tyr Val Ala Ile Leu Ser Phe Ala Phe Leu Leu Leu
1               5                   10                  15

Leu His Tyr Leu Val Gly Arg Ser Gly Gly Asn Ser Asn Val Lys Lys
            20                  25                  30

Lys Asp Val Gln Leu Pro Pro Ser Pro Ala Ala Ile Pro Phe Leu Gly
        35                  40                  45

His Leu His Leu Val Glu Lys Pro Phe His Ala Ala Leu Ser Arg Leu
    50                  55                  60

Ala Ala Arg His Gly Pro Val Phe Ser Leu Arg Leu Gly Ser Arg Asn
65                  70                  75                  80

Thr Val Val Val Ser Ser Pro Ala Cys Ala Arg Glu Cys Phe Thr Glu
                85                  90                  95

His Asp Val Ser Phe Ala Asn Arg Pro Leu Phe Pro Ser Gln Leu Leu
            100                 105                 110

Val Ser Phe Asn Gly Thr Ala Leu Ala Ala Ser Ser Tyr Gly Pro Tyr
        115                 120                 125

Trp Arg Asn Leu Arg Arg Ile Ala Thr Val Gln Leu Leu Ser Ala His
    130                 135                 140

Arg Val Ser Cys Met Ser Gly Val Ile Ser Ala Glu Val Arg Ala Met
145                 150                 155                 160

Val Leu Arg Met Tyr Arg Ala Ala Ala Ala Pro Gly Ser Ala Ala
                165                 170                 175

Arg Ile Leu Leu Lys Arg Arg Leu Glu Leu Ser Leu Ser Val Leu
        180                 185                 190

Met Glu Thr Ile Ala Lys Thr Lys Ala Thr Arg Pro Glu Ala Asp Ala
    195                 200                 205

Asp Thr Asp Met Ser Val Glu Ala Gln Glu Phe Lys Lys Met Ser Asp
    210                 215                 220

Glu Ile Ile Pro Gln Leu Gly Thr Ala Asn Leu Trp Asp Tyr Leu Pro
225                 230                 235                 240

Val Leu Arg Trp Phe Asp Val Phe Gly Val Arg Asn Lys Val Leu Asp
                245                 250                 255

Ala Val Arg Arg Arg Asp Ala Phe Leu Arg Arg Leu Ile Asp Ala Glu
            260                 265                 270

Arg Gln Arg Leu Asp Asp Gly Ser Glu Ser Glu Lys Ser Ser Met Ile
        275                 280                 285

Ala Val Leu Leu Thr Leu Gln Arg Thr Glu Pro Glu Val Tyr Thr Asp
    290                 295                 300

Ala Met Ile Thr Ala Leu Cys Gly Asn Leu Phe Gly Ala Gly Thr Glu
305                 310                 315                 320

Thr Ile Ser Ile Thr Thr Glu Trp Ala Met Ser Leu Leu Asn His
                325                 330                 335

Pro Glu Thr Leu Arg Lys Ala Gln Ala Glu Ile Asp Ala Ser Val Gly
            340                 345                 350

Ser Ser Arg Leu Val Ser Ala Asp Asp Met Pro Arg Leu Ser Tyr Leu
        355                 360                 365

Gln Cys Ile Val Ser Glu Thr Leu Arg Leu Tyr Pro Ala Ala Pro Leu
    370                 375                 380

Leu Leu Pro His Glu Ser Ser Thr Asp Cys Lys Val Gly Gly Tyr Asn
385                 390                 395                 400

Ile Pro Ser Gly Thr Met Leu Leu Val Asn Ala Tyr Ala Ile Gln Arg
                405                 410                 415

Asp Pro Thr Val Trp Glu Pro Thr Lys Phe Lys Pro Glu Arg Phe
            420                 425                 430

Glu Asp Gly Lys Ala Glu Gly Leu Phe Met Ile Pro Phe Gly Met Gly
                435                 440                 445

Arg Arg Lys Cys Pro Gly Glu Thr Leu Ala Leu Arg Thr Ile Gly Leu
        450                 455                 460

Val Leu Gly Thr Leu Ile Gln Cys Phe Asp Trp Asp Thr Val Asp Gly
465                 470                 475                 480

Val Glu Val Asp Met Thr Glu Ser Gly Gly Ile Ser Met Pro Lys Ala
                485                 490                 495

Val Pro Leu Glu Ala Ile Cys Lys Pro Arg Ala Ala Met Tyr Gly Val
            500                 505                 510

Leu Gln Asn Leu
        515

<210> SEQ ID NO 15
<211> LENGTH: 732
<212> TYPE: PRT
<213> ORGANISM: Oryza sativa

<400> SEQUENCE: 15

Met Ala Phe Leu Gly Trp Ala Val Asp Ile Ala Arg Asp Ser Gly Ala
1               5                   10                  15

Ser Ser Ser Val Val Leu Thr Cys Asp Gly Tyr Gly Ser Ala Leu Tyr
                20                  25                  30

Phe Ser Pro Trp Asp Ser Val Pro Leu Pro Ala Thr Ala Ser Pro Asp
            35                  40                  45

Asp Gly Phe Leu Leu Pro Arg Phe Pro Asp Val Cys Val Gln Arg Ser
        50                  55                  60

Gln Phe Thr Asn His Leu Ala Pro Ala Asn Gly Thr Gly Gly Gly Gly
65                  70                  75                  80

Ser Arg Thr Gly Val Lys Glu Glu Ala Ser Glu Val Leu Ser Trp Pro
                85                  90                  95

Pro Thr Ser Lys Gln Ser Val Arg Arg Leu Glu Val Ala Glu His Trp
            100                 105                 110

Tyr Arg Leu Tyr Lys Thr Asp Asn Gln Arg Leu Ser Pro Asp Ser Gln
        115                 120                 125

Gln Val Ser Val Leu Ala Glu Ser His Cys Asp Leu Ala Ser Gly Asn
    130                 135                 140

Trp Lys Glu Ile Ser Ile His His Lys Lys Met Pro Ser Ser Thr Thr
145                 150                 155                 160

Thr Lys Thr Thr Thr Pro Ser Arg Asp Ala Trp Ile Val Ser Ala Arg
                165                 170                 175

Ser Asp Pro Phe His Leu Leu Glu Ala Gln Ala Pro Leu Gly Ile
            180                 185                 190

Lys Ala Asp Ala Leu Ser Gln Ile Ala Ala Val His Gln Ser His Arg
        195                 200                 205

Asn Thr Ser His Ile Arg Glu Leu Ser Leu Ala Met Asp Asn Ala Tyr
    210                 215                 220

Ile Ile Ala Ile Leu Ser Val Ala Ile Leu Phe Leu Leu His Tyr Tyr
225                 230                 235                 240

Leu Leu Gly Arg Gly Asn Gly Gly Ala Ala Arg Leu Pro Pro Gly Pro
                245                 250                 255

Pro Ala Val Pro Ile Leu Gly His Leu His Leu Val Lys Lys Pro Met
                260                 265                 270

His Ala Thr Met Ser Arg Leu Ala Glu Arg Tyr Gly Pro Val Phe Ser
            275                 280                 285

Leu Arg Leu Gly Ser Arg Arg Ala Val Val Ser Ser Pro Gly Cys
        290                 295                 300

Ala Arg Glu Cys Phe Thr Glu His Asp Val Thr Phe Ala Asn Arg Pro
305                 310                 315                 320

Arg Phe Glu Ser Gln Leu Leu Val Ser Phe Asn Gly Ala Ala Leu Ala
                325                 330                 335

Thr Ala Ser Tyr Gly Ala His Trp Arg Asn Leu Arg Arg Ile Val Ala
            340                 345                 350

Val Gln Leu Leu Ser Ala His Arg Val Gly Leu Met Ser Gly Leu Ile
        355                 360                 365

Ala Gly Glu Val Arg Ala Met Val Arg Arg Met Tyr Arg Ala Ala Ala
    370                 375                 380

Ala Ser Pro Ala Gly Ala Ala Arg Ile Gln Leu Lys Arg Arg Leu Phe
385                 390                 395                 400

Glu Val Ser Leu Ser Val Leu Met Glu Thr Ile Ala His Thr Lys Ala
                405                 410                 415

Thr Arg Pro Glu Thr Asp Pro Asp Thr Asp Met Ser Val Glu Ala Gln
            420                 425                 430

Glu Phe Lys Gln Val Val Asp Glu Ile Ile Pro His Ile Gly Ala Ala
        435                 440                 445

Asn Leu Trp Asp Tyr Leu Pro Ala Leu Arg Trp Phe Asp Val Phe Gly
    450                 455                 460

Val Arg Arg Lys Ile Leu Ala Ala Val Ser Arg Arg Asp Ala Phe Leu
465                 470                 475                 480

Arg Arg Leu Ile Asp Ala Glu Arg Arg Leu Asp Asp Gly Asp Glu
                485                 490                 495

Gly Glu Lys Lys Ser Met Ile Ala Val Leu Leu Thr Leu Gln Lys Thr
                500                 505                 510

Glu Pro Glu Val Tyr Thr Asp Asn Met Ile Thr Ala Leu Thr Ala Asn
            515                 520                 525

Leu Phe Gly Ala Gly Thr Glu Thr Thr Ser Thr Thr Ser Glu Trp Ala
        530                 535                 540

Met Ser Leu Leu Leu Asn His Pro Asp Thr Leu Lys Lys Ala Gln Ala
545                 550                 555                 560

Glu Ile Asp Ala Ser Val Gly Asn Ser Arg Leu Ile Thr Ala Asp Asp
                565                 570                 575

Val Thr Arg Leu Gly Tyr Leu Gln Cys Ile Val Arg Glu Thr Leu Arg
            580                 585                 590

Leu Tyr Pro Ala Ala Pro Met Leu Leu Pro His Glu Ser Ser Ala Asp
        595                 600                 605

Cys Lys Val Gly Gly Tyr Asn Ile Pro Arg Gly Ser Met Leu Leu Ile
    610                 615                 620

Asn Ala Tyr Ala Ile His Arg Asp Pro Ala Val Trp Glu Glu Pro Glu
625                 630                 635                 640

Lys Phe Met Pro Glu Arg Phe Glu Asp Gly Cys Asp Gly Asn Leu
                645                 650                 655

Leu Met Pro Phe Gly Met Gly Arg Arg Cys Pro Gly Glu Thr Leu
            660                 665                 670

```
Ala Leu Arg Thr Val Gly Leu Val Leu Gly Thr Leu Ile Gln Cys Phe
            675                 680                 685

Asp Trp Glu Arg Val Asp Gly Val Glu Val Asp Met Thr Glu Gly Gly
        690                 695                 700

Gly Leu Thr Ile Pro Lys Val Val Pro Leu Glu Ala Met Cys Arg Pro
705                 710                 715                 720

Arg Asp Ala Met Gly Gly Val Leu Arg Glu Leu Val
                725                 730

<210> SEQ ID NO 16
<211> LENGTH: 518
<212> TYPE: PRT
<213> ORGANISM: Hordeum vulgare

<400> SEQUENCE: 16

Met Asp Lys Ala Tyr Ile Ala Ile Leu Ser Phe Thr Phe Leu Phe Leu
1               5                   10                  15

Leu His Tyr Ile Leu Gly Lys Val Ser Asn Gly Arg Arg Ser Lys Gly
            20                  25                  30

Asp Val Gln Leu Pro Pro Ser Pro Arg Pro Ile Pro Phe Leu Gly His
        35                  40                  45

Leu His Leu Leu Glu Lys Pro Phe His Val Ala Leu Cys Arg Leu Ala
    50                  55                  60

Ala Arg Leu Gly Pro Val Phe Ser Leu Arg Leu Gly Ser Arg Arg Ala
65                  70                  75                  80

Val Val Val Ser Ser Ala Asp Cys Ala Arg Glu Cys Phe Thr Glu His
                85                  90                  95

Asp Val Ile Phe Ala Asn Arg Pro Gln Phe Pro Ser Gln Leu Leu Val
            100                 105                 110

Ser Phe Asp Gly Thr Ala Leu Ser Thr Ser Ser Tyr Gly Pro His Trp
        115                 120                 125

Arg Asn Leu Arg Arg Val Ala Ala Val Gln Leu Leu Ser Ala His Arg
    130                 135                 140

Val Ala Cys Met Ser Gly Val Ile Ala Gly Glu Val Arg Ala Met Ala
145                 150                 155                 160

Arg Arg Leu Phe Arg Ser Ala Glu Ala Ser Pro Gly Gly Gly Gly Ala
                165                 170                 175

Ala Arg Val Gln Leu Lys Arg Arg Leu Phe Glu Leu Ser Leu Ser Val
            180                 185                 190

Leu Met Glu Thr Ile Ala Gln Thr Lys Gly Thr Arg Ser Glu Ala Asp
        195                 200                 205

Ala Asp Thr Asp Met Ser Val Glu Ala Gln Glu Phe Lys Lys Val Val
    210                 215                 220

Asp Glu Ile Ile Pro Tyr Leu Gly Ala Ala Asn Thr Trp Asp Tyr Leu
225                 230                 235                 240

Pro Val Val Arg Trp Phe Asp Val Phe Gly Val Arg Asn Lys Ile Leu
                245                 250                 255

Ala Ala Val Ser Arg Arg Asp Ala Phe Leu His Arg Leu Ile Asp Ala
            260                 265                 270

Glu Arg Arg Arg Leu Asp Gly Gly Ala Glu Ala Asp Lys Lys Ser
        275                 280                 285

Met Ile Ala Val Leu Leu Thr Leu Gln Lys Thr Glu Pro Glu Val Tyr
    290                 295                 300

Thr Asp Thr Met Ile Thr Ala Leu Cys Ser Asn Leu Phe Gly Ala Gly
305                 310                 315                 320
```

```
Thr Glu Thr Thr Ser Thr Thr Thr Glu Trp Ala Met Ser Leu Leu Leu
                325                 330                 335

Asn His Pro Ala Ala Leu Arg Lys Ala Gln Ala Glu Ile Asp Ala Ala
            340                 345                 350

Val Gly Thr Ser Arg Leu Val Thr Ala Asp Val Pro Arg Leu Ala
        355                 360                 365

Tyr Leu Gln Cys Ile Val Ser Glu Thr Leu Arg Leu Tyr Pro Ala Thr
    370                 375                 380

Pro Met Leu Leu Pro His Gln Ser Ser Ala Asp Cys Lys Val Gly Gly
385                 390                 395                 400

Tyr Asn Val Pro Ser Gly Thr Met Leu Met Val Asn Ala Tyr Ala Ile
                405                 410                 415

His Arg Asp Pro Ala Ala Trp Glu Arg Pro Leu Glu Phe Val Pro Glu
            420                 425                 430

Arg Phe Glu Asp Gly Lys Ala Glu Gly Arg Phe Met Ile Pro Phe Gly
        435                 440                 445

Met Gly Arg Arg Arg Cys Pro Gly Glu Thr Leu Ala Leu Arg Thr Ile
    450                 455                 460

Gly Met Val Leu Ala Thr Leu Val Gln Cys Phe Asp Trp Asp Arg Val
465                 470                 475                 480

Asp Gly Lys Glu Val Asp Met Thr Glu Ser Gly Gly Leu Thr Ile Pro
                485                 490                 495

Lys Ala Val Pro Leu Glu Ala Val Cys Arg Pro Arg Ala Ala Met Arg
            500                 505                 510

Asp Val Leu Gln Ser Leu
            515

<210> SEQ ID NO 17
<211> LENGTH: 513
<212> TYPE: PRT
<213> ORGANISM: Oryza sativa

<400> SEQUENCE: 17

Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
                20                  25                  30

Leu Pro Pro Gly Pro Pro Ala Val Pro Ile Leu Gly His Leu His Leu
            35                  40                  45

Val Lys Lys Pro Met His Ala Thr Met Ser Arg Leu Ala Glu Arg Tyr
    50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
    130                 135                 140

Met Ser Gly Leu Ile Ala Gly Glu Val Arg Ala Met Val Arg Arg Met
145                 150                 155                 160

Tyr Arg Ala Ala Ala Ala Ser Pro Ala Gly Ala Ala Arg Ile Gln Leu
```

```
                    165                 170                 175
Lys Arg Arg Leu Phe Glu Val Ser Leu Ser Val Leu Met Glu Thr Ile
                180                 185                 190
Ala His Thr Lys Ala Thr Arg Pro Glu Thr Asp Pro Asp Thr Asp Met
            195                 200                 205
Ser Val Glu Ala Gln Glu Phe Lys Gln Val Val Asp Glu Ile Ile Pro
        210                 215                 220
His Ile Gly Ala Ala Asn Leu Trp Asp Tyr Leu Pro Ala Leu Arg Trp
225                 230                 235                 240
Phe Asp Val Phe Gly Val Arg Arg Lys Ile Leu Ala Ala Val Ser Arg
                245                 250                 255
Arg Asp Ala Phe Leu Arg Arg Leu Ile Asp Ala Glu Arg Arg Arg Leu
            260                 265                 270
Asp Asp Gly Asp Glu Gly Glu Lys Lys Ser Met Ile Ala Val Leu Leu
        275                 280                 285
Thr Leu Gln Lys Thr Glu Pro Glu Val Tyr Thr Asp Asn Met Ile Thr
        290                 295                 300
Ala Leu Thr Ala Asn Leu Phe Gly Ala Gly Thr Glu Thr Thr Ser Thr
305                 310                 315                 320
Thr Ser Glu Trp Ala Met Ser Leu Leu Leu Asn His Pro Asp Thr Leu
                325                 330                 335
Lys Lys Ala Gln Ala Glu Ile Asp Ala Ser Val Gly Asn Ser Arg Leu
            340                 345                 350
Ile Thr Ala Asp Asp Val Thr Arg Leu Gly Tyr Leu Gln Cys Ile Val
        355                 360                 365
Arg Glu Thr Leu Arg Leu Tyr Pro Ala Ala Pro Met Leu Leu Pro His
    370                 375                 380
Glu Ser Ser Ala Asp Cys Lys Val Gly Gly Tyr Asn Ile Pro Arg Gly
385                 390                 395                 400
Ser Met Leu Leu Ile Asn Ala Tyr Ala Ile His Arg Asp Pro Ala Val
                405                 410                 415
Trp Glu Glu Pro Glu Lys Phe Met Pro Glu Arg Phe Glu Asp Gly Gly
            420                 425                 430
Cys Asp Gly Asn Leu Leu Met Pro Phe Gly Met Gly Arg Arg Arg Cys
        435                 440                 445
Pro Gly Glu Thr Leu Ala Leu Arg Thr Val Gly Leu Val Leu Gly Thr
    450                 455                 460
Leu Ile Gln Cys Phe Asp Trp Glu Arg Val Asp Gly Val Glu Val Asp
465                 470                 475                 480
Met Thr Glu Gly Gly Gly Leu Thr Ile Pro Lys Val Val Pro Leu Glu
                485                 490                 495
Ala Met Cys Arg Pro Arg Asp Ala Met Gly Gly Val Leu Arg Glu Leu
            500                 505                 510
Val

<210> SEQ ID NO 18
<211> LENGTH: 518
<212> TYPE: PRT
<213> ORGANISM: Hordeum vulgare

<400> SEQUENCE: 18

Met Asp Lys Ala Ser Ile Ala Val Leu Ser Leu Ala Phe Leu Phe Leu
1               5                   10                  15

Leu His Tyr Ile Leu Gly Lys Arg Ser Asp Gly Arg Arg Gly Lys Gly
```

```
                20                  25                  30
Lys Gly Ala Val Gln Leu Pro Pro Ser Pro Pro Ala Val Pro Phe Phe
                35                  40                  45

Gly His Leu His Leu Val Glu Lys Pro Leu His Ala Ala Leu Cys Arg
    50                  55                  60

Leu Gly Ala Arg His Gly Pro Val Phe Ser Leu Arg Leu Gly Ala Arg
65                  70                  75                  80

Asn Ala Val Val Val Ser Ser Pro Ala Cys Ala Arg Glu Cys Phe Thr
                85                  90                  95

Asp His Asp Val Ala Phe Ala Asn Arg Pro Gln Phe Pro Ser Gln Met
                100                 105                 110

Leu Val Ser Tyr Gly Gly Thr Ser Leu Val Ser Ser Tyr Gly Pro
                115                 120                 125

His Trp Arg Asn Leu Arg Arg Val Ala Ala Val Arg Leu Leu Ser Ala
                130                 135                 140

His Arg Val Ala Gly Met Ser Gly Val Ile Ala Ala Glu Val Arg Ala
145                 150                 155                 160

Met Ala Arg Arg Leu Tyr Arg Ala Ala Ala Ser Pro Gly Gly Ala
                165                 170                 175

Ala Arg Val Glu Leu Lys Arg Ser Leu Phe Glu Leu Ser Leu Ser Val
                180                 185                 190

Leu Met Glu Thr Ile Ala Arg Thr Lys Gly Thr Arg Ser Glu Ala Asp
                195                 200                 205

Ala Asp Thr Asp Met Ser Leu Glu Ala Gln Glu Phe Lys Gln Val Val
                210                 215                 220

Asp Glu Ile Ile Pro Leu Ile Gly Ala Ala Asn Leu Trp Asp Tyr Leu
225                 230                 235                 240

Pro Val Met Arg Trp Phe Asp Val Ser Gly Val Arg Ser Arg Ile Leu
                245                 250                 255

Ala Thr Val Ser Arg Arg Asp Ala Phe Leu His Arg Leu Ile Asp Ala
                260                 265                 270

Glu Arg Arg Arg Met Glu Glu Gly Gly Asp Glu Gly Glu Lys Lys Ser
                275                 280                 285

Met Ile Ala Val Leu Leu Thr Leu Gln Lys Thr Glu Pro Glu Leu Tyr
                290                 295                 300

Thr Asp Gln Met Ile Ile Ala Leu Cys Ala Asn Met Phe Val Ala Gly
305                 310                 315                 320

Thr Glu Thr Thr Ser Thr Thr Ile Glu Trp Ala Met Ser Leu Leu Leu
                325                 330                 335

Asn His Pro Ala Ala Leu Lys Lys Ala Gln Ala Glu Ile Asp Ala Ser
                340                 345                 350

Ile Gly Thr Ser Arg Met Val Ala Asp Asp Val Pro Arg Leu Ser
                355                 360                 365

Tyr Leu Gln Cys Ile Ile Asn Glu Thr Leu Arg Met Tyr Pro Ala Ala
                370                 375                 380

Pro Leu Leu Leu Pro His Glu Ser Ser Ala Asp Cys Lys Val Gly Gly
385                 390                 395                 400

Tyr Asp Val Pro Ser Gly Thr Met Leu Ile Val Asn Ala Tyr Ala Ile
                405                 410                 415

His Arg Asp Pro Ala Thr Trp Glu Asp Pro Thr Ala Phe Arg Pro Glu
                420                 425                 430

Arg Phe Glu Asp Gly Lys Gly Asp Gly Leu Leu Leu Met Pro Phe Gly
                435                 440                 445
```

```
Met Gly Arg Arg Cys Pro Gly Glu Ala Leu Ala Leu Gln Thr Val
    450             455                 460

Gly Val Val Leu Gly Met Leu Val Gln Cys Phe Asp Trp Asp Arg Val
465             470                 475                 480

Asp Gly Val Glu Val Asp Met Thr Glu Gly Val Gly Ile Thr Met Pro
                485                 490                 495

Lys Ser Val Ala Leu Glu Ala Val Cys Arg Pro Arg Ala Ala Met Arg
                500                 505                 510

Asp Val Leu His Lys Leu
            515

<210> SEQ ID NO 19
<211> LENGTH: 517
<212> TYPE: PRT
<213> ORGANISM: Lolium rigidum

<400> SEQUENCE: 19

Met Asp Lys Ala Tyr Ile Ala Ile Leu Ser Cys Ala Phe Leu Phe Leu
1               5                   10                  15

Val His Tyr Val Leu Gly Lys Val Ser His Gly Arg Arg Gly Lys Lys
                20                  25                  30

Gly Ala Val Gln Leu Pro Pro Ser Pro Ala Ile Pro Phe Ile Gly
            35                  40                  45

His Leu His Leu Val Glu Lys Pro Ile His Ala Thr Met Cys Arg Leu
    50                  55                  60

Ala Ala Arg Leu Gly Pro Val Phe Ser Leu Arg Leu Gly Ser Arg Arg
65              70                  75                  80

Ala Val Val Val Ser Ser Ser Glu Cys Ala Arg Glu Cys Phe Thr Glu
                85                  90                  95

His Asp Val Thr Phe Ala Asn Arg Pro Lys Phe Pro Ser Gln Leu Leu
                100                 105                 110

Ala Ser Phe Asn Gly Thr Ala Leu Val Thr Pro Ser Tyr Gly Pro His
            115                 120                 125

Trp Arg Asn Leu Arg Arg Val Ala Thr Val Gln Leu Leu Ser Ala His
    130                 135                 140

Arg Val Ala Cys Met Ser Gly Val Ile Ala Ala Glu Val Arg Ala Met
145                 150                 155                 160

Ala Arg Arg Leu Phe His Ala Ala Glu Ala Ser Pro Gly Gly Ala Ala
                165                 170                 175

Arg Val Gln Leu Lys Arg Gly Pro Phe Glu Leu Ser Leu Ser Val Leu
            180                 185                 190

Met Glu Thr Ile Ala Gln Thr Lys Ala Thr Arg Ser Glu Ala Asp Ala
        195                 200                 205

Asp Thr Asp Met Ser Val Glu Ala Gln Glu Phe Lys Glu Val Val Asp
    210                 215                 220

Lys Pro Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
```

```
                290                 295                 300
Asp Thr Met Ile Thr Ala Leu Cys Ala Asn Leu Phe Gly Ala Gly Thr
305                 310                 315                 320

Glu Thr Thr Ser Thr Thr Glu Arg Ala Met Ser Leu Leu Leu Asn
            325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Met Pro Ser Leu Ala Tyr
            355                 360                 365

Leu Gln Cys Ile Val Asn Glu Thr Leu Arg Leu Tyr Pro Ala Ala Pro
    370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu His Pro Leu Glu Phe Arg Pro Glu Arg
                420                 425                 430

Phe Glu Asp Gly Lys Ala Glu Gly Leu Phe Met Ile Pro Phe Gly Met
            435                 440                 445

Gly Arg Arg Cys Pro Gly Glu Thr Leu Ala Leu Arg Thr Ile Gly
    450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Ala Val Met Arg Asp
                500                 505                 510

Val Leu Gln Asn Leu
            515

<210> SEQ ID NO 20
<211> LENGTH: 517
<212> TYPE: PRT
<213> ORGANISM: Lolium rigidum

<400> SEQUENCE: 20

Met Asp Lys Ala Tyr Ile Ala Ile Leu Ser Cys Ala Phe Leu Phe Leu
1               5                   10                  15

Val His Tyr Val Leu Gly Lys Val Ser His Gly Arg Arg Gly Lys Lys
                20                  25                  30

Gly Ala Val Gln Leu Pro Pro Ser Pro Pro Ala Ile Pro Phe Ile Gly
            35                  40                  45

His Leu His Leu Val Glu Lys Pro Ile His Ala Thr Met Cys Arg Leu
    50                  55                  60

Ala Ala Arg Leu Gly Pro Val Phe Ser Leu Arg Leu Gly Ser Arg Arg
65                  70                  75                  80

Ala Val Val Val Ser Ser Ser Glu Cys Ala Arg Glu Cys Phe Thr Glu
                85                  90                  95

His Asp Val Thr Phe Ala Asn Arg Pro Ser Ser Arg Arg Lys Leu Leu
                100                 105                 110

Ala Ser Phe Asn Gly Thr Ala Leu Val Thr Ser Ser Tyr Gly Pro His
            115                 120                 125

Trp Arg Asn Leu Arg Arg Val Ala Thr Val Gln Leu Leu Ser Ala His
    130                 135                 140
```

```
Arg Val Ala Cys Met Ser Gly Val Ile Ala Ala Glu Val Arg Ala Met
145                 150                 155                 160

Ala Arg Arg Leu Phe His Ala Ala Glu Ala Ser Pro Asp Gly Ala Thr
            165                 170                 175

Arg Val Gln Leu Lys Arg Arg Leu Phe Glu Leu Ser Leu Ser Val Leu
        180                 185                 190

Met Glu Thr Ile Ala Gln Thr Lys Ala Thr Arg Ser Glu Ala Asp Ala
    195                 200                 205

Asp Thr Asp Met Ser Val Glu Ala Gln Glu Phe Lys Glu Val Val Asp
        210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
290                 295                 300

Asp Thr Met Ile Thr Ala Leu Cys Ala Asn Leu Phe Gly Ala Gly Thr
305                 310                 315                 320

Glu Thr Thr Ser Thr Thr Glu Trp Ala Met Ser Leu Leu Leu Asn
                325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Leu Ser Leu Ala Tyr
        355                 360                 365

Leu Gln Cys Ile Val Ser Glu Thr Leu Arg Leu Tyr Pro Ala Ala Pro
    370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu His Pro Leu Glu Phe Arg Pro Glu Arg
            420                 425                 430

Phe Glu Asp Gly Lys Ala Glu Gly Leu Phe Met Ile Pro Phe Gly Met
        435                 440                 445

Gly Arg Arg Arg Cys Pro Gly Glu Thr Leu Ala Leu Arg Thr Ile Gly
    450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Thr Val Met Arg Asp
            500                 505                 510

Val Leu Gln Asn Leu
        515

<210> SEQ ID NO 21
<211> LENGTH: 517
<212> TYPE: PRT
<213> ORGANISM: Lolium rigidum

<400> SEQUENCE: 21
```

```
Met Asp Lys Ala Tyr Ile Ala Ile Leu Ser Cys Ala Phe Leu Phe Leu
1               5                   10                  15

Val His Tyr Val Leu Gly Lys Val Ser Asp Gly Arg Arg Gly Lys Lys
            20                  25                  30

Gly Ala Val Gln Leu Pro Pro Ser Pro Pro Ala Ile Pro Phe Ile Gly
            35                  40                  45

His Leu His Leu Val Glu Lys Pro Ile His Ala Thr Met Cys Arg Leu
        50                  55                  60

Ala Ala Arg Leu Gly Pro Val Phe Ser Leu Arg Leu Gly Ser Arg Arg
65                  70                  75                  80

Ala Val Val Val Pro Ser Ser Glu Cys Ala Arg Glu Cys Phe Thr Glu
                85                  90                  95

His Asp Val Thr Phe Ala Asn Arg Pro Lys Phe Pro Ser Gln Leu Leu
            100                 105                 110

Ala Ser Phe Asn Gly Thr Ala Leu Val Thr Ser Ser Tyr Gly Pro His
            115                 120                 125

Trp Arg Asn Leu Arg Arg Val Ala Thr Val Gln Leu Leu Ser Ala His
        130                 135                 140

Arg Val Ala Cys Met Ser Gly Val Ile Ala Ala Glu Val Arg Ala Met
145                 150                 155                 160

Ala Arg Arg Leu Phe His Ala Ala Glu Ala Ser Pro Asp Gly Ala Ala
                165                 170                 175

Arg Val Gln Leu Lys Arg Arg Leu Phe Glu Leu Ser Leu Ser Val Leu
            180                 185                 190

Met Glu Thr Ile Ala Gln Thr Lys Ala Thr Arg Ser Glu Ala Asp Ala
        195                 200                 205

Asp Thr Asp Met Ser Val Glu Ala Gln Glu Phe Lys Glu Val Val Asp
210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
            245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
        290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
            325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Pro Ser Leu Ala Tyr
            355                 360                 365

Leu Gln Cys Ile Val Asn Glu Thr Leu Arg Leu Tyr Pro Ala Ala Pro
        370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
            405                 410                 415
```

```
Arg Asp Pro Ala Ala Trp Glu His Pro Leu Glu Phe Arg Pro Glu Arg
            420                 425                 430

Phe Glu Asp Gly Lys Ala Glu Gly Leu Phe Met Ile Pro Phe Gly Val
            435                 440                 445

Gly Arg Arg Arg Cys Pro Gly Glu Thr Leu Ala Leu Arg Thr Ile Ser
450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Ala Val Met Arg Asp
            500                 505                 510

Val Leu Gln Asn Leu
            515

<210> SEQ ID NO 22
<211> LENGTH: 540
<212> TYPE: PRT
<213> ORGANISM: Hordeum vulgare

<400> SEQUENCE: 22

Leu Thr Gln His Thr Ser Asn Gln Pro Gln Thr Ser Ser Val Lys Thr
1               5                   10                  15

Arg Asp Thr Ser Leu Pro Met Asp Lys Ala Tyr Ile Ala Ile Leu Thr
            20                  25                  30

Ile Val Phe Leu Phe Leu Leu His Tyr Ile Leu Arg Arg Val Ser Asn
            35                  40                  45

Gly Arg Arg Gly Lys Gly Ala Val Gln Leu Pro Pro Ser Pro Pro Ala
50                  55                  60

Val Pro Phe Leu Gly His Leu His Leu Leu Glu Lys Pro Phe His Ala
65                  70                  75                  80

Ala Leu Gly Arg Leu Ala Ala Arg Leu Gly Pro Val Phe Ser Leu Arg
            85                  90                  95

Leu Gly Ser Arg Arg Ala Val Val Ser Ser Ala Glu Cys Ala Arg
            100                 105                 110

Glu Cys Phe Thr Glu His Asp Val Thr Phe Ala Asn Arg Pro Arg Phe
            115                 120                 125

Pro Ser Gln Leu Leu Val Ser Phe Asn Gly Ala Ala Leu Ala Thr Ser
            130                 135                 140

Ser Tyr Gly Pro His Trp Arg Asn Leu Arg Arg Val Ala Ala Val Gln
145                 150                 155                 160

Leu Leu Ser Ala His Arg Val Ala Cys Met Ser Gly Val Ile Ala Gly
            165                 170                 175

Glu Val Arg Ala Met Ala Arg Arg Leu Phe Arg Ala Ala Glu Ala Ser
            180                 185                 190

Pro Gly Gly Gly Gly Ala Ala Arg Val Gln Leu Lys Arg Arg Leu Phe
            195                 200                 205

Glu Leu Ser Leu Ser Val Leu Met Glu Thr Ile Ala Gln Thr Lys Gly
            210                 215                 220

Thr Arg Ser Glu Ala Asp Ala Asp Thr Asp Met Ser Val Glu Ala Gln
225                 230                 235                 240

Glu Phe Lys Lys Val Val Asp Glu Ile Ile Pro Tyr Leu Gly Ala Ala
            245                 250                 255

Asn Thr Trp Asp Tyr Leu Pro Val Met Arg Trp Phe Asp Val Phe Gly
            260                 265                 270
```

Val Arg Asn Lys Ile Leu Ala Ala Val Ser Arg Arg Asp Ala Phe Leu
            275                 280                 285

His Arg Leu Ile Asp Ala Glu Arg Arg Leu Asp Gly Gly Gly Ala
        290                 295                 300

Glu Ala Asp Lys Lys Ser Met Ile Ala Val Leu Leu Thr Leu Gln Lys
305                 310                 315                 320

Thr Glu Pro Glu Val Tyr Thr Asp Thr Met Ile Thr Ala Leu Cys Ala
                325                 330                 335

Asn Leu Phe Gly Ala Gly Thr Glu Thr Thr Ser Ser Thr Thr Glu Trp
                340                 345                 350

Ala Met Ser Leu Leu Asn His Pro Ala Ala Leu Arg Lys Ala Gln
            355                 360                 365

Ala Glu Ile Asp Val Ala Val Gly Thr Ser Arg Leu Val Thr Ala Asp
        370                 375                 380

Asp Val Pro Arg Leu Ala Tyr Leu Gln Cys Ile Val Ser Glu Thr Leu
385                 390                 395                 400

Arg Leu Tyr Pro Ala Ala Pro Met Leu Leu Pro His Gln Ser Ser Ala
                405                 410                 415

Asp Cys Lys Val Gly Gly Tyr Asn Val Pro Ser Gly Thr Met Leu Met
            420                 425                 430

Val Asn Ala Tyr Ala Ile His Arg Asp Pro Ala Ala Trp Glu Arg Pro
            435                 440                 445

Leu Glu Phe Val Pro Glu Arg Phe Glu Asp Gly Lys Ala Glu Gly Arg
        450                 455                 460

Phe Met Ile Pro Phe Gly Met Gly Arg Arg Cys Pro Gly Glu Thr
465                 470                 475                 480

Leu Ala Leu Arg Thr Ile Gly Met Val Leu Ala Thr Leu Val Gln Cys
                485                 490                 495

Phe Asp Trp Asp Arg Val Asp Gly Lys Glu Val Asp Met Thr Glu Ser
            500                 505                 510

Gly Gly Leu Thr Ile Pro Lys Ala Val Pro Leu Glu Ala Val Cys Arg
            515                 520                 525

Pro Arg Ala Ala Met Arg Asp Val Leu Gln Ser Leu
            530                 535                 540

<210> SEQ ID NO 23
<211> LENGTH: 517
<212> TYPE: PRT
<213> ORGANISM: Lolium rigidum

<400> SEQUENCE: 23

Met Asp Lys Ala Tyr Ile Ala Ile Leu Ser Cys Ala Phe Leu Phe Leu
1               5                   10                  15

Val His Tyr Val Leu Gly Lys Val Ser Asp Gly Arg Arg Gly Lys Lys
            20                  25                  30

Gly Ala Val Gln Leu Pro Ser Pro Ala Val Pro Phe Leu Gly
            35                  40                  45

His Leu His Leu Val Asp Lys Pro Ile His Ala Thr Met Cys Arg Leu
    50                  55                  60

Ala Ala Arg Leu Gly Pro Val Phe Ser Leu Leu Gly Ser Arg Arg
65                  70                  75                  80

Ala Val Val Val Ser Ser Ser Glu Cys Ala Arg Glu Cys Phe Thr Glu
                85                  90                  95

His Asp Val Thr Phe Ala Asn Arg Pro Lys Phe Pro Ser Gln Leu Leu

```
                100             105             110
Val Ser Phe Asn Gly Thr Ala Leu Val Thr Ser Ser Tyr Gly Pro His
        115             120             125

Trp Arg Asn Leu Arg Arg Val Ala Thr Val Gln Leu Leu Ser Ala His
        130             135             140

Arg Val Ala Cys Met Ser Gly Val Ile Ala Ala Glu Val Arg Ala Met
145             150             155             160

Ala Arg Arg Leu Phe His Ala Thr Glu Ala Ser Pro Asp Gly Ala Ala
                165             170             175

Arg Val Gln Leu Lys Arg Leu Phe Glu Leu Ser Leu Ser Val Leu
                180             185             190

Met Glu Thr Ile Ala Gln Thr Lys Ala Thr Arg Ser Glu Ala Asp Ala
        195             200             205

Asp Thr Asp Met Ser Val Glu Ala Gln Glu Phe Lys Glu Val Val Asp
        210             215             220

Lys Leu Ile Pro His Leu Gly Ala Ala Asn Met Trp Asp Tyr Leu Pro
225             230             235             240

Val Met Arg Trp Phe Asp Val Phe Gly Val Arg Asn Lys Ile Leu His
                245             250             255

Ala Val Ser Arg Arg Asp Ala Phe Leu Arg Arg Leu Ile Asp Ala Glu
                260             265             270

Arg Arg Arg Leu Ala Asp Gly Gly Ser Asp Gly Asp Lys Lys Ser Met
        275             280             285

Ile Ala Val Leu Leu Thr Leu Gln Lys Thr Glu Pro Lys Val Tyr Thr
        290             295             300

Asp Thr Met Ile Thr Ala Leu Cys Ala Asn Leu Phe Gly Ala Gly Thr
305             310             315             320

Glu Thr Thr Ser Thr Thr Thr Glu Trp Ala Met Ser Leu Leu Leu Asn
                325             330             335

His Pro Ala Ala Leu Lys Lys Ala Gln Ala Glu Ile Asp Ala Ser Val
                340             345             350

Gly Thr Ser Arg Leu Val Ser Val Asp Asp Val Pro Ser Leu Ala Tyr
                355             360             365

Leu Gln Cys Ile Val Ser Glu Thr Leu Arg Leu Tyr Pro Ala Ala Pro
        370             375             380

Leu Leu Leu Pro His Glu Ser Ser Ala Asp Cys Lys Val Gly Gly Tyr
385             390             395             400

Asn Val Pro Ala Asp Thr Met Leu Ile Val Asn Ala Tyr Ala Ile His
                405             410             415

Arg Asp Pro Ala Ala Trp Glu Asp Pro Leu Glu Phe Arg Pro Glu Arg
                420             425             430

Phe Glu Asp Gly Lys Ala Glu Gly Leu Phe Met Ile Pro Phe Gly Met
        435             440             445

Gly Arg Arg Arg Cys Pro Gly Glu Thr Leu Ala Leu Arg Thr Ile Gly
        450             455             460

Met Val Leu Ala Thr Leu Val Gln Cys Phe Asp Trp Glu Pro Val Asp
465             470             475             480

Gly Val Lys Val Asp Met Thr Glu Gly Gly Phe Thr Ile Pro Lys
                485             490             495

Ala Val Pro Leu Glu Ala Val Cys Arg Pro Arg Ala Val Met Arg Asp
                500             505             510

Val Leu Gln Asn Leu
        515
```

<210> SEQ ID NO 24
<211> LENGTH: 513
<212> TYPE: PRT
<213> ORGANISM: Oryza sativa

<400> SEQUENCE: 24

```
Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
            20                  25                  30

Leu Pro Pro Gly Pro Pro Ala Val Pro Ile Leu Gly His Leu His Leu
        35                  40                  45

Val Lys Lys Pro Met His Ala Thr Met Ser Arg Leu Ala Glu Arg Tyr
    50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
    130                 135                 140

Met Ser Gly Leu Ile Ala Gly Glu Val Arg Ala Met Val Arg Arg Met
145                 150                 155                 160

Tyr Arg Ala Ala Ala Ser Pro Ala Gly Ala Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
        195                 200                 205

Ser Val Glu Ala Gln Glu Phe Lys Gln Val Val Asp Glu Ile Ile Pro
    210                 215                 220

His Ile Gly Ala Ala Asn Leu Trp Asp Tyr Leu Pro Ala Leu Arg Trp
225                 230                 235                 240

Phe Asp Val Phe Gly Val Arg Arg Lys Ile Leu Ala Ala Val Ser Arg
                245                 250                 255

Arg Asp Ala Phe Leu Arg Arg Leu Ile Asp Ala Glu Arg Arg Arg Leu
            260                 265                 270

Asp Asp Gly Asp Glu Gly Glu Lys Lys Ser Met Ile Ala Val Leu Leu
        275                 280                 285

Thr Leu Gln Lys Thr Glu Pro Glu Val Tyr Thr Asp Asn Met Ile Thr
    290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Thr Arg Leu Gly Tyr Leu Gln Cys Ile Val
        355                 360                 365

Arg Glu Thr Leu Arg Leu Tyr Pro Ala Ala Pro Met Leu Leu Pro His
```

```
                370                 375                 380
Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
                420                 425                 430

Cys Asp Gly Asn Leu Leu Met Pro Phe Gly Met Gly Arg Arg Arg Cys
                435                 440                 445

Pro Gly Glu Thr Leu Ala Leu Arg Thr Val Gly Leu Val Leu Gly Thr
                450                 455                 460

Leu Ile Gln Cys Phe Asp Trp Glu Arg Val Asp Gly Val Glu Val Asp
465                 470                 475                 480

Met Thr Glu Gly Gly Leu Thr Ile Pro Lys Val Val Pro Leu Glu
                485                 490                 495

Ala Met Cys Arg Pro Arg Asp Ala Met Gly Gly Val Leu Arg Glu Leu
                500                 505                 510

Val

<210> SEQ ID NO 25
<211> LENGTH: 517
<212> TYPE: PRT
<213> ORGANISM: Zea mays

<400> SEQUENCE: 25

Met Asp Lys Ala Tyr Ile Ala Ala Leu Ser Ala Ala Leu Phe Leu
1               5                   10                  15

Leu His Tyr Leu Leu Gly Arg Arg Ala Gly Gly Glu Gly Lys Thr Lys
                20                  25                  30

Gly Ser Gln Arg Arg Leu Pro Pro Ser Pro Ala Ile Pro Phe Leu
                35                  40                  45

Gly His Leu His Leu Val Lys Ala Pro Phe His Ala Ala Leu Ala Arg
    50                  55                  60

Leu Ala Ala Arg His Gly Pro Val Phe Ser Met Arg Leu Gly Thr Arg
65                  70                  75                  80

Arg Ala Val Val Ser Ser Pro Asp Cys Ala Arg Glu Cys Phe Thr
                85                  90                  95

Glu His Asp Val Asn Phe Ala Asn Arg Pro Leu Phe Pro Ser Met Arg
                100                 105                 110

Leu Ala Ser Phe Asp Gly Ala Met Leu Ser Val Ser Ser Tyr Gly Pro
                115                 120                 125

Tyr Trp Arg Asn Leu Arg Val Ala Ala Val Gln Leu Leu Ser Ala
130                 135                 140

His Arg Val Ala Cys Met Ala Pro Ala Ile Glu Ala Gln Val Arg Ala
145                 150                 155                 160

Met Val Arg Arg Met Asp Arg Ala Ala Ala Gly Gly Gly Ala
                165                 170                 175

Ala Arg Val Gln Leu Lys Arg Leu Phe Glu Leu Ser Leu Ser Val
                180                 185                 190

Leu Met Glu Thr Ile Ala His Thr Lys Thr Ser Arg Ala Glu Ala Asp
                195                 200                 205

Ala Asp Ser Asp Met Ser Pro Glu Ala His Glu Phe Lys Gln Ile Val
                210                 215                 220

Asp Glu Leu Val Pro Tyr Ile Gly Thr Ala Asn Arg Trp Asp Tyr Leu
```

Pro Val Leu Arg Trp Phe Asp Val Phe Gly Val Arg Asn Lys Ile Leu
225                 230                 235                 240

Asp Ala Val Gly Arg Asp Ala Phe Leu Arg Arg Leu Ile Asp Gly
        245                 250                 255

Glu Arg Arg Leu Asp Ala Gly Asp Ser Glu Ser Lys Ser Met
260                 265                 270

Ile Ala Val Leu Leu Thr Leu Gln Lys Ser Glu Pro Glu Val Tyr Thr
275                 280                 285

Asp Thr Val Ile Thr Ala Leu Cys Ala Asn Leu Phe Gly Ala Gly Thr
290                 295                 300

Glu Thr Thr Ser Thr Thr Thr Glu Trp Ala Met Ser Leu Leu Leu Asn
305                 310                 315                 320

His Arg Glu Ala Leu Lys Lys Ala Gln Ala Glu Ile Asp Ala Ala Val
            325                 330                 335

Gly Thr Ser Arg Leu Val Thr Ala Asp Asp Val Pro His Leu Thr Tyr
            340                 345                 350

Leu Gln Cys Ile Val Asp Glu Thr Leu Arg Leu His Pro Ala Ala Pro
            355                 360                 365

Leu Leu Leu Pro His Glu Ser Ala Ala Asp Cys Thr Val Gly Gly Tyr
370                 375                 380

Asp Val Pro Arg Gly Thr Met Leu Leu Val Asn Val His Ala Val His
385                 390                 395                 400

Arg Asp Pro Ala Val Trp Asp Asp Pro Asp Arg Phe Val Pro Glu Arg
            405                 410                 415

Phe Glu Gly Gly Lys Ala Glu Gly Arg Leu Leu Met Pro Phe Gly Met
            420                 425                 430

Gly Arg Arg Lys Cys Pro Gly Glu Thr Leu Ala Leu Arg Thr Val Gly
            435                 440                 445

Leu Val Leu Gly Thr Leu Leu Gln Cys Phe Asp Trp Asp Thr Val Asp
465                 470                 475                 480

Gly Ala Gln Val Asp Met Lys Ala Ser Gly Gly Leu Thr Met Pro Arg
            485                 490                 495

Ala Val Pro Leu Glu Ala Met Cys Arg Pro Arg Thr Ala Met Arg Asp
            500                 505                 510

Val Leu Lys Arg Leu
            515

<210> SEQ ID NO 26
<211> LENGTH: 1799
<212> TYPE: DNA
<213> ORGANISM: Alopecurus

<400> SEQUENCE: 26
gcagtggtat caacgcagag tacatgggga cagcccagtg acccagtctg tgaatccggc     60
tatacgatca gacaactctt acgaaacctc agcggcagag ccaaagcctg tgttttcctc    120
tagttcaccg ccccgatgac gatggccacc cgagctctcc acatactggg tgaggcctct    180
ccgtggagcc tagccggtgc ggcggcggcc atggcgctgc tgtggctggc cgcctggatc    240
ctcgagtggg catggtggac cccgcggcgg ctgggtcggg ccctgcaggc tcagggcctc    300
acgggcaccc ggtaccgcct attaccggag acgtcacgg agaacgcccg gctcaacagg    360
gcggcccggt ccaagcccct gccgctcggc tcccacgaca tcattcctcg cgtgcagcca    420
atgctcagca acgccgttaa ggagaacggg aaactgtcgt tcacttggtt tggcccaaca    480

```
ccaagggtga tgattcatga cccagaatta gtgagagaaa ttctgtccaa caagtttgga    540
cactacggta aaccacagac tagccgtttg tttaagctgc tagccgacgg gcttgtcaat    600
catgaaggcg agaaatgggc aaagcaccgg agaatcctaa atcctgcctt tcacagtgag    660
aagataaaga ggatgctgcc agttttttca acctgtagcg aagaaatgat cacgagatgg    720
gagaattcag tgtcctctga aggattatct gaggtggacg tctggcctga gttccagaat    780
ctgactggag atgtcatctc gagaacagcg ttcggtagca gttatcagga ggggatgaaa    840
atattccagc tccaaggaga gctagctgaa cggctgatac aagcttttca gacactttt     900 atcccaggct attggttctt accgactaga acaacagaa gaatgagagc aatcgaccgt     960
gagatctgca caattctgcg aggaattatt gagaagaaaa acagagctat taaaaatggt   1020
gatgctagaa gcgatgactt gctaggattg ctgctggagt caaatatgcg ggaatcaaat   1080
gggaaagcag atctaggaat gagcactgaa gacacaatgg aggaatgcaa gctatttat   1140 tttgcaggca tggagacaac atcagtcttg ctcacatgga cactaattct gctgagcatg   1200 caccccggagt ggcaagagca ggcaagaaag gaagtgttgc accacttcgg aagaaccaca   1260
ccagattttg agaacttgag tcgcctgaaa atagtaacta tgattctata tgaagttctc   1320
aggctgtacc caccggcagt ctttatgacc agaagaacat acaaggcaat ggagcttggc   1380
ggcatcacat atccggcagg agtgaacttt atgttgcccg ttctctttat ccaccatgat   1440
cccactatat ggggaaaaga tgcaagcgaa ttcaatccac agaggtttgc tgatggcatc   1500
tcgaatgcgg caaagcatcc ggctgcgttc ttcccatttg gaggtggtcc tcggatctgc   1560
atcggccaga actttgcgtt actggaagct aagatggctc ttagcaccat cctccagcgc   1620
ttctcgttcc agctctcgcc gtcctacacc cacgctccgt acaccgtgtt aaccctccac   1680
ccgcagcacg gtgctccaat tatgctgaag aagatatgac catgcttaca tgttgtgtgt   1740
aatttgaagt tgaagctttg agctgaataa acatagcacc gagtttacat gtgtgttttt   1799
```

<210> SEQ ID NO 27
<211> LENGTH: 527
<212> TYPE: PRT
<213> ORGANISM: Alopecurus

<400> SEQUENCE: 27

```
Met Thr Met Ala Thr Arg Ala Leu His Ile Leu Gly Glu Ala Ser Pro
1               5                   10                  15

Trp Ser Leu Ala Gly Ala Ala Ala Met Ala Leu Leu Trp Leu Ala
            20                  25                  30

Ala Trp Ile Leu Glu Trp Ala Trp Trp Thr Pro Arg Arg Leu Gly Arg
        35                  40                  45

Ala Leu Gln Ala Gln Gly Leu Thr Gly Thr Arg Tyr Arg Leu Phe Thr
    50                  55                  60

Gly Asp Val Thr Glu Asn Ala Arg Leu Asn Arg Ala Ala Arg Ser Lys
65                  70                  75                  80

Pro Leu Pro Leu Gly Ser His Asp Ile Ile Pro Arg Val Gln Pro Met
                85                  90                  95

Leu Ser Asn Ala Val Lys Glu Asn Gly Lys Leu Ser Phe Thr Trp Phe
            100                 105                 110

Gly Pro Thr Pro Arg Val Met Ile His Asp Pro Glu Leu Val Arg Glu
        115                 120                 125

Ile Leu Ser Asn Lys Phe Gly His Tyr Gly Lys Pro Gln Thr Ser Arg
    130                 135                 140
```

Leu Phe Lys Leu Leu Ala Asp Gly Leu Val Asn His Glu Gly Glu Lys
145                 150                 155                 160

Trp Ala Lys His Arg Arg Ile Leu Asn Pro Ala Phe His Ser Glu Lys
            165                 170                 175

Ile Lys Arg Met Leu Pro Val Phe Ser Thr Cys Ser Glu Glu Met Ile
            180                 185                 190

Thr Arg Trp Glu Asn Ser Val Ser Ser Glu Gly Leu Ser Glu Val Asp
            195                 200                 205

Val Trp Pro Glu Phe Gln Asn Leu Thr Gly Asp Val Ile Ser Arg Thr
210                 215                 220

Ala Phe Gly Ser Ser Tyr Gln Glu Gly Met Lys Ile Phe Gln Leu Gln
225                 230                 235                 240

Gly Glu Leu Ala Glu Arg Leu Ile Gln Ala Phe Gln Thr Leu Phe Ile
            245                 250                 255

Pro Gly Tyr Trp Phe Leu Pro Thr Arg Asn Asn Arg Arg Met Arg Ala
            260                 265                 270

Ile Asp Arg Glu Ile Cys Thr Ile Leu Arg Gly Ile Ile Glu Lys Lys
            275                 280                 285

Asn Arg Ala Ile Lys Asn Gly Asp Ala Arg Ser Asp Asp Leu Leu Gly
290                 295                 300

Leu Leu Leu Glu Ser Asn Met Arg Glu Ser Asn Gly Lys Ala Asp Leu
305                 310                 315                 320

Gly Met Ser Thr Glu Asp Thr Met Glu Glu Cys Lys Leu Phe Tyr Phe
            325                 330                 335

Ala Gly Met Glu Thr Thr Ser Val Leu Leu Thr Trp Thr Leu Ile Leu
            340                 345                 350

Leu Ser Met His Pro Glu Trp Gln Gln Ala Arg Lys Glu Val Leu
            355                 360                 365

His His Phe Gly Arg Thr Thr Pro Asp Phe Glu Asn Leu Ser Arg Leu
            370                 375                 380

Lys Ile Val Thr Met Ile Leu Tyr Glu Val Leu Arg Leu Tyr Pro Pro
385                 390                 395                 400

Ala Val Phe Met Thr Arg Arg Thr Tyr Lys Ala Met Glu Leu Gly Gly
            405                 410                 415

Ile Thr Tyr Pro Ala Gly Val Asn Phe Met Leu Pro Val Leu Phe Ile
            420                 425                 430

His His Asp Pro Thr Ile Trp Gly Lys Asp Ala Ser Glu Phe Asn Pro
            435                 440                 445

Gln Arg Phe Ala Asp Gly Ile Ser Asn Ala Ala Lys His Pro Ala Ala
            450                 455                 460

Phe Phe Pro Phe Gly Gly Gly Pro Arg Ile Cys Ile Gly Gln Asn Phe
465                 470                 475                 480

Ala Leu Leu Glu Ala Lys Met Ala Leu Ser Thr Ile Leu Gln Arg Phe
            485                 490                 495

Ser Phe Gln Leu Ser Pro Ser Tyr Thr His Ala Pro Tyr Thr Val Leu
            500                 505                 510

Thr Leu His Pro Gln His Gly Ala Pro Ile Met Leu Lys Lys Ile
            515                 520                 525

<210> SEQ ID NO 28
<211> LENGTH: 525
<212> TYPE: PRT
<213> ORGANISM: Lolium rigidum

<400> SEQUENCE: 28

```
Met Ala Thr Arg Ala Leu Gln Met Leu Gly Glu Ala Ser Pro Trp Asn
1               5                   10                  15

Leu Ala Cys Ala Ala Ala Met Ala Leu Leu Trp Leu Ala Ala Trp
            20                  25                  30

Ile Leu Glu Trp Ala Trp Trp Thr Pro Arg Arg Leu Gly Arg Ala Leu
        35                  40                  45

Glu Ala Gln Gly Leu Lys Gly Thr Arg Tyr Arg Leu Phe Thr Gly Asp
    50                  55                  60

Val Pro Glu Asn Ala Arg Leu Asn Lys Glu Ala Arg Ser Lys Pro Leu
65                  70                  75                  80

Pro Leu Gly Ser His Asp Ile Ile Pro Arg Val Gln Pro Met Ile Ser
                85                  90                  95

Asn Ala Ile Lys Glu Asn Gly Lys Leu Ser Phe Thr Trp Phe Gly Pro
            100                 105                 110

Glu Pro Arg Val Thr Ile Leu Asp Pro Glu Ser Val Arg Glu Ile Leu
        115                 120                 125

Ser Asn Lys Phe Gly His Tyr Gly Lys Pro Arg Ser Ser Arg Phe Gly
    130                 135                 140

Lys Leu Leu Ala Asn Gly Leu Val Asn His Gln Gly Glu Lys Trp Ala
145                 150                 155                 160

Lys His Arg Arg Ile Leu Asn Pro Ala Phe His His Glu Lys Ile Lys
                165                 170                 175

Arg Met Leu Pro Val Phe Ser Ala Cys Ser Glu Glu Met Ile Thr Arg
            180                 185                 190

Trp Glu Asn Ser Met Ser Ser Gln Gly Val Ser Glu Val Asp Val Trp
        195                 200                 205

Pro Glu Phe Gln Asn Leu Thr Gly Asp Val Ile Ser Arg Thr Ala Phe
    210                 215                 220

Gly Ser Ser Tyr Gln Glu Gly Thr Lys Ile Phe Gln Leu Gln Gly Glu
225                 230                 235                 240

Gln Ala Glu Arg Leu Met Gln Ala Phe Gln Thr Leu Phe Ile Pro Gly
                245                 250                 255

Tyr Trp Phe Leu Pro Thr Lys Asn Asn Arg Arg Met Arg Ala Ile Asp
            260                 265                 270

Arg Glu Ile Cys Thr Ile Leu Arg Gly Ile Ile Glu Lys Lys Asp Arg
        275                 280                 285

Ala Ile Lys Ser Gly Glu Ala Ser Ser Asp Asp Leu Leu Gly Leu Leu
    290                 295                 300

Leu Glu Ser Asn Arg Arg Glu Ser Asn Gly Lys Ala Asn Leu Gly Met
305                 310                 315                 320

Ser Thr Glu Asp Ile Ile Glu Glu Cys Lys Leu Phe Tyr Phe Ala Gly
                325                 330                 335

Met Glu Thr Thr Ser Val Leu Leu Thr Trp Thr Leu Ile Val Leu Ser
            340                 345                 350

Met His Pro Glu Trp Gln Glu Gln Ala Arg Lys Glu Val Leu His His
        355                 360                 365

Phe Gly Arg Thr Thr Pro Asp Phe Glu Asn Leu Ser Arg Leu Lys Ile
    370                 375                 380

Val Thr Met Val Leu Tyr Glu Val Leu Arg Leu Tyr Pro Pro Ala Ile
385                 390                 395                 400

Phe Val Thr Arg Arg Thr Tyr Lys Ala Met Glu Leu Gly Gly Ile Thr
                405                 410                 415
```

```
Tyr Pro Ala Gly Val Asn Leu Met Leu Pro Ile Leu Phe Ile His His
            420                 425                 430

Asp Pro Asn Ile Trp Gly Lys Asp Ala Ser Glu Phe Asn Pro Gln Arg
        435                 440                 445

Phe Ala Asp Gly Ile Ser Asn Ala Val Lys Asn Pro Ala Ala Phe Phe
450                 455                 460

Pro Phe Gly Gly Pro Arg Ile Cys Ile Gly Gln Asn Phe Ala Leu
465                 470                 475                 480

Leu Glu Ala Lys Met Ala Leu Ser Thr Ile Leu Gln Arg Phe Ser Phe
                485                 490                 495

Glu Leu Ser Pro Ser Tyr Thr His Ser Pro Tyr Thr Val Leu Thr Leu
            500                 505                 510

His Pro Gln His Gly Ala Pro Ile Val Leu Arg Lys Ile
        515                 520                 525

<210> SEQ ID NO 29
<211> LENGTH: 528
<212> TYPE: PRT
<213> ORGANISM: Zea mays

<400> SEQUENCE: 29

Met Ala Thr Leu Pro Leu Leu His Leu Leu Trp Glu Ala Ser Pro
1               5                   10                  15

Trp Ala Arg Ala Gly Ala Ala Thr Ala Val Val Leu Val Trp Leu
            20                  25                  30

Ala Ala Trp Thr Leu Glu Trp Ala Trp Trp Thr Pro Arg Arg Leu Asp
            35                  40                  45

Arg Ala Leu Arg Ala Gln Gly Leu Lys Gly Thr Arg Tyr Arg Leu Leu
        50                  55                  60

Thr Gly Asp Val Arg Glu Asn Ala Arg Leu Asn Arg Glu Ala Arg Thr
65                  70                  75                  80

Lys Pro Leu Pro Leu Gly Ser His Asp Ile Pro Arg Val Leu Pro
                85                  90                  95

Met Phe His Asn Ala Val Lys Glu Asn Gly Thr Asn Ser Phe Thr Trp
            100                 105                 110

Phe Gly Pro Ile Pro Arg Val Ile Ile Pro Asp Pro Glu Leu Met Arg
        115                 120                 125

Glu Val Leu Ser Asn Lys Phe Gly His Phe Gly Lys Pro Leu Phe Ser
130                 135                 140

Arg Val Gly Lys Leu Leu Ala Asn Gly Leu Ala Asn His Glu Gly Glu
145                 150                 155                 160

Lys Trp Ala Lys His Arg Arg Ile Leu Asn Pro Ala Phe His His Glu
                165                 170                 175

Lys Ile Lys Gly Met Leu Pro Val Phe Ala Thr Cys Cys Ala Asp Met
            180                 185                 190

Ile Asn Arg Trp Glu Asn Ser Met Ser Ser Lys Glu Pro Ser Glu Met
        195                 200                 205

Asp Val Trp Pro Glu Phe Gln Asn Leu Thr Gly Asp Val Ile Ser Arg
210                 215                 220

Thr Ala Phe Gly Ser Asn Tyr Gln Glu Gly Arg Asn Ile Phe Gln Leu
225                 230                 235                 240

Gln Gly Glu Gln Ala Glu Arg Leu Ile Gln Ser Phe Gln Thr Ile Phe
                245                 250                 255

Ile Pro Gly Tyr Trp Phe Leu Pro Thr Lys Asn Asn Arg Arg Met Lys
```

```
                   260                 265                 270
Glu Ile Asp Arg Glu Ile Arg Lys Ile Leu His Gly Ile Ile Arg Lys
            275                 280                 285

Arg Glu Arg Ala Phe Ile Asp Ser Glu Gly Thr Asn Asp Leu Leu
        290                 295                 300

Gly Leu Leu Val Glu Ser Asn Met Arg Glu Ser Asn Gly Asn Ala Lys
305                 310                 315                 320

Leu Gly Met Thr Thr Glu Asp Ile Ile Glu Glu Cys Lys Leu Phe Tyr
                325                 330                 335

Phe Ala Gly Met Glu Thr Thr Ser Val Leu Leu Thr Trp Thr Leu Ile
            340                 345                 350

Leu Leu Ser Met His Pro Glu Trp Gln Glu Gln Ala Arg Glu Glu Val
            355                 360                 365

Leu Asn His Phe Gly Met Gly Thr Pro Asp Phe Asp Asn Leu Asn Arg
            370                 375                 380

Leu Lys Ile Val Thr Met Ile Leu Tyr Glu Val Leu Arg Leu Tyr Pro
385                 390                 395                 400

Pro Val Val Phe Leu Ser Arg Arg Thr Tyr Lys Glu Met Glu Leu Gly
                405                 410                 415

Gly Ile Lys Tyr Pro Ser Gly Val Ser Leu Leu Leu Pro Ile Ile Phe
                420                 425                 430

Ile His His Asp Pro Asn Ile Trp Gly Lys Asp Ala Ser Glu Phe Asn
            435                 440                 445

Pro Gln Arg Phe Glu Asp Gly Ile Ser Asn Ala Thr Lys His Gln Ala
        450                 455                 460

Ala Phe Phe Pro Phe Gly Trp Gly Pro Arg Ile Cys Ile Gly Gln Asn
465                 470                 475                 480

Phe Ala Leu Leu Glu Ala Lys Met Ala Leu Ser Thr Ile Leu Gln Arg
                485                 490                 495

Phe Ser Phe Glu Leu Ser Ser Ser Tyr Thr His Ala Pro Tyr Thr Val
                500                 505                 510

Ile Thr Leu His Pro Gln His Gly Ala Gln Ile Arg Leu Lys Lys Leu
            515                 520                 525

<210> SEQ ID NO 30
<211> LENGTH: 523
<212> TYPE: PRT
<213> ORGANISM: Oryza sativa

<400> SEQUENCE: 30

Met Leu Met Met Leu Gly Ala Ala Ser Gln Trp Ile Leu Ala Ala Ala
1               5                   10                  15

Ala Ala Ala Val Ala Ala Leu Leu Trp Leu Ala Val Ser Thr Leu
            20                  25                  30

Glu Trp Ala Trp Trp Thr Pro Arg Arg Leu Glu Arg Ala Leu Arg Ala
        35                  40                  45

Gln Gly Ile Arg Gly Asn Arg Tyr Arg Leu Phe Thr Gly Asp Val Pro
    50                  55                  60

Glu Asn Val Arg Leu Asn Arg Glu Ala Arg Lys Lys Pro Leu Pro Leu
65                  70                  75                  80

Gly Cys His Asp Ile Ile Pro Arg Val Leu Pro Met Phe Ser Lys Ala
                85                  90                  95

Val Glu Glu His Gly Lys Pro Ser Phe Thr Trp Phe Gly Pro Thr Pro
            100                 105                 110
```

-continued

Arg Val Met Ile Ser Asp Pro Glu Ser Ile Arg Glu Val Met Ser Asn
            115                 120                 125

Lys Phe Gly His Tyr Gly Lys Pro Lys Pro Thr Arg Leu Gly Lys Leu
    130                 135                 140

Leu Ala Ser Gly Val Val Ser Tyr Glu Gly Glu Lys Trp Ala Lys His
145                 150                 155                 160

Arg Arg Ile Leu Asn Pro Ala Phe His His Glu Lys Ile Lys Arg Met
                165                 170                 175

Leu Pro Val Phe Ser Asn Cys Cys Thr Glu Met Val Thr Arg Trp Glu
            180                 185                 190

Asn Ser Met Ser Ile Glu Gly Met Ser Glu Val Asp Val Trp Pro Glu
        195                 200                 205

Phe Gln Asn Leu Thr Gly Asp Val Ile Ser Lys Thr Ala Phe Gly Ser
    210                 215                 220

Ser Tyr Glu Glu Gly Arg Arg Ile Phe Gln Leu Gln Ala Glu Ser Ala
225                 230                 235                 240

Glu Arg Ile Ile Gln Ala Phe Arg Thr Ile Phe Ile Pro Gly Tyr Trp
                245                 250                 255

Phe Leu Pro Thr Lys Asn Asn Arg Arg Leu Arg Glu Ile Glu Arg Glu
            260                 265                 270

Val Ser Lys Leu Leu Arg Gly Ile Ile Gly Lys Arg Glu Arg Ala Ile
        275                 280                 285

Lys Asn Gly Glu Thr Ser Asn Gly Asp Leu Leu Gly Leu Leu Val Glu
    290                 295                 300

Ser Asn Met Arg Glu Ser Asn Gly Lys Ala Glu Leu Gly Met Thr Thr
305                 310                 315                 320

Asp Glu Ile Ile Glu Glu Cys Lys Leu Phe Tyr Phe Ala Gly Met Glu
                325                 330                 335

Thr Thr Ser Val Leu Leu Thr Trp Thr Leu Ile Val Leu Ser Met His
            340                 345                 350

Pro Glu Trp Gln Glu Arg Ala Arg Glu Glu Val Leu His His Phe Gly
        355                 360                 365

Arg Thr Thr Pro Asp Tyr Asp Ser Leu Ser Arg Leu Lys Ile Val Thr
    370                 375                 380

Met Ile Leu Tyr Glu Val Leu Arg Leu Tyr Pro Pro Val Val Phe Leu
385                 390                 395                 400

Thr Arg Arg Thr Tyr Lys Glu Met Glu Leu Gly Gly Ile Lys Tyr Pro
                405                 410                 415

Ala Glu Val Thr Leu Met Leu Pro Ile Leu Phe Ile His His Asp Pro
            420                 425                 430

Asp Ile Trp Gly Lys Asp Ala Gly Glu Phe Asn Pro Gly Arg Phe Ala
        435                 440                 445

Asp Gly Ile Ser Asn Ala Thr Lys Tyr Gln Thr Ser Phe Phe Pro Phe
    450                 455                 460

Gly Trp Gly Pro Arg Ile Cys Ile Gly Gln Asn Phe Ala Leu Leu Glu
465                 470                 475                 480

Ala Lys Met Ala Ile Cys Thr Ile Leu Gln Arg Phe Ser Phe Glu Leu
                485                 490                 495

Ser Pro Ser Tyr Ile His Ala Pro Phe Thr Val Ile Thr Leu His Pro
            500                 505                 510

Gln His Gly Ala Gln Ile Lys Leu Lys Lys Ile
        515                 520

```
<210> SEQ ID NO 31
<211> LENGTH: 519
<212> TYPE: PRT
<213> ORGANISM: Oryza sativa

<400> SEQUENCE: 31
```

| | | | | | | | | | | | | | | |
|---|---|---|---|---|---|---|---|---|---|---|---|---|---|---|
| Met | Leu | Gly | Glu | Ala | Ala | Ser | Pro | Trp | Ser | Leu | Ala | Gly | Ala | Ala |
| 1 | | | | 5 | | | | | 10 | | | | | 15 |
| Ala | Val | Ala | Leu | Leu | Trp | Leu | Cys | Ala | Trp | Thr | Leu | Gln | Trp | Ala | Trp |
| | | | 20 | | | | | 25 | | | | | 30 | | |
| Trp | Thr | Pro | Arg | Arg | Leu | Glu | Arg | Ala | Leu | Arg | Ala | Gln | Gly | Leu | Arg |
| | | | 35 | | | | | 40 | | | | | 45 | | |
| Gly | Thr | Arg | Tyr | Arg | Leu | Phe | Ile | Gly | Asp | Val | Ala | Glu | Asn | Gly | Arg |
| | 50 | | | | | 55 | | | | | 60 | | | | |
| Leu | Asn | Arg | Glu | Ala | Ala | Ser | Arg | Pro | Leu | Pro | Leu | Gly | Ser | His | Asp |
| 65 | | | | | 70 | | | | | 75 | | | | | 80 |
| Val | Val | Pro | Arg | Val | Met | Pro | Phe | Phe | Cys | Asn | Val | Leu | Lys | Glu | His |
| | | | | 85 | | | | | 90 | | | | | 95 | |
| Gly | Lys | Leu | Ser | Phe | Val | Trp | Thr | Gly | Pro | Lys | Pro | Phe | Val | Ile | Ile |
| | | | 100 | | | | | 105 | | | | | 110 | | |
| Arg | Asp | Pro | Asp | Leu | Ala | Arg | Glu | Ile | Leu | Ser | Asn | Lys | Ser | Gly | Asn |
| | | | 115 | | | | | 120 | | | | | 125 | | |
| Phe | Ala | Lys | Gln | Thr | Thr | Ala | Gly | Ile | Ala | Lys | Phe | Val | Val | Gly | Gly |
| | 130 | | | | | 135 | | | | | 140 | | | | |
| Val | Val | Thr | Tyr | Glu | Gly | Glu | Lys | Trp | Ala | Lys | His | Arg | Arg | Ile | Leu |
| 145 | | | | | 150 | | | | | 155 | | | | | 160 |
| Asn | Pro | Ala | Phe | His | Gln | Glu | Lys | Ile | Lys | Arg | Met | Leu | Pro | Val | Phe |
| | | | | 165 | | | | | 170 | | | | | 175 | |
| Leu | Ala | Cys | Cys | Thr | Lys | Met | Ile | Thr | Arg | Trp | Val | Asn | Ser | Met | Ser |
| | | | 180 | | | | | 185 | | | | | 190 | | |
| Ser | Glu | Gly | Ile | Ser | Glu | Leu | Asp | Val | Trp | Asp | Glu | Phe | Gln | Asn | Leu |
| | | | 195 | | | | | 200 | | | | | 205 | | |
| Thr | Gly | Asp | Val | Ile | Ser | Arg | Thr | Ala | Phe | Gly | Ser | Ser | Tyr | Gln | Glu |
| | 210 | | | | | 215 | | | | | 220 | | | | |
| Gly | Trp | Arg | Ile | Phe | Gln | Leu | Gln | Glu | Glu | Gln | Ala | Lys | Arg | Val | Leu |
| 225 | | | | | 230 | | | | | 235 | | | | | 240 |
| Lys | Ala | Phe | Gln | Arg | Ile | Phe | Ile | Pro | Gly | Tyr | Trp | Tyr | Leu | Pro | Ile |
| | | | | 245 | | | | | 250 | | | | | 255 | |
| Glu | Asn | Asn | Arg | Arg | Ile | Arg | Glu | Ile | Asp | Gln | Glu | Ile | Arg | Thr | Ile |
| | | | 260 | | | | | 265 | | | | | 270 | | |
| Leu | Arg | Gly | Ile | Ile | Val | Lys | Arg | Asp | Lys | Ala | Val | Arg | Asn | Gly | Glu |
| | | | 275 | | | | | 280 | | | | | 285 | | |
| Gly | Ser | Asn | Asp | Asp | Leu | Leu | Gly | Leu | Leu | Val | Glu | Ser | Asn | Met | Arg |
| | 290 | | | | | 295 | | | | | 300 | | | | |
| Gln | Ser | Asn | Glu | Lys | Glu | Asp | Val | Gly | Met | Ser | Ile | Glu | Asp | Met | Ile |
| 305 | | | | | 310 | | | | | 315 | | | | | 320 |
| Glu | Glu | Cys | Lys | Leu | Phe | Tyr | Ala | Ala | Gly | Ser | Glu | Thr | Thr | Ser | Met |
| | | | | 325 | | | | | 330 | | | | | 335 | |
| Leu | Leu | Thr | Trp | Thr | Leu | Ile | Leu | Leu | Ser | Met | His | Pro | Glu | Trp | Gln |
| | | | 340 | | | | | 345 | | | | | 350 | | |
| Glu | Gln | Ala | Arg | Glu | Glu | Val | Met | His | His | Phe | Gly | Arg | Thr | Thr | Pro |
| | | | 355 | | | | | 360 | | | | | 365 | | |
| Asp | His | Asp | Gly | Leu | Ser | Arg | Leu | Lys | Ile | Val | Thr | Met | Ile | Leu | His |
| | 370 | | | | | 375 | | | | | 380 | | | | |

```
Glu Val Leu Arg Leu Tyr Pro Pro Val Val Phe Leu Gln Arg Thr Thr
385                 390                 395                 400

His Lys Glu Ile Glu Leu Gly Gly Ile Lys Tyr Pro Glu Gly Val Asn
                405                 410                 415

Phe Thr Leu Pro Val Leu Ser Ile His His Asp Pro Ser Ile Trp Gly
            420                 425                 430

Gln Asp Ala Ile Lys Phe Asn Pro Glu Arg Phe Ala Asn Gly Val Ser
        435                 440                 445

Lys Ala Thr Lys Phe Gln Thr Ala Phe Phe Ser Phe Ala Trp Gly Pro
450                 455                 460

Arg Ile Cys Leu Gly Gln Ser Phe Ala Ile Leu Glu Ala Lys Met Ala
465                 470                 475                 480

Leu Ala Thr Ile Leu Gln Ser Phe Ser Phe Glu Leu Ser Pro Ser Tyr
                485                 490                 495

Thr His Ala Pro His Thr Val Leu Thr Leu Gln Pro Gln Tyr Gly Ser
            500                 505                 510

Pro Ile Lys Leu Lys Lys Leu
            515

<210> SEQ ID NO 32
<211> LENGTH: 519
<212> TYPE: PRT
<213> ORGANISM: Oryza sativa

<400> SEQUENCE: 32

Met Leu Ile Met Leu Gly Leu Gly Leu Val Pro Ala Gly Ala Ala Ala
1               5                   10                  15

Ala Leu Ala Val Ala Leu Val Cys Leu Ala Ala Ala Ala Trp Trp Thr
                20                  25                  30

Val Glu Arg Ala Pro Arg Arg Leu Glu Arg Ala Leu Arg Ala Gln Gly
            35                  40                  45

Val Gly Gly Gly Arg Tyr Gln Leu Leu Leu Gly Gly Asp Val Ala Glu
        50                  55                  60

Asn Gly Arg Leu Asn Arg Glu Ala Trp Ser Arg Pro Leu Pro Leu Gly
65                  70                  75                  80

Cys His Arg Ile Ala Pro Arg Val Leu Pro Leu Leu Trp Asn Ala Val
                85                  90                  95

Arg Asp His Gly Lys Leu Ser Phe Ile Trp Phe Gly Pro Val Pro Arg
            100                 105                 110

Val Met Ile Pro Asp Pro Glu Leu Val Arg Glu Val Phe Asn Lys Phe
        115                 120                 125

Asp Gln Phe Gly Lys Pro Lys Met Ile Arg Val Gly Lys Leu Leu Ala
    130                 135                 140

Thr Gly Val Val Ser Tyr Glu Gly Glu Lys Trp Ala Lys His Arg Arg
145                 150                 155                 160

Ile Leu Asn His Ala Phe His His Glu Lys Ile Lys Arg Met Leu Pro
                165                 170                 175

Val Phe Ala Asn Cys Cys Thr Glu Met Val Thr Arg Trp Glu Asn Ser
            180                 185                 190

Ile Ser Leu Glu Ala Ala Ser Gly Ile Asp Val Trp Pro Glu Phe Arg
        195                 200                 205

Asn Leu Thr Gly Asp Val Ile Ser Arg Thr Ala Phe Gly Ser Ser Tyr
    210                 215                 220

Gln Glu Gly Arg Arg Ile Phe Gln Leu Gln Glu Glu Leu Ala Gln Tyr
225                 230                 235                 240
```

```
Leu Thr Glu Ala Leu Gln Lys Leu Phe Ile Pro Gly Tyr Trp Tyr Leu
                245                 250                 255

Pro Thr Lys Asn Asn Arg Arg Met Arg Glu Ile Asp Arg Glu Val Arg
            260                 265                 270

Lys Ile Leu Leu Glu Ile Ile Gly Asn Lys Glu Arg Ala Ile Thr Asn
        275                 280                 285

Gly Glu Asn Ser Asn Asp Asp Met Leu Gly Leu Leu Val Glu Ser Asn
    290                 295                 300

Thr Lys Gln Pro Glu Leu Arg Met Ser Thr Asp Asp Ile Ile Glu Glu
305                 310                 315                 320

Cys Lys Leu Phe Tyr Phe Ala Gly Met Glu Thr Thr Ser Val Leu Leu
                325                 330                 335

Thr Trp Thr Leu Ile Val Leu Ser Met His Pro Glu Trp Gln Glu Arg
            340                 345                 350

Ala Arg Glu Glu Val Leu His His Phe Gly Arg Thr Thr Pro Asp
        355                 360                 365

Tyr Asp Ser Leu Ser Arg Leu Lys Ile Val Thr Met Ile Leu Tyr Glu
    370                 375                 380

Val Leu Arg Leu Tyr Pro Pro Val Val Leu Asn Arg Arg Thr Phe
385                 390                 395                 400

Lys Glu Thr Asn Leu Gly Gly Ile Lys Phe Pro Ala Asp Met Asn Leu
                405                 410                 415

Ile Leu Pro Ile Leu Phe Ile His His Asp Pro Glu Ile Trp Gly Lys
            420                 425                 430

Asp Ala Ser Glu Phe Asn Pro Gly Arg Phe Ala Asp Gly Ile Ser Asn
        435                 440                 445

Ala Ser Lys Tyr His Asp Ala Ser Phe Phe Pro Phe Gly Trp Gly Pro
    450                 455                 460

Arg Ile Cys Ile Gly Gln Ser Phe Ala Leu Leu Glu Ala Lys Met Ala
465                 470                 475                 480

Leu Ser Met Ile Leu Gln Arg Phe Ser Leu Glu Leu Ser Pro Ser Tyr
                485                 490                 495

Ile His Ala Pro Tyr Ile Val Leu Thr Leu Arg Pro His Gly Ala
            500                 505                 510

Gln Ile Lys Leu Lys Arg Ile
        515

<210> SEQ ID NO 33
<211> LENGTH: 519
<212> TYPE: PRT
<213> ORGANISM: Oryza sativa

<400> SEQUENCE: 33

Met Leu Gly Glu Ala Ala Ser Pro Trp Ser Leu Ala Gly Ala Gly Ala
1               5                   10                  15

Ala Val Ala Leu Leu Trp Leu Cys Ala Trp Thr Leu Gln Trp Ala Trp
            20                  25                  30

Trp Thr Pro Arg Arg Leu Glu Arg Ala Leu Arg Ala Gln Gly Leu Arg
        35                  40                  45

Gly Thr Arg Tyr Arg Leu Phe Ile Gly Asp Val Ala Glu Asn Gly Arg
    50                  55                  60

Leu Asn Arg Glu Ala Ala Ser Arg Pro Leu Pro Leu Gly Ser His Asp
65              70                  75                  80

Val Val Pro Arg Val Met Pro Phe Phe Cys Asn Val Leu Lys Glu His
```

-continued

```
                85                  90                  95
Gly Lys Leu Ser Phe Val Trp Thr Gly Pro Lys Pro Phe Val Ile Ile
            100                 105                 110
Arg Asp Pro Asp Leu Ala Arg Glu Ile Leu Ser Asn Lys Ser Gly Asn
            115                 120                 125
Phe Ala Lys Gln Thr Thr Ala Gly Ile Ala Lys Phe Val Val Gly Gly
            130                 135                 140
Val Val Thr Tyr Glu Gly Glu Lys Trp Ala Lys His Arg Arg Ile Leu
145                 150                 155                 160
Asn Pro Ala Phe His Gln Glu Lys Ile Lys Arg Met Leu Pro Val Phe
                165                 170                 175
Leu Ala Cys Cys Thr Lys Met Ile Thr Arg Trp Val Asn Ser Met Ser
                180                 185                 190
Ser Glu Gly Ile Ser Glu Leu Asp Val Trp Asp Glu Phe Gln Asn Leu
                195                 200                 205
Thr Gly Asp Val Ile Ser Arg Thr Ala Phe Gly Ser Ser Tyr Gln Glu
                210                 215                 220
Gly Trp Arg Ile Phe Gln Leu Gln Glu Glu Gln Ala Lys Arg Val Leu
225                 230                 235                 240
Lys Ala Phe Gln Arg Ile Phe Ile Pro Gly Tyr Trp Tyr Leu Pro Ile
                245                 250                 255
Glu Asn Asn Arg Arg Ile Arg Glu Ile Asp Gln Glu Ile Arg Thr Ile
                260                 265                 270
Leu Arg Gly Ile Ile Val Lys Arg Asp Lys Ala Val Arg Asn Gly Glu
                275                 280                 285
Gly Ser Asn Asp Asp Leu Leu Gly Leu Leu Val Glu Ser Asn Met Arg
                290                 295                 300
Gln Ser Asn Glu Lys Glu Asp Val Gly Met Ser Ile Glu Asp Met Ile
305                 310                 315                 320
Glu Glu Cys Lys Leu Phe Tyr Ala Ala Gly Ser Glu Thr Thr Ser Met
                325                 330                 335
Leu Leu Thr Trp Thr Leu Ile Leu Leu Ser Met His Pro Glu Trp Gln
                340                 345                 350
Glu Gln Ala Arg Glu Glu Val Met His His Phe Gly Arg Thr Thr Pro
                355                 360                 365
Asp His Asp Gly Leu Ser Arg Leu Lys Ile Val Thr Met Ile Leu His
                370                 375                 380
Glu Val Leu Arg Leu Tyr Pro Pro Val Val Phe Leu Gln Arg Thr Thr
385                 390                 395                 400
His Lys Glu Ile Glu Leu Gly Gly Ile Lys Tyr Pro Glu Gly Val Asn
                405                 410                 415
Phe Thr Leu Pro Val Leu Ser Ile His His Asp Pro Ser Ile Trp Gly
                420                 425                 430
Gln Asp Ala Ile Lys Phe Asn Pro Glu Arg Phe Ala Asn Gly Ile Ser
                435                 440                 445
Lys Ala Thr Lys Phe Gln Thr Ala Phe Phe Ser Phe Ala Trp Gly Pro
                450                 455                 460
Arg Ile Cys Leu Gly Gln Ser Phe Ala Ile Leu Glu Ala Lys Met Ala
465                 470                 475                 480
Leu Ala Thr Ile Leu Gln Ser Phe Ser Phe Glu Leu Ser Pro Ser Tyr
                485                 490                 495
Thr His Ala Pro His Thr Val Leu Thr Leu Gln Pro Gln Tyr Gly Ser
                500                 505                 510
```

```
Pro Ile Lys Leu Lys Lys Leu
        515

<210> SEQ ID NO 34
<211> LENGTH: 525
<212> TYPE: PRT
<213> ORGANISM: Lolium rigidum

<400> SEQUENCE: 34

Met Ala Thr Arg Ala Leu Gln Met Leu Arg Glu Ala Ser Pro Trp Ser
1               5                   10                  15

Leu Ala Gly Ala Ala Ala Met Ala Leu Leu Trp Leu Ala Ala Trp
            20                  25                  30

Ile Val Glu Trp Ala Trp Trp Thr Pro Arg Arg Leu Arg Arg Ala Leu
        35                  40                  45

Gln Ala Gln Gly Leu Arg Gly Thr Gln Tyr Arg Leu Phe Thr Gly Asp
    50                  55                  60

Val Pro Glu Asn Ala Arg Leu Asn Arg Glu Ala Arg Ser Lys Pro Leu
65                  70                  75                  80

Pro Leu Gly Ser His Asp Ile Ile Gln Arg Val Gln Pro Met Phe Ser
                85                  90                  95

Asn Val Ile Lys Glu Asn Gly Lys Phe Ser Phe Thr Trp Phe Gly Pro
            100                 105                 110

Thr Pro Arg Val Met Ile Pro Asp Pro Glu Leu Val Arg Glu Val Leu
        115                 120                 125

Ser Asn Lys Phe Gly His Tyr Gly Lys Gln Lys Ser Ser Arg Leu Gly
    130                 135                 140

Lys Leu Leu Ala Asn Gly Leu Ala Asn His Gln Gly Glu Lys Trp Ala
145                 150                 155                 160

Lys His Arg Arg Ile Leu Asn Pro Ala Phe His Asn Glu Lys Ile Lys
                165                 170                 175

Arg Met Leu Pro Val Phe Ala Thr Cys Cys Glu Glu Met Ile Thr Arg
            180                 185                 190

Trp Asp Asn Ser Met Ser Thr Glu Gly Ser Ser Glu Ile Asp Ile Trp
        195                 200                 205

Pro Glu Phe Gln Asn Leu Thr Gly Asp Val Ile Ser Arg Thr Ala Phe
    210                 215                 220

Gly Ser Asn Tyr Gln Glu Gly Met Lys Ile Phe Gln Leu Gln Gly Glu
225                 230                 235                 240

Leu Ala Glu Arg Leu Ile Met Ala Phe Gln Thr Ile Phe Ile Pro Gly
                245                 250                 255

Tyr Trp Phe Leu Pro Thr Lys Asn Asn Lys Arg Met Arg Ala Ile Asp
            260                 265                 270

Cys Glu Ile Arg Thr Ile Leu Arg Val Ile Arg Lys Lys Asp Lys
        275                 280                 285

Ala Ile Lys Asn Gly Glu Ala Ile Ser Asp Leu Leu Gly Leu Leu
    290                 295                 300

Leu Glu Ser Asn Met Arg Glu Ser Asn Gly Lys Ala Asp Leu Gly Met
305                 310                 315                 320

Ser Thr Glu Glu Ile Ile Gln Glu Cys Lys Leu Phe Tyr Phe Ala Gly
                325                 330                 335

Met Glu Thr Thr Ser Val Leu Thr Trp Thr Leu Ile Leu Leu Ser
            340                 345                 350

Met His Pro Glu Trp Gln Glu Lys Ala Arg Asp Glu Val Leu Tyr His
```

```
                  355                 360                 365
Phe Gly Arg Thr Thr Pro Asp Phe Glu His Leu Ser Arg Leu Lys Ile
        370                 375                 380

Val Thr Met Ile Leu Tyr Glu Val Leu Arg Leu Tyr Pro Pro Ile Thr
385                 390                 395                 400

Ile Leu Thr Arg Arg Thr Tyr Lys Ala Met Glu Leu Gly Gly Ile Lys
                405                 410                 415

Tyr Pro Ala Gly Val Asn Leu Met Leu Pro Ile Leu Phe Ile His His
            420                 425                 430

Asp Pro Asn Leu Trp Gly Lys Asp Ala Ser Glu Phe Asn Pro Glu Arg
        435                 440                 445

Phe Ala Asp Gly Ile Ser Asn Ala Ala Lys His Pro Gly Ser Phe Phe
    450                 455                 460

Pro Phe Gly Gly Gly Pro Arg Ile Cys Ile Gly Gln Asn Phe Ala Leu
465                 470                 475                 480

Leu Glu Ala Lys Met Ala Leu Ser Thr Ile Leu Gln His Phe Ser Leu
                485                 490                 495

Glu Leu Ser Pro Ser Tyr Thr His Ala Pro Tyr Thr Val Ile Thr Leu
            500                 505                 510

His Pro Gln His Gly Ala Gln Ile Arg Met Lys Lys Ile
        515                 520                 525

<210> SEQ ID NO 35
<211> LENGTH: 527
<212> TYPE: PRT
<213> ORGANISM: Oryza sativa

<400> SEQUENCE: 35

Met Gln Ser Ser Gly Phe Ile Pro Glu Lys Gly Gly Thr Ser Ala Pro
1               5                   10                  15

Ser Thr Gln Val Met Val Pro Glu Ser Asn Gly Leu Thr Leu Ser
                20                  25                  30

Asp Glu Glu Tyr Asp Gly Leu Val Glu Gln Ser Lys Arg Arg Ala Ser
            35                  40                  45

Asp Ser Asp Gln Pro Ile Leu Gln Arg Ala Glu Lys Met Lys Ala Glu
        50                  55                  60

Arg Asn Leu Asp Asn Gln Lys Thr Thr Asp Arg Ala Ala Gln Leu Gln
65                  70                  75                  80

Lys Cys Asp Glu Asp Ile Lys Leu Ile Lys Thr Ala Cys Arg Ile His
                85                  90                  95

Glu Thr Met Val Met Gln Phe Phe Ala Asn Tyr Gly Lys Leu Ser Phe
                100                 105                 110

Ile Trp Phe Gly Pro Val Pro Arg Val Met Ile Pro Asp Pro Glu Leu
        115                 120                 125

Val Arg Glu Val Phe Asn Lys Phe Asp Gln Phe Gly Lys Pro Lys Met
    130                 135                 140

Ile Arg Val Gly Lys Leu Leu Ala Thr Gly Val Val Ser Tyr Glu Gly
145                 150                 155                 160

Glu Lys Trp Ala Lys His Arg Arg Ile Leu Asn His Ala Phe His His
                165                 170                 175

Glu Lys Ile Lys Arg Met Leu Pro Val Phe Ala Asn Cys Cys Thr Glu
            180                 185                 190

Met Val Thr Arg Trp Glu Asn Ser Ile Ser Leu Glu Ala Ala Ser Glu
        195                 200                 205
```

```
Ile Asp Val Trp Pro Glu Phe Arg Asn Leu Thr Gly Asp Val Ile Ser
    210                 215                 220

Arg Thr Ala Phe Gly Ser Ser Tyr Gln Glu Gly Arg Arg Ile Phe Gln
225                 230                 235                 240

Leu Gln Glu Glu Leu Ala Gln Tyr Leu Thr Glu Ala Leu Gln Lys Leu
                245                 250                 255

Phe Ile Pro Gly Tyr Trp Tyr Leu Pro Thr Lys Asn Asn Arg Arg Met
                    260                 265                 270

Arg Glu Ile Asp Arg Glu Val Arg Lys Ile Leu Leu Glu Ile Ile Gly
                275                 280                 285

Asn Lys Glu Arg Ala Ile Thr Asn Gly Glu Asn Ser Asn Asp Asp Met
290                 295                 300

Leu Gly Leu Leu Val Glu Ser Asn Thr Lys Gln Pro Glu Leu Arg Met
305                 310                 315                 320

Ser Thr Asp Asp Ile Ile Glu Glu Cys Lys Leu Phe Tyr Phe Ala Gly
                    325                 330                 335

Met Glu Thr Thr Ser Val Leu Leu Thr Trp Thr Leu Ile Val Leu Ser
                340                 345                 350

Met His Pro Glu Trp Gln Glu Arg Ala Arg Glu Glu Val Leu His His
                355                 360                 365

Phe Gly Arg Thr Thr Thr Pro Asp Tyr Asp Ser Leu Ser Arg Leu Lys
370                 375                 380

Ile Val Thr Met Ile Leu Tyr Glu Val Leu Arg Leu Tyr Pro Pro Val
385                 390                 395                 400

Val Leu Leu Asn Arg Arg Thr Phe Lys Glu Thr Asn Leu Gly Gly Ile
                    405                 410                 415

Lys Phe Pro Ala Asp Met Asn Leu Ile Leu Pro Ile Leu Phe Ile His
                420                 425                 430

His Asp Pro Glu Ile Trp Gly Lys Asp Ala Ser Glu Phe Asn Pro Gly
                435                 440                 445

Arg Phe Ala Asp Gly Ile Ser Asn Ala Ser Lys Tyr His Asp Ala Ser
        450                 455                 460

Phe Phe Pro Phe Gly Trp Gly Pro Arg Ile Cys Ile Gly Gln Ser Phe
465                 470                 475                 480

Ala Leu Leu Glu Ala Lys Met Ala Leu Ser Met Ile Leu Gln Arg Phe
                485                 490                 495

Ser Leu Glu Leu Ser Pro Ser Tyr Ile His Ala Pro Tyr Ile Val Leu
                500                 505                 510

Thr Leu Arg Pro Gln His Gly Ala Gln Ile Lys Leu Lys Arg Ile
                515                 520                 525

<210> SEQ ID NO 36
<211> LENGTH: 525
<212> TYPE: PRT
<213> ORGANISM: Lolium rigidum

<400> SEQUENCE: 36

Met Ala Thr Arg Ala Leu Gln Met Leu Gly Glu Ala Ser Pro Trp Asn
1               5                   10                  15

Leu Ala Cys Ala Ala Ala Met Ala Val Leu Trp Leu Ala Ala Trp
                20                  25                  30

Ile Leu Glu Trp Ala Trp Trp Thr Pro Arg Arg Leu Gly Arg Ala Leu
            35                  40                  45

Glu Ala Gln Gly Leu Lys Gly Thr Arg Tyr Arg Leu Phe Thr Gly Asp
50                  55                  60
```

```
Val Pro Glu Asn Ala Arg Leu Asn Lys Glu Ala Arg Ser Lys Pro Leu
 65                  70                  75                  80

Pro Leu Gly Ser His Asp Ile Ile Pro Arg Val Gln Pro Met Ile Ser
                 85                  90                  95

Asn Ala Ile Lys Glu Asn Gly Lys Leu Ser Phe Thr Trp Phe Gly Pro
            100                 105                 110

Glu Pro Arg Val Thr Ile Leu Asp Pro Glu Ser Val Arg Glu Ile Leu
        115                 120                 125

Ser Asn Lys Phe Gly His Tyr Gly Lys Pro Arg Ser Ser Arg Phe Gly
    130                 135                 140

Lys Leu Leu Ala Asn Gly Leu Val Asn His Gln Gly Glu Lys Trp Ala
145                 150                 155                 160

Lys His Arg Arg Ile Leu Asn Pro Ala Phe His His Glu Lys Ile Lys
                165                 170                 175

Arg Met Leu Pro Val Phe Ser Ala Cys Ser Glu Glu Met Ile Thr Arg
            180                 185                 190

Trp Glu Asn Ser Met Ser Ser Gln Gly Val Ser Glu Val Asp Val Trp
        195                 200                 205

Pro Glu Phe Gln Asn Leu Thr Gly Asp Val Ile Ser Arg Thr Ala Phe
    210                 215                 220

Gly Ser Ser Tyr Gln Glu Gly Thr Lys Ile Phe Gln Leu Gln Gly Glu
225                 230                 235                 240

Gln Ala Glu Arg Leu Met Gln Ala Phe Gln Thr Leu Phe Ile Pro Gly
                245                 250                 255

Tyr Trp Phe Leu Pro Thr Lys Asn Asn Arg Arg Met Arg Glu Ile Asp
            260                 265                 270

Arg Glu Ile Cys Thr Ile Leu Arg Gly Ile Ile Glu Lys Lys Asp Arg
        275                 280                 285

Ala Ile Lys Ser Gly Glu Ala Ser Ser Asp Asp Leu Leu Gly Leu Leu
    290                 295                 300

Leu Glu Ser Asn Arg Arg Glu Ser Asn Gly Lys Ala Asp Leu Gly Met
305                 310                 315                 320

Ser Thr Glu Asp Ile Ile Glu Gly Cys Lys Leu Phe Tyr Phe Ala Gly
                325                 330                 335

Met Glu Thr Thr Ser Val Leu Leu Thr Trp Thr Leu Ile Val Leu Ser
            340                 345                 350

Met His Pro Glu Trp Gln Glu Gln Ala Arg Lys Glu Val Leu His His
        355                 360                 365

Phe Gly Arg Thr Thr Pro Asp Phe Glu Asn Leu Ser Arg Leu Lys Ile
    370                 375                 380

Val Thr Met Val Leu Tyr Glu Val Leu Arg Leu Tyr Pro Pro Ala Ile
385                 390                 395                 400

Phe Val Thr Arg Arg Thr Tyr Lys Ala Met Glu Leu Gly Gly Ile Thr
                405                 410                 415

Tyr Pro Ala Gly Val Asn Leu Met Leu Pro Ile Leu Phe Ile His His
            420                 425                 430

Asp Pro Asn Ile Trp Gly Lys Asp Ala Ser Glu Phe Asn Pro Gln Arg
        435                 440                 445

Phe Ala Asp Gly Ile Ser Asn Ala Val Lys His Pro Ala Ala Phe Phe
    450                 455                 460

Pro Phe Gly Gly Gly Pro Arg Ile Cys Ile Gly Gln Asn Phe Ala Leu
465                 470                 475                 480
```

```
Leu Glu Ala Lys Met Ala Leu Ser Thr Ile Leu Gln Arg Phe Ser Phe
                485                 490                 495

Glu Leu Ser Pro Ser Tyr Thr His Ala Pro Tyr Thr Val Leu Thr Leu
            500                 505                 510

His Pro Gln His Gly Ala Pro Ile Val Leu Arg Lys Ile
        515                 520                 525

<210> SEQ ID NO 37
<211> LENGTH: 525
<212> TYPE: PRT
<213> ORGANISM: Sorghum bicolor

<400> SEQUENCE: 37

Met Ala Thr Arg Val Leu Leu Met Leu Arg Glu Thr Ser Pro Trp Ala
1               5                   10                  15

Leu Ala Gly Ala Ala Ser Val Ala Leu Leu Trp Leu Val Ala Trp
            20                  25                  30

Thr Leu Glu Trp Ala Trp Trp Thr Pro Arg Arg Leu Asp Arg Ala Leu
        35                  40                  45

Arg Ala Gln Gly Leu Lys Gly Thr Arg Tyr Arg Leu Phe Thr Gly Asp
    50                  55                  60

Leu Arg Glu Thr Ala Arg Val Asn Arg Glu Ala Arg Lys Asn Pro Leu
65                  70                  75                  80

Pro Leu Gly Cys His Asp Ile Ala Pro Arg Val Gln Pro Met Leu His
                85                  90                  95

Ser Ala Met Lys Glu Tyr Gly Lys Leu Ser Phe Thr Trp Phe Gly Pro
            100                 105                 110

Thr Pro Arg Val Met Ile Pro Asp Pro Glu Leu Val Lys Glu Val Leu
        115                 120                 125

Ser Asn Lys Phe Gly His Phe Gly Lys Pro Arg Ser Ser Arg Ile Gly
    130                 135                 140

Lys Leu Leu Ala Asn Gly Val Val Asn His Asp Gly Glu Lys Trp Ala
145                 150                 155                 160

Lys His Arg Arg Ile Leu Asn Pro Ala Phe His His Glu Lys Ile Lys
                165                 170                 175

Arg Met Leu Pro Val Phe Ser Thr Cys Cys Ile Glu Thr Ile Ile Arg
            180                 185                 190

Trp Glu Asn Ser Met Pro Ser Glu Gly Ser Ser Glu Ile Asp Val Trp
        195                 200                 205

Pro Glu Phe Gln Asn Leu Thr Gly Asp Val Ile Ser Arg Thr Ala Phe
    210                 215                 220

Gly Ser Asn Tyr Gln Glu Gly Arg Arg Ile Phe Gln Leu Gln Gly Glu
225                 230                 235                 240

Leu Ala Glu Arg Leu Ile Gln Ser Ile Gln Thr Ile Phe Ile Pro Gly
                245                 250                 255

Tyr Trp Phe Leu Pro Thr Lys Asn Asn Arg Arg Met Lys Glu Ile Asp
            260                 265                 270

Leu Glu Ile Arg Lys Ile Leu Arg Glu Ile Ile Gly Lys Arg Glu Lys
        275                 280                 285

Ala Thr Arg Asn Gly Glu Thr Asn Asn Asp Asp Leu Leu Gly Leu Leu
    290                 295                 300

Leu Glu Ser Asn Thr Arg Gln Ser Asn Gly Asn Ala Ser Leu Gly Leu
305                 310                 315                 320

Thr Thr Glu Asp Val Ile Glu Glu Cys Lys Leu Phe Tyr Phe Ala Gly
                325                 330                 335
```

Met Glu Thr Thr Ser Val Leu Leu Thr Trp Thr Leu Ile Val Leu Ser
              340                 345                 350

Met His Pro Glu Trp Gln Glu Arg Ala Arg Glu Val Leu Ser His
          355                 360                 365

Phe Gly Arg Thr Arg Pro Asp Phe Asp Ser Leu Ser Arg Leu Lys Ile
      370                 375                 380

Val Thr Met Ile Leu His Glu Val Leu Arg Leu Tyr Pro Pro Ala Thr
385                 390                 395                 400

Phe Leu Thr Arg Arg Thr Tyr Lys Glu Met Glu Leu Gly Gly Ile Lys
              405                 410                 415

Tyr Pro Ala Gly Val Asn Leu Leu Pro Ile Ile Phe Ile His His
          420                 425                 430

Asp Pro Asp Ile Trp Gly Lys Asp Ala Ser Glu Phe Asn Pro Glu Arg
              435                 440                 445

Phe Ala Asn Gly Ile Ser Asn Ala Thr Arg His Gln Ala Ala Phe Phe
          450                 455                 460

Pro Phe Gly Gly Gly Pro Arg Ile Cys Ile Gly Gln Ser Phe Ala Leu
465                 470                 475                 480

Leu Glu Ala Lys Met Ala Leu Cys Thr Ile Leu Gln Arg Phe Ser Phe
              485                 490                 495

Glu Leu Ser Pro Ser Tyr Thr His Ala Pro Tyr Thr Val Ile Thr Leu
          500                 505                 510

His Pro Gln His Gly Ala Gln Ile Arg Leu Lys Lys Leu
              515                 520                 525

<210> SEQ ID NO 38
<211> LENGTH: 538
<212> TYPE: PRT
<213> ORGANISM: Sorghum bicolor

<400> SEQUENCE: 38

Met Pro Leu Pro Phe Leu Cys Phe Ser Ser Thr Ala Pro Met Val Thr
1               5                   10                  15

Ser Val Leu Leu Ile Leu Arg Glu Thr Ser Pro Trp Ala Leu Val Gly
              20                  25                  30

Ala Ala Ala Ser Val Ala Leu Leu Trp Leu Val Ala Trp Thr Leu Glu
          35                  40                  45

Trp Ala Trp Trp Thr Pro Arg Arg Leu Asp Arg Ala Leu Arg Ala Gln
      50                  55                  60

Gly Leu Lys Gly Thr Lys Tyr Arg Leu Leu Thr Gly Asp Val Arg Glu
65                  70                  75                  80

Asn Ala Arg Leu Asn Arg Glu Ala Arg Thr Lys Pro Leu Ala Leu Gly
              85                  90                  95

Ser His Asp Ile Ile Pro Arg Val Leu Pro Met Leu His Asn Val Val
          100                 105                 110

Lys Glu Tyr Gly Thr Asn Ser Phe Thr Trp Phe Gly Pro Val Pro Arg
      115                 120                 125

Val Ile Ile Pro Asp Pro Glu Leu Val Arg Glu Val Leu Ser Asn Lys
130                 135                 140

Phe Gly His Phe Gly Lys Pro Arg Phe Ser Arg Leu Gly Lys Leu Leu
145                 150                 155                 160

Ala Asn Gly Leu Ala Asn His Glu Gly Glu Lys Trp Ala Lys His Arg
              165                 170                 175

Arg Ile Leu Asn Pro Ala Phe His His Glu Lys Ile Lys Arg Met Leu 180                 185                 190
Pro Val Phe Ala Thr Cys Cys Thr Asp Met Ile Asn Arg Trp Glu Asn
            195                 200                 205

Ser Met Ser Ser Glu Gly Ser Ser Glu Ile Asp Val Trp Pro Glu Phe
        210                 215                 220

Gln Asn Leu Thr Gly Asp Val Ile Ser Arg Thr Ala Phe Gly Ser Asn
225                 230                 235                 240

Tyr Gln Glu Gly Arg Asn Ile Phe Gln Leu Gln Gly Glu Gln Ala Glu
                245                 250                 255

Arg Leu Ile Gln Ser Phe Gln Thr Ile Phe Ile Pro Gly Tyr Trp Phe
            260                 265                 270

Leu Pro Thr Lys Asn Asn Arg Arg Met Lys Glu Ile Asp Arg Glu Ile
        275                 280                 285

Cys Lys Val Leu His Gly Ile Ile Arg Lys Arg Glu Arg Ala Phe Ile
    290                 295                 300

Asp Gly Glu Gly Ser Asn Asp Asp Leu Leu Gly Leu Leu Val Glu Ser
305                 310                 315                 320

Asn Met Arg Glu Ser Asn Gly Asn Ala Lys Leu Gly Met Ser Thr Lys
                325                 330                 335

Asp Ile Ile Glu Glu Cys Lys Leu Phe Tyr Phe Ala Gly Met Glu Thr
            340                 345                 350

Thr Ser Val Leu Leu Thr Trp Thr Leu Ile Val Leu Ser Met His Pro
        355                 360                 365

Glu Trp Gln Glu Arg Ala Arg Asp Glu Val Leu Asn His Phe Gly Arg
    370                 375                 380

Gly Arg Pro Asp Phe Asp Ser Leu Asn Arg Leu Lys Ile Val Thr Met
385                 390                 395                 400

Ile Leu Tyr Glu Val Leu Arg Leu Tyr Pro Pro Val Ile Leu Leu Thr
                405                 410                 415

Arg Arg Thr Tyr Lys Glu Met Glu Leu Gly Gly Ile Thr Tyr Pro Ser
            420                 425                 430

Gly Val Ser Leu Leu Leu Pro Ile Ile Phe Ile His His Asp Pro Asn
        435                 440                 445

Ile Trp Gly Lys Asp Ala Ser Glu Phe Asn Pro Gln Arg Phe Glu Asp
    450                 455                 460

Gly Ile Ser Asn Ala Thr Lys His Gln Ala Ala Phe Phe Pro Phe Gly
465                 470                 475                 480

Trp Gly Pro Arg Ile Cys Ile Gly Gln Asn Phe Ala Leu Leu Glu Ala
                485                 490                 495

Lys Met Ala Leu Cys Thr Ile Leu Gln Arg Phe Ser Phe Glu Leu Ser
            500                 505                 510

Pro Ser Tyr Thr His Ala Pro Tyr Thr Val Ile Thr Leu His Pro Gln
        515                 520                 525

His Gly Ala Gln Ile Arg Leu Lys Lys Leu
    530                 535

<210> SEQ ID NO 39
<211> LENGTH: 525
<212> TYPE: PRT
<213> ORGANISM: Lolium rigidum

<400> SEQUENCE: 39

Met Ala Thr Arg Ala Leu Gln Met Leu Arg Glu Ala Ser Pro Trp Ser
1               5                   10                  15

-continued

```
Leu Ala Gly Ala Ala Ala Met Ala Leu Leu Trp Leu Ala Trp
            20                  25                  30

Ile Val Glu Trp Ala Trp Trp Thr Pro Arg Arg Leu Arg Arg Ala Leu
        35                  40                  45

Gln Ala Gln Gly Leu Arg Gly Thr Gln Tyr Arg Leu Phe Thr Gly Asp
    50                  55                  60

Val Pro Glu Asn Ala Arg Leu Asn Arg Glu Ala Arg Ser Lys Pro Leu
65                  70                  75                  80

Pro Leu Gly Ser His Asp Ile Ile Gln Arg Val Gln Pro Met Phe Ser
                85                  90                  95

Asn Val Ile Lys Glu Asn Gly Lys Phe Ala Phe Thr Trp Phe Gly Pro
            100                 105                 110

Thr Pro Arg Val Met Ile Pro Asp Pro Glu Leu Val Arg Glu Val Leu
        115                 120                 125

Ser Asn Lys Phe Gly His Tyr Gly Lys Gln Lys Ser Ser Arg Leu Gly
    130                 135                 140

Lys Leu Leu Ala Asn Gly Leu Ala Asn His Gln Gly Glu Lys Trp Ala
145                 150                 155                 160

Lys His Arg Arg Ile Leu Asn Pro Ala Phe His Asn Glu Lys Ile Lys
                165                 170                 175

Arg Met Leu Pro Val Phe Ala Thr Cys Cys Glu Glu Met Ile Thr Arg
            180                 185                 190

Trp Asp Asn Ser Met Ser Thr Gln Gly Ser Ser Glu Ile Asp Ile Trp
        195                 200                 205

Pro Glu Phe Gln Asn Leu Thr Gly Asp Val Ile Ser Arg Thr Ala Phe
    210                 215                 220

Gly Ser Asn Tyr Gln Glu Gly Met Lys Ile Phe Gln Leu Gln Gly Glu
225                 230                 235                 240

Leu Ala Glu Arg Leu Ile Met Ala Phe Gln Thr Ile Phe Ile Pro Gly
                245                 250                 255

Tyr Trp Phe Leu Pro Thr Lys Asn Asn Lys Arg Met Arg Ala Ile Asp
            260                 265                 270

Cys Glu Ile Arg Thr Ile Leu Arg Gly Ile Ile Gly Lys Lys Asp Lys
        275                 280                 285

Ala Ile Lys Asn Gly Glu Ala Ile Ser Asp Asp Leu Leu Gly Leu Leu
    290                 295                 300

Leu Glu Ser Asn Met Arg Glu Ser Asn Gly Lys Ala Asp Leu Glu Met
305                 310                 315                 320

Ser Thr Glu Glu Ile Ile Gln Glu Cys Lys Leu Phe Tyr Phe Ala Gly
                325                 330                 335

Met Glu Thr Thr Ser Val Leu Leu Thr Trp Thr Leu Ile Leu Leu Ser
            340                 345                 350

Met His Pro Glu Trp Gln Glu Lys Ala Arg Asp Glu Val Leu Tyr His
        355                 360                 365

Phe Gly Arg Thr Thr Pro Asp Phe Glu His Leu Ser Arg Leu Lys Ile
    370                 375                 380

Val Thr Met Ile Leu Tyr Glu Val Leu Arg Leu Tyr Pro Pro Ile Thr
385                 390                 395                 400

Ile Leu Thr Arg Arg Thr Tyr Lys Ala Met Glu Leu Gly Gly Ile Lys
                405                 410                 415

Tyr Pro Ala Gly Val Asn Leu Met Leu Pro Ile Leu Phe Ile His His
            420                 425                 430

Asp Pro Asn Leu Trp Gly Lys Asp Ala Ser Glu Phe Asn Pro Glu Arg
```

```
                435              440              445
Phe Ala Asp Gly Ile Ser Asn Ala Ala Lys His Pro Gly Ser Phe Phe
        450                 455                 460
Pro Phe Gly Gly Gly Pro Arg Ile Cys Ile Gly Gln Asn Phe Ala Leu
465                 470                 475                 480
Leu Glu Ala Lys Met Ala Leu Ser Thr Ile Leu Gln His Phe Ser Leu
                485                 490                 495
Glu Leu Ser Pro Ser Tyr Thr His Ala Pro Tyr Thr Val Ile Thr Leu
            500                 505                 510
His Pro Gln His Gly Ala Gln Ile Arg Ile Lys Lys Ile
            515                 520                 525

<210> SEQ ID NO 40
<211> LENGTH: 527
<212> TYPE: PRT
<213> ORGANISM: Zea mays

<400> SEQUENCE: 40

Met Ala Thr Cys Val Leu Leu Met Leu Arg Glu Val Ser Pro Trp Ala
1               5                   10                  15
Leu Ala Ser Val Val Ala Ser Val Ser Leu Leu Trp Leu Val Val Trp
            20                  25                  30
Thr Leu Glu Trp Ala Trp Trp Thr Pro Trp Arg Leu Glu Arg Ala Leu
        35                  40                  45
Arg Val Gln Gly Leu Lys Gly Thr Arg Tyr Arg Leu Phe Thr Gly Asp
    50                  55                  60
Leu Arg Glu Thr Ala Arg Ala Asn Arg Glu Ala Arg Lys Lys Pro Leu
65                  70                  75                  80
Pro Leu Gly Ser His Asp Ile Ala Pro Arg Val Gln Pro Met His His
                85                  90                  95
Ser Thr Ile Lys Glu Tyr Gly Lys Leu Ser Phe Thr Trp Phe Gly Pro
            100                 105                 110
Thr Pro Arg Val Met Ile Pro Asp Pro Glu Leu Val Lys Glu Val Leu
        115                 120                 125
Ser Asn Lys Phe Gly His Phe Gly Lys Pro Arg Ser Asn Arg Ile Gly
    130                 135                 140
Arg Leu Leu Ala Asn Gly Leu Val Asn His Asp Gly Glu Lys Trp Ala
145                 150                 155                 160
Lys His Arg Arg Ile Leu Asn Pro Ala Phe His His Glu Lys Ile Lys
                165                 170                 175
Gly Met Met Pro Val Phe Ser Thr Cys Cys Ile Glu Met Ile Thr Arg
            180                 185                 190
Trp Asp Asn Ser Met Pro Ser Glu Gly Ser Ser Glu Ile Asp Val Trp
        195                 200                 205
Pro Glu Phe Gln Asn Leu Thr Gly Asp Val Ile Ser Arg Thr Ala Phe
    210                 215                 220
Gly Ser Asn Tyr Gln Glu Gly Arg Arg Ile Phe Glu Leu Gln Gly Glu
225                 230                 235                 240
Leu Ala Glu Arg Leu Ile Gln Ser Val Gln Thr Ile Phe Ile Pro Gly
                245                 250                 255
Tyr Trp Phe Leu Pro Thr Lys Asn Asn Arg Arg Met Arg Ala Ile Asp
            260                 265                 270
Val Glu Ile Arg Lys Ile Leu Arg Glu Ile Ile Gly Lys Arg Glu Lys
        275                 280                 285
```

```
Asp Thr Lys Asn Arg Glu Thr Asn Asn Asp Asp Leu Leu Gly Leu Leu
    290                 295                 300

Leu Glu Ser Asn Thr Arg Gln Ser Asn Gly Asn Ala Ser Leu Gly Leu
305                 310                 315                 320

Thr Thr Glu Asp Val Ile Glu Glu Cys Lys Leu Phe Tyr Phe Ala Gly
                325                 330                 335

Met Glu Thr Thr Ser Val Leu Leu Thr Trp Thr Leu Ile Val Leu Ser
            340                 345                 350

Met His Pro Glu Trp Gln Glu Arg Ala Arg Glu Val Leu Ser His
        355                 360                 365

Phe Gly Arg Thr Thr Pro Asp Tyr Asp Ser Leu Ser Arg Leu Lys Thr
    370                 375                 380

Ile Thr Met Ile Leu His Glu Val Leu Arg Leu Tyr Pro Pro Ala Thr
385                 390                 395                 400

Phe Leu Thr Arg Arg Thr Tyr Lys Glu Met Glu Leu Gly Gly Ile Lys
                405                 410                 415

Tyr Pro Ala Gly Val Asp Leu Leu Pro Val Ile Phe Ile His His
            420                 425                 430

Asp Pro Asp Ile Trp Gly Lys Asp Ala Ser Glu Phe Asn Pro Glu Arg
        435                 440                 445

Phe Ala Asn Gly Ile Ser Ser Ala Thr Arg His Gln Ala Ala Phe Phe
    450                 455                 460

Pro Phe Gly Gly Gly Pro Arg Ile Cys Ile Gly Gln Ser Phe Ala Leu
465                 470                 475                 480

Leu Glu Ala Lys Met Thr Leu Cys Thr Ile Leu Gln Arg Phe Ser Phe
                485                 490                 495

Glu Leu Ser Pro Ser Tyr Thr His Ala Pro Tyr Thr Val Ile Thr Leu
            500                 505                 510

His Pro Gln His Gly Ala Gln Ile Arg Leu Lys Lys Leu Ser Pro
        515                 520                 525

<210> SEQ ID NO 41
<211> LENGTH: 528
<212> TYPE: PRT
<213> ORGANISM: Zea mays

<400> SEQUENCE: 41

Met Ala Thr Leu Pro Leu Leu His Leu Leu Trp Glu Ala Ser Pro
1               5                   10                  15

Trp Ala Arg Ala Gly Ala Ala Thr Ala Ala Val Val Leu Val Trp Leu
            20                  25                  30

Ala Ala Trp Thr Leu Glu Trp Ala Trp Trp Thr Pro Arg Arg Leu Asp
        35                  40                  45

Arg Ala Leu Arg Ala Gln Gly Leu Lys Gly Thr Arg Tyr Arg Leu Leu
    50                  55                  60

Thr Gly Asp Val Arg Glu Asn Ala Arg Leu Asn Arg Glu Ala Arg Thr
65                  70                  75                  80

Lys Pro Leu Pro Leu Gly Ser His Asp Ile Ile Pro Arg Val Leu Pro
                85                  90                  95

Met Phe His Asn Ala Val Lys Glu Asn Gly Thr Asn Ser Phe Thr Trp
            100                 105                 110

Phe Gly Pro Ile Pro Arg Val Ile Ile Pro Asp Pro Glu Leu Met Arg
        115                 120                 125

Glu Val Leu Ser Asn Lys Phe Gly His Phe Gly Lys Pro Leu Phe Ser
    130                 135                 140
```

```
Arg Val Gly Lys Leu Leu Ala Asn Gly Leu Ala Asn His Glu Gly Glu
145                 150                 155                 160

Lys Trp Ala Lys His Arg Arg Ile Leu Asn Pro Ala Phe His His Glu
            165                 170                 175

Lys Ile Lys Arg Met Leu Pro Val Phe Ala Thr Cys Cys Ala Asp Met
        180                 185                 190

Ile Asn Arg Trp Glu Asn Ser Met Ser Ser Lys Glu Pro Ser Glu Met
    195                 200                 205

Asp Val Trp Pro Glu Phe Gln Asn Leu Thr Gly Asp Val Ile Ser Arg
210                 215                 220

Thr Ala Phe Gly Ser Asn Tyr Gln Glu Gly Arg Asn Ile Phe Gln Leu
225                 230                 235                 240

Gln Gly Glu Gln Ala Glu Arg Leu Ile Gln Ser Phe Gln Thr Ile Phe
                245                 250                 255

Ile Pro Gly Tyr Trp Leu Leu Pro Thr Lys Asn Asn Arg Arg Met Lys
            260                 265                 270

Glu Ile Asp Arg Glu Ile Arg Lys Ile Leu His Gly Ile Ile Arg Lys
        275                 280                 285

Arg Glu Arg Ala Phe Ile Asp Ser Gly Thr Asn Asp Asp Leu Leu
290                 295                 300

Gly Leu Leu Val Glu Ser Asn Met Arg Glu Ser Asn Gly Asn Ala Lys
305                 310                 315                 320

Leu Gly Met Thr Thr Glu Asp Ile Ile Glu Glu Cys Lys Leu Phe Tyr
                325                 330                 335

Phe Ala Gly Met Glu Thr Thr Ser Val Leu Leu Thr Trp Thr Leu Ile
                340                 345                 350

Leu Leu Ser Met His Pro Glu Trp Gln Glu Gln Ala Arg Glu Glu Val
                355                 360                 365

Leu Asn His Phe Gly Met Gly Thr Pro Asp Phe Asp Asn Leu Asn Arg
370                 375                 380

Leu Lys Ile Val Thr Met Ile Leu Tyr Glu Val Leu Arg Leu Tyr Pro
385                 390                 395                 400

Pro Val Val Phe Leu Ser Arg Arg Thr Tyr Lys Glu Met Glu Leu Gly
                405                 410                 415

Gly Ile Lys Tyr Pro Ser Gly Val Ser Leu Leu Leu Pro Ile Ile Phe
                420                 425                 430

Ile His His Asp Pro Asn Ile Trp Gly Lys Asp Ala Ser Glu Phe Asn
            435                 440                 445

Pro Gln Arg Phe Glu Asp Gly Ile Ser Asn Ala Thr Lys His Gln Ala
            450                 455                 460

Ala Phe Phe Pro Phe Gly Trp Gly Pro Arg Ile Cys Ile Gly Gln Asn
465                 470                 475                 480

Phe Ala Leu Leu Glu Ala Lys Met Ala Leu Ser Thr Ile Leu Gln Arg
                485                 490                 495

Phe Ser Phe Glu Leu Ser Ser Ser Tyr Thr His Ala Pro Tyr Thr Val
            500                 505                 510

Ile Thr Leu His Pro Gln His Gly Ala Gln Ile Arg Leu Lys Lys Leu
515                 520                 525
```

<210> SEQ ID NO 42
<211> LENGTH: 525
<212> TYPE: PRT
<213> ORGANISM: Lolium rigidum

<400> SEQUENCE: 42

```
Met Ala Thr Arg Ala Leu Gln Met Leu Gly Glu Ala Ser Pro Trp Asn
1               5                   10                  15

Leu Ala Cys Ala Ala Ala Met Ala Val Leu Trp Leu Ala Ala Trp
            20                  25                  30

Ile Leu Glu Trp Ala Trp Trp Thr Pro Arg Arg Leu Gly Arg Ala Leu
            35                  40                  45

Glu Ala Gln Gly Leu Lys Gly Thr Arg Tyr Arg Leu Phe Thr Gly Asp
        50                  55                  60

Val Pro Glu Asn Ala Arg Leu Asn Lys Glu Ala Arg Ser Lys Pro Leu
65                  70                  75                  80

Pro Leu Gly Ser His Asp Ile Ile Pro Arg Val Gln Pro Met Ile Ser
                85                  90                  95

Asn Ala Ile Lys Glu Asn Gly Lys Leu Ser Phe Thr Trp Phe Gly Pro
            100                 105                 110

Glu Pro Arg Val Thr Ile Leu Asp Pro Glu Ser Val Arg Glu Ile Leu
        115                 120                 125

Ser Asn Lys Phe Gly His Tyr Gly Lys Pro Arg Ser Ser Arg Phe Gly
    130                 135                 140

Lys Leu Leu Ala Asn Gly Leu Val Asn His Gln Gly Glu Lys Trp Ala
145                 150                 155                 160

Lys His Arg Arg Ile Leu Asn Pro Ala Phe His His Glu Lys Ile Lys
                165                 170                 175

Arg Met Leu Pro Val Phe Ser Ala Cys Ser Glu Glu Met Ile Thr Arg
            180                 185                 190

Trp Glu Asn Ser Met Ser Ser Gln Gly Val Ser Glu Val Asp Val Trp
        195                 200                 205

Pro Glu Phe Gln Asn Leu Thr Gly Asp Val Ile Ser Arg Thr Ala Phe
    210                 215                 220

Gly Ser Ser Tyr Gln Glu Gly Thr Lys Ile Phe Gln Leu Gln Gly Glu
225                 230                 235                 240

Gln Ala Glu Arg Leu Met Gln Ala Phe Gln Thr Leu Phe Ile Pro Gly
                245                 250                 255

Tyr Trp Phe Leu Pro Thr Lys Asn Asn Arg Arg Met Arg Ala Ile Asp
            260                 265                 270

Arg Glu Ile Cys Thr Ile Leu Arg Gly Ile Ile Glu Lys Lys Asp Arg
        275                 280                 285

Ala Ile Lys Ser Gly Glu Ala Ser Ser Asp Asp Leu Leu Gly Leu Leu
    290                 295                 300

Leu Glu Ser Asn Arg Arg Glu Ser Asn Gly Lys Ala Asp Leu Gly Met
305                 310                 315                 320

Ser Thr Glu Asp Ile Ile Glu Glu Cys Lys Leu Phe Tyr Phe Ala Gly
                325                 330                 335

Met Glu Thr Thr Ser Val Leu Leu Thr Trp Thr Leu Ile Val Leu Ser
            340                 345                 350

Met His Pro Glu Trp Gln Glu Gln Ala Arg Lys Glu Val Leu His His
        355                 360                 365

Phe Gly Arg Thr Lys Pro Asp Phe Glu Asn Leu Ser Arg Leu Lys Ile
    370                 375                 380

Val Thr Met Val Leu Tyr Glu Val Leu Arg Leu Tyr Pro Pro Ala Ile
385                 390                 395                 400

Phe Val Thr Arg Arg Thr Tyr Lys Ala Met Glu Leu Gly Gly Ile Thr
                405                 410                 415
```

```
Tyr Pro Ala Gly Val Asn Leu Met Leu Pro Ile Leu Phe Ile His His
            420                 425                 430

Asp Pro Asn Ile Trp Gly Lys Asp Ala Ser Glu Phe Asn Pro Gln Arg
            435                 440                 445

Phe Ala Asp Gly Ile Ser Asn Ala Val Lys His Pro Ala Ala Phe Phe
450                 455                 460

Pro Phe Gly Gly Pro Arg Ile Cys Ile Gly Gln Asn Phe Ala Leu
465                 470                 475                 480

Leu Glu Ala Lys Met Ala Leu Ser Thr Ile Leu Gln Arg Phe Ser Phe
            485                 490                 495

Glu Leu Ser Pro Ser Tyr Thr His Ala Pro Tyr Thr Val Leu Thr Leu
            500                 505                 510

His Pro Gln His Gly Ala Pro Ile Val Leu Arg Lys Ile
            515                 520                 525

<210> SEQ ID NO 43
<211> LENGTH: 523
<212> TYPE: PRT
<213> ORGANISM: Oryza sativa

<400> SEQUENCE: 43

Met Leu Met Met Leu Gly Ala Ala Ser Gln Trp Ile Leu Ala Ala Ala
1               5                   10                  15

Ala Ala Ala Val Ala Ala Leu Leu Trp Leu Ala Val Ser Thr Leu
            20                  25                  30

Glu Trp Ala Trp Trp Thr Pro Arg Arg Leu Glu Arg Ala Leu Arg Ala
            35                  40                  45

Gln Gly Ile Arg Gly Asn Arg Tyr Arg Leu Phe Thr Gly Asp Val Pro
    50                  55                  60

Glu Asn Val Arg Leu Asn Arg Glu Ala Arg Lys Lys Pro Leu Pro Leu
65                  70                  75                  80

Gly Cys His Asp Ile Ile Pro Arg Val Leu Pro Met Phe Ser Lys Ala
                85                  90                  95

Val Glu Glu His Gly Lys Pro Ser Phe Thr Trp Phe Gly Pro Thr Pro
            100                 105                 110

Arg Val Met Ile Ser Asp Pro Glu Ser Ile Arg Glu Val Met Ser Asn
            115                 120                 125

Lys Phe Gly His Tyr Gly Lys Pro Lys Pro Thr Arg Leu Gly Lys Leu
            130                 135                 140

Leu Ala Ser Gly Val Val Ser Tyr Glu Gly Glu Lys Trp Ala Lys His
145                 150                 155                 160

Arg Arg Ile Leu Asn Pro Ala Phe His His Glu Lys Ile Lys Arg Met
                165                 170                 175

Leu Pro Val Phe Ser Asn Cys Cys Thr Glu Met Val Thr Arg Trp Glu
            180                 185                 190

Asn Ser Met Ser Ile Glu Gly Met Ser Glu Val Asp Val Trp Pro Glu
            195                 200                 205

Phe Gln Asn Leu Thr Gly Asp Val Ile Ser Lys Thr Ala Phe Gly Ser
            210                 215                 220

Ser Tyr Glu Glu Gly Arg Arg Ile Phe Gln Leu Gln Ala Glu Ser Ala
225                 230                 235                 240

Glu Arg Ile Ile Gln Ala Phe Arg Thr Ile Phe Ile Pro Gly Tyr Trp
                245                 250                 255

Phe Leu Pro Thr Lys Asn Asn Arg Arg Leu Arg Glu Ile Glu Arg Glu
```

```
                    260                 265                 270
     Val Ser Lys Leu Leu Arg Gly Ile Ile Gly Lys Arg Glu Arg Ala Ile
                275                 280                 285

Lys Asn Gly Glu Thr Ser Asn Gly Asp Leu Leu Gly Leu Leu Val Glu
                290                 295                 300

Ser Asn Met Arg Glu Ser Asn Gly Lys Ala Glu Leu Gly Met Thr Thr
     305                 310                 315                 320

Asp Glu Ile Ile Glu Glu Cys Lys Leu Phe Tyr Phe Ala Gly Met Glu
                    325                 330                 335

Thr Thr Ser Val Leu Leu Thr Trp Thr Leu Ile Val Leu Ser Met His
                340                 345                 350

Pro Glu Trp Gln Glu Arg Ala Arg Glu Val Leu His His Phe Gly
                355                 360                 365

Arg Thr Thr Pro Asp Tyr Asp Ser Leu Ser Arg Leu Lys Ile Val Thr
                370                 375                 380

Met Ile Leu Tyr Glu Val Leu Arg Leu Tyr Pro Pro Val Val Phe Leu
     385                 390                 395                 400

Thr Arg Arg Thr Tyr Lys Glu Met Glu Leu Gly Gly Ile Lys Tyr Pro
                    405                 410                 415

Ala Glu Val Thr Leu Met Leu Pro Ile Leu Phe Ile His His Asp Pro
                420                 425                 430

Asp Ile Trp Gly Lys Asp Ala Gly Glu Phe Asn Pro Gly Arg Phe Ala
                435                 440                 445

Asp Gly Ile Ser Asn Ala Thr Lys Tyr Gln Thr Ser Phe Phe Pro Phe
                450                 455                 460

Gly Trp Gly Pro Arg Ile Cys Ile Gly Gln Asn Phe Ala Leu Leu Glu
     465                 470                 475                 480

Ala Lys Met Ala Ile Cys Thr Ile Leu Gln Arg Phe Ser Phe Glu Leu
                    485                 490                 495

Ser Pro Ser Tyr Ile His Ala Pro Phe Thr Val Ile Thr Leu His Pro
                500                 505                 510

Gln His Gly Ala Gln Ile Lys Leu Lys Lys Ile
                515                 520

<210> SEQ ID NO 44
<211> LENGTH: 1668
<212> TYPE: DNA
<213> ORGANISM: Alopecurus

<400> SEQUENCE: 44
gcgtgtcgtg cagactgcag agtccccgct cctgagagaa ccaccatgtc cacgggcctc      60
gtctggatgg tggcggcggc catcgcggcg gtgctggcga cgtgggcgtt caacgcgctg     120
gtgcgcctcg tgtggaggcc gcgcgccatc accaggcagc tccgcgcgca gggcgtgggc     180
gggccggcgt acaagctctt cgccgggaac ctcggcgaga tcaagcagct ccgcgccgag     240
accgccggcg ccgcgctgga cgtcggctcc cacgacttcg tccccctcgt gcagccgcac     300
ttccgcaaat ggatccccat tcacggacgc acgttcctgt actggttcgg cgcgaggccg     360
accctgtgca tcgccgacgt gaacgtggtg aaacaggtcc tcttcgaccg caacgggctc     420
taccccaaga acaccggcaa cccgcacatc gcccgcctgc tcggcaaggg gctcgtgctc     480
atcgacggcg acgactggaa cgccaccgc aaggtcgtcc accggcctt caacatggac     540 aagctcaaga tgatgaccgt gaccatgtcc gactgcgctg gtcaatgat gtcggagtgg     600 aaagccaagc tggagaaggg cggcgaagcg gagattgacc tcagcaggca gtttgaggag     660
```

```
ctaaccgcgg acgtgatctc ccacacggcg ttcggcagca gctacacgga ggggaaaaag      720
gtctttctgg cgcagaggga cctccagttt ctggcatttt ccactgtatt cagcgtccaa      780
atcccagcat tcaggtacat tccgacccaa aagaaccgtc agatatggaa gctcgacagg      840
gaggtgagga ccatgctcac caacatcatc aaaacccggc tcgcgaccaa agacaccatg      900
ggctacggaa acgacctgct cgggctcatg ctggaggcgt gcgcgccaga gcacggggag      960
actccgattc tgagcatgga cgagatcatc gacgagtgca agaccttctt cttcgccggg     1020
cacgacacca gctcgcacct gctcacgtgg accatgttct tgctgagcac gcacccggag     1080
tggcaggaga agctcaggga ggaggtgctg acagagtgtg caatgaggt tcccaccggc      1140
gacatgctca acaagctcaa gttggtcaac atgttcctac tggaaactct caggttatac     1200
tcccctgtgt ccgtaattca gaggaagaca ggttcagata tggaggtcgg tggcatcaaa     1260
gtgccccaag gaactgtcct gaccatcccc atcgcgacga tgcatcgtga caaggaggtc     1320
tggggtgagg atgcggatga attcaagcct atgaggttcg agaaaggtgt gaccatggct     1380
gccaagcacc ccaatgcctt gttgtctttc tccagcgggc cgaggtcgtg catagggcag     1440
aacttcgcga tgatcgaagc caaggctgtg atcgctgtga ttcttcagag gttctccttc     1500
tccctgtccc ctaagtacgt ccatgcaccg atggacgtga tcacgctgcg gcccaagttt     1560
ggtcttccca tggtcctgaa gagcctggag atgtagagac atgcatacag tgtattcagg     1620
ttgagtaaca cgaagtactt cactagggtt tacattacta gattgtac                  1668
```

<210> SEQ ID NO 45
<211> LENGTH: 516
<212> TYPE: PRT
<213> ORGANISM: Alopecurus

<400> SEQUENCE: 45

```
Met Ser Thr Gly Leu Val Trp Met Val Ala Ala Ile Ala Ala Val
1               5                   10                  15

Leu Ala Thr Trp Ala Phe Asn Ala Leu Val Arg Leu Val Trp Arg Pro
                20                  25                  30

Arg Ala Ile Thr Arg Gln Leu Arg Ala Gln Gly Val Gly Gly Pro Ala
            35                  40                  45

Tyr Lys Leu Phe Ala Gly Asn Leu Gly Glu Ile Lys Gln Leu Arg Ala
        50                  55                  60

Glu Thr Ala Gly Ala Ala Leu Asp Val Gly Ser His Asp Phe Val Pro
65                  70                  75                  80

Leu Val Gln Pro His Phe Arg Lys Trp Ile Pro Ile His Gly Arg Thr
                85                  90                  95

Phe Leu Tyr Trp Phe Gly Ala Arg Pro Thr Leu Cys Ile Ala Asp Val
            100                 105                 110

Asn Val Val Lys Gln Val Leu Phe Asp Arg Asn Gly Leu Tyr Pro Lys
        115                 120                 125

Asn Thr Gly Asn Pro His Ile Ala Arg Leu Leu Gly Lys Gly Leu Val
    130                 135                 140

Leu Ile Asp Gly Asp Asp Trp Lys Arg His Arg Lys Val Val His Pro
145                 150                 155                 160

Ala Phe Asn Met Asp Lys Leu Lys Met Met Thr Val Thr Met Ser Asp
                165                 170                 175

Cys Ala Gly Ser Met Met Ser Glu Trp Lys Ala Lys Leu Glu Lys Gly
            180                 185                 190
```

Gly Glu Ala Glu Ile Asp Leu Ser Arg Gln Phe Glu Leu Thr Ala
            195                 200                 205

Asp Val Ile Ser His Thr Ala Phe Gly Ser Ser Tyr Thr Glu Gly Lys
210                 215                 220

Lys Val Phe Leu Ala Gln Arg Asp Leu Gln Phe Leu Ala Phe Ser Thr
225                 230                 235                 240

Val Phe Ser Val Gln Ile Pro Ala Phe Arg Tyr Ile Pro Thr Gln Lys
            245                 250                 255

Asn Arg Gln Ile Trp Lys Leu Asp Arg Glu Val Arg Thr Met Leu Thr
            260                 265                 270

Asn Ile Ile Lys Thr Arg Leu Ala Thr Lys Asp Thr Met Gly Tyr Gly
            275                 280                 285

Asn Asp Leu Leu Gly Leu Met Leu Glu Ala Cys Ala Pro Glu His Gly
            290                 295                 300

Glu Thr Pro Ile Leu Ser Met Asp Glu Ile Ile Asp Glu Cys Lys Thr
305                 310                 315                 320

Phe Phe Phe Ala Gly His Asp Thr Ser Ser His Leu Leu Thr Trp Thr
            325                 330                 335

Met Phe Leu Leu Ser Thr His Pro Glu Trp Gln Glu Lys Leu Arg Glu
            340                 345                 350

Glu Val Leu Thr Glu Cys Gly Asn Glu Val Pro Thr Gly Asp Met Leu
            355                 360                 365

Asn Lys Leu Lys Leu Val Asn Met Phe Leu Leu Glu Thr Leu Arg Leu
            370                 375                 380

Tyr Ser Pro Val Ser Val Ile Gln Arg Lys Thr Gly Ser Asp Met Glu
385                 390                 395                 400

Val Gly Gly Ile Lys Val Pro Gln Gly Thr Val Leu Thr Ile Pro Ile
            405                 410                 415

Ala Thr Met His Arg Asp Lys Glu Val Trp Gly Glu Asp Ala Asp Glu
            420                 425                 430

Phe Lys Pro Met Arg Phe Glu Lys Gly Val Thr Met Ala Ala Lys His
            435                 440                 445

Pro Asn Ala Leu Leu Ser Phe Ser Ser Gly Pro Arg Ser Cys Ile Gly
450                 455                 460

Gln Asn Phe Ala Met Ile Glu Ala Lys Ala Val Ile Ala Val Ile Leu
465                 470                 475                 480

Gln Arg Phe Ser Phe Ser Leu Ser Pro Lys Tyr Val His Ala Pro Met
            485                 490                 495

Asp Val Ile Thr Leu Arg Pro Lys Phe Gly Leu Pro Met Val Leu Lys
            500                 505                 510

Ser Leu Glu Met
        515

<210> SEQ ID NO 46
<211> LENGTH: 460
<212> TYPE: PRT
<213> ORGANISM: Oryza sativa

<400> SEQUENCE: 46

Met Val Ala Ala Ala Ala Ala Val Leu Ala Ser Trp Ala Phe Ser
1               5                   10                  15

Ala Val Val His Leu Val Trp Arg Pro His Ala Ile Ser Arg Arg Leu
                20                  25                  30

Arg Ala Gln Gly Val Gly Gly Pro Gly Tyr Arg Phe Phe Ser Gly Asn
            35                  40                  45

```
Leu Gly Glu Ile Lys Arg Phe Arg Gly Asp Gly Ala Gly Val Val Leu
         50                  55                  60

Asn Val Ser Ser His Asp Phe Leu Pro Ile Val Gln Pro His Phe Arg
 65                  70                  75                  80

Lys Trp Ile Ser Leu Tyr Asp Arg Thr Gly Ile Tyr Pro Lys Asn Leu
                 85                  90                  95

Thr Asn Ser His Phe Val Arg Leu Leu Gly Lys Gly Leu Val Leu Thr
                100                 105                 110

Asp Gly Asp Glu Trp Lys Arg His Arg Lys Val Val His Pro Ala Phe
            115                 120                 125

Asn Met Asp Lys Leu Lys Met Met Thr Met Thr Met Ser Asp Cys Ser
        130                 135                 140

Arg Ser Met Met Ser Glu Trp Glu Ser Glu Leu Ala Ala Lys Gly Gly
145                 150                 155                 160

Leu Val Glu Ile Glu Leu Ser Arg Arg Phe Glu Glu Leu Thr Ala Asp
                165                 170                 175

Val Ile Ser His Thr Ala Phe Gly Ser Ser Tyr Lys Glu Gly Lys Gln
                180                 185                 190

Leu Pro Ser Asp His Glu Lys Leu Phe Lys Thr Trp Ser Leu Asp Lys
            195                 200                 205

Lys Val Arg Gly Met Leu Met Asp Ile Ile Lys Thr Arg His Ala Asn
210                 215                 220

Lys Asn Val Ala Trp Tyr Gly Asn Asp Leu Leu Gly Leu Met Leu Glu
225                 230                 235                 240

Ala Cys Ala Pro Glu His Gly Glu Ser Cys Pro Gln Leu Ser Met Asp
                245                 250                 255

Glu Ile Ile Asp Glu Cys Lys Thr Phe Phe Ala Gly His Asp Thr
            260                 265                 270

Thr Ser His Leu Leu Thr Trp Thr Met Phe Leu Leu Ser Thr His Pro
            275                 280                 285

Asp Trp Gln Glu Lys Leu Arg Glu Glu Ile Ala Met Glu Cys Gly Asp
        290                 295                 300

Lys Val Pro Ala Gly Asp Met Leu Asn Lys Leu Lys Met Val Asn Met
305                 310                 315                 320

Phe Leu Leu Glu Thr Leu Arg Leu Tyr Ser Pro Val Ser Leu Ile Arg
                325                 330                 335

Arg Lys Val Gly Thr Asp Ile Glu Leu Gly Gly Ile Lys Met Pro Glu
                340                 345                 350

Gly Ala Leu Leu Thr Ile Pro Ile Ala Thr Ile His Arg Asp Lys Glu
            355                 360                 365

Val Trp Gly Glu Asp Ala Asp Glu Phe Arg Pro Glu Arg Phe Glu Asn
        370                 375                 380

Gly Val Thr Arg Ala Ala Lys His Pro Asn Ala Leu Leu Ser Phe Ser
385                 390                 395                 400

Ser Gly Pro Arg Ser Cys Ile Gly Gln Asn Phe Ala Met Ile Glu Ala
                405                 410                 415

Lys Ala Val Ile Ala Met Ile Leu Gln Arg Phe Ser Phe Thr Leu Ser
                420                 425                 430

Pro Lys Tyr Val His Ala Pro Thr Asp Val Ile Thr Leu Arg Pro Lys
            435                 440                 445

Tyr Gly Leu Pro Met Ile Leu Lys Ser Leu Lys Leu
450                 455                 460
```

<210> SEQ ID NO 47
<211> LENGTH: 528
<212> TYPE: PRT
<213> ORGANISM: Zea mays

<400> SEQUENCE: 47

```
Met Gly Leu Ala Trp Met Val Thr Ala Val Ala Val Leu Ala
1               5                   10                  15

Ser Trp Ala Phe Asn Ala Leu Val His Leu Val Trp Arg Pro Tyr Ala
            20                  25                  30

Ile Thr Arg Arg Leu Arg Ala His Gly Val Arg Gly Pro Pro Tyr Thr
        35                  40                  45

Phe Phe Thr Gly Ser Leu Gly Glu Ile Lys Arg Leu Arg Ala Lys Gly
    50                  55                  60

Ala Thr Val Thr Leu Asp Val Asp Asp His Asp Phe Ile Pro Met Val
65                  70                  75                  80

Gln Pro His Leu Arg Lys Trp Ile Ala Leu Tyr Gly Arg Thr Phe Val
                85                  90                  95

Tyr Trp Thr Gly Ala Arg Pro Asn Val Cys Val Ala Asp Val Asn Val
            100                 105                 110

Val Arg Gln Val Leu Phe Asp Arg Thr Gly Leu Tyr Pro Lys Asn Leu
        115                 120                 125

Met Asn Pro His Ile Ser Arg Leu Leu Gly Lys Gly Leu Val Leu Thr
    130                 135                 140

Asp Gly Asn Asp Trp Lys Arg His Arg Lys Val Val His Pro Ala Phe
145                 150                 155                 160

Asn Met Asp Lys Leu Lys Leu Met Thr Ala Thr Met Ser Asp Cys Ala
                165                 170                 175

Arg Ser Met Ile Ser Glu Trp Asp Ala Gln Leu Gln Lys Glu Ser
            180                 185                 190

Gly Arg Asp Gly His Gly His Gly His Val Glu Glu Leu Ser Ser
        195                 200                 205

Arg Phe Glu Glu Leu Thr Ala Asp Val Ile Ser His Thr Ala Phe Gly
    210                 215                 220

Ser Ser Tyr Ser Glu Gly Lys Arg Val Phe Leu Ala Gln Arg Glu Leu
225                 230                 235                 240

Gln His Ile Ala Phe Ser Thr Ile Phe Asn Val Gln Ile Pro Ala Leu
                245                 250                 255

Lys Tyr Leu Pro Thr Glu Lys Asn Leu Arg Thr Arg Lys Leu Asp Arg
            260                 265                 270

Gln Val Arg Ala Met Leu Met Asp Ile Ile Glu Ala Arg Leu Ala Ser
        275                 280                 285

Lys Asp Thr Ala Gly Gly Tyr Gly Asn Asp Leu Leu Gly Leu Met Leu
    290                 295                 300

Glu Ala Cys Ala Pro Pro Glu His His Gly Glu Met Ala Pro Thr
305                 310                 315                 320

Thr Leu Ser Met Asp Glu Ile Val Asp Glu Cys Lys Thr Phe Phe Phe
                325                 330                 335

Ala Gly His Asp Thr Thr Ser His Leu Leu Thr Trp Ala Ser Phe Leu
            340                 345                 350

Leu Ser Thr His Pro Glu Trp Gln His Arg Leu Arg Asp Glu Val Arg
        355                 360                 365

Arg Glu Cys Gly Asp Asp Glu Val Pro Thr Gly Asp Ala Leu Asn Arg
    370                 375                 380
```

```
Leu Lys Leu Val Asn Met Phe Leu Leu Glu Thr Leu Arg Leu Tyr Gly
385                 390                 395                 400

Pro Val Ser Leu Ile Gln Arg Lys Ala Gly Ser Asp Leu Asp Leu Gly
            405                 410                 415

Gly Ile Arg Val Pro Glu Gly Ala Ile Leu Thr Ile Pro Ile Ala Thr
            420                 425                 430

Ile His Arg Asp Lys Glu Val Trp Gly Glu Asp Ala Gly Glu Phe Arg
            435                 440                 445

Pro Glu Arg Phe Glu Asn Gly Val Thr Arg Ala Ala Lys His Pro Asn
            450                 455                 460

Ala Leu Leu Ser Phe Ser Ser Gly Pro Arg Ser Cys Ile Gly Gln Asn
465                 470                 475                 480

Phe Ala Met Ile Glu Ala Lys Ala Val Ala Met Ile Leu Gln Arg
                485                 490                 495

Phe Ala Leu Glu Leu Ser Pro Lys Tyr Val His Ala Pro Met Asp Leu
                500                 505                 510

Ile Thr Leu Arg Pro Arg His Gly Leu Pro Met Leu Leu Lys Arg Leu
            515                 520                 525

<210> SEQ ID NO 48
<211> LENGTH: 517
<212> TYPE: PRT
<213> ORGANISM: Zea mays

<400> SEQUENCE: 48

Met Gly Pro Ala Trp Met Val Ala Ser Val Ala Ala Val Leu Ala
1               5                   10                  15

Ser Trp Ala Phe Asn Ala Leu Val Arg Leu Val Trp Arg Pro Tyr Ala
                20                  25                  30

Val Ala Arg Arg Leu Arg Ala Gln Gly Val Arg Gly Pro Ala Tyr Arg
            35                  40                  45

Phe Leu Ala Gly Asn Leu Ala Glu Met Lys Arg Leu Arg Ala Glu Gly
        50                  55                  60

Ala Arg Ala Thr Leu Asp Val Gly Asp His Asp Phe Val Pro Met Val
65                  70                  75                  80

Gln Pro His His Arg Lys Trp Ile Ser Leu Tyr Gly Arg Thr Phe Leu
                85                  90                  95

Tyr Trp Asn Gly Ala Thr Pro Asn Leu Cys Leu Ala Asp Val Asn Leu
                100                 105                 110

Val Arg Gln Val Leu Phe Asp Arg Thr Gly Leu Tyr Pro Lys Asn His
            115                 120                 125

Ile Asn Gln Tyr Val Thr Arg Leu Leu Gly Arg Gly Leu Leu Leu Thr
    130                 135                 140

Asp Gly Asp Glu Trp Lys Arg His Arg Lys Val Val His Pro Ala Phe
145                 150                 155                 160

Asn Met Asp Lys Leu Lys Thr Met Thr Ala Thr Met Ser Asp Cys Ala
                165                 170                 175

Leu Ser Met Ile Ser Glu Trp Glu Ala Lys Leu Ala Lys Gly Gly Asp
                180                 185                 190

Ala Glu Val Val Glu Leu Ser Gln Phe Glu Leu Thr Ala Asp
            195                 200                 205

Val Ile Ser Arg Thr Ala Phe Gly Ser Ser Tyr Arg Glu Gly Arg Gln
            210                 215                 220

Val Phe Leu Ala Gln Arg Glu Leu Gln Phe Leu Ala Phe Ser Thr Ala
```

```
            225                 230                 235                 240
        Phe Asp Val Gln Ile Pro Ala Leu Arg Tyr Leu Pro Thr Arg Asn Asn
                        245                 250                 255

Leu Arg Thr Arg Glu Leu Asp Arg Arg Val Arg Gly Met Leu Met Asp
                        260                 265                 270

Ile Ile Lys Ala Arg Leu Ala Val Ala Gly Lys Asp Thr Ala Gly Gly
                        275                 280                 285

Gly Tyr Gly His Asp Leu Leu Gly Leu Met Leu Glu Ala Ala Glu His
                        290                 295                 300

Gly Gly Glu Ala Pro Thr Leu Ser Met Asp Glu Ile Val Asp Glu Cys
        305                 310                 315                 320

Lys Thr Phe Phe Phe Ala Gly Tyr Asp Thr Thr Ser His Leu Leu Thr
                        325                 330                 335

Trp Ala Cys Phe Leu Leu Ser Thr His Pro Glu Trp Gln Gly Arg Leu
                        340                 345                 350

Arg Glu Glu Val Arg Gln Glu Cys Gly Ala Asp Glu Val Pro Thr Gly
                        355                 360                 365

Asp Ala Leu Asn Arg Leu Arg Leu Val Asn Met Phe Leu Leu Glu Thr
                        370                 375                 380

Leu Arg Leu Tyr Gly Pro Val Ser Leu Ile Gln Arg Lys Ala Gly Thr
        385                 390                 395                 400

Asp Leu Asp Leu Gly Gly Val Arg Val Pro Glu Gly Ala Ile Leu Thr
                        405                 410                 415

Ile Pro Ile Ala Thr Ile His Arg Asp Thr Glu Val Trp Gly Asp Asp
                        420                 425                 430

Ala Gly Glu Phe Arg Pro Glu Arg Phe Gln Asn Gly Val Thr Arg Ala
                        435                 440                 445

Ala Lys His Pro Asn Ala Leu Leu Ala Phe Ser Ser Gly Pro Arg Ser
                        450                 455                 460

Cys Ile Gly Gln Asn Phe Ala Met Ile Glu Ala Lys Ala Val Val Ala
        465                 470                 475                 480

Ile Ile Leu Gln Arg Phe Ala Leu Glu Leu Ser Pro Thr Tyr Val His
                        485                 490                 495

Ala Pro Met Asp Val Ile Thr Leu Arg Pro Arg His Gly Leu Pro Met
                        500                 505                 510

Leu Leu Arg Ser Leu
                515

<210> SEQ ID NO 49
<211> LENGTH: 514
<212> TYPE: PRT
<213> ORGANISM: Sorghum bicolor

<400> SEQUENCE: 49

Met Asp Leu Ala Trp Met Val Ala Ala Val Ala Ser Val Leu Ala
        1               5                   10                  15

Ser Trp Ala Phe Asn Ala Leu Leu His Leu Val Trp Arg Pro Tyr Ala
                        20                  25                  30

Ile Thr Arg Ser Leu Arg Ala Gln Gly Val Arg Gly Pro Asp Tyr Arg
                        35                  40                  45

Phe Leu Thr Gly Asn Leu Ala Glu Met Lys Arg Leu Arg Ala Asp Gly
                        50                  55                  60

Ala Ala Val Thr Leu Asp Val Gly Asp His Asp Phe Ile Pro Met Val
        65                  70                  75                  80
```

```
Gln Pro His His Arg Lys Trp Ile Ser Leu Tyr Gly Arg Thr Phe Val
                 85                  90                  95
Tyr Trp Asn Gly Ala Thr Pro Asn Val Cys Leu Ala Asp Val Asn Val
            100                 105                 110
Val Arg Gln Val Leu Phe Asp Arg Thr Gly Leu Tyr Pro Lys Asn Leu
        115                 120                 125
Met Asn Pro His Val Ser Arg Leu Leu Gly Lys Gly Leu Val Leu Thr
    130                 135                 140
Asp Gly Asp Asp Trp Lys Arg His Arg Lys Val His Pro Ala Phe
145                 150                 155                 160
Asn Met Asp Lys Leu Lys Met Met Thr Ala Thr Met Ser Asn Cys Ala
                165                 170                 175
Leu Ser Met Met Ser Glu Trp Glu Ala Gln Leu Ala Lys Gly Ala Gly
            180                 185                 190
Asp Ala Glu Val Glu Leu Ser Thr Arg Phe Glu Leu Thr Ala Asp
        195                 200                 205
Val Ile Ser His Thr Ala Phe Gly Ser Ser Tyr Glu Asp Gly Lys Arg
    210                 215                 220
Val Phe Leu Ala Gln Arg Glu Leu Gln Phe Leu Ala Phe Ser Thr Phe
225                 230                 235                 240
Phe Asn Val Gln Ile Pro Ala Leu Arg Tyr Leu Pro Thr Glu Lys Asn
                245                 250                 255
Arg Arg Thr Trp Lys Leu Asp Lys Gln Val Arg Gly Met Leu Met Asp
            260                 265                 270
Ile Ile Lys Ala Arg Val Ala Asn Lys Asp Thr Ala Gly Tyr Gly Asn
        275                 280                 285
Asp Leu Leu Gly Leu Met Leu Glu Ala Cys Ala Pro Glu His Gly Glu
    290                 295                 300
Thr Pro Val Leu Ser Met Asp Glu Ile Ile Asp Glu Cys Lys Thr Phe
305                 310                 315                 320
Phe Phe Ala Gly His Asp Thr Thr Ser His Leu Leu Thr Trp Ala Ala
                325                 330                 335
Phe Leu Leu Ser Thr His Pro Glu Trp Gln Asp Arg Leu Arg Glu Glu
            340                 345                 350
Val Arg Arg Glu Cys Gly Asp Glu Val Pro Thr Arg Gly Asp Ala Leu
        355                 360                 365
Asn Lys Leu Ala Leu Val Asn Met Phe Leu Leu Glu Thr Leu Arg Leu
    370                 375                 380
Tyr Gly Pro Val Ser Leu Ile Gln Arg Lys Ala Gly Ser Asp Leu Asp
385                 390                 395                 400
Leu Gly Gly Ile Arg Val Pro Glu Gly Ala Ile Phe Thr Ile Pro Ile
                405                 410                 415
Ala Thr Ile His Arg Asp Lys Glu Val Trp Gly Asp Asp Ala Gly Glu
            420                 425                 430
Phe Lys Pro Glu Arg Phe Glu Asn Gly Val Thr Arg Ala Ala Lys His
        435                 440                 445
Pro Asn Ala Leu Leu Ser Phe Ser Gly Pro Arg Ser Cys Ile Gly
    450                 455                 460
Gln Asn Phe Ala Met Ile Glu Ala Lys Ala Val Ala Met Ile Leu
465                 470                 475                 480
Gln Arg Phe Ala Leu Glu Leu Ser Pro Lys Tyr Val His Ala Pro Met
                485                 490                 495
Asp Val Ile Thr Leu Arg Pro Arg His Gly Leu Pro Met Leu Leu Arg
```

<210> SEQ ID NO 50
<211> LENGTH: 491
<212> TYPE: PRT
<213> ORGANISM: Oryza sativa

<400> SEQUENCE: 50

```
Met Ala Met Gly Phe Leu Ala Trp Met Val Ala Ala Ala Ala Ala
 1               5                  10                  15

Val Leu Ala Ser Trp Ala Phe Ser Ala Val Val His Leu Val Trp Arg
                20                  25                  30

Pro Arg Ala Ile Ser Arg Arg Leu Arg Ala Gln Gly Val Gly Gly Pro
            35                  40                  45

Gly Tyr Arg Phe Phe Ser Gly Asn Leu Gly Glu Ile Lys Arg Phe Arg
        50                  55                  60

Gly Asp Gly Ala Gly Val Val Leu Asn Val Ser Ser His Asp Phe Leu
 65                  70                  75                  80

Pro Ile Val Gln Pro His Phe Arg Lys Trp Ile Pro Leu Tyr Gly Arg
                85                  90                  95

Thr Phe Leu Tyr Trp Phe Gly Ala Gln Pro Asn Ile Cys Leu Ala Asp
            100                 105                 110

Val Ser Met Val Trp Gln Val Leu Ser Asp Arg Thr Gly Ile Tyr Pro
        115                 120                 125

Lys Asn Leu Thr Asn Pro His Phe Val Arg Leu Leu Gly Lys Gly Leu
130                 135                 140

Val Leu Thr Asp Gly Asp Glu Trp Lys Arg His Arg Lys Trp Glu Ser
145                 150                 155                 160

Glu Leu Ala Ala Lys Gly Gly Leu Val Glu Ile Glu Leu Ser Arg Arg
                165                 170                 175

Phe Glu Glu Leu Thr Ala Asp Val Ile Ser His Thr Ala Phe Gly Ser
            180                 185                 190

Ser Tyr Lys Glu Gly Lys Gln Val Phe Leu Ala Gln Arg Glu Leu Gln
        195                 200                 205

Phe Leu Ala Phe Ser Thr Phe Leu Thr Val Gln Ile Pro Gly Phe Ser
    210                 215                 220

Tyr Leu Pro Thr Met Lys Asn Phe Lys Thr Trp Ser Leu Asp Lys Lys
225                 230                 235                 240

Val Arg Gly Met Leu Met Asp Ile Ile Lys Thr Arg His Ala Asn Lys
                245                 250                 255

Asp Val Ala Gly Tyr Gly Asn Asp Leu Leu Gly Leu Met Leu Glu Ala
            260                 265                 270

Cys Ala Pro Glu His Gly Glu Ser Cys Pro Gln Leu Ser Met Asp Glu
        275                 280                 285

Ile Ile Asp Glu Cys Lys Thr Phe Phe Ala Gly His Asp Thr Thr
    290                 295                 300

Ser His Leu Leu Thr Trp Thr Met Phe Leu Leu Ser Thr His Pro Asp
305                 310                 315                 320

Trp Gln Glu Lys Leu Arg Glu Glu Ile Ala Met Glu Cys Gly Asp Lys
                325                 330                 335

Val Pro Thr Gly Asp Met Leu Asn Lys Leu Lys Met Val Asn Met Phe
            340                 345                 350

Leu Leu Glu Thr Leu Arg Leu Tyr Ser Pro Val Ser Leu Ile Arg Arg
```

```
              355                 360                 365
Lys Val Asp Thr Asp Ile Glu Leu Gly Gly Ile Lys Met Pro Glu Gly
370                 375                 380

Ala Leu Leu Thr Ile Pro Ile Ala Thr Ile His Arg Asp Lys Glu Val
385                 390                 395                 400

Trp Gly Glu Asp Ala Asp Glu Phe Arg Pro Glu Arg Phe Glu Asn Gly
                405                 410                 415

Val Thr Arg Ala Ala Lys His Pro Asn Ala Leu Leu Ser Phe Ser Ser
                420                 425                 430

Gly Pro Arg Ser Cys Ile Gly Gln Asn Phe Ala Met Ile Glu Ala Lys
                435                 440                 445

Ala Val Ile Ala Met Ile Leu Gln Arg Phe Ser Phe Thr Leu Ser Pro
                450                 455                 460

Lys Tyr Val His Ala Pro Thr Asp Val Ile Thr Leu Arg Pro Lys Tyr
465                 470                 475                 480

Gly Leu Pro Met Ile Leu Lys Ser Leu Lys Leu
                485                 490

<210> SEQ ID NO 51
<211> LENGTH: 514
<212> TYPE: PRT
<213> ORGANISM: Triticum aestivum

<400> SEQUENCE: 51

Met Gly Leu Val Trp Leu Val Ala Ala Val Ala Val Val Leu Ala
1               5                   10                  15

Ser Trp Ala Phe Asn Ala Leu Val Tyr Leu Val Trp Arg Pro Arg Ala
                20                  25                  30

Ile Thr Arg Gln Leu Arg Ala Gln Gly Val Gly Gly Pro Gly Tyr Arg
                35                  40                  45

Phe Phe Ala Gly Asn Leu Ala Glu Ile Lys Gln Leu Arg Ala Asp Ser
                50                  55                  60

Ala Gly Ala Ala Leu Asp Ile Gly Asn His Asp Phe Val Pro Arg Val
65                  70                  75                  80

Gln Pro His Phe Arg Lys Trp Ile Pro His Gly Arg Thr Phe Leu
                85                  90                  95

Tyr Trp Phe Gly Ala Arg Pro Ser Leu Cys Val Ala Asp Val Asn Thr
                100                 105                 110

Val Lys Gln Val Leu Ser Asp Arg Ser Gly Leu Tyr Pro Lys Ser Ile
                115                 120                 125

Gly Asn Pro His Ile Ala Arg Leu Leu Gly Lys Gly Leu Val Leu Thr
                130                 135                 140

Asp Gly Asp Asp Trp Lys Arg His Arg Lys Val Val His Pro Ala Phe
145                 150                 155                 160

Asn Met Asp Lys Leu Lys Met Met Thr Val Thr Met Ser Asp Cys Ala
                165                 170                 175

Gly Ser Met Met Ser Glu Trp Lys Ala Lys Met Asp Lys Gly Gly Ser
                180                 185                 190

Val Glu Ile Asp Leu Ser His Gln Phe Glu Glu Leu Thr Ala Asp Val
                195                 200                 205

Ile Ser His Thr Ala Phe Gly Ser Ser Tyr Glu Gln Gly Lys Lys Val
                210                 215                 220

Phe Leu Ala Gln Arg Glu Leu Gln Phe Leu Ala Phe Ser Thr Val Phe
225                 230                 235                 240
```

Asn Val Gln Ile Pro Ala Phe Arg Tyr Leu Pro Thr Glu Lys Asn Val
            245                 250                 255

Lys Ile Trp Lys Leu Asp Lys Glu Val Arg Thr Met Leu Met Asn Ile
        260                 265                 270

Ile Lys Gly Arg Leu Ala Thr Lys Asp Ile Met Gly Tyr Gly Asn Asp
            275                 280                 285

Leu Leu Gly Leu Met Leu Glu Ala Cys Ala Pro Glu Asp Arg Gln Asn
        290                 295                 300

Pro Leu Leu Ser Met Asp Glu Ile Ile Asp Glu Cys Lys Thr Phe Phe
305                 310                 315                 320

Phe Ala Gly His Asp Thr Ser Ser His Leu Leu Thr Trp Thr Met Phe
                325                 330                 335

Leu Leu Ser Thr His Pro Lys Trp Gln Glu Lys Leu Arg Glu Glu Val
            340                 345                 350

Leu Arg Glu Cys Gly Asn Gly Val Pro Thr Gly Asp Met Leu Asn Lys
        355                 360                 365

Leu Gln Leu Val Asn Met Phe Leu Leu Glu Thr Leu Arg Leu Tyr Ala
    370                 375                 380

Pro Val Ser Ala Ile Gln Arg Lys Ala Gly Ser Asp Leu Glu Val Gly
385                 390                 395                 400

Gly Ile Lys Val Pro Glu Gly Thr Val Leu Thr Ile Pro Ile Ala Thr
                405                 410                 415

Ile His Arg Asp Lys Glu Val Trp Gly Glu Asp Ala Asn Glu Phe Lys
            420                 425                 430

Pro Met Arg Phe Glu Asn Gly Val Thr Arg Ala Gly Lys His Pro Asn
        435                 440                 445

Ala Leu Leu Ser Phe Ser Ser Gly Pro Arg Ser Cys Ile Gly Gln Asn
    450                 455                 460

Phe Ala Met Ile Glu Ala Lys Ala Val Ile Ala Val Ile Leu Gln Arg
465                 470                 475                 480

Phe Ser Phe Ser Leu Ser Pro Lys Tyr Val His Ala Pro Met Asp Val
                485                 490                 495

Ile Thr Leu Arg Pro Lys Phe Gly Leu Pro Met Val Leu Lys Ser Leu
            500                 505                 510

Glu Met

<210> SEQ ID NO 52
<211> LENGTH: 521
<212> TYPE: PRT
<213> ORGANISM: Oryza sativa

<400> SEQUENCE: 52

Met Gly Asn Phe Val Trp Met Val Ala Ala Ala Ala Ala Val Ala
1               5                   10                  15

Ser Trp Ala Phe Ile Ala Val Val Lys Leu Val Trp Arg Pro Arg
            20                  25                  30

Ala Ile Ser Arg Arg Leu Arg Ala Gln Ala Val Gly Pro Gly Tyr
        35                  40                  45

Arg Phe Phe Ser Gly Asn Leu Gly Glu Ile Arg Arg Leu Arg Ala Glu
    50                  55                  60

Gly Ala Gly Val Val Leu Asp Val Ser Ser His Asp Phe Val Pro Ile
65                  70                  75                  80

Val Gln Pro His Phe Arg Lys Trp Val Ser Leu Tyr Gly Lys Thr Phe
                85                  90                  95

```
Leu Phe Trp Phe Gly Ala Gln Pro Asn Ile Cys Leu Ala Asp Ile Asn
            100                 105                 110

Ile Val Arg Gln Val Leu Ser Asp Arg Thr Gly Met Tyr Pro Lys Asp
        115                 120                 125

Leu Thr Asn Pro Tyr Phe Ala His Leu Leu Gly Lys Gly Leu Val Leu
    130                 135                 140

Ile Asp Gly Asp Glu Trp Lys Arg His Tyr Lys Val Val His Pro Ala
145                 150                 155                 160

Phe Asp Met Asp Lys Leu Lys Met Met Thr Val Thr Ile Ser Asp Cys
                165                 170                 175

Thr Gly Ser Met Met Ser Glu Trp Glu Ser Glu Leu Gly Met Lys Gly
            180                 185                 190

Gly Ser Ala Glu Ile Glu Leu Ser Gln Arg Phe Gln Glu Leu Thr Ala
        195                 200                 205

Asp Val Ile Ser Arg Thr Ala Phe Gly Ser Ser Tyr Ser Glu Gly Lys
    210                 215                 220

Gln Val Phe Leu Ala Gln Arg Lys Leu Gln Phe Leu Ala Phe Ser Met
225                 230                 235                 240

Phe Leu Thr Ile Gln Ile Pro Gly Phe Arg Tyr Leu Pro Thr Lys Lys
                245                 250                 255

Asn Leu Lys Ile Trp Ser Leu Asp Lys Lys Val Arg Ser Met Leu Arg
            260                 265                 270

Asn Ile Ile Lys Ile Arg Leu Ala Asn Lys Asp Thr Met Gly Tyr Gly
        275                 280                 285

Asn Asp Leu Leu Gly Leu Met Leu Glu Thr Cys Ala Pro Glu His Asp
290                 295                 300

Glu Ser Gln Gln Leu Ser Met Asp Glu Ile Ile Ala Glu Cys Lys Thr
305                 310                 315                 320

Phe Phe Phe Gly Gly His Asp Thr Thr Ser His Leu Leu Thr Trp Thr
                325                 330                 335

Met Phe Leu Leu Ser Thr His Pro Glu Trp Met Arg Lys Ile Arg Lys
            340                 345                 350

Glu Val Thr Thr Met Cys Gly Asp Glu Val Pro Thr Gly Asp Met Leu
        355                 360                 365

Asn Lys Met Asn Leu Leu Asn Met Phe Leu Leu Glu Thr Leu Arg Leu
370                 375                 380

Tyr Ser Pro Val Ser Leu Ile Ser Arg Arg Thr Gly Thr Asn Ala Lys
385                 390                 395                 400

Phe Gly Gly Ile Lys Val Pro Glu Gly Thr Ile Leu Arg Ile Pro Ile
                405                 410                 415

Ala Thr Ile His Arg Asp Lys Glu Val Trp Gly Glu Asp Ala Asp Glu
            420                 425                 430

Phe Lys Pro Ala Arg Phe Glu Asn Gly Val Ser Lys Ala Ala Lys His
        435                 440                 445

Pro Asn Ala Leu Leu Ser Phe Ser Asn Gly Pro Arg Ser Cys Ile Gly
450                 455                 460

Gln Asn Phe Ala Met Ile Glu Ala Lys Ala Val Ile Thr Met Ile Leu
465                 470                 475                 480

Gln Arg Phe Ser Phe Thr Leu Ser Pro Lys Tyr Val His Thr Pro Ile
                485                 490                 495

Ser Val Ile Thr Leu Arg Pro Lys Tyr Gly Leu Pro Met Ile Leu Arg
            500                 505                 510

Ser Leu Lys Leu Tyr Lys Ile Gly Met
```

```
                515                 520

<210> SEQ ID NO 53
<211> LENGTH: 529
<212> TYPE: PRT
<213> ORGANISM: Zea mays

<400> SEQUENCE: 53

Met Gly Leu Ala Trp Met Val Ala Ala Val Ala Ala Val Leu Ala
1               5                  10                  15

Ser Trp Ala Phe Asn Ala Leu Val His Leu Val Trp Arg Pro Tyr Ala
            20                  25                  30

Ile Thr Arg Arg Leu Arg Ala Gln Gly Val Arg Gly Pro Pro Tyr Thr
        35                  40                  45

Phe Phe Thr Gly Ser Leu Gly Glu Ile Lys Arg Leu Arg Gly Glu Gly
    50                  55                  60

Ala Ala Val Thr Leu Asp Val Asp Asp His Asp Phe Ile Pro Met Val
65                  70                  75                  80

Gln Pro His Leu Arg Lys Trp Ile Ala Leu Tyr Gly Arg Thr Phe Val
                85                  90                  95

Tyr Trp Thr Gly Ala Arg Pro Asn Val Cys Val Ala Asp Val Asn Val
            100                 105                 110

Val Arg Gln Val Leu Phe Asp Arg Thr Gly Leu Tyr Pro Lys Asn Leu
        115                 120                 125

Met Asn Pro His Ile Ser Arg Leu Leu Gly Lys Gly Leu Val Leu Thr
130                 135                 140

Asp Gly Asp Asp Trp Lys Arg His Arg Lys Val His Pro Ala Phe
145                 150                 155                 160

Asn Met Asp Lys Leu Lys Leu Met Thr Ala Thr Met Ser Asp Cys Ala
                165                 170                 175

Arg Ser Met Ile Ser Glu Trp Asp Ala Gln Leu Gln Lys Glu Glu Ser
            180                 185                 190

Gly Arg Asp Gly His Gly His Gly His Val Glu Val Glu Leu Ser Ser
        195                 200                 205

Arg Phe Glu Glu Leu Thr Ala Asp Val Ile Ser His Thr Ala Phe Gly
    210                 215                 220

Ser Ser Tyr Ser Glu Gly Lys Arg Val Phe Leu Ala Gln Arg Glu Leu
225                 230                 235                 240

Gln His Ile Ala Phe Ser Thr Ile Phe Asn Val Gln Ile Pro Ala Leu
                245                 250                 255

Lys Tyr Leu Pro Thr Lys Lys Asn Val Arg Thr Arg Lys Leu Asp Arg
            260                 265                 270

Gln Val Arg Ala Met Leu Met Gly Ile Ile Glu Ala Arg Leu Ala Ser
        275                 280                 285

Lys Asp Thr Ala Gly Gly Tyr Gly Asn Asp Leu Leu Gly Leu Met Leu
    290                 295                 300

Glu Ala Cys Ala Pro Pro Glu His His Gly Glu Met Ala Leu Thr
305                 310                 315                 320

Thr Leu Ser Met Asp Glu Ile Val Asp Glu Cys Lys Thr Phe Phe
                325                 330                 335

Ala Gly His Asp Thr Thr Ser His Leu Leu Thr Trp Ala Thr Phe Leu
            340                 345                 350

Leu Ser Thr His Pro Glu Trp Gln His Arg Leu Arg Asp Glu Val Arg
        355                 360                 365
```

```
Arg Glu Cys Gly Asp Asp Asp Glu Val Pro Thr Gly Asp Ala Leu Asn
370                 375                 380

Arg Leu Lys Leu Val Asn Met Phe Leu Leu Glu Thr Leu Arg Leu Tyr
385                 390                 395                 400

Gly Pro Val Ser Leu Ile Gln Arg Lys Ala Gly Ser Asp Leu Asp Leu
                405                 410                 415

Gly Gly Ile Arg Val Pro Glu Gly Ala Ile Leu Thr Ile Pro Ile Ala
                420                 425                 430

Thr Ile His Arg Asp Lys Glu Val Trp Gly Asp Ala Gly Glu Phe
            435                 440                 445

Arg Pro Glu Arg Phe Glu Asn Gly Val Thr Arg Ala Ala Lys His Pro
450                 455                 460

Asn Ala Leu Leu Ser Phe Ser Ser Gly Pro Arg Ser Cys Ile Gly Gln
465                 470                 475                 480

Asn Phe Ala Met Ile Glu Ala Lys Ala Val Ala Met Ile Leu Gln
                485                 490                 495

Arg Phe Ala Leu Glu Leu Ser Pro Lys Tyr Val His Ala Pro Met Asp
                500                 505                 510

Leu Ile Thr Leu Arg Pro Arg His Gly Leu Pro Met Leu Leu Lys Arg
                515                 520                 525

Leu
```

<210> SEQ ID NO 54
<211> LENGTH: 512
<212> TYPE: PRT
<213> ORGANISM: Sorghum bicolor

<400> SEQUENCE: 54

```
Met Asp Leu Ala Trp Met Val Ala Ala Val Ala Ala Val Leu Ala
1               5                   10                  15

Ser Trp Ala Phe Asn Ala Leu Val His Leu Val Trp Arg Pro Tyr Ala
                20                  25                  30

Ile Thr Arg Ser Leu Arg Ala Gln Gly Val Arg Gly Pro Asp Tyr Arg
                35                  40                  45

Phe Phe Thr Gly Ser Leu Gly Glu Ile Lys Arg Leu Arg Gly Glu Gly
            50                  55                  60

Ala Ala Val Thr Leu Asp Val Asp His Asp Phe Ile Pro Met Val
65                  70                  75                  80

Gln Pro His Leu Arg Lys Trp Ile Ala Leu Tyr Gly Arg Thr Phe Val
                85                  90                  95

Tyr Trp Thr Ala Ala Arg Pro Asn Val Cys Val Ala Asp Val Asn Val
                100                 105                 110

Val Arg Gln Val Leu Phe Asp Arg Thr Gly Leu Tyr Pro Lys Asn Leu
                115                 120                 125

Met Asn Pro His Val Ser Arg Leu Leu Gly Lys Gly Leu Val Leu Thr
130                 135                 140

Asp Gly Asp Asp Trp Lys Arg His Arg Lys Val His Pro Ala Phe
145                 150                 155                 160

Asn Met Asp Lys Leu Lys Met Met Thr Val Thr Met Ser Asp Cys Ala
                165                 170                 175

Arg Ser Met Met Ser Glu Trp Glu Ala Gln Leu Ala Lys Gly Gly Glu
                180                 185                 190

Val Glu Val Glu Leu Ser Ser Arg Phe Glu Glu Leu Thr Ala Asp Val
                195                 200                 205
```

```
Ile Ser His Thr Ala Phe Gly Ser Ser Tyr Asn Glu Gly Lys Gln Val
    210                 215                 220

Phe Leu Ala Gln Arg Glu Leu Gln Tyr Ile Ala Phe Ser Thr Val Phe
225                 230                 235                 240

Asn Val Gln Ile Pro Ala Leu Lys Tyr Leu Pro Thr Glu Lys Asn Leu
                245                 250                 255

Lys Thr Arg Lys Leu Asp Arg Gln Val Arg Gly Met Leu Met Asp Ile
            260                 265                 270

Ile Lys Ala Arg Leu Thr Ser Lys Asp Thr Ala Gly Tyr Gly Asn Asp
        275                 280                 285

Leu Leu Gly Leu Met Leu Glu Ala Cys Ala Pro Glu His Gly Glu Thr
    290                 295                 300

Pro Val Leu Ser Met Asp Glu Ile Ile Asp Glu Cys Lys Thr Phe Phe
305                 310                 315                 320

Phe Ala Gly His Asp Thr Thr Ser His Leu Leu Thr Trp Ala Ser Phe
                325                 330                 335

Leu Leu Ser Thr His Pro Glu Trp Gln Asp Arg Leu Arg Glu Glu Val
            340                 345                 350

Arg Arg Glu Cys Gly Asp Glu Val Pro Thr Gly Asp Ala Leu Asn Lys
        355                 360                 365

Leu Lys Leu Val Asn Met Phe Leu Leu Glu Thr Leu Arg Leu Tyr Gly
    370                 375                 380

Pro Val Ser Leu Ile Gln Arg Lys Ala Gly Ser Asp Leu Asp Leu Gly
385                 390                 395                 400

Gly Ile Arg Val Pro Glu Gly Ala Ile Leu Thr Ile Pro Ile Ala Thr
                405                 410                 415

Ile His Arg Asp Lys Glu Val Trp Gly Asp Ala Gly Glu Phe Lys
            420                 425                 430

Pro Glu Arg Phe Glu Asn Gly Val Thr Arg Ala Ala Lys His Pro Asn
        435                 440                 445

Ala Leu Leu Ser Phe Ser Ser Gly Pro Arg Ser Cys Ile Gly Gln Asn
    450                 455                 460

Phe Ala Met Ile Glu Ala Lys Ala Val Val Ala Met Ile Leu Gln Arg
465                 470                 475                 480

Phe Ala Leu Glu Leu Ser Pro Lys Tyr Val His Ala Pro Met Asp Val
                485                 490                 495

Ile Thr Leu Arg Pro Arg His Gly Leu Pro Met Leu Leu Lys Arg Leu
            500                 505                 510

<210> SEQ ID NO 55
<211> LENGTH: 520
<212> TYPE: PRT
<213> ORGANISM: Oryza sativa

<400> SEQUENCE: 55

Met Gly Asn Phe Val Trp Met Val Ala Ala Ala Ala Ala Ala Val Ala
1               5                   10                  15

Ser Trp Ala Phe Ile Ala Val Val Lys Leu Val Trp Arg Pro Arg
                20                  25                  30

Ala Ile Ser Arg Arg Leu Arg Ala Gln Ala Val Gly Gly Pro Gly Tyr
            35                  40                  45

Arg Phe Phe Ser Gly Asn Leu Gly Glu Ile Arg Arg Leu Arg Ala Glu
        50                  55                  60

Gly Ala Gly Val Val Leu Asp Val Ser Ser His Asp Phe Val Pro Ile
65                  70                  75                  80
```

```
Val Gln Pro His Phe Arg Lys Trp Val Ser Leu Tyr Gly Lys Thr Phe
                 85                  90                  95

Leu Phe Trp Phe Gly Ala Gln Pro Asn Ile Cys Leu Ala Asp Ile Asn
            100                 105                 110

Ile Val Arg Gln Val Leu Ser Asp Arg Thr Gly Met Tyr Pro Lys Asp
        115                 120                 125

Leu Thr Asn Pro Tyr Phe Ala His Leu Leu Gly Lys Gly Leu Val Leu
    130                 135                 140

Ile Asp Gly Asp Glu Trp Lys Arg His Tyr Lys Val Val His Pro Ala
145                 150                 155                 160

Phe Asp Met Asp Lys Leu Lys Met Met Thr Val Thr Ile Ser Asp Cys
                165                 170                 175

Thr Gly Ser Met Met Ser Glu Trp Glu Ser Glu Leu Gly Met Lys Gly
            180                 185                 190

Gly Ser Ala Glu Ile Glu Leu Ser Gln Arg Phe Gln Glu Leu Thr Ala
        195                 200                 205

Asp Val Ile Ser Arg Thr Ala Phe Gly Ser Ser Tyr Ser Glu Gly Lys
    210                 215                 220

Gln Val Phe Leu Ala Gln Arg Lys Leu Gln Phe Leu Ala Phe Ser Met
225                 230                 235                 240

Phe Leu Thr Ile Gln Ile Pro Gly Phe Arg Tyr Leu Pro Thr Lys Lys
                245                 250                 255

Asn Leu Lys Ile Trp Ser Leu Asp Lys Lys Val Arg Ser Met Leu Arg
            260                 265                 270

Asn Ile Ile Lys Ile Arg Leu Ala Asn Lys Asp Thr Met Gly Tyr Gly
        275                 280                 285

Asn Asp Leu Leu Gly Leu Met Leu Glu Thr Cys Ala Pro Glu His Asp
    290                 295                 300

Glu Ser Gln Gln Leu Ser Met Asp Glu Ile Ile Ala Glu Cys Lys Thr
305                 310                 315                 320

Phe Phe Phe Gly Gly His Asp Thr Thr Ser His Leu Leu Thr Trp Thr
                325                 330                 335

Met Phe Leu Leu Ser Thr His Pro Glu Trp Met Arg Lys Ile Arg Lys
            340                 345                 350

Glu Val Thr Thr Met Cys Gly Asp Glu Val Pro Thr Gly Asp Met Leu
        355                 360                 365

Asn Lys Met Asn Leu Leu Asn Met Phe Leu Leu Glu Thr Leu Arg Leu
    370                 375                 380

Tyr Ser Pro Val Ser Leu Ile Ser Arg Arg Thr Gly Thr Asn Ala Lys
385                 390                 395                 400

Phe Gly Gly Ile Lys Val Pro Glu Gly Thr Ile Leu Arg Ile Pro Ile
                405                 410                 415

Ala Thr Ile His Arg Asp Lys Glu Val Trp Gly Glu Asp Ala Asp Glu
            420                 425                 430

Phe Lys Pro Ala Arg Phe Glu Asn Gly Val Ser Lys Ala Ala Lys His
        435                 440                 445

Pro Asn Ala Leu Leu Ser Phe Ser Asn Gly Pro Arg Ser Cys Ile Gly
    450                 455                 460

Gln Asn Phe Ala Met Ile Glu Ala Lys Ala Val Ile Thr Met Ile Leu
465                 470                 475                 480

Gln Arg Phe Ser Phe Thr Leu Ser Pro Lys Tyr Val His Thr Pro Ile
                485                 490                 495
```

Ser Val Ile Thr Leu Arg Pro Lys Tyr Gly Leu Pro Met Ile Leu Arg
            500                 505                 510

Ser Leu Lys Val Lys Arg Asp Leu
            515                 520

<210> SEQ ID NO 56
<211> LENGTH: 509
<212> TYPE: PRT
<213> ORGANISM: Oryza sativa

<400> SEQUENCE: 56

Met Gly Phe Glu Trp Thr Val Ala Thr Ala Ala Ala Val Ala Arg
1               5                   10                  15

Arg Gly Arg Ser Ser Arg Trp Trp Arg Leu Gly Ala Gln Gly Val Ala
            20                  25                  30

Gly Pro Gly Tyr Arg Phe Phe Ser Gly Asn Leu Ser Glu Ile Arg Arg
            35                  40                  45

Leu Arg Ala Glu Gly Ala Asn Leu Val Leu Asp Val Ser Ser His Asp
50                  55                  60

Phe Val Pro Ile Val Gln Pro His Ile Arg Thr Trp Ile Pro Leu Tyr
65                  70                  75                  80

Gly Lys Thr Phe Leu Tyr Trp Phe Gly Thr Arg Pro Asn Ile Cys Leu
            85                  90                  95

Ala Asp Met Asn Met Val Arg Gln Val Leu Ser Asp Arg Thr Gly Met
            100                 105                 110

Phe Pro Lys Tyr Ile Asp Asn Met Gln Phe Ala Arg Leu Leu Gly Lys
            115                 120                 125

Gly Leu Val Leu Thr Asp Asp Glu Trp Lys Arg His Tyr Lys Val
            130                 135                 140

Val His Pro Ala Phe Asp Met Asp Lys Leu Lys Met Met Thr Glu Thr
145                 150                 155                 160

Ile Ser Asp Cys Ala Arg Ser Met Met Phe Glu Trp Glu Ser Glu Leu
            165                 170                 175

Gly Met Lys Gly Gly Ser Thr Glu Ile Glu Leu Ser Arg Trp Phe Glu
            180                 185                 190

Glu Leu Thr Val Asp Val Ile Ser Arg Thr Ala Phe Gly Ser Ile Tyr
            195                 200                 205

Arg Glu Gly Lys Gln Val Phe Leu Ala Gln Arg Lys Leu Gln Phe Leu
            210                 215                 220

Ala Phe Ser Ala Phe Leu Thr Ile Gln Ile Pro Gly Phe Ser Tyr Leu
225                 230                 235                 240

Leu Thr Lys Lys Asn Met Lys Thr Trp Ser Leu Asp Lys Lys Val Arg
            245                 250                 255

Ser Met Leu Met Asn Ile Ile Lys Ser Arg Leu Thr Asn Lys Glu Thr
            260                 265                 270

Met Gly Tyr Gly Asn Asp Leu Leu Gly Leu Met Leu Glu Ala Cys Val
            275                 280                 285

Pro Glu His Gly Gly Ser Gln Pro Gln Leu Ser Met Asp Asp Ile Ile
            290                 295                 300

Ala Glu Cys Lys Thr Phe Phe Ala Gly His Asp Thr Thr Ser Gln
305                 310                 315                 320

Leu Leu Thr Trp Thr Met Phe Leu Leu Ser Thr His Gln His Trp Met
            325                 330                 335

Glu Lys Leu Arg Lys Glu Val Arg Met Val Cys Asn Asp Glu Val Pro
            340                 345                 350

```
Thr Gly Asp Met Leu Asn Lys Leu Lys Leu Val Asn Met Phe Leu Leu
            355                 360                 365

Glu Thr Leu Arg Leu Tyr Gly Pro Val Ser Leu Val Thr Arg Arg Asp
    370                 375                 380

Gly Thr Asp Val Lys Leu Gly Ser Ile Lys Val Pro Lys Gly Thr Ile
385                 390                 395                 400

Leu Thr Ile Pro Ile Ala Thr Ile His Arg Asp Lys Glu Val Trp Gly
                405                 410                 415

Glu Asp Ala Asp Glu Phe Lys Pro Glu Arg Phe Glu Asn Gly Val Leu
            420                 425                 430

Lys Ala Ala Lys His Pro Ser Ala Leu Leu Ser Phe Ser Ile Gly Leu
                435                 440                 445

Arg Ser Cys Ile Gly Gln Asn Phe Ala Met Ile Glu Ala Lys Thr Ile
            450                 455                 460

Ile Ala Met Ile Leu Gln Arg Phe Ser Phe Thr Leu Ser Pro Lys Tyr
465                 470                 475                 480

Val His Thr Pro Ile Ser Val Ile Thr Leu Arg Pro Lys Tyr Gly Leu
                485                 490                 495

Pro Met Ile Leu Arg Ser Leu Lys Val Lys Arg Asp Arg
                500                 505

<210> SEQ ID NO 57
<211> LENGTH: 517
<212> TYPE: PRT
<213> ORGANISM: Oryza sativa

<400> SEQUENCE: 57

Met Gly Asn Leu Gly Trp Met Val Ala Ala Val Ala Ala Val Val
1               5                   10                  15

Ala Ser Trp Ala Phe Asp Ala Val Lys Leu Val Trp Arg Pro Arg
                20                  25                  30

Ala Ile Thr Arg Arg Leu Arg Ala Gln Gly Val Gly Gly Pro Gly Tyr
            35                  40                  45

Arg Phe Phe Ser Gly Asn Leu Gly Glu Ile Arg Arg Leu Arg Asp Glu
    50                  55                  60

Gly Ala Gly Val Val Leu Asp Val Ser Ser His Asp Phe Val Pro Ile
65                  70                  75                  80

Val Gln Pro His Phe Arg Lys Trp Ile Pro Leu Tyr Gly Lys Thr Phe
                85                  90                  95

Met Tyr Trp Phe Gly Ala Arg Pro Thr Ile Cys Leu Ala Asp Val Ser
            100                 105                 110

Met Val Arg Gln Val Leu Ser Asp Arg Thr Gly Met Tyr Pro Lys Asn
        115                 120                 125

Val Ser Asn Pro Tyr Phe Ala Arg Leu Leu Gly Lys Gly Leu Val Leu
    130                 135                 140

Thr Asp Gly Asp Glu Trp Lys Arg His Arg Lys Val Val His Pro Ala
145                 150                 155                 160

Phe Asn Met Asp Lys Leu Lys Met Met Thr Val Thr Met Ser Asp Cys
                165                 170                 175

Ala Gln Ser Met Ile Ser Glu Trp Glu Ser Leu Gly Thr Lys Gly
            180                 185                 190

Asp Ile Val Glu Ile Glu Leu Ser Arg Arg Phe Glu Glu Leu Thr Ala
        195                 200                 205

Asp Val Ile Ser His Thr Ala Phe Gly Ser Ser Tyr Lys Glu Gly Lys
```

```
               210                 215                 220
Gln Val Phe Leu Ala Gln Arg Glu Leu Gln Phe Leu Ala Phe Ser Thr
225                 230                 235                 240

Phe Leu Ser Ile Gln Ile Pro Gly Ser Ser Tyr Leu Pro Thr Lys Lys
                245                 250                 255

Asn Leu Lys Thr Trp Ser Val Asp Lys Val Arg Ser Met Leu Thr
                260                 265                 270

Asp Ile Ile Lys Ser Arg Leu Asn Asn Lys Asp Val Ala Gly Tyr Gly
                275                 280                 285

Asn Asp Leu Leu Gly Leu Met Leu Glu Ala Cys Ala Pro Glu His Gly
                290                 295                 300

Glu Ser Gln Pro Gln Leu Ser Met Asp Glu Ile Ala Glu Cys Lys
305                 310                 315                 320

Thr Phe Phe Phe Ala Gly His Asp Thr Thr Ser His Leu Leu Thr Trp
                325                 330                 335

Thr Met Phe Leu Leu Ser Thr His Pro Glu Trp Gln Glu Lys Leu Arg
                340                 345                 350

Glu Glu Val Ala Thr Glu Cys Asp Gly Lys Val Pro Thr Gly Asp Met
                355                 360                 365

Leu Asn Lys Leu Lys Leu Val Asn Met Phe Leu Leu Glu Thr Leu Arg
370                 375                 380

Leu Tyr Gly Pro Val Ala Phe Ile Gln Arg Arg Val Asn Ala Glu Leu
385                 390                 395                 400

Glu Leu Gly Gly Ile Thr Val Pro Glu Gly Thr Val Leu Ser Ile Pro
                405                 410                 415

Ile Ala Thr Ile His Arg Asp Lys Glu Val Trp Gly Glu Asp Ala Asp
                420                 425                 430

Ile Phe Lys Pro Glu Arg Phe Lys Asn Gly Val Ser Lys Ala Gly Lys
                435                 440                 445

Tyr Pro Asn Ala Leu Leu Ser Phe Ser Ser Gly Pro Arg Ala Cys Ile
                450                 455                 460

Gly Gln Asn Phe Ala Met Ile Glu Ala Lys Ala Val Ile Ala Met Ile
465                 470                 475                 480

Leu Gln Arg Phe Ser Phe Thr Leu Ser Pro Lys Tyr Val His Val Pro
                485                 490                 495

Thr Asp Val Ile Thr Leu Arg Pro Lys Tyr Gly Leu Pro Met Ile Leu
                500                 505                 510

Lys Ser Leu Lys Val
                515

<210> SEQ ID NO 58
<211> LENGTH: 502
<212> TYPE: PRT
<213> ORGANISM: Oryza sativa

<400> SEQUENCE: 58

Met Gly Phe Glu Trp Thr Val Ala Thr Ala Ala Ala Val Ala Ala
1               5                   10                  15

Ser Arg Leu Gly Ala Gln Gly Val Ala Gly Pro Gly Tyr Arg Phe Phe
                20                  25                  30

Ser Gly Asn Leu Ser Glu Ile Arg Arg Leu Arg Ala Glu Gly Ala Asn
                35                  40                  45

Leu Val Leu Asp Val Ser His Asp Phe Val Pro Ile Val Gln Pro
50                  55                  60
```

```
His Ile Arg Lys Trp Ile Pro Leu Tyr Gly Lys Thr Phe Leu Tyr Trp
 65                  70                  75                  80

Phe Gly Thr Arg Pro Asn Ile Cys Leu Ala Asp Met Asn Met Val Arg
                 85                  90                  95

Gln Val Leu Ser Asp Arg Thr Gly Met Phe Pro Lys Tyr Ile Asp Asn
            100                 105                 110

Met Gln Phe Ala Arg Leu Leu Gly Lys Gly Leu Val Leu Thr Asp Asp
        115                 120                 125

Asp Glu Trp Lys Arg His Tyr Lys Val Val His Pro Ala Phe Asp Met
130                 135                 140

Asp Lys Leu Lys Met Met Thr Glu Thr Ile Ser Asp Tyr Ala Gln Ser
145                 150                 155                 160

Met Met Phe Glu Trp Glu Ser Glu Leu Gly Met Lys Gly Gly Ser Thr
                165                 170                 175

Glu Ile Glu Leu Ser Arg Trp Phe Glu Glu Leu Thr Ala Asp Val Ile
            180                 185                 190

Ser Arg Thr Ala Phe Gly Ser Ser Tyr Arg Glu Gly Lys Gln Val Phe
        195                 200                 205

Leu Ala Gln Arg Lys Leu Gln Phe Leu Ala Phe Ser Val Phe Leu Thr
210                 215                 220

Ile Gln Ile Pro Gly Phe Ser Tyr Leu Leu Thr Lys Lys Asn Leu Lys
225                 230                 235                 240

Thr Trp Ser Leu Asp Lys Lys Val Arg Ser Met Leu Met Asn Ile Ile
                245                 250                 255

Lys Ser Arg Leu Thr Asn Lys Glu Thr Met Gly Tyr Gly Asn Asp Leu
            260                 265                 270

Leu Gly Leu Met Leu Glu Ala Cys Val Pro Glu His Gly Gly Ser Gln
        275                 280                 285

Pro Gln Leu Ser Met Asp Asp Ile Ile Ala Glu Cys Lys Thr Phe Phe
290                 295                 300

Phe Ala Gly His Asp Thr Thr Ser Gln Leu Leu Thr Trp Thr Met Phe
305                 310                 315                 320

Leu Leu Ser Thr His Gln His Trp Met Glu Lys Leu Arg Lys Glu Val
                325                 330                 335

Arg Met Val Cys Asn Asp Glu Val Pro Thr Gly Asp Met Leu Asn Lys
            340                 345                 350

Leu Lys Leu Val Asn Met Phe Leu Leu Glu Thr Leu Arg Leu Tyr Gly
        355                 360                 365

Pro Val Ser Leu Val Thr Arg Arg Ala Gly Thr Asp Val Lys Leu Gly
370                 375                 380

Ser Ile Lys Val Pro Lys Gly Thr Ile Leu Thr Ile Pro Ile Ala Thr
385                 390                 395                 400

Ile His Arg Asp Lys Glu Val Trp Gly Glu Asp Ala Asp Glu Phe Lys
                405                 410                 415

Pro Glu Arg Ser Glu Asn Gly Val Leu Asn Ala Ala Lys His Pro Ser
            420                 425                 430

Ala Leu Leu Ser Phe Ser Ile Gly Leu Arg Ser Cys Ile Gly Gln Asn
        435                 440                 445

Phe Ala Met Ile Glu Ala Arg Thr Ile Ile Ala Met Ile Leu Gln Arg
450                 455                 460

Phe Ser Phe Thr Leu Ser Pro Lys Tyr Val His Thr Pro Ile Ser Val
465                 470                 475                 480

Ile Thr Leu Arg Pro Lys Tyr Gly Leu Pro Met Ile Leu Arg Ser Leu
```

Lys Val Lys Arg Asp Arg
            500

<210> SEQ ID NO 59
<211> LENGTH: 520
<212> TYPE: PRT
<213> ORGANISM: Oryza sativa

<400> SEQUENCE: 59

Met Gly Asn Phe Val Trp Met Val Ala Ala Ala Ala Val Ala
1               5                   10                  15

Ser Trp Ala Phe Ile Ala Val Val Lys Leu Val Trp Arg Pro Arg
            20                  25                  30

Ala Ile Ser Arg Arg Leu Arg Ala Gln Ala Val Gly Gly Pro Gly Tyr
            35                  40                  45

Arg Phe Phe Ser Gly Asn Leu Gly Glu Ile Arg Arg Leu Arg Ala Glu
            50                  55                  60

Gly Ala Gly Val Val Leu Asp Val Ser Ser His Asp Phe Val Pro Ile
65                  70                  75                  80

Val Gln Pro His Phe Arg Lys Trp Val Ser Leu Tyr Gly Lys Thr Phe
            85                  90                  95

Leu Phe Trp Phe Gly Ala Gln Pro Asn Ile Cys Leu Ala Asp Ile Asn
            100                 105                 110

Ile Val Arg Gln Val Leu Ser Asp Arg Thr Gly Met Tyr Pro Lys Asp
            115                 120                 125

Leu Thr Asn Pro Tyr Phe Ala His Leu Leu Gly Lys Gly Leu Val Leu
            130                 135                 140

Ile Asp Gly Asp Glu Trp Lys Arg His Tyr Lys Val Val His Pro Ala
145                 150                 155                 160

Phe Asp Met Asp Lys Leu Lys Met Met Thr Val Thr Ile Ser Asp Cys
                165                 170                 175

Thr Gly Ser Met Met Ser Glu Trp Glu Ser Glu Leu Gly Met Lys Gly
            180                 185                 190

Gly Ser Ala Glu Ile Glu Leu Ser Gln Arg Phe Gln Glu Leu Thr Ala
            195                 200                 205

Asp Val Ile Ser Arg Thr Ala Phe Gly Ser Ser Tyr Ser Glu Gly Lys
            210                 215                 220

Gln Val Phe Leu Ala Gln Arg Lys Leu Gln Phe Leu Ala Phe Ser Met
225                 230                 235                 240

Phe Leu Thr Ile Gln Ile Pro Gly Phe Arg Tyr Leu Pro Thr Lys Lys
            245                 250                 255

Asn Leu Lys Ile Trp Ser Leu Asp Lys Lys Val Arg Ser Met Leu Thr
            260                 265                 270

Asn Ile Ile Lys Ile Arg Leu Ala Asn Lys Asp Thr Met Gly Tyr Gly
            275                 280                 285

Asn Asp Leu Leu Gly Leu Met Leu Glu Thr Cys Ala Pro Glu His Asp
            290                 295                 300

Glu Ser Gln Gln Leu Ser Met Asp Glu Ile Ile Ala Glu Cys Lys Thr
305                 310                 315                 320

Phe Phe Phe Gly Gly His Asp Thr Thr Ser His Leu Leu Thr Trp Thr
            325                 330                 335

Met Phe Leu Leu Ser Thr His Pro Glu Trp Met Arg Lys Ile Arg Lys
            340                 345                 350

```
Glu Val Thr Thr Met Cys Gly Asp Glu Val Pro Thr Gly Asp Met Leu
            355                 360                 365

Asn Lys Met Asn Leu Leu Asn Met Phe Leu Leu Glu Thr Leu Arg Leu
370                 375                 380

Tyr Gly Pro Val Ser Leu Ile Ser Arg Arg Thr Gly Thr Asn Ala Lys
385                 390                 395                 400

Phe Gly Gly Ile Lys Val Pro Glu Gly Thr Ile Leu Arg Ile Pro Ile
                405                 410                 415

Ala Thr Ile His Arg Asp Lys Glu Val Trp Gly Glu Asp Ala Asp Glu
                420                 425                 430

Phe Lys Pro Ala Arg Phe Glu Asn Gly Val Ser Lys Ala Ala Lys His
            435                 440                 445

Pro Asn Ala Leu Leu Ser Phe Ser Asn Gly Pro Arg Ser Cys Ile Gly
            450                 455                 460

Gln Asn Phe Ala Met Ile Glu Ala Lys Ala Val Ile Thr Met Ile Leu
465                 470                 475                 480

Gln Arg Phe Ser Phe Thr Leu Ser Pro Lys Tyr Val His Thr Pro Ile
                485                 490                 495

Ser Val Ile Thr Leu Arg Pro Lys Tyr Gly Leu Pro Met Ile Leu Arg
                500                 505                 510

Ser Leu Lys Val Lys Arg Asp Leu
            515                 520

<210> SEQ ID NO 60
<211> LENGTH: 519
<212> TYPE: PRT
<213> ORGANISM: Oryza sativa

<400> SEQUENCE: 60

Met Ala Met Gly Leu Leu Ala Trp Met Val Ala Ala Ala Ala Ala Ala
1               5                   10                  15

Val Leu Ala Ser Trp Ala Phe Ser Ala Val His Leu Val Trp Arg
                20                  25                  30

Pro Arg Ala Ile Ser Arg Arg Leu Arg Ala Gln Gly Val Gly Gly Pro
                35                  40                  45

Gly Tyr Arg Phe Phe Ser Gly Asn Leu Gly Glu Ile Lys Arg Phe Arg
50                  55                  60

Gly Asp Gly Ala Gly Val Val Leu Asn Val Ser Ser His Asp Phe Leu
65                  70                  75                  80

Pro Ile Val Gln Pro His Phe Arg Lys Trp Ile Pro Leu Tyr Gly Arg
                85                  90                  95

Thr Phe Leu Tyr Trp Phe Gly Ala Gln Pro Asn Ile Cys Leu Ala Asp
                100                 105                 110

Val Ser Met Val Trp Gln Val Leu Ser Asp Arg Thr Gly Ile Tyr Pro
                115                 120                 125

Lys Asn Leu Thr Asn Pro His Phe Val Arg Leu Leu Gly Lys Gly Leu
130                 135                 140

Val Leu Thr Asp Gly Asp Glu Trp Lys Arg His Arg Lys Val Val His
145                 150                 155                 160

Pro Ala Phe Asn Met Asp Lys Leu Lys Met Met Thr Thr Met Ser
                165                 170                 175

Asp Cys Ser Arg Ser Met Met Ser Glu Trp Glu Ser Glu Leu Ala Ala
                180                 185                 190

Lys Gly Gly Leu Val Glu Ile Glu Leu Ser Arg Arg Phe Glu Glu Leu
                195                 200                 205
```

```
Thr Ala Asp Val Ile Ser His Thr Ala Phe Gly Ser Tyr Lys Glu
        210                 215                 220

Gly Lys Gln Val Phe Leu Ala Gln Arg Glu Leu Gln Phe Leu Ala Phe
225                 230                 235                 240

Ser Thr Phe Leu Thr Val Gln Ile Pro Gly Phe Ser Tyr Leu Pro Thr
                245                 250                 255

Met Lys Asn Phe Lys Thr Trp Ser Leu Asp Lys Lys Val Arg Gly Met
                260                 265                 270

Leu Met Asp Ile Ile Lys Thr Arg His Ala Asn Lys Asp Val Ala Gly
            275                 280                 285

Tyr Gly Asn Asp Leu Leu Gly Leu Met Leu Glu Ala Cys Ala Pro Glu
        290                 295                 300

His Gly Glu Ser Cys Pro Gln Leu Ser Met Asp Glu Ile Ile Asp Glu
305                 310                 315                 320

Cys Lys Thr Phe Phe Phe Ala Gly His Asp Thr Thr Ser His Leu Leu
                325                 330                 335

Thr Trp Thr Met Phe Leu Leu Ser Thr His Pro Asp Trp Gln Glu Lys
                340                 345                 350

Leu Arg Glu Glu Ile Ala Met Glu Cys Gly Asp Lys Val Pro Thr Gly
            355                 360                 365

Asp Met Leu Asn Lys Leu Lys Met Val Asn Met Phe Leu Leu Glu Thr
        370                 375                 380

Leu Arg Leu Tyr Ser Pro Val Ser Leu Ile Arg Arg Lys Val Asp Thr
385                 390                 395                 400

Asp Ile Glu Leu Gly Gly Ile Lys Met Pro Glu Gly Ala Leu Leu Thr
                405                 410                 415

Ile Pro Ile Ala Thr Ile His Arg Asp Lys Glu Val Trp Gly Glu Asp
                420                 425                 430

Ala Asp Glu Phe Arg Pro Glu Arg Phe Glu Asn Gly Val Thr Arg Ala
            435                 440                 445

Ala Lys His Pro Asn Ala Leu Leu Ser Phe Ser Gly Pro Arg Ser
        450                 455                 460

Cys Ile Gly Gln Asn Phe Ala Met Ile Glu Ala Lys Ala Val Ile Ala
465                 470                 475                 480

Met Ile Leu Gln Arg Phe Ser Phe Thr Leu Ser Pro Lys Tyr Val His
                485                 490                 495

Ala Pro Thr Asp Val Ile Thr Leu Arg Pro Lys Tyr Gly Leu Pro Met
                500                 505                 510

Ile Leu Lys Ser Leu Lys Leu
        515

<210> SEQ ID NO 61
<211> LENGTH: 514
<212> TYPE: PRT
<213> ORGANISM: Hordeum vulgare

<400> SEQUENCE: 61

Met Gly Leu Leu Trp Met Ala Ala Ala Val Ala Ala Val Leu Ala
1               5                   10                  15

Ser Trp Ala Phe Asn Ala Leu Val His Leu Val Trp Arg Pro Arg Ala
                20                  25                  30

Ile Thr Arg Gln Leu Arg Ala Gln Gly Val Gly Gly Pro Gly Tyr Ser
            35                  40                  45

Phe Phe Ala Gly Asn Leu Gly Glu Ile Lys Arg Leu Leu Ala Asp Thr
```

```
            50              55              60
Ala Gly Ala Val Leu Asp Val Gly Asp His Asp Phe Val Pro Arg Val
 65              70              75              80

Gln Pro His Phe Arg Lys Trp Ile Pro Ile His Gly Arg Thr Phe Leu
             85              90              95

Tyr Trp Phe Gly Ala Arg Pro Thr Leu Cys Val Ala Asp Val Asn Val
            100             105             110

Val Lys Gln Val Leu Ala Asp Arg Ser Gly Met Tyr Pro Lys Asn Val
            115             120             125

Gly Asn Pro His Ile Ala Arg Leu Leu Gly Lys Gly Leu Val Leu Thr
130             135             140

Asp Gly Asp Asp Trp Lys Arg His Arg Lys Val Val His Pro Ala Phe
145             150             155             160

Asn Met Asp Lys Leu Lys Met Met Thr Met Thr Met Ser Asp Cys Ala
            165             170             175

Gly Ser Met Met Ser Glu Trp Lys Ala Lys Met Glu Lys Gly Gly Asn
            180             185             190

Met Glu Ile Glu Leu Ser Arg Gln Phe Glu Glu Leu Thr Ala Asp Val
            195             200             205

Ile Ser His Thr Ala Phe Gly Ser Ser Tyr Gln Gln Gly Lys Lys Val
210             215             220

Phe Leu Ala Gln Arg Glu Leu Gln Phe Leu Ala Phe Ser Thr Val Phe
225             230             235             240

Asn Val Gln Ile Pro Ala Phe Arg Tyr Leu Pro Thr Glu Lys Asn Leu
            245             250             255

Lys Ile Trp Lys Leu Asp Lys Glu Val Arg Gly Met Leu Met Asn Ile
            260             265             270

Ile Lys Thr Arg Leu Asp Thr Lys Asp Thr Met Gly Tyr Gly Asn Asp
            275             280             285

Leu Leu Gly Leu Met Leu Glu Ala Cys Ala Leu Glu His Gly Gln Asn
290             295             300

Pro Ile Leu Ser Met Asp Glu Ile Ile Asp Glu Cys Lys Thr Phe Phe
305             310             315             320

Phe Ala Gly His Asp Thr Ser Ser His Leu Leu Thr Trp Thr Met Phe
            325             330             335

Leu Leu Ser Met His Pro Glu Trp Gln Glu Lys Leu Arg Glu Glu Val
            340             345             350

Leu Arg Glu Cys Gly Asn Gly Ala Pro Thr Gly Asp Met Leu Asn Lys
            355             360             365

Leu His Leu Val Asn Met Phe Leu Leu Glu Thr Leu Arg Leu Tyr Gly
370             375             380

Pro Val Ala Ala Ile Gln Arg Lys Ala Gly Ser Asp Leu Glu Val Gly
385             390             395             400

Gly Ile Lys Val Pro Lys Gly Thr Val Ile Thr Ile Pro Ile Ala Thr
            405             410             415

Ile His Arg Asp Lys Glu Val Trp Gly Glu Asp Ala Asn Glu Phe Lys
            420             425             430

Pro Met Arg Phe Glu Asn Gly Val Thr Arg Ala Gly Lys His Pro Asn
            435             440             445

Ala Leu Leu Ser Phe Ser Ser Gly Pro Arg Ser Cys Ile Gly Gln Asn
            450             455             460

Phe Ala Met Ile Glu Ala Lys Ala Val Ile Ala Met Ile Leu Gln Arg
465             470             475             480
```

```
Phe Ser Phe Ser Leu Ser Pro Lys Tyr Val His Ala Pro Met Asp Val
                485                 490                 495

Ile Thr Leu Arg Pro Lys Phe Gly Leu Pro Met Ile Leu Lys Ser Leu
                500                 505                 510

Glu Met

<210> SEQ ID NO 62
<211> LENGTH: 401
<212> TYPE: PRT
<213> ORGANISM: Zea mays

<400> SEQUENCE: 62

Met Asn Pro His Ile Ser Arg Leu Leu Gly Lys Gly Leu Val Leu Thr
1               5                   10                  15

Asp Gly Asp Asp Trp Lys Arg His Arg Lys Val Val His Pro Ala Phe
                20                  25                  30

Asn Met Asp Lys Leu Lys Leu Met Thr Ala Thr Met Ser Asp Cys Ala
                35                  40                  45

Arg Ser Met Ile Ser Glu Trp Asp Ala Gln Leu Gln Lys Glu Glu Ser
            50                  55                  60

Gly Arg Asp Gly His Gly His Gly His Val Glu Val Glu Leu Ser Ser
65                  70                  75                  80

Arg Phe Glu Glu Leu Thr Ala Asp Val Ile Ser His Thr Ala Phe Gly
                85                  90                  95

Ser Ser Tyr Ser Glu Gly Lys Arg Val Phe Leu Ala Gln Arg Glu Leu
                100                 105                 110

Gln His Ile Ala Phe Ser Thr Ile Phe Asn Val Gln Ile Pro Ala Leu
            115                 120                 125

Lys Tyr Leu Pro Thr Lys Lys Asn Val Arg Thr Arg Lys Leu Asp Arg
            130                 135                 140

Gln Val Arg Ala Met Leu Met Gly Ile Ile Glu Ala Arg Leu Ala Ser
145                 150                 155                 160

Lys Asp Thr Ala Gly Gly Tyr Gly Asn Asp Leu Leu Gly Leu Met Leu
                165                 170                 175

Glu Ala Cys Ala Pro Pro Glu His His Gly Glu Met Ala Leu Thr
                180                 185                 190

Thr Leu Ser Met Asp Glu Ile Val Asp Glu Cys Lys Thr Phe Phe Phe
            195                 200                 205

Ala Gly His Asp Thr Thr Ser His Leu Leu Thr Trp Ala Thr Phe Leu
            210                 215                 220

Leu Ser Thr His Pro Glu Trp Gln His Arg Leu Arg Asp Glu Val Arg
225                 230                 235                 240

Arg Glu Cys Gly Asp Asp Asp Glu Val Pro Thr Gly Asp Ala Leu Asn
                245                 250                 255

Arg Leu Lys Leu Val Asn Met Phe Leu Leu Glu Thr Leu Arg Leu Tyr
                260                 265                 270

Gly Pro Val Ser Leu Ile Gln Arg Lys Ala Gly Ser Asp Leu Asp Leu
            275                 280                 285

Gly Gly Ile Arg Val Pro Glu Gly Ala Ile Leu Thr Ile Pro Ile Ala
            290                 295                 300

Thr Ile His Arg Asp Lys Glu Val Trp Gly Glu Asp Ala Gly Glu Phe
305                 310                 315                 320

Arg Pro Glu Arg Phe Glu Asn Gly Val Thr Arg Ala Ala Lys His Pro
                325                 330                 335
```

```
Asn Ala Leu Leu Ser Phe Ser Ser Gly Pro Arg Ser Cys Ile Gly Gln
            340                 345                 350

Asn Phe Ala Met Ile Glu Ala Lys Ala Val Val Ala Met Ile Leu Gln
            355                 360                 365

Arg Phe Ala Leu Glu Leu Ser Pro Lys Tyr Val His Ala Pro Met Asp
            370                 375                 380

Leu Ile Thr Leu Arg Pro Arg His Gly Leu Pro Met Leu Leu Lys Arg
385                 390                 395                 400

Leu

<210> SEQ ID NO 63
<211> LENGTH: 491
<212> TYPE: PRT
<213> ORGANISM: Oryza sativa

<400> SEQUENCE: 63

Pro Arg Ala Ile Thr Arg Arg Leu Gly Ala Gln Gly Val Ala Gly Pro
1               5                   10                  15

Gly Tyr Arg Phe Phe Ser Gly Asn Leu Ser Glu Ile Arg Arg Leu Arg
            20                  25                  30

Ala Glu Gly Ala Asn Leu Val Leu Asp Val Ser Ser His Asp Phe Val
            35                  40                  45

Pro Ile Val Gln Pro His Ile Arg Lys Trp Ile Pro Leu Tyr Gly Lys
50                  55                  60

Thr Phe Leu Tyr Trp Phe Gly Thr Arg Pro Asn Ile Cys Leu Ala Asp
65                  70                  75                  80

Met Asn Met Val Arg Gln Val Leu Ser Asp Arg Thr Gly Met Phe Pro
            85                  90                  95

Lys Tyr Ile Asp Asn Met Gln Phe Ala Arg Leu Leu Gly Lys Gly Leu
            100                 105                 110

Val Leu Thr Asp Asp Asp Glu Trp Lys Arg His Tyr Lys Val Val His
            115                 120                 125

Pro Ala Phe Asp Met Asp Lys Leu Lys Met Met Thr Glu Thr Ile Ser
130                 135                 140

Asp Tyr Ala Gln Ser Met Met Phe Glu Trp Glu Ser Glu Leu Gly Met
145                 150                 155                 160

Lys Gly Gly Ser Thr Glu Ile Glu Leu Ser Arg Trp Phe Glu Glu Leu
            165                 170                 175

Thr Ala Asp Val Ile Ser Arg Thr Ala Phe Gly Ser Ser Tyr Arg Glu
            180                 185                 190

Gly Lys Gln Val Phe Leu Ala Gln Arg Lys Leu Gln Phe Leu Ala Phe
            195                 200                 205

Ser Val Phe Leu Thr Ile Gln Ile Pro Gly Phe Ser Tyr Leu Leu Thr
            210                 215                 220

Lys Lys Asn Leu Lys Thr Trp Ser Leu Asp Lys Lys Val Arg Ser Met
225                 230                 235                 240

Leu Met Asn Ile Ile Lys Ser Arg Leu Thr Asn Lys Glu Thr Met Gly
            245                 250                 255

Tyr Gly Asn Asp Leu Leu Gly Leu Met Leu Glu Ala Cys Val Pro Glu
            260                 265                 270

His Gly Gly Ser Gln Pro Gln Leu Ser Met Asp Asp Ile Ile Ala Glu
            275                 280                 285

Cys Lys Thr Phe Phe Phe Ala Gly His Asp Thr Thr Ser Gln Leu Leu
            290                 295                 300
```

```
Thr Trp Thr Met Phe Leu Leu Ser Thr His Gln His Trp Met Glu Lys
305                 310                 315                 320

Leu Arg Lys Glu Val Arg Met Val Cys Asn Asp Glu Val Pro Thr Gly
            325                 330                 335

Asp Met Leu Asn Lys Leu Lys Leu Val Asn Met Phe Leu Leu Glu Thr
        340                 345                 350

Leu Arg Leu Tyr Gly Pro Val Ser Leu Val Thr Arg Arg Ala Gly Thr
    355                 360                 365

Asp Val Lys Leu Gly Ser Ile Lys Val Pro Lys Gly Thr Ile Leu Thr
370                 375                 380

Ile Pro Ile Ala Thr Ile His Arg Asp Lys Glu Val Trp Gly Glu Asp
385                 390                 395                 400

Ala Asp Glu Phe Lys Pro Glu Arg Ser Glu Asn Gly Val Leu Asn Ala
            405                 410                 415

Ala Lys His Pro Ser Ala Leu Leu Ser Phe Ser Ile Gly Leu Arg Ser
        420                 425                 430

Cys Ile Gly Gln Asn Phe Ala Met Ile Glu Ala Arg Thr Ile Ile Ala
    435                 440                 445

Met Ile Leu Gln Arg Phe Ser Phe Thr Leu Ser Pro Lys Tyr Val His
450                 455                 460

Thr Pro Ile Ser Val Ile Thr Leu Arg Pro Lys Tyr Gly Leu Pro Met
465                 470                 475                 480

Ile Leu Arg Ser Leu Lys Val Lys Arg Asp Arg
            485                 490

<210> SEQ ID NO 64
<211> LENGTH: 337
<212> TYPE: PRT
<213> ORGANISM: Oryza sativa

<400> SEQUENCE: 64

Met Ser Glu Trp Glu Ser Glu Leu Gly Ala Lys Gly Gly Leu Ala Glu
1               5                   10                  15

Ile Glu Leu Ser Arg Arg Phe Glu Glu Leu Thr Ala Asp Val Ile Ser
            20                  25                  30

His Thr Ala Phe Gly Ser Ser Tyr Lys Glu Gly Lys Gln Val Phe Leu
        35                  40                  45

Ala Gln Arg Glu Leu Gln Phe Leu Ala Phe Ser Thr Phe Leu Thr Val
    50                  55                  60

Gln Ile Leu Gly Tyr Ser Tyr Leu Leu Thr Met Lys Asn Phe Lys Thr
65                  70                  75                  80

Trp Ser Leu Asp Lys Lys Val Arg Gly Met Leu Met Asp Ile Ile Lys
                85                  90                  95

Thr Arg His Ala Asn Lys Asp Val Val Gly Tyr Gly Asn Asp Leu Leu
            100                 105                 110

Gly Leu Leu Leu Glu Ala Cys Ala Pro Glu His Gly Glu Ser His Pro
        115                 120                 125

Gln Leu Ser Met Asp Glu Ile Ile Asp Glu Cys Lys Thr Phe Phe Phe
    130                 135                 140

Ala Gly His Asp Thr Thr Ser His Leu Leu Thr Trp Thr Met Phe Leu
145                 150                 155                 160

Leu Ser Thr His Pro Asp Trp Gln Glu Lys Leu Arg Glu Asp Ile Ala
                165                 170                 175

Met Glu Cys Gly Asp Glu Val Pro Thr Gly Asp Met Leu Asn Lys Leu
```

```
                180             185             190
Lys Met Val Asn Met Phe Leu Leu Glu Thr Leu Arg Leu Tyr Ser Pro
            195                 200             205

Val Leu Leu Ile Arg Arg Lys Val Gly Thr Asp Ile Glu Leu Gly Gly
            210                 215             220

Ile Lys Met Pro Glu Gly Ala Leu Leu Thr Ile Pro Ile Ala Thr Ile
225                 230                 235                 240

His Arg Asp Lys Glu Val Trp Gly Glu Asp Ala Asp Glu Phe Arg Leu
                245                 250                 255

Glu Arg Phe Glu Asn Gly Val Thr Arg Ala Ala Lys His Pro Asp Ala
            260                 265                 270

Leu Leu Ser Phe Ser Ser Gly Pro Arg Ser Cys Ile Gly Gln Asn Phe
            275                 280                 285

Ala Met Ile Glu Ala Lys Ala Val Ile Ala Met Ile Leu Gln Arg Phe
            290                 295                 300

Ser Phe Thr Leu Ser Pro Lys Tyr Val His Ala Pro Thr Asp Val Ile
305                 310                 315                 320

Thr Leu Arg Pro Lys Tyr Gly Leu Pro Met Ile Leu Lys Ser Leu Lys
                325                 330                 335

Leu

<210> SEQ ID NO 65
<211> LENGTH: 514
<212> TYPE: PRT
<213> ORGANISM: Hordeum vulgare

<400> SEQUENCE: 65

Met Gly Leu Val Trp Met Val Ala Ala Val Val Ala Val Leu Ala
1               5                   10                  15

Ser Trp Ala Phe Asn Ala Leu Val His Leu Val Trp Arg Pro Arg Ala
            20                  25                  30

Ile Thr Arg Gln Leu Arg Ala Gln Gly Val Gly Gly Pro Gly Tyr Arg
            35                  40                  45

Phe Phe Ala Gly Asn Leu Gly Glu Ile Lys Arg Leu Arg Asp Asp Thr
        50                  55                  60

Ala Gly Ala Ala Leu Asp Val Gly Asp His Asp Phe Val Pro Met Val
65                  70                  75                  80

Gln Pro His Phe Arg Lys Trp Ile Pro Ile His Gly Arg Thr Phe Leu
                85                  90                  95

Tyr Trp Phe Gly Ala Arg Pro Ser Leu Cys Val Ala Asp Val Asn Val
            100                 105                 110

Val Lys Gln Val Leu Ala Asp Arg Asn Gly Met Tyr Pro Lys Asn Ile
            115                 120                 125

Gly Asn Pro His Ile Ala Arg Leu Leu Gly Lys Gly Leu Val Leu Thr
        130                 135                 140

Asp Gly Asp Asp Trp Lys Arg His Arg Lys Val Val His Pro Ala Phe
145                 150                 155                 160

Asn Met Asp Lys Leu Lys Met Met Thr Val Thr Met Ser Glu Cys Ala
                165                 170                 175

Gly Ser Met Met Ser Glu Trp Glu Thr Lys Met Asp Lys Gly Gly Ser
            180                 185                 190

Val Glu Ile Asp Leu Ser Thr Gln Phe Glu Glu Ile Thr Ala Asp Val
            195                 200                 205

Ile Ser His Thr Ala Phe Gly Ser Ser Tyr Glu Gln Gly Lys Lys Val
```

Phe Leu Ala Gln Arg Glu Leu Gln Phe Leu Ala Phe Ser Thr Val Phe
225                 230                 235                 240

Ser Val Gln Ile Pro Ala Phe Arg Tyr Leu Pro Thr Glu Lys Asn Leu
            245                 250                 255

Lys Ile Trp Lys Leu Asp Lys Glu Val Arg Thr Met Leu Met Asn Ile
        260                 265                 270

Ile Glu Ser Arg Leu Ala Thr Lys Asp Thr Met Gly Tyr Gly Asn Asp
    275                 280                 285

Leu Leu Gly Leu Met Leu Glu Ala Cys Ala Ala Glu Gly Gly His Thr
290                 295                 300

Pro Ile Leu Ser Met Asp Glu Ile Ile Asp Glu Cys Lys Thr Phe Phe
305                 310                 315                 320

Phe Ala Gly His Asp Thr Ser Ser His Leu Leu Thr Trp Thr Val Phe
                325                 330                 335

Leu Leu Ser Thr His Pro Glu Trp Gln Glu Lys Leu Arg Glu Glu Val
            340                 345                 350

Leu Arg Glu Cys Gly Ser Glu Val Pro Thr Gly Asp Met Leu Asn Lys
    355                 360                 365

Leu His Leu Val Asn Met Phe Leu Leu Glu Thr Leu Arg Leu Tyr Ala
370                 375                 380

Pro Val Ser Leu Ile Gln Arg Lys Ala Gly Ser Asp Leu Glu Val Gly
385                 390                 395                 400

Gly Ile Lys Val Pro Glu Gly Thr Val Leu Thr Ile Pro Ile Ala Thr
                405                 410                 415

Ile His Arg Asp Lys Glu Val Trp Gly Glu Asp Ala Asn Glu Phe Lys
            420                 425                 430

Pro Met Arg Phe Glu Asn Gly Val Ala Arg Ala Gly Lys His Pro Asn
    435                 440                 445

Ala Leu Leu Ser Phe Ser Ser Gly Pro Arg Ser Cys Ile Gly Gln Ser
450                 455                 460

Phe Ala Met Ile Glu Ala Lys Ala Val Ile Ala Val Ile Leu Gln Arg
465                 470                 475                 480

Phe Ser Phe Ser Leu Ser Pro Lys Tyr Val His Ala Pro Met Asp Val
                485                 490                 495

Ile Thr Leu Arg Pro Lys Phe Gly Leu Pro Met Ile Leu Lys Ser Ile
            500                 505                 510

Glu Ile

<210> SEQ ID NO 66
<211> LENGTH: 514
<212> TYPE: PRT
<213> ORGANISM: Triticum aestivum

<400> SEQUENCE: 66

Met Gly Leu Val Trp Met Val Ala Ala Val Ala Ala Val Leu Ala
1               5                   10                  15

Ser Trp Ala Phe Asp Ala Leu Val Tyr Leu Val Trp Arg Pro Arg Ala
            20                  25                  30

Ile Thr Arg Gln Leu Arg Ala Gln Gly Val Gly Pro Gly Tyr Arg
        35                  40                  45

Phe Phe Ala Gly Asn Leu Ala Glu Ile Lys Gln Leu Arg Ala Asp Ser
    50                  55                  60

Ala Gly Ala Ala Leu Asp Ile Gly Asp His Asp Phe Val Pro Arg Val

```
                65                  70                  75                  80
Gln Pro His Phe Arg Lys Trp Ile Pro Ile His Gly Arg Thr Phe Leu
                        85                  90                  95
Tyr Trp Phe Gly Ala Lys Pro Thr Leu Cys Ile Ala Asp Val Asn Val
                    100                 105                 110
Val Lys Gln Val Leu Ser Asp Arg Gly Leu Tyr Pro Lys Ser Ile
                115                 120                 125
Gly Asn Pro His Ile Ala Arg Leu Leu Gly Lys Gly Leu Val Leu Thr
            130                 135                 140
Asp Gly Asp Asp Trp Lys Arg His Arg Lys Val Val His Pro Ala Phe
145                 150                 155                 160
Asn Met Asp Lys Leu Lys Met Met Thr Val Thr Met Ser Asp Cys Ala
                    165                 170                 175
Gly Ser Met Met Ser Glu Trp Lys Ala Lys Met Asp Lys Gly Gly Ser
                180                 185                 190
Val Glu Ile Asp Leu Ser Ser Gln Phe Glu Glu Leu Thr Ala Asp Val
            195                 200                 205
Ile Ser His Thr Ala Phe Gly Ser Ser Tyr Glu Gln Gly Lys Lys Val
        210                 215                 220
Phe Leu Ala Gln Arg Glu Leu Gln Phe Leu Ala Phe Ser Thr Val Phe
225                 230                 235                 240
Asn Val Gln Ile Pro Ser Phe Arg Tyr Leu Pro Thr Glu Lys Asn Leu
                    245                 250                 255
Lys Ile Trp Lys Leu Asp Lys Glu Val Arg Thr Met Leu Met Asn Ile
                260                 265                 270
Ile Lys Gly Arg Leu Ala Thr Lys Asp Thr Met Gly Tyr Gly Asn Asp
            275                 280                 285
Leu Leu Gly Leu Met Leu Glu Ala Cys Ala Pro Glu Asp Gly Gln Asn
        290                 295                 300
Pro Leu Leu Ser Met Asp Glu Ile Ile Asp Glu Cys Lys Thr Phe Phe
305                 310                 315                 320
Phe Ala Gly His Asp Thr Ser Ser His Leu Leu Thr Trp Thr Met Phe
                    325                 330                 335
Leu Leu Ser Thr His Pro Glu Trp Gln Glu Lys Leu Arg Glu Glu Val
                340                 345                 350
Leu Arg Glu Cys Gly Asn Gly Ile Pro Thr Gly Asp Met Leu Asn Lys
            355                 360                 365
Leu Gln Leu Val Asn Met Phe Leu Leu Glu Thr Leu Arg Leu Tyr Ala
        370                 375                 380
Pro Val Ser Ala Ile Gln Arg Lys Ala Gly Ser Asp Leu Glu Val Gly
385                 390                 395                 400
Gly Ile Lys Val Thr Glu Gly Thr Phe Leu Thr Ile Pro Ile Ala Thr
                    405                 410                 415
Ile His Arg Asp Lys Glu Val Trp Gly Glu Asp Ala Asn Lys Phe Lys
                420                 425                 430
Pro Met Arg Phe Glu Asn Gly Val Thr Arg Ala Gly Lys His Pro Asn
            435                 440                 445
Ala Leu Leu Ser Phe Ser Gly Pro Arg Ser Cys Ile Gly Gln Asn
        450                 455                 460
Phe Ala Met Ile Glu Ala Lys Ala Val Ile Ala Val Ile Leu Gln Arg
465                 470                 475                 480
Phe Ser Phe Ser Leu Ser Pro Lys Tyr Val His Ala Pro Met Asp Val
                    485                 490                 495
```

Ile Thr Leu Arg Pro Lys Phe Gly Leu Pro Met Ile Leu Lys Ser Leu
                500                 505                 510

Glu Met

<210> SEQ ID NO 67
<211> LENGTH: 454
<212> TYPE: PRT
<213> ORGANISM: Oryza sativa

<400> SEQUENCE: 67

Asn Ala Met Ser Thr Asn Tyr Phe Asn Leu Leu Ala Tyr Ile Tyr Ile
1               5                   10                  15

Tyr Ile Ile Val Cys Leu Leu Cys Val Val Gly Lys Thr Phe Leu Phe
                20                  25                  30

Trp Phe Gly Ala Gln Pro Asn Ile Cys Leu Ala Asp Ile Asn Ile Val
            35                  40                  45

Arg Gln Val Leu Ser Asp Arg Thr Gly Met Tyr Pro Lys Asp Leu Thr
50                  55                  60

Asn Pro Tyr Phe Ala His Leu Leu Gly Lys Gly Leu Val Leu Ile Asp
65                  70                  75                  80

Gly Asp Glu Trp Lys Arg His Tyr Lys Val Val His Pro Ala Phe Asp
                85                  90                  95

Met Asp Lys Leu Lys Met Met Thr Val Thr Ile Ser Asp Cys Thr Gly
            100                 105                 110

Ser Met Met Ser Glu Trp Glu Ser Glu Leu Gly Met Lys Gly Gly Ser
        115                 120                 125

Ala Glu Ile Glu Leu Ser Gln Arg Phe Gln Glu Leu Thr Ala Asp Val
    130                 135                 140

Ile Ser Arg Thr Ala Phe Gly Ser Ser Tyr Ser Glu Gly Lys Gln Val
145                 150                 155                 160

Phe Leu Ala Gln Arg Lys Leu Gln Phe Leu Ala Phe Ser Met Phe Leu
                165                 170                 175

Thr Ile Gln Ile Pro Gly Phe Arg Tyr Leu Pro Thr Lys Lys Asn Leu
            180                 185                 190

Lys Ile Trp Ser Leu Asp Lys Lys Val Arg Ser Met Leu Arg Asn Ile
        195                 200                 205

Ile Lys Ile Arg Leu Ala Asn Lys Asp Thr Met Gly Tyr Gly Asn Asp
    210                 215                 220

Leu Leu Gly Leu Met Leu Glu Thr Cys Ala Pro Glu His Asp Glu Ser
225                 230                 235                 240

Gln Gln Leu Ser Met Asp Glu Ile Ile Ala Glu Cys Lys Thr Phe Phe
                245                 250                 255

Phe Gly Gly His Asp Thr Thr Ser His Leu Leu Thr Trp Thr Met Phe
            260                 265                 270

Leu Leu Ser Thr His Pro Glu Trp Met Arg Lys Ile Arg Lys Glu Val
        275                 280                 285

Thr Thr Met Cys Gly Asp Glu Val Pro Thr Gly Asp Met Leu Asn Lys
    290                 295                 300

Met Asn Leu Leu Asn Met Phe Leu Leu Glu Thr Leu Arg Leu Tyr Ser
305                 310                 315                 320

Pro Val Ser Leu Ile Ser Arg Arg Thr Gly Thr Asn Ala Lys Phe Gly
                325                 330                 335

Gly Ile Lys Val Pro Glu Gly Thr Ile Leu Arg Ile Pro Ile Ala Thr
            340                 345                 350

```
Ile His Arg Asp Lys Glu Val Trp Gly Glu Asp Ala Asp Glu Phe Lys
        355                 360                 365

Pro Ala Arg Phe Glu Asn Gly Val Ser Lys Ala Ala Lys His Pro Asn
    370                 375                 380

Ala Leu Leu Ser Phe Ser Asn Gly Pro Arg Ser Cys Ile Gly Gln Asn
385                 390                 395                 400

Phe Ala Met Ile Glu Ala Lys Ala Val Ile Thr Met Ile Leu Gln Arg
                405                 410                 415

Phe Ser Phe Thr Leu Ser Pro Lys Tyr Val His Thr Pro Ile Ser Val
            420                 425                 430

Ile Thr Leu Arg Pro Lys Tyr Gly Leu Pro Met Ile Leu Arg Ser Leu
        435                 440                 445

Lys Val Lys Arg Asp Leu
    450
```

<210> SEQ ID NO 68
<211> LENGTH: 517
<212> TYPE: PRT
<213> ORGANISM: Oryza sativa

<400> SEQUENCE: 68

```
Met Gly Asn Leu Gly Trp Met Val Ala Ala Val Ala Ala Val Val
1               5                   10                  15

Ala Ser Trp Ala Phe Asp Ala Val Lys Leu Val Trp Arg Pro Arg
            20                  25                  30

Ala Ile Thr Arg Arg Leu Arg Ala Gln Gly Val Gly Gly Pro Gly Tyr
        35                  40                  45

Arg Phe Phe Ser Gly Asn Leu Gly Glu Ile Lys Arg Leu Arg Asp Glu
    50                  55                  60

Gly Ala Gly Val Val Leu Asp Val Ser Ser His Asp Phe Val Pro Ile
65                  70                  75                  80

Val Gln Pro His Phe Arg Lys Trp Ile Pro Leu Tyr Gly Lys Thr Phe
                85                  90                  95

Met Tyr Trp Phe Gly Ala Arg Pro Thr Ile Cys Leu Ala Asp Val Ser
            100                 105                 110

Met Val Arg Gln Val Leu Ser Asp Arg Thr Gly Met Tyr Pro Lys Asn
        115                 120                 125

Val Ser Asn Pro Tyr Phe Ala Arg Leu Leu Gly Lys Gly Leu Val Leu
    130                 135                 140

Thr Asp Gly Asp Glu Trp Lys Arg His Arg Lys Val Val His Pro Ala
145                 150                 155                 160

Phe Asn Met Asp Lys Leu Lys Met Met Thr Val Thr Met Ser Asp Cys
                165                 170                 175

Ala Gln Ser Met Ile Ser Glu Trp Glu Ser Glu Leu Gly Thr Lys Gly
            180                 185                 190

Asp Ile Val Glu Ile Glu Leu Ser Arg Arg Phe Glu Glu Leu Thr Ala
        195                 200                 205

Asp Val Ile Ser His Thr Ala Phe Gly Ser Ser Tyr Lys Glu Gly Lys
    210                 215                 220

Gln Val Phe Leu Ala Gln Arg Glu Leu Gln Phe Leu Ala Phe Ser Thr
225                 230                 235                 240

Phe Leu Ser Ile Gln Ile Pro Gly Ser Ser Tyr Leu Pro Thr Lys Lys
                245                 250                 255

Asn Leu Lys Thr Trp Ser Val Asp Lys Lys Val Arg Ser Met Leu Thr
```

```
                  260                 265                 270
Asp Ile Ile Lys Ser Arg Leu Asn Asn Lys Asp Val Ala Gly Tyr Gly
            275                 280                 285

Asn Asp Leu Leu Gly Leu Met Leu Glu Ala Cys Ala Pro Glu His Gly
        290                 295                 300

Glu Ser Gln Pro Gln Leu Ser Met Asp Glu Ile Ala Glu Cys Lys
305                 310                 315                 320

Thr Phe Phe Phe Ala Gly His Asp Thr Thr Ser His Leu Leu Thr Trp
            325                 330                 335

Thr Met Phe Leu Leu Ser Thr His Pro Glu Trp Gln Glu Lys Leu Arg
            340                 345                 350

Glu Glu Val Ala Met Glu Cys Asp Gly Lys Val Pro Thr Gly Asp Met
            355                 360                 365

Leu Asn Lys Leu Lys Leu Val Asn Met Phe Leu Leu Glu Thr Leu Arg
        370                 375                 380

Leu Tyr Gly Pro Val Ala Phe Ile Gln Arg Arg Val Asn Ala Glu Leu
385                 390                 395                 400

Glu Leu Gly Gly Ile Thr Val Pro Glu Gly Thr Val Leu Ser Ile Pro
            405                 410                 415

Ile Ala Thr Ile His Arg Asp Lys Glu Val Trp Gly Glu Asp Ala Asp
            420                 425                 430

Ile Phe Lys Pro Glu Arg Phe Glu Asn Gly Val Ser Lys Ala Gly Lys
            435                 440                 445

Tyr Pro Asn Ala Leu Leu Ser Phe Ser Ser Gly Pro Arg Ala Cys Ile
        450                 455                 460

Gly Gln Asn Phe Ala Met Ile Glu Ala Lys Ala Val Ile Ala Met Ile
465                 470                 475                 480

Leu Gln Arg Phe Ser Phe Thr Leu Ser Pro Lys Tyr Val His Ala Pro
            485                 490                 495

Thr Asp Val Ile Thr Leu Arg Pro Lys Tyr Gly Leu Pro Met Ile Leu
            500                 505                 510

Lys Ser Leu Lys Val
        515

<210> SEQ ID NO 69
<211> LENGTH: 512
<212> TYPE: PRT
<213> ORGANISM: Sorghum bicolor

<400> SEQUENCE: 69

Met Asp Leu Ala Trp Met Val Ala Ala Val Ala Ser Val Leu Ala
1               5                   10                  15

Ser Trp Ala Phe Asn Ala Leu Val His Leu Val Trp Arg Pro Tyr Ala
            20                  25                  30

Ile Thr Arg Ser Leu Arg Ala Gln Gly Val Arg Gly Pro Asp Tyr Arg
        35                  40                  45

Phe Phe Thr Gly Ser Leu Gly Glu Ile Lys Arg Leu Arg Ala Glu Gly
    50                  55                  60

Ala Ala Val Thr Leu Asp Val Asp Asp His Asp Phe Ile Pro Met Val
65                  70                  75                  80

Gln Pro His Leu Arg Lys Trp Ile Ala Leu Tyr Gly Arg Thr Phe Val
            85                  90                  95

Tyr Trp Thr Gly Ala Arg Pro Asn Val Cys Val Ala Asp Val Asn Val
            100                 105                 110
```

Val Arg Gln Val Leu Phe Asp Arg Thr Gly Leu Tyr Pro Lys Asn Leu
115                 120                 125

Met Asn Pro His Val Ser Arg Leu Leu Gly Lys Gly Phe Val Leu Thr
130                 135                 140

Asp Gly Asp Asp Trp Lys Arg His Arg Lys Val Val His Pro Ala Phe
145                 150                 155                 160

Asn Met Asp Lys Leu Lys Met Met Thr Val Thr Met Ser Asp Cys Ala
                165                 170                 175

Arg Ser Met Met Ser Glu Trp Glu Ala Gln Leu Ala Lys Gly Gly Glu
                180                 185                 190

Val Glu Val Glu Leu Ser Ser Arg Phe Glu Glu Leu Thr Ala Asp Val
                195                 200                 205

Ile Ser His Thr Ala Phe Gly Ser Ser Tyr Asn Glu Gly Lys Gln Val
210                 215                 220

Phe Leu Ala Gln Arg Glu Leu Gln Tyr Ile Ala Phe Ser Thr Val Phe
225                 230                 235                 240

Asn Val Gln Ile Pro Val Phe Arg Tyr Leu Pro Thr Glu Lys Asn Leu
                245                 250                 255

Lys Thr Arg Lys Leu Asp Arg Gln Val Arg Gly Met Leu Met Asp Ile
                260                 265                 270

Ile Lys Thr Arg Leu Ala Ser Lys Asp Thr Ala Gly Tyr Gly Asn Asp
            275                 280                 285

Leu Leu Gly Leu Met Leu Glu Ala Cys Ala Pro Glu His Gly Glu Thr
            290                 295                 300

Pro Val Leu Ser Met Asp Glu Ile Ile Asp Glu Cys Lys Thr Phe Phe
305                 310                 315                 320

Phe Ala Gly His Asp Thr Thr Ser His Leu Leu Thr Trp Ala Ser Phe
                325                 330                 335

Leu Leu Ser Thr His Pro Glu Trp Gln Asp Arg Leu Arg Glu Glu Val
                340                 345                 350

Arg Arg Glu Cys Gly Asp Glu Val Pro Thr Gly Asp Ala Leu Asn Lys
                355                 360                 365

Leu Lys Leu Val Asn Met Phe Leu Leu Glu Thr Leu Arg Leu Tyr Gly
            370                 375                 380

Pro Val Ser Leu Ile Gln Arg Lys Ala Gly Ser Asp Leu Asp Leu Gly
385                 390                 395                 400

Gly Ile Arg Val Pro Glu Gly Ala Ile Leu Thr Ile Pro Ile Ala Thr
                405                 410                 415

Ile His Arg Asp Lys Glu Val Trp Gly Asp Asp Ala Gly Glu Phe Lys
                420                 425                 430

Pro Glu Arg Phe Glu Asn Gly Val Thr Arg Ala Ala Lys His Pro Asn
            435                 440                 445

Ala Leu Leu Ser Phe Ser Ser Gly Pro Arg Ser Cys Ile Gly Gln Asn
            450                 455                 460

Phe Ala Met Ile Glu Ala Lys Ala Val Val Ala Met Ile Leu Gln Arg
465                 470                 475                 480

Phe Ala Leu Glu Leu Ser Pro Lys Tyr Val His Ala Pro Met Asp Val
                485                 490                 495

Ile Thr Leu Arg Pro Arg His Gly Leu Pro Met Leu Leu Lys Arg Leu
                500                 505                 510

<210> SEQ ID NO 70
<211> LENGTH: 1567
<212> TYPE: DNA

<213> ORGANISM: Alopecurus

<400> SEQUENCE: 70

```
ggcgcgccac catgatgatg dataaggctt atatcgctat attcttcttc tttacattcg      60
tgttcttgct caggcagatc ctcagaggaa agacctctaa cggagataac aacaggggag     120
tgcagttgcc tccatctcct ccagctattc ctttcctcgg acatctccat ctcgtggcta     180
agaaacctct ccacgctact cttagaggac tcgctgatca ctacggacct atcttctcac     240
ttagactcgg agctagaaac gctgtggtgg tttcttctgc tgcttgtgct actgagtgct     300
tcactgagca cgatgtgatc ttcgctaaca ggcctcagtt cccatctcag cagcttgttt     360
ctttcggagg aacctctctc atcttctcat cttacggacc taggtggagg accctcagaa     420
gagttgctgc tgttcagctc ttgtctcctc atagagtggc ttgcatgtct ggtgtgatcg     480
cttctgagat cagggctatg actagaaggc tctgtagagc tgctgctgct ggtgctagag     540
ttcatctcaa gagaaggctt ttcgagcttt ctctctctgt gctcatggaa actatcgcta     600
acaccaaggg aaccaggcct gttgctgatg ctgataccga tatgtctatg gaagctcaag     660
agttcaagaa agtgatggat gagatcatcc cttacatcgg atctgctaat atgtgggatt     720
tcttgcctgt gatgagatgg ttcgatgtgt tcggagtgag gaacaagatc ctcgctgtgg     780
tgtctagaag ggatgctttc cttagaaggc tcatcgatgc tgagagacag agacttgaag     840
atggtggtgg acagggtgat aagaaatcta tgatcgctgt gctcctcacc ctccaaaaga     900
ctgaacctga ggtgtacacc gataccatga tcacttcact ctgcgctaac ctcttcggag     960
ctggaactga gactacttct actatgaccg agtgggctat gtctctcctc cttaaccatc    1020
ctgctgtgat caagaaggct caggctgaga tcgatgcttc tgtgggaaac tctagactcg    1080
tggctgctga tgatgttcct agacttgctt acctccagtg catcatctct gagactctta    1140
gactttgccc tcctgctcca cttctcttgg ctcatgaatc ttcagctgat gcaaggtgg    1200
gaggatacaa cgtgccaaga gataccatgc tcatcgtgtc tgcttacgct atccacagag    1260
atcctgctac ttgggaggat cctactgtgt tcagacctga gagattcgag gatggaaagg    1320
gtgatgagat gctcgtgatc cctttcggaa tgggaagaag aggttgtcct ggagagactc    1380
tcgctagaca gatggttgga atggtgctcg gaactatgct ccagtgtttc gattgggaga    1440
gagtggattc tgttgaagtg gatatgaccg agggtggtgg tgtgactatg cctaaggctg    1500
ttcctcttga ggctatgtgc tcaccaagag cttctatgtg caaggtgctc gagaagctcc    1560
ctgcagg                                                              1567
```

<210> SEQ ID NO 71
<211> LENGTH: 1564
<212> TYPE: DNA
<213> ORGANISM: Alopcurus

<400> SEQUENCE: 71

```
ggcgcgccac catggataag gctgcttaca ttgctgtgtt ctgctttacc ttcttgttct      60
tgctccacag gatcctcagg ggatctaagt ctaacggagg aaactcttct aagggagttc     120
agctccctcc atctcctcca gctattcctt ccttggaca tctccatctc gtggctgaga     180
agcctcttca tgctactctt agaaggctcg ctgataggta cggacctgtg ttctctctta     240
gactcggtgc tagaaacgct ctcgtggttt ctactgctgc tggtgctaga gaatgcttca     300
ctgagcacga tgtgaccttc gctaacagac tcagttccc atctcagctc ctcgtttctt     360
tcggaggaac ttctctcatc cactctaact acggacctag gtggaggatc ctcagaagag     420
```

```
ttgctgctgt tcagttgctc tctacccata gagtggcttg catgtctggt gtgatcgctg      480
ctgaaatcag ggctatgact agaaggctct gtagagctgc tgcagctggt gcaagagttc      540
atctcaagag aaggcttttc gagctttctc tctctgtgct catggaaact atcgctaaca      600
ccaagggaac caggcctgtt gctgatgctg ataccgatat gtctatggaa gctcaagagt      660
tcaagaaagt gatggatgag atcatccctt acatcggatc tgctaatatg tgggatttct      720
tgcctgtgat gagatggttc gatgtgttcg gagtgaggaa caagatcctc gctgtggtgt      780
ctagaaggga tgctttcttg agaaggctca tcgatgctga gacacagaga cttgaagatg      840
gtggtggaca gggtgataag aaatctatga tcgctgtgct cctcacccct caaaagactg      900
aacctgaggt gtacaccgat accatgatca cttcactctg cgctaacctc ttcggagctg      960
gaactgagac tacttctact atgaccgagt gggctatgtc tctcctcctt aaccatcctg     1020
ctgtgatcaa gaaggctcag gctgagatcg atgcttctgt gggaaactct agactcgtgg     1080
ctgctgatga tgttcctaga cttgcttacc tccagtgcat catctctgag actcttagac     1140
tttgccctcc tgctccactt ctcttggctc atgaatcttc agctgattgc aaggtgggag     1200
gatacaacgt gccaagagat accatgctca tcgtgtctgc ttacgctatc cacagagatc     1260
ctgctacttg ggaggatcct actgtgttca gacctgagag attcgaggat ggaaagggtg     1320
atggaatgct cgtgatccct ttcggaatgg aagaagagg ttgtcctgga gagactctcg     1380
ctagacagat ggttggaatg gtgctcggaa ctatgctcca gtgtttcgat gggagcgtg     1440 tggatggtgt ggaagtggat atgactgagg gtggtggtgt gactatgcct aaggctgttc     1500
ctcttgaggc aatgtgctca ccaagagctt ctatgtgcaa ggtgctcgag aagctccctg     1560
cagg                                                                 1564
```

<210> SEQ ID NO 72
<211> LENGTH: 1564
<212> TYPE: DNA
<213> ORGANISM: Alopecurus

<400> SEQUENCE: 72

```
ggcgcgccac catggataag gctgcttaca ttgctgtgtt ctgctttacc ttcttgttct       60
tgctccacag gatcctcagg ggatctaagt ctaacggagg aaactcttct aagggagttc      120
agctccctcc atctcctcca gctattcctt tccttggaca tctccatctc gtggctgaga      180
agcctcttca tgctactctt agaaggctcg ctgataggta cggacctgtg ttctctctta      240
gactcggtgc tagaaacgct ctcgtggttt ctactgctgc tggtgctaga gaatgcttca      300
ctgagcacga tgtgaccttc gctaacagac ctcagttccc atctcagctc ctcgtttctt      360
tcggaggaac ttctctcatc cactctaact acgacctag tggagaacc ctcagaagag       420 ttgctgctgt tcagttgctc tctacccata gagtggcttg catgtctggt gtgatcgctt      480
ctgagatcag ggctatgact agaaggctct gtagagctgc tgcagctggt gcaagagttc      540
atctcaagag aaggcttttc gagctttctc tctctgtgct catggaaact atcgctaaca      600
ccaagggaac caggcctgtt gctgatgctg ataccgatat gtctctcgag gctcaagagt      660
tcaagaaagt gatggatgag atcatccctt acatcggagc tgctaatatg tgggatttct      720
tgcctgtgat gagatggttc gatgtgttcg gagtgaggaa caagatcctc gctgctgtgt      780
ctagaaggga tgctttcttg agaaggctca tcgatgctga gacacagaga ctcgatcatg     840
gtggtggaca gggtgataag aaatctatga tcgctgtgct cctcacccct caaaagactg      900
```

```
aacctgaggt gtacaccgat accatgatca ctgctttgtg cgctaacctc ttcgctgctg   960
gaactgagac tacttctact atgaccgagt gggctatgac cctccttctt aaccatcctg  1020
ctgtgatcaa gaaggctcag gctgagatcg atggatctgt gggaaactct agactcgtgg  1080
ctgctgatga tcttcctaga cttgcttacc tccagtgcat catctctgag gctcttagac  1140
tttaccctcc agctccactt ctcttgcctc atgagtcatc tgctgattgc aaggtgggag  1200
gatcaacgt gccaagagat accatgctca tcgtgtctgc ttacgctatc cacagggatc  1260
ctgctatttg gggagatcct actgtgttca gacctgagag attcgaggat ggaaagggtg  1320
agggacttct cgttatccct ttcggaatgg aagaagagg ttgccctgga gagactcttg  1380
ctagacagat ggttggaatg gtgctcggaa ctatgctcca gtgttttgat gggagaggg  1440
aagatggtat ggaagtggat atgaccgagg aagggtat cactatggct aaggctgttc  1500
ctcttgaggc tatgtgctct cctagagcta tatgtgcaa cttcctcgag aagctccctg  1560
cagg                                                             1564

<210> SEQ ID NO 73
<211> LENGTH: 1600
<212> TYPE: DNA
<213> ORGANISM: Alpecurus

<400> SEQUENCE: 73
ggcgcgccac catgactatg gctactagag cacttcatat cctcggagag gcttctcctt    60
ggtctttggc tggtgctgct gctgctatgg ctcttttgtg gcttgctgct tggattcttg   120
aatgggcttg gtggactcct agaaggcttg gtagagcatt gcaagctcag ggactcactg   180
gaaccagata cagactcttc actggtgatg tgaccgagaa cgctagactc aacagagctg   240
ctagatctaa gcctctccct ctcggatctc acgatatcat ccctagagtt cagcctatgc   300
tctctaacgc tgtgaaagag aacggaaagc tctctttcac ctggttcgga cctactccta   360
gagtgatgat ccacgatcct gagcttgtga gagagatcct ctcaaacaag ttcggacact   420
acggaaagcc tcagacctct agactttca agctcctcgc tgatggactc gtgaatcatg   480
aaggtgagaa gtgggctaag cacagaagga tccttaaccc tgctttccac tctgagaaga   540
tcaagaggat gctccctgtg ttctctacct gctctgaaga gatgatcacc aggtgggaga   600
actctgtgtc atctgaggga ctcagtgaag tggatgtttg gcctgagttc agaaccctca   660
ccggtgatgt gatctctaga accgctttcg gatcttctta ccaagaggga atgaagatct   720
tccagctcca gggtgaactt gctgagagac ttatccaggc tttccagacc cttttcatcc   780
ctggatactg gttcctccca accagaaaca acagaaggat gagggctatc gatagagaga  840
tctgcaccat cctcagggga atcatcgaga gaagaacag ggctatcaag aacggtgatg   900
ctaggtctga tgatctcctt ggattgctcc tcgagtctaa catgagagag tctaacggaa   960
aggctgatct cggaatgtct accgaggata ccatggaaga gtgcaagctt ttctacttcg  1020
ctggaatgga aactacctct gtgctcctta cttggaccct catcctcctt tcaatgcacc  1080
ctgaatggca agagcaggct agaaaagagg tgctccatca cttcggaaga accaccctg  1140
atttcgagaa cctctctagg ctcaagatcg tgaccatgat cctctacgag gtgctcagac  1200
tttaccctcc tgctgtgttc atgactagaa ggacctacaa ggctatggaa ctcggaggaa  1260
tcacttaccc tgctggtgtg aacttcatgc tccctgttct cttcatccac cacgatccta  1320
ctatctgggg aaaggatgct tctgagttca accctcagag gttcgctgat ggaatctcaa  1380
acgctgctaa gcaccctgct gcattcttcc cttttggtgg tggacctaga atctgcatcg  1440
```

```
gacagaactt cgctctcctc gaagctaaga tggctctctc tactatcctc cagaggttca   1500
gtttccagct ctctccttct tacacccacg ctccatacac tgtgcttact cttcatcctc   1560
agcacggtgc tcctattatg ctcaagaaga tccctgcagg                         1600
```

<210> SEQ ID NO 74
<211> LENGTH: 1567
<212> TYPE: DNA
<213> ORGANISM: Alopecurus

<400> SEQUENCE: 74

```
ggcgcgccac catgtctact ggacttgttt ggatggttgc tgctgctatc gctgctgttc     60
ttgctacttg ggcttttcaac gctctcgtga gattggtttg gaggcctaga gctatcacta   120
gacagcttag ggctcaaggt gttggaggac ctgcttacaa gcttttcgct ggaaacctcg   180
gagagatcaa gcagttgaga gctgaaactg ctggtgctgc tctcgatgtg ggatctcatg   240
atttcgttcc tctcgtgcag cctcacttca gaaagtggat tcctatccac ggaaggacat   300
tcctctactg gtttggagct agacctaccc tctgtatcgc tgatgttaac gtggtgaagc   360
aggttctctt cgataggaac ggactctacc ctaagaacac cggaaaccct catatcgcta   420
gactcctcgg aaagggactc gttctcatcg atggtgatga ttggaagagg cacagaaagg   480
tggtgcaccc tgcttttcaac atggataagc tcaagatgat daccgtgacc atgtctgatt   540
gcgctggatc tatgatgtct gagtggaagg ctaagctcga aagggtggt gaagctgaga   600 tcgatctttc taggcagttc gaggaactca ccgctgatgt gatctctcac actgctttcg   660
gatcttcata caccgaggga agaaggtgt tcctcgctca gagagatctt cagttcctcg   720
ctttctctac cgtgttctct gttcagatcc ctgcttcag atatatccct acccagaaga   780
acaggcagat ctggaagctc gatagagaag tgagaaccat gctcaccaac atcatcaaga   840
ccaggctcgc taccaaggat accatgggat acggaaacga tctcctcgga cttatgcttg   900
aggcttgtgc tcctgaacat ggtgagactc ctatcctctc tatggatgag atcatcgatg   960
agtgcaagac cttcttcttc gctggacacg atacctcttc tcacctcctt acctggacta  1020
tgttcctcct ctcaactcac cctgagtggc aagagaagct cagagaagag gttctcactg  1080
agtgcggaaa cgaggttcca actggtgata tgctcaacaa gctcaagctc gtgaacatgt  1140
tcttgctcga gactctcagg ctctactctc ctgtttctgt gatccagaga aagaccggat  1200
ctgatatgga agtgggagga atcaaggtgc cacagggaac tgttctcact atccctatcg  1260
ctaccatgca cagggataag gaagtttggg gagaggacgc tgatgagttc aagcctatga  1320
ggtttgagaa gggtgtgacc atggctgcta agcaccctaa cgctttgctc tcattctctt  1380
caggacctag gtcttgcatc ggacagaact cgctatgat cgaggctaag gctgtgatcg  1440
ctgttatcct ccagaggttc tctttctcac tctctccaaa gtacgtgcac gcacctatgg  1500
acgtgataac cctcagacct aagttcggac tccctatggt tctcaagtct ctcgagatgc  1560
ctgcagg                                                             1567
```